US010501438B2

(12) United States Patent
Jacquemot et al.

(10) Patent No.: US 10,501,438 B2
(45) Date of Patent: Dec. 10, 2019

(54) ARYL-SUBSTITUTED DIHYDROQUINOLINONES, THEIR PREPARATION AND THEIR USE AS PHARMACEUTICALS

(71) Applicant: NEOMED Institute, Montreal, Quebec (CA)

(72) Inventors: Guillaume Jacquemot, Montreal (CA); Malken Bayrakdarian, Montreal (CA); Shawn Johnstone, Montreal (CA); Jeffrey S. Albert, Montreal (CA); Andrew Griffin, Montreal (CA)

(73) Assignee: Neomed Institute, Montreal, Quebec (CA)

( * ) Notice: Subject to any disclaimer, the term of this patent is extended or adjusted under 35 U.S.C. 154(b) by 0 days.

(21) Appl. No.: 15/751,800

(22) PCT Filed: Aug. 11, 2016

(86) PCT No.: PCT/CA2016/050943
§ 371 (c)(1),
(2) Date: Feb. 9, 2018

(87) PCT Pub. No.: WO2017/024408
PCT Pub. Date: Feb. 16, 2017

(65) Prior Publication Data
US 2018/0230130 A1 Aug. 16, 2018

Related U.S. Application Data

(60) Provisional application No. 62/356,579, filed on Jun. 30, 2016, provisional application No. 62/203,623, filed on Aug. 11, 2015.

(51) Int. Cl.
*C07D 401/14* (2006.01)
*C07D 405/14* (2006.01)
*C07D 413/14* (2006.01)
*C07D 401/04* (2006.01)
*C07D 417/14* (2006.01)

(52) U.S. Cl.
CPC ......... *C07D 401/14* (2013.01); *C07D 401/04* (2013.01); *C07D 405/14* (2013.01); *C07D 413/14* (2013.01); *C07D 417/14* (2013.01)

(58) Field of Classification Search
CPC .. C07D 401/14; C07D 405/14; C07D 413/14; C07D 417/14; C07D 401/04
USPC .................................................. 514/255.05
See application file for complete search history.

(56) References Cited

U.S. PATENT DOCUMENTS 4,550,166 A 10/1985 Moran et al.
4,785,005 A * 11/1988 Campbell ............ C07D 401/04
514/312

| 6,162,804 A | 12/2000 | Bilodeau et al. |
| 6,465,484 B1 | 10/2002 | Bilodeau et al. |
| 8,557,841 B2 | 10/2013 | Yu et al. |
| 2005/0153985 A1 | 7/2005 | Kehrli, Jr. et al. |
| 2014/0094456 A1 | 4/2014 | Buckman et al. |
| 2014/0349990 A1 | 11/2014 | Blank et al. |
| 2015/0051208 A1 | 2/2015 | Engelhardt et al. |
| 2015/0148342 A1 | 5/2015 | Yue et al. |
| 2015/0148375 A1 | 5/2015 | Yue et al. |

FOREIGN PATENT DOCUMENTS

| CA | 2098243 A1 | 12/1993 |
| CA | 2657327 A1 | 1/2008 |
| CA | 2701355 A1 | 4/2009 |
| CA | 2760084 A1 | 11/2010 |
| CA | 2874953 A1 | 12/2013 |
| CA | 2875016 A1 | 12/2013 |
| CA | 2895404 A1 | 6/2014 |
| CA | 2917562 A1 | 1/2015 |
| CA | 2932030 A1 | 6/2015 |
| WO | 2000012089 | 3/2000 |

(Continued)

OTHER PUBLICATIONS

Brand et al., "Small Molecule Inhibitors of Bromodomain-Acetyl-lysine Interactions", ACS Chem. Biol., 2015, vol. 10, pp. 22-39.
Ember et al., "Acetyl-lysine Binding Site of Bromodomain-Containing Protein 4 (BRD4) Interacts with Diverse Kinase Inhibitors", ACS Chem. Biol, 2014, vol. 9, pp. 1160-1171.
Garnier et al. "BET bromodomain inhibitors: a patent review", Expert Opinion on Theurapeutic Patents, 2014, 24(2), pp. 185-199.
Hay et al., "Discovery and Optimization of Small-Molecule Ligands for the CBP/p300 Bromodomains" Journal of the American Chemical Society, 2014, vol. 136, pp. 9308-9319.

(Continued)

Primary Examiner — Kahsay Habte
(74) Attorney, Agent, or Firm — Brinks Gilson & Lione

(57) ABSTRACT

This application relates to aryl-substituted dihydroquinolinones of formula (I), compositions comprising them and their uses in the treatment of diseases and conditions in which inhibition of a bromodomain is indicated. For example, the application relates to aryl-substituted dihydroquinolinones and to their use as bromodomain inhibitors. The present application is also related to the treatment or prevention of proliferative disorders, auto-immune disorders, inflammatory disorders, dermal disorders, and neoplasms, including tumors and/or cancers.

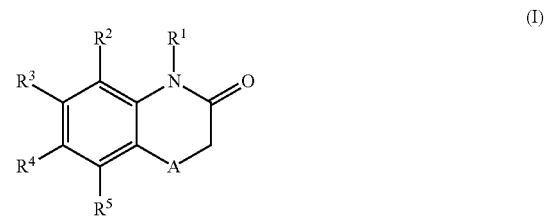

25 Claims, No Drawings

(56) References Cited

FOREIGN PATENT DOCUMENTS

| WO | 2005089763 | | 9/2005 |
|---|---|---|---|
| WO | 2008078091 | | 7/2008 |
| WO | 2009050183 | | 4/2009 |
| WO | 2011054846 | A1 | 5/2011 |
| WO | 2011060235 | | 5/2011 |
| WO | 2012082689 | | 6/2012 |
| WO | 2013024104 | A1 | 2/2013 |
| WO | 2013186229 | A1 | 12/2013 |
| WO | 2014051698 | A1 | 4/2014 |
| WO | 2014055548 | A1 | 4/2014 |
| WO | 2014096965 | A2 | 6/2014 |
| WO | 2014128655 | A1 | 8/2014 |
| WO | 2014145051 | A1 | 9/2014 |
| WO | 2014152029 | A1 | 9/2014 |
| WO | 2014159837 | A1 | 10/2014 |
| WO | 2014191896 | A1 | 12/2014 |
| WO | 2015002754 | A2 | 1/2015 |
| WO | 2015004533 | A2 | 1/2015 |
| WO | 2015004534 | A2 | 1/2015 |
| WO | 2015022332 | A1 | 2/2015 |
| WO | 2015049629 | A1 | 4/2015 |
| WO | 2015086526 | | 6/2015 |
| WO | 2015104653 | A1 | 7/2015 |
| WO | 2015153683 | A1 | 10/2015 |
| WO | 2015164480 | A1 | 10/2015 |
| WO | 2016077656 | A2 | 5/2016 |
| WO | 2016087936 | A1 | 6/2016 |
| WO | 2016097863 | A1 | 6/2016 |
| WO | 2016097870 | A1 | 6/2016 |
| WO | 2016139292 | A1 | 9/2016 |
| WO | 2016146738 | A1 | 9/2016 |
| WO | 2016168682 | A2 | 10/2016 |
| WO | 2016170323 | A1 | 10/2016 |
| WO | 2016170324 | A1 | 10/2016 |
| WO | 2017066876 | | 4/2017 |

OTHER PUBLICATIONS

Mirguet et al. "From ApoA1 upregulation to BET family bromodomain inhibition: Discovery of I-BET151", Bioorganic & Medicinal Chemisty Letters, 2012, vol. 22, pp. 2963-2967.

Nakamura et al., "Enantioselective Synthesis and Enhanced Circularly Polarized Luminescence of S-Shaped Double Azahelicenes", Journal of the American Chemical Society, 2014, vol. 136, pp. 5555-5558.

Johnstone et al. "EG-04. Development of Highly Potent, Selective Bet Bromodomain inhibitors that are CNS Penetrant and Effective in Rodent Models of Brain Cancer", Neuro-Oncology, 2014, 16: supplement 5, Epigenetics EG-04. Abstracts from the 19th Annual Scientific Meeting of the Society for Neuro-Oncology, Miami, Florida, Nov. 13-16, 2014.

Picaud et al., "PFI-1, a Highly Selective Protein Interaction Inhibitor, Targeting BET Bromodomains", Therapeutics, Targets, and Chemical Biology, Cancer Research, 73(11), 2013, pp. 3336-3346.

Sastry et al., "Synthesis of 6-(1,4,5,6-tetrahydro-6-oxo-3-pyridazinyl)-2H-1,4-benzoxazin-3(4H)-ones as possible cardiotonic agents", Indian Journal of Chemistry, vol. 28B, 1989, pp. 882-884.

Romero et al., "Disrupting Acetyl-Lysine Recognition: Progess in the Development of Bromodomain Inhibitors", Journal of Medicinal Chemistry, 2016, vol. 59, pp. 1271-1298.

Rooney et al., "A Series of Potent CREBBP Bromodomain Ligands Reveals an Induced-Fit Pocket Stabilized by a Cation-π Interaction", Angew. Chem. Int. Ed., 2014, 53, pp. 6126-6130.

Seal et al. Identification of a novel series of BET family bromodomain inhibitors: Binding mode and profile of I-BET151 (GSK1210151A), Bioorganic & Medicinal Chemistry Letters, 22, 2012, pp. 2968-2972.

Swords et al., "Novel BET Bromodomain Inhibitors EP31670, EP11313 and EP11336 Have Potent Anti-Leukemic Activity in Acute Myeloid Leukemia (AML) and Augment the Effects of All-Trans-Retinoic Acid (ATRA) in Vitro", ASH 57th Annual Meeting, Orlando, FL, Dec. 5-8, 2015.

Vidler et al. "Discovery of Novel Small-Molecule Inhibitors of BRD4 Using Structure-Based Virtual Screening" Journal of Medicinal Chemistry, 2013, vol. 56, pp. 8073-8088.

Yamanaka et al., "Imidazo[1,2-a]pyridines.I. Synthesis and Inotropic Activity of New 5-Imidazo[1,2-a]pyridinyl-2(1H)-pyridinone Derivatives", Chem. Pharm. Bull., 1991, vol. 39. No. 6, pp. 1556-1567.

Yamanaka et al., "Imidazo[1,2-a]pyridines. III. Synthesis and Bradycardic Activity of New 5-Imidazo[1,2-a]pyridin-6-ylpyridine Derivatives", Chem. Pharm. Bull., 1992, vol. 40, No. 6, pp. 1486-1493.

European Search Report dated Jan. 14, 2019 for corresponding EP Application No. 16834368.9.

Bilodeau et al., "Design and Synthesis of 1,5-Diarylbenzimidazoles as Inhibitors of the VEGF-Receptor KDR," Bioorganic & Medicinal Chemistry Letters, 2003, vol. 13, pp. 2485-2488.

Banker et al., "Prodrugs," Modern Pharmaceutics, 3rd edition, Revised and Expanded, 1986, pp. 451 and 596.

Bernstein, "Polymorphism in Molecular Crystals," 2002, pp. 115-118, 272.

Braga et al., "Making Crystals from Crystals: A Green Route to Crystal Engineering and Polymorphism," Royal Society of Chemistry, Chem. Commun., 2005, pp. 3635-3645.

Bundgaard, Design of Prodrugs, 1985, Chapter 1, p. 1.

Chemical Abstract Service, Database Accession No. 1781658-56-7, dated Jun. 17, 2015.

Chemical Abstract Service, Database Accession No. 1782034-46-1, dated Jun. 17, 2015.

Davidovich et al., "Detection of Polymorphism by Powder X-Ray Diffraction: Interference by Preferred Orientation," Am. Pharm. Rev., 2004, vol. 7, No. 1, pp. 10, 12, 14, 16, and 100).

Dean, "Analytical Chemistry Handbook," 1995, pp. 10.24-10.26.

Ettmayer et al., "Lessons Learned from Marketed and Investigational Prodrugs," J. Med. Chem., 2004, vol. 47, No. 10, pp. 2393-2404.

Guillory (in Brittain ed.), "Polymorphism in Pharmaceutical Solids," NY: Marcel Dekker, Inc., 1999, pp. 1-2 and 183-226.

Hackam et al., "Translation of Research Evidence from Animals to Humans," JAMA, 2006, vol. 296, No. 14, pp. 1731-1732.

Ivanisevic et al. "Use of X-Ray Powder Diffraction in the Pharmaceutical Industry," Pharm. Sci. Encycl., 2010, pp. 1-42.

Jain et al., "Polymorphism in Pharmacy," Indian Drugs, 1986, vol. 23, No. 6, pp. 315-329.

Jordan, "Tamoxifen: A Most Unlikely Pioneering Medicine," Nature Reviews, 2003, vol. 2, pp. 205-213.

Kirk-Othmer, "Crystallization," Encyclopedia of Chemical Technology, 2002, vol. 8, pp. 95-147.

Seddon, "Pseudopolymorph: A Polemic," Crystal Growth & Design, 2004, vol. 4, No. 6, p. 1087 (2 pages from Internet).

Silverman, Prodrugs and Drug Delivery Systems, The Organic Chemistry of Drug Design and Drug Action, Chapter 3, 1992, pp. 352-400.

Stella, "Prodrugs as Therapeutics," Expert Opin. Ther. Patents, 2004, vol. 14, No. 3, pp. 277-280.

Testa, "Prodrug Research: Futile or Fertile?," Biochemical Pharmacology, 2004, vol. 68, pp. 2097-2106.

Vippagunta et al., "Crystalline Solids," 2001, Advanced Drug Delivery Reviews, vol. 48, pp. 3-26.

Wolff, ed. Burger's Medicinal Chemistry and Drug Discovery, 5th Edition, New York: John Wiley & Sons, 1994, vol. 1, pp. 975-977.

Wolff, ed., Burger's Medicinal Chemistry and Drug Discovery, 5th edition, New York: John Wiley & Sons, 1996, vol. 1, pp. 949-976.

Yu et al., "Physical Characterization of Polymorphic Drugs: An Integrated Characterization Strategy," PSTT, 1998, vol. 1, No. 3, pp. 118-127.

Zaragoza, "Side Reactions in Organic Synthesis: A Guide to Successful Synthesis Design," Weinheim: Wiley-VCH Verlag GmbH & Co. KGaA, 2005, Preface pp. IX-X.

Andrieu, "Clinical Trials for BET Inhibitors Run Ahead of the Science," Drug Discovery Today: Technologies, 2016, vol. 19, pp. 45-50.

(56) References Cited

OTHER PUBLICATIONS

Kharenko, "Novel Approaches to Targeting BRD4," Drug Discovery Today: Technologies, 2017, vol. 24, pp. 19-24.
Pervaiz, "Bromodomain Drug Discovery—the Past, the Present, and the Future," The Chemical Record, 2018, vol. 18, pp. 1808-1817.
Ramadoss, "Targeting the Cancer Epigenome: Synergistic Therapy with Bromodomain Inhibitors," Drug Discover Today, 2018, vol. 23, pp. 76-89.
Shi, "The Mechanisms Behind the Therapeutic Activity of BET Bromodomain Inhibition," Molecular Cell, 2014, vol. 54, pp. 728-736.
Venkatesh, "Role of the Development Scientist in Compound Lead Selection and Optimization," Journal of Pharmaceutical Sciences, 2000, vol. 89, No. 2, pp. 145-154.
West, Solid State Chemistry and Its Applications, John Wiley & Sons, 1984.

* cited by examiner

ARYL-SUBSTITUTED DIHYDROQUINOLINONES, THEIR PREPARATION AND THEIR USE AS PHARMACEUTICALS

RELATED APPLICATION

This application is a National Stage application of International Application No. PCT/CA2016/050943 filed on Aug. 11, 2016, which claims priority to U.S. provisional application No. 62/203,623 filed on Aug. 11, 2015, and to U.S. provisional application No. 62/356,579 filed on Jun. 30, 2016, the contents of which are incorporated herein by reference in their entirety for all purposes.

This application claims priority to United States provisional application No. 62/203,623 filed on Aug. 11, 2015, and to United States provisional application No. 62/356,579 filed on Jun. 30, 2016, the contents of which are incorporated herein by reference in their entirety for all purposes.

TECHNICAL FIELD

The technical field generally compounds, compositions and their uses in the treatment of diseases and conditions in which inhibition of bromodomains is indicated. For example, the application relates to aryl-substituted dihydroquinolinones, to pharmaceutical compositions comprising the same, and to their use as bromodomain inhibitors. The present application is also related to the treatment or prevention of proliferative disorders, auto-immune disorders, inflammatory disorders, dermal disorders, and neoplasms, including tumors and/or cancers.

BACKGROUND

Bromodomains are found in a variety of mammalian DNA-binding proteins. The bromodomain, which is the conserved structural module in chromatin-associated proteins and histone acetyltransferases, is known to recognize acetyl-lysine residues on proteins. Bromodomain inhibitors are believed to be useful in the treatment of a variety of diseases or conditions, such as cancer as well as chronic autoimmune and inflammatory conditions. There is therefore a need for compounds that could inhibit bromodomains.

SUMMARY

According to one aspect, the present application relates to compounds of Formula (I), and pharmaceutically acceptable salts, solvates, esters or prodrugs thereof:

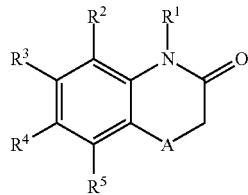

wherein:
A is —CH$_2$— or oxygen;
R$^1$ is hydrogen or C$_1$-C$_6$ alkyl;
R$^2$ and R$^5$ independently represent hydrogen, halogen, —CH$_3$, —C(R$^a$)(R$^b$)(R$^c$), —N(R$^d$)(R$^e$) or —O(R$^f$), wherein
R$^a$ is hydrogen or C$_1$-C$_6$ alkyl;
R$^b$ is hydrogen, hydroxyl or C$_1$-C$_6$ alkyl;
R$^c$ is C$_3$-C$_6$ cycloalkyl, C$_6$-C$_{10}$ aryl, 3-7 membered heterocycloalkyl, 5-10 membered heteroaryl, (C$_3$-C$_6$ cycloalkyl)C$_1$-C$_6$ alkyl, (3-7 membered heterocycloalkyl)C$_1$-C$_6$ alkyl, (C$_6$-C$_{10}$ aryl)C$_1$-C$_6$ alkyl or (5-10 membered heteroaryl)C$_1$-C$_6$ alkyl, —O(R$^g$) or —N(R$^g$)(R$^h$);
R$^d$ is hydrogen or C$_1$-C$_6$ alkyl;
R$^e$ is C$_1$-C$_6$ alkyl, C$_3$-C$_6$ cycloalkyl, C$_6$-C$_{10}$ aryl, 3-7 membered heterocycloalkyl, 5-10 membered heteroaryl, (C$_3$-C$_6$ cycloalkyl)C$_1$-C$_6$ alkyl, (3-7 membered heterocycloalkyl)C$_1$-C$_6$ alkyl, (C$_6$-C$_{10}$ aryl)C$_1$-C$_6$ alkyl, (5-10 membered heteroaryl)C$_1$-C$_6$ alkyl, keto(C$_6$-C$_{10}$ aryl) or keto(5-10 membered heteroaryl);
R$^f$ is C$_1$-C$_6$ alkyl, C$_3$-C$_6$ cycloalkyl, 3-7 membered heterocycloalkyl, C$_6$-C$_{10}$ aryl, 5-10 membered heteroaryl, (C$_3$-C$_6$ cycloalkyl)C$_1$-C$_6$ alkyl, (3-7 membered heterocycloalkyl)C$_1$-C$_6$ alkyl, (C$_6$-C$_{10}$ aryl)C$_1$-C$_6$ alkyl or (5-10 membered heteroaryl)C$_1$-C$_6$ alkyl;
R$^g$ is C$_1$-C$_6$ alkyl, C$_3$-C$_6$ cycloalkyl, C$_6$-C$_{10}$ aryl, 3-7 membered heterocycloalkyl, 5-10 membered heteroaryl, (C$_3$-C$_6$ cycloalkyl)C$_1$-C$_6$ alkyl, (3-7 membered heterocycloalkyl)C$_1$-C$_6$ alkyl, (C$_6$-C$_{10}$ aryl)C$_1$-C$_6$ alkyl or (5-10 membered heteroaryl)C$_1$-C$_6$ alkyl;
R$^h$ is hydrogen, C$_1$-C$_4$ alkyl, —C(O)(R$^6$); —C(O)NH$_2$, —C(O)NH(R$^6$) or —C(O)N(R$^6$)(R$^{6'}$); one of R$^3$ and R$^4$ represents a group of formula (II), provided that when R$^3$ is a group of formula (II), then R$^4$ has the same definition than R$^2$ and R$^5$, and when R$^4$ is a group of formula (II), then R$^3$ has the same definition than R$^2$ and R$^5$;
the group of formula (II) has the following structure:

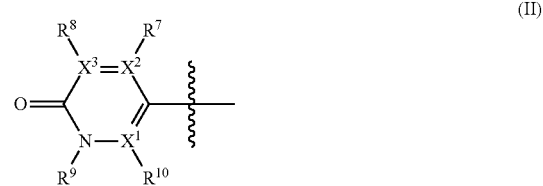

wherein:
X$^1$, X$^2$ and X$^3$ are each independently N or C, wherein when X$^1$, X$^2$ or X$^3$ is N, then the R$^7$, R$^8$ or R$^{10}$ attached thereto is absent, provided that at least two of X$^1$, X$^2$ and X$^3$ is C;
R$^7$ and R$^{10}$ are each independently hydrogen, halogen (such as F, Cl), CN, linear or branched C$_1$-C$_6$alkyl, C$_3$-C$_6$cycloalkyl, OR$^6$, SR$^6$, NHR$^6$, N(R$^6$)(R$^{6'}$), NHC(O)R$^6$ or N(R$^6$)C(O)R$^{6'}$;
R$^8$ is halogen (such as F, Cl), CN, linear or branched C$_1$-C$_6$alkyl, C$_3$-C$_6$cycloalkyl, OR$^6$, SR$^6$, NHR$^6$, N(R$^6$)(R$^{6'}$), NHC(O)R$^6$ or N(R$^6$)C(O)R$^{6'}$;
R$^6$ and R$^{6'}$, which are the same or different, represent a C$_1$-C$_6$ alkyl group;
R$^9$ is a C$_1$-C$_3$alkyl or C$_3$-C$_5$cycloalkyl group;
each alkyl group is linear or branched and optionally substituted, and each of cycloalkyl, aryl, heterocycloalkyl and heteroaryl is optionally substituted;
and when $R^3$ is the group of formula (II), one of $R^2$, $R^4$ and $R^5$ is —C($R^a$)($R^b$)($R^c$), —N($R^d$)($R^e$) or —O($R^f$) and the other two of $R^2$, $R^4$ and $R^5$ are independently hydrogen, halogen or —CH$_3$; or when $R^4$ is the group of formula (II), one of $R^2$, $R^3$ and $R^5$ is —C($R^a$)($R^b$)($R^c$), —N($R^d$)($R^e$) or —O($R^f$) and the other two of $R^2$, $R^3$ and $R^5$ are independently hydrogen, halogen or —CH$_3$.

In one embodiment, when a substituent in Formula (I) comprises an alkyl group, this group can be unsubstituted or substituted with 1 to 3 groups being halogen, CN, alkoxy or haloalkoxy. In another embodiment, when a substituent in Formula (I) comprises a cycloalkyl, aryl, heterocycloalkyl and/or heteroaryl group, such group can be unsubstituted or substituted by 1 to 3 groups being halogen, CN, alkyl, haloalkyl, alkoxy or haloalkoxy.

According to another embodiment, the application relates to compounds of Formula (III), and pharmaceutically acceptable salts, solvates, esters or prodrugs thereof:

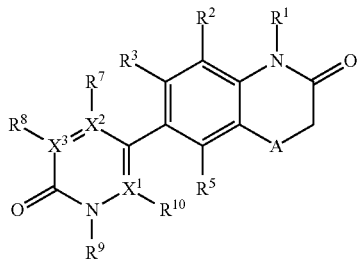

(III)

wherein A, $R^1$, $R^2$, $R^3$, $R^5$, $R^7$, $R^8$, $R^9$, $R^{10}$, $X^1$, $X^2$ and $X^3$ are as defined herein.

According to another embodiment, the application also relates to compounds of Formula (IIIa), and pharmaceutically acceptable salts, solvates, esters or prodrugs thereof:

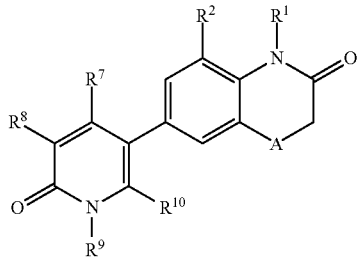

(IIIa)

wherein A, $R^1$, $R^2$ $R^7$, $R^8$, $R^9$ and $R^{10}$ are as herein defined.

In another embodiment, the present application relates to compounds of Formula (IIIb), and pharmaceutically acceptable salts, solvates, esters or prodrugs thereof:

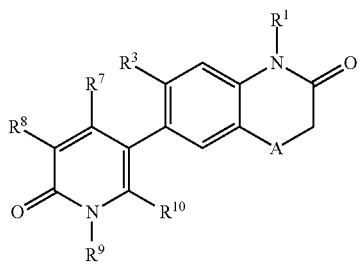

(IIIb)

wherein A, $R^1$, $R^3$, $R^7$, $R^8$, $R^9$ and $R^{10}$ are as defined herein.

Another embodiment of the application relates to compounds of Formula (IIIc), and pharmaceutically acceptable salts, solvates, esters or prodrugs thereof:

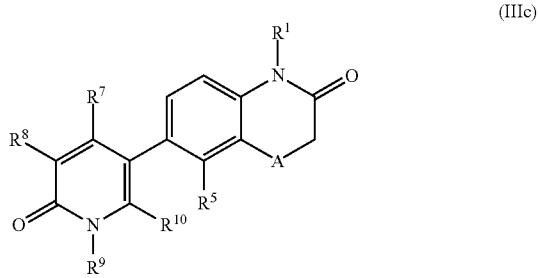

(IIIc)

wherein A, $R^1$, $R^5$, $R^7$, $R^8$, $R^9$ and $R^{10}$ are as defined herein.

According to another embodiment, the application also relates to compounds of Formula (IV), and pharmaceutically acceptable salts, solvates, esters or prodrugs thereof:

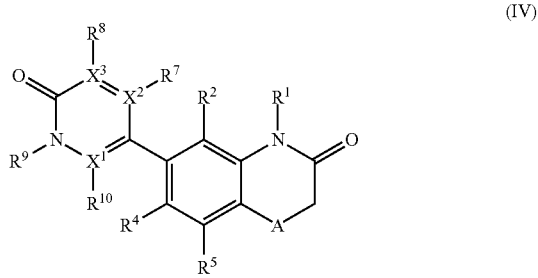

(IV)

wherein A, $R^1$, $R^2$, $R^4$, $R^5$, $R^7$, $R^8$, $R^9$, $R^{10}$, $X^1$, $X^2$ and $X^3$ are as herein defined.

According to another embodiment, the application also relates to compounds of Formula (IVa), and pharmaceutically acceptable salts, solvates, esters or prodrugs thereof:

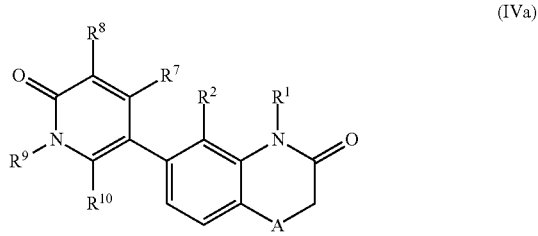

(IVa)

wherein A, $R^1$, $R^2$, $R^7$, $R^8$, $R^9$, $R^{10}$ are as defined herein.

According to another embodiment, the application also relates to compounds of Formula (IVb), and pharmaceutically acceptable salts, solvates, esters or prodrugs thereof:

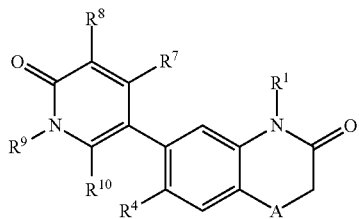

(IVb)

wherein A, $R^1$, $R^4$, $R^7$, $R^8$, $R^9$ and $R^{10}$ are as defined herein.

According to another embodiment, the application also relates to compounds of Formula (IVc), and pharmaceutically acceptable salts, solvates, esters or prodrugs thereof:

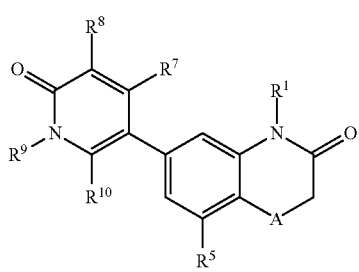

(IVc)

wherein A, $R^1$, $R^5$, $R^7$, $R^8$, $R^9$ and $R^{10}$ are as defined herein.

According to another embodiment, the application also relates to compounds of Formula (IIId), and pharmaceutically acceptable salts, solvates, esters or prodrugs thereof:

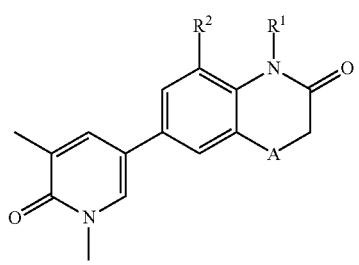

(IIId)

wherein A, $R^1$ and $R^2$ are as herein defined.

According to another embodiment, the application also relates to compounds of Formula (IVd), and pharmaceutically acceptable salts, solvates, esters or prodrugs thereof:

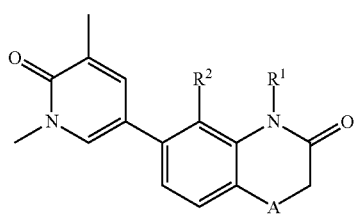

(IVd)

wherein A, $R^1$ and $R^2$ are as herein defined.

According to another embodiment, the application also relates to compounds of Formula (IIIe), and pharmaceutically acceptable salts, solvates, esters or prodrugs thereof:

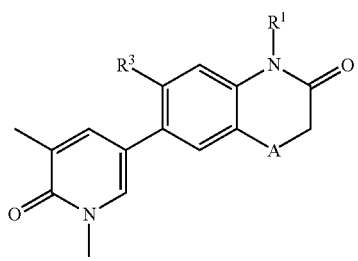

(IIIe)

wherein A, $R^1$ and $R^3$ are as herein defined.

According to another embodiment, the application also relates to compounds of Formula (IVe), and pharmaceutically acceptable salts, solvates, esters or prodrugs thereof:

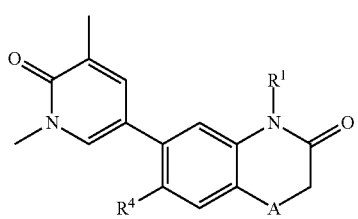

(IVe)

wherein A, $R^1$ and $R^4$ are as herein defined.

According to another embodiment, the application also relates to compounds of Formula (IIIf), and pharmaceutically acceptable salts, solvates, esters or prodrugs thereof:

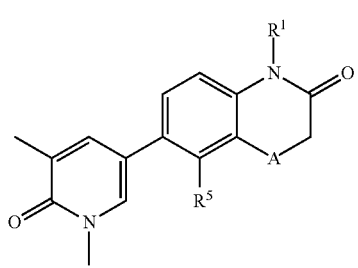

(IIIf)

wherein A, $R^1$ and $R^5$ are as herein defined.

According to another embodiment, the application also relates to compounds of Formula (IVf), and pharmaceutically acceptable salts, solvates, esters or prodrugs thereof:

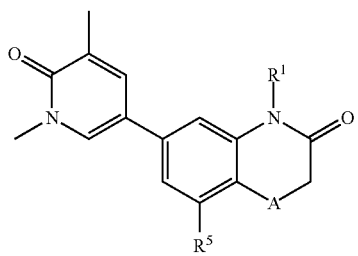

(IVf)

wherein A, $R^1$ and $R^5$ are as herein defined.

Another aspect relates to pharmaceutical compositions, comprising a compound as defined in the present application, together with a pharmaceutically acceptable carrier, diluent or excipient.

A further aspect relates to the use of a compound as defined in the present application, or such a compound for use, in the treatment or prevention of a disease or condition for which a bromodomain inhibitor is indicated. Similarly, this aspect relates to the use of a compound of the present application in the manufacture of a medicament for the treatment or prevention of a disease or condition for which a bromodomain inhibitor is indicated. This aspect also further relates to a method for treating a disease or condition for which a bromodomain inhibitor is indicated, which comprises administering to a subject in need thereof, a therapeutically effective amount of a compound as herein defined. In one embodiment, the disease or condition for which a bromodomain inhibitor is indicated is an autoimmune disorder, an inflammatory disorder (such as rheumatoid arthritis, irritable bowel syndrome, or psoriasis), a dermal disorder, or cancer (for instance, brain cancer, pancreatic cancer, breast cancer, lung cancer, or prostate cancer). For instance the disease or condition is brain cancer, such as glioblastoma multiforme.

According to a further aspect, the application relates to the use of a compound as herein defined, or such a compound for use, in the treatment of a disease or condition selected from auto-immune disorders, inflammatory disorders, dermal disorders, and neoplasms. This aspect also relates to a method for the treatment or prevention of a disease or condition selected from auto-immune disorders, inflammatory disorders, dermal disorders, and neoplasms, which comprises administering to a subject in need thereof, a therapeutically effective amount of a compound as herein defined. For instance, the inflammatory disorder is rheumatoid arthritis, irritable bowel syndrome, or psoriasis. For example, the disease or condition is a neoplasm which is brain cancer (e.g. glioblastoma multiforme), pancreatic cancer, breast cancer, lung cancer, or prostate cancer.

Additional objects and features of the present compounds, compositions, methods and uses will become more apparent upon reading of the following non-restrictive description of exemplary embodiments, which should not be interpreted as limiting the scope of the invention.

DESCRIPTION

All technical and scientific terms used herein have the same meaning as commonly understood by one ordinary skilled in the art to which the present technology pertains. For convenience, the meaning of certain terms and phrases used herein are provided below.

To the extent the definitions of terms in the publications, patents, and patent applications incorporated herein by reference are contrary to the definitions set forth in this specification, the definitions in this specification control. The section headings used herein are for organizational purposes only, and are not to be construed as limiting the subject matter disclosed.

i. Definitions

The terminology used herein is for the purpose of describing particular embodiments only and is not intended to be limiting. It should be noted that, the singular forms "a", "an", and "the" include plural forms as well, unless the content clearly dictates otherwise. Thus, for example, reference to a composition containing "a compound" also contemplates a mixture of two or more compounds. It should also be noted that the term "or" is generally employed in its sense including "and/or" unless the content clearly dictates otherwise. Furthermore, to the extent that the terms "including", "includes", "having", "has", "with", or variants thereof are used in either the detailed description and/or the claims, such terms are intended to be inclusive in a manner similar to the term "comprising".

The term "about" or "approximately" means within an acceptable error range for the particular value as determined by one of ordinary skill in the art, which will depend in part on how the value is measured or determined, i.e., the limitations of the measurement system. For example, "about" can mean within 1 or more than 1 standard deviation, per the practice in the art. Alternatively, "about" can mean a range of up to 20%, preferably up to 10%, more preferably up to 5%, and more preferably still up to 1% of a given value. Alternatively, particularly with respect to biological systems or processes, the term can mean within an order of magnitude, preferably within 5-fold, and more preferably within 2-fold, of a value. Where particular values are described in the application and claims, unless otherwise stated the term "about" meaning within an acceptable error range for the particular value should be assumed.

As used herein, the terms "compounds herein described", "compounds of the present application" and equivalent expressions refer to compounds described in the present application, e.g., those encompassed by structural Formulae such as Formulae I, III, IIIa-IIIf, IV and IVa-IVd, optionally with reference to any of the applicable embodiments, and also includes exemplary compounds, for example, Compounds 1-101, as well as their pharmaceutically acceptable salts, solvates, esters, and prodrugs when applicable. When a zwitterionic form is possible, the compound may be drawn as its neutral form for practical purposes, but the compound is understood to also include its zwitterionic form. Embodiments herein may also exclude one or more of the compounds. Compounds may be identified either by their chemical structure or their chemical name. In a case where the chemical structure and chemical name would conflict, the chemical structure will prevail.

Unless otherwise stated, structures depicted herein are also meant to include all isomeric (e.g., enantiomeric, diastereomeric, and geometric (or conformational)) forms of the structure; for example, the R and S configurations for each asymmetric center, Z and E double bond isomers, and Z and E conformational isomers. Therefore, single stereochemical isomers as well as enantiomeric, diastereomeric, and geometric (or conformational) mixtures of the present compounds are within the scope of the present description. Unless otherwise stated, all tautomeric forms of the compounds are within the scope of the present description. Additionally, unless otherwise stated, structures depicted herein are also meant to include compounds that differ only in the presence of one or more isotopically enriched atoms. For example, compounds having the present structures including the replacement of hydrogen by deuterium or tritium, or the replacement of a carbon by a $^{13}$C- or $^{14}$C-enriched carbon are within the scope of the present description. Such compounds are useful, for example, as analytical tools, as probes in biological assays, or as therapeutic agents in accordance with the present description.

Where a particular enantiomer is preferred, it may, in some embodiments be provided substantially free of the corresponding enantiomer, and may also be referred to as "optically enriched." "Optically-enriched," as used herein, means that the compound is made up of a significantly greater proportion of one enantiomer. In certain embodiments the compound is made up of at least about 90% by weight of a preferred enantiomer. In other embodiments the compound is made up of at least about 95%, 98%, or 99% by weight of a preferred enantiomer. Preferred enantiomers may be isolated from racemic mixtures by any method known to those skilled in the art, including chiral high pressure liquid chromatography (HPLC) and the formation and crystallization of chiral salts or prepared by asymmetric syntheses. See, for example, Jacques et al., *Enantiomers, Racemates and Resolutions* (Wiley Interscience, New York, 1981); Wilen, et al., *Tetrahedron* 33:2725 (1977); Eliel, E. L. *Stereochemistry of Carbon Compounds* (McGraw-Hill, N Y, 1962); Wilen, S. H. *Tables of Resolving Agents and Optical Resolutions*, p. 268 (E. L. Eliel, Ed., Univ. of Notre Dame Press, Notre Dame, Ind. 1972).

Definitions of specific functional groups and chemical terms are described in more detail below. For purposes of the present description, the chemical elements are identified in accordance with the Periodic Table of the Elements, CAS version, *Handbook of Chemistry and Physics*, 75$^{th}$, Ed., inside cover, and specific functional groups are generally defined as described therein. Additionally, general principles of organic chemistry, as well as specific functional moieties and reactivity, are described in *Organic Chemistry*, Thomas Sorrell, University Science Books, Sausalito, 1999; Smith and March *March's Advanced Organic Chemistry*, 5$^{th}$, Edition, John Wiley & Sons, Inc., New York, 2001; Larock, *Comprehensive Organic Transformations*, VCH Publishers, Inc., New York, 1989; Carruthers, *Some Modern Methods of Organic Synthesis*, 3$^{rd}$ Edition, Cambridge University Press, Cambridge, 1987.

The chemical structures herein are drawn according to the conventional standards known in the art. Thus, where an atom, such as a carbon atom, as drawn appears to have an unsatisfied valency, then that valency is assumed to be satisfied by a hydrogen atom even though that hydrogen atom is not necessarily explicitly drawn. Hydrogen atoms should be inferred to be part of the compound.

Abbreviations may also be used throughout the application, unless otherwise noted, such abbreviations are intended to have the meaning generally understood by the field. Examples of such abbreviations include Me (methyl), Et (ethyl), Pr (propyl), i-Pr (isopropyl), Bu (butyl), t-Bu (tert-butyl), i-Bu (iso-butyl), s-Bu (sec-butyl), c-Bu (cyclobutyl), Ph (phenyl), Bn (benzyl), Bz (benzoyl), CBz or Cbz or Z (carbobenzyloxy), Boc or BOC (tert-butoxycarbonyl), and Su or Suc (succinimide). For greater certainty, examples of abbreviations used in the present application are listed in a table in the Examples section.

The number of carbon atoms in a hydrocarbyl substituent can be indicated by the prefix "$C_x$-$C_y$," where x is the minimum and y is the maximum number of carbon atoms in the substituent. When reference is made to "x to y membered" heterocyclic ring (e.g., heterocycloalkyl or heteroaryl), then x and y define respectively, the minimum and maximum number of atoms in the cycle, including carbons as well as heteroatom(s).

The prefix "halo" indicates that the substituent to which the prefix is attached is substituted with one or more independently selected halogen atoms. More specifically, the terms "halo" and "halogen" as used herein refer to an atom selected from fluorine (fluoro, —F), chlorine (chloro, —Cl), bromine (bromo, —Br), and iodine (iodo, —I). For example, "haloalkyl" means an alkyl substituent wherein at least one hydrogen atom is replaced with a halogen atom and "haloalkoxy" means an alkoxy substituent wherein at least one hydrogen atom is replaced with a halogen atom.

The term "heteroatom" means one or more of oxygen, sulfur, nitrogen, phosphorus, or silicon (including, any oxidized form of nitrogen, sulfur, phosphorus, or silicon; the quaternized form of any basic nitrogen or; a substitutable nitrogen of a heterocyclic ring, for example N (as in 3,4-dihydro-2H-pyrrolyl), NH (as in pyrrolidinyl) or NR+ (as in N-substituted pyrrolidinyl).

As used herein a "direct bond" or "covalent bond" refers to a single, double or triple bond. In certain embodiments, a "direct bond" or "covalent bond" refers to a single bond.

The term "aliphatic" or "aliphatic group", as used herein, denotes a hydrocarbon moiety that may be straight-chain (i.e., unbranched), branched, or cyclic (including fused, bridging, and spiro-fused polycyclic) and may be completely saturated or may contain one or more units of unsaturation, but which is not aromatic. Unless otherwise specified, aliphatic groups contain 1-6 carbon atoms. In some embodiments, aliphatic groups contain 1-4 carbon atoms, and in yet other embodiments aliphatic groups contain 1-3 carbon atoms. Aliphatic groups include, but are not limited to, alkyl, alkenyl, alkynyl, carbocycle. Suitable aliphatic groups include, but are not limited to, linear or branched, alkyl, alkenyl, and alkynyl groups, and hybrids thereof such as (cycloalkyl)alkyl, (cycloalkenyl)alkyl or (cycloalkyl)alkenyl.

The term "alkyl" as used herein, refers to a saturated, straight- or branched-chain hydrocarbon radical typically containing from 1 to 20 carbon atoms. For example, "$C_1$-$C_6$ alkyl" contains from one to six carbon atoms. Examples of alkyl radicals include, but are not limited to, methyl, ethyl, propyl, isopropyl, n-butyl, sec-butyl, tert-butyl, neopentyl, n-hexyl, heptyl, octyl radicals and the like.

The term "alkenyl" as used herein, denotes a straight- or branched-chain hydrocarbon radical containing one or more double bonds and typically from 2 to 20 carbon atoms. For example, "$C_2$-$C_8$ alkenyl" contains from two to eight carbon atoms. Alkenyl groups include, but are not limited to, for example, ethenyl, propenyl, butenyl, I-methyl-2-buten-1-yl, heptenyl, octenyl and the like.

The term "alkynyl" as used herein, denotes a straight- or branched-chain hydrocarbon radical containing one or more triple bonds and typically from 2 to 20 carbon atoms. For example, "$C_2$-$C_8$ alkynyl" contains from two to eight carbon atoms. Representative alkynyl groups include, but are not limited to, for example, ethynyl, 1-propynyl, 1-butynyl, heptynyl, octynyl and the like.

The term "alkoxy" as used herein, refers to group —Oalkyl, wherein alkyl is as defined herein. For example, the alkoxy group may be —O($C_1$-$C_6$ alkyl). Examples of alkoxy groups include, without being limited to, —OMe, —OEt, —O$^i$Pr etc.

The term "haloalkyl" as used herein, refers to an alkyl group as defined herein (e.g., $C_1$-$C_6$ alkyl), wherein one or more hydrogen atoms has been replaced with a halogen atom (e.g. F or Cl). For example, the haloalkyl group may be —$CF_3$, —$CH_2CH_2F$, —$CH_2CHF_2$, —$CH_2CF_3$ etc.

The term "haloalkoxy" as used herein, refers to a group alkoxy as defined herein, where one or more hydrogen atoms has been replaced with a halogen atom (e.g. F or Cl). For example, the haloalkoxy group may be —$OCF_3$, —$OCH_2CH_2F$, —$OCH_2CHF_2$, —$OCH_2CF_3$ etc.

The terms "cycloalkyl", "alicyclic", "carbocyclic" and equivalent expressions refer to a group comprising a saturated or partially unsaturated (non-aromatic) carbocyclic ring in a monocyclic or polycyclic ring system, including spiro (sharing one atom), fused (sharing at least one bond) or bridged (sharing two or more bonds) carbocyclic ring systems, having from three to fifteen ring members. Examples of cycloalkyl groups include, without limitation, cyclopropyl, cyclobutyl, cyclopentyl, cyclopenten-1-yl, cyclopenten-2-yl, cyclopenten-3-yl, cyclohexyl, cyclohexen-1-yl, cyclohexen-2-yl, cyclohexen-3-yl, cycloheptyl, bicyclo[4,3,0]nonanyl, norbornyl, and the like. The term "cycloalkyl" includes both unsubstituted cycloalkyl groups and substituted cycloalkyl groups. The term "$C_3$-$C_n$cycloalkyl" refers to a cycloalkyl group having from 3 to the indicated "n" number of carbon atoms in the ring structure. Unless the number of carbons is otherwise specified, "lower cycloalkyl" groups as herein used, have at least 3 and equal or less than 8 carbon atoms in their ring structure.

The term "alkylcycloalkyl" refers to an alkyl group substituted by a cycloalkyl group as defined herein, wherein the alkyl and cycloalkyl portions independently are optionally substituted. In the present description, an alkylcycloalkyl group can be referred to as "($C_3$-$C_n$ cycloalkyl)$C_x$-$C_y$ alkyl", where n is the maximum number of carbon atoms in the cycloalkyl group, x is the minimum and y is the maximum number of carbon atoms in the alkyl group. In other words, ($C_3$-$C_n$ cycloalkyl)$C_x$-$C_y$ alkyl represents a $C_x$-$C_y$ alkyl group substituted with a group $C_3$-$C_n$ cycloalkyl and the $C_x$-$C_y$ alkyl portion is directly attached to the atom (e.g. C or N) to be substituted. An example of alkylcycloalkyl includes, without being limited to, ($C_3$-$C_6$ cycloalkyl)$C_1$-$C_6$ alkyl.

As used herein, the terms "heterocycle", "heterocycloalkyl", "heterocyclyl", "heterocyclic radical" and "heterocyclic ring" are used interchangeably and refer to a chemically stable 3- to 7-membered monocyclic or 7-10-membered bicyclic heterocyclic moiety that is either saturated or partially unsaturated, and having, in addition to carbon atoms, one or more, preferably one to four, heteroatoms, as defined above. When used in reference to a ring atom of a heterocycle, the term "nitrogen" includes a substituted nitrogen. As an example, in a saturated or partially unsaturated ring having 1-3 heteroatoms selected from oxygen, sulfur or nitrogen, the nitrogen may be N (as in 3,4-dihydro-2H-pyrrolyl), NH (as in pyrrolidinyl), or +NR (as in N-substituted pyrrolidinyl). A heterocyclic ring can be attached to its pendant group at any heteroatom or carbon atom that results in a chemically stable structure and any of the ring atoms can be optionally substituted. Examples of heterocycloalkyl groups include, but are not limited to, 1,3-dioxolanyl, pyrrolidinyl, pyrrolidonyl, pyrazolinyl, pyrazolidinyl, imidazolinyl, imidazolidinyl, piperidinyl, piperazinyl, oxazolidinyl, isoxazolidinyl, morpholinyl, thiazolidinyl, isothiazolidinyl, tetrahydrofuranyl, tetrahydropyranyl, tetrahydrothiopyranyl, tetrahydrodithienyl, tetrahydrothienyl, thiomorpholino, thioxanyl, azetidinyl, oxetanyl, thietanyl, homopiperidinyl, oxepanyl, thiepanyl, oxazepinyl, diazepinyl, thiazepinyl, 1,2,3,6-tetrahydropyridinyl, 2-pyrrolinyl, 3-pyrrolinyl, 2H-pyranyl, 4H-pyranyl, dioxanyl, dithianyl, dithiolanyl, dihydropyranyl, dihydrothienyl, dihydrofuranyl, 3-azabicyclo[3,1,0]hexanyl, 3-azabicyclo[4,1,0] heptanyl, quinolizinyl, quinuclidinyl, tetrahydroquinolinyl, tetrahydroisoquinolinyl, decahydroquinolinyl, and the like. Heterocyclic groups also include groups in which a heterocyclic ring is fused to one or more aryl, heteroaryl, or cycloaliphatic rings, such as indolinyl, 3H-indolyl, chromanyl, chromenyl, phenanthridinyl, 2-azabicyclo[2.2.1]heptanyl, octahydroindolyl, or tetrahydroquinolinyl, where the radical or point of attachment is on the heterocyclyl ring. A heterocyclyl group may be mono- or bicyclic.

The term "alkylheterocycloalkyl" refers to an alkyl group substituted by a heterocycloalkyl group as defined herein. The alkyl and heterocycloalkyl portions independently are optionally substituted. In the present description, an alkylheterocycloalkyl group can be referred to as a "(3-n membered heterocycloalkyl)$C_x$-$C_y$ alkyl", where n is the maximum number of atoms (including carbons and heteroatoms) in the heterocycloalkyl group, and x is the minimum and y is the maximum number of carbon atoms in the alkyl group. In other words, a (3-n membered heterocycloalkyl)$C_x$-$C_y$ alkyl represents a $C_x$-$C_y$ alkyl group substituted with a heterocycloalkyl group having 3 to n atoms and the $C_x$-$C_y$ alkyl portion is directly attached to the atom (e.g. C or N) to be substituted. An example of a (3-n membered heterocycloalkyl)$C_x$-$C_y$ alkyl group can be, without being limited to, a (3-7 membered heterocycloalkyl)$C_1$-$C_6$ alkyl.

As used herein, the term "partially unsaturated" refers to a ring moiety that includes at least one double or triple bond between ring atoms but is not aromatic. The term "partially unsaturated" is intended to encompass rings having multiple sites of unsaturation, but is not intended to include aryl or heteroaryl moieties, as herein defined.

The term "aryl" used alone or as part of a larger moiety as in "aralkyl", "aralkoxy", or "aryloxyalkyl", refers to a monocyclic moiety or to a bicyclic or tricyclic fused ring system having a total of six to 15 ring members, wherein at least one ring in the system is aromatic and wherein each ring in the system contains three to seven ring members. The term "aryl" may be used interchangeably with the term "aryl ring". In certain embodiments of the present description, "aryl" refers to an aromatic ring system which includes, but not limited to, phenyl, biphenyl, naphthyl, azulenyl, anthracyl and the like, which may bear one or more substituents.

The term "aralkyl" or "arylalkyl" refers to an alkyl residue substituted with an aryl ring. Examples of aralkyl include, but are not limited to, benzyl, phenethyl, 1-phenylethyl, and the like. Also included within the scope of the term "aryl", as it is used herein, is a group in which an aromatic ring is fused to one or more non-aromatic rings, such as indanyl, indenyl, phthalimidyl, naphthimidyl, fluorenyl, phenanthridinyl, or tetrahydronaphthyl, and the like. In the present description, aralkyl groups can also be referred to as ($C_v$-$C_w$ aryl)$C_x$-$C_y$ alkyl wherein x is the minimum and y the maximum number of carbon atoms in the alkyl group, and v is the minimum and w the maximum number of carbon atoms in the aryl group. In other words, a ($C_v$-$C_w$ aryl)$C_x$-$C_y$ alkyl represents a $C_x$-$C_y$ alkyl group substituted with a $C_v$-$C_w$ aryl group and the $C_x$-$C_y$ alkyl portion is directly attached to the atom (e.g. C or N) to be substituted. An example of ($C_v$-$C_w$ aryl)$C_x$-$C_y$ alkyl group can be ($C_6$-$C_{10}$ aryl)$C_1$-$C_6$ alkyl.

The terms "heteroaryl" and "heteroar-", used alone or as part of a larger moiety, e.g., "heteroaralkyl", or "heteroaralkoxy", refer to groups having 5 to 18 ring atoms, preferably 5, 6, or 9 ring atoms; having 6, 10, or 14 π electrons shared in a cyclic array; and having, in addition to carbon atoms, from one to five heteroatoms. The term "heteroatom" includes but is not limited to nitrogen, oxygen, or sulfur, and includes any oxidized form of nitrogen or sulfur, and any quaternized form of a basic nitrogen. A heteroaryl may be a single ring, or two or more fused rings. Heteroaryl groups include, without limitation, thienyl, furanyl (furyl), thienyl, pyrrolyl, imidazolyl, pyrazolyl, triazolyl, tetrazolyl, oxazolyl, isoxazolyl, oxadiazolyl, thiazolyl, isothiazolyl, thiadiazolyl, pyridyl, pyridazinyl, pyrimidinyl, pyrazinyl, triazinyl, furopyridinyl, indolizinyl, purinyl, naphthyridinyl, and pteridinyl. The terms "heteroaryl" and "heteroar-", as used herein, also include groups in which a heteroaromatic ring is fused to one or more aryl, cycloaliphatic, or heterocyclyl rings, where the radical or point of attachment is on the heteroaromatic ring. Non-limiting examples include indolyl, 3H-indolyl, isoindolyl, benzothienyl (benzothiophenyl), benzofuranyl, dibenzofuranyl, indazolyl, benzimidazolyl, benzoxazolyl, benzothiazolyl, quinolyl (quinolinyl), isoquinolyl (isoquinolinyl), quinolonyl, isoquinolonyl, cinnolinyl, phthalazinyl, quinazolinyl, quinoxalinyl, 4H-quinolizinyl, carbazolyl, acridinyl, phenanthridinyl, phenazinyl, phenothiazinyl, phenoxazinyl, tetrahydroquinolinyl, tetrahydroisoquinolinyl, and pyrido[2,3-b]-1,4-oxazin-3(4H)-one. A heteroaryl group can be attached to its pendant group at any heteroatom or carbon atom that results in a chemically stable structure. A heteroaryl group may be mono- or bicyclic. Heteroaryl groups include rings that are optionally substituted.

The term "heteroaralkyl" refers to an alkyl group substituted by a heteroaryl, wherein the alkyl and heteroaryl portions independently are optionally substituted. Examples include, but are not limited to, pyridinylmethyl, pyrimidinylethyl and the like. In the present description, heteroaralkyl groups can also be referred to as (5-n membered heteroaryl)$C_x$-$C_y$ alkyl, wherein n is the maximum number of atoms (including carbons and heteroatoms) in the heteroaryl group, and x is the minimum and y the maximum number of carbon atoms in the alkyl group. In other words, a (5-n membered heteroaryl)$C_x$-$C_y$ alkyl represents a $C_x$-$C_y$ alkyl group substituted with a heteroaryl group having 5 to n atoms and the $C_x$-$C_y$ alkyl portion is directly attached to the atom (e.g. C or N) to be substituted. An example of a (3-n membered heteroaryl)$C_x$-$C_y$ alkyl can be, without being limited to, a (5-10 membered heteroaryl)$C_1$-$C_6$ alkyl.

The term "bivalent hydrocarbon" refers to a bivalent saturated or unsaturated hydrocarbon group. Such bivalent hydrocarbon groups include alkylene, alkenylene, and alkynylene groups.

The term "alkylene" refers to a divalent group derived from a straight or branched saturated hydrocarbyl chain typically containing from 1 to 20 carbon atoms, more typically from 1 to 8 carbon atoms. Examples of an "alkylene" include a polymethylene group, i.e., —$(CH_2)_n$—, wherein n is a positive integer, preferably from 1 to 6, from 1 to 4, from 1 to 3, from 1 to 2, or from 2 to 3; or —$CH_2$—, —$CH_2CH_2$—, —$CH_2CH_2CH_2$—, —$CH_2CH_2CH_2CH_2$—, and —$CH_2CH(CH_3)CH_2$—. A substituted alkylene chain is a polymethylene group in which one or more methylene hydrogen atoms are replaced with a substituent. Suitable substituents include those described below for a substituted aliphatic group.

The term "alkenylene" refers to a divalent unsaturated hydrocarbyl group which may be linear or branched and which has at least one carbon-carbon double bond. An alkenylene group typically contains 2 to 20 carbon atoms, more typically from 2 to 8 carbon atoms. Non-limiting examples of alkenylene groups include —C(H)=C(H)—, —C(H)=C(H)—$CH_2$—, —C(H)=C(H)—$CH_2$—$CH_2$—, —$CH_2$—C(H)=C(H)—$CH_2$—, —C(H)=C(H)—CH($CH_3$)—, and —$CH_2$—C(H)=C(H)—CH($CH_2CH_3$)—.

The term "alkynylene" refers to a divalent unsaturated hydrocarbon group which may be linear or branched and which has at least one carbon-carbon triple bond. Examples of alkynylene groups include, without limitation, —C≡C—, —C≡C—$CH_2$—, —C≡C—$CH_2$—$CH_2$—, —$CH_2$—C≡C—$CH_2$—, —C≡C—CH($CH_3$)—, and —$CH_2$—C≡C—CH($CH_2CH_3$)—.

As described herein, compounds of the present description may contain "optionally substituted" moieties. In general, the term "substituted", whether preceded by the term "optionally" or not, means that one or more hydrogens of the designated moiety are replaced with a suitable substituent. Unless otherwise indicated, an "optionally substituted" group may have a suitable substituent at each substitutable position of the group, and when more than one position in any given structure may be substituted with more than one substituent selected from a specified group, the substituent may be either the same or different at each position. Combinations of substituents envisioned under the present description are preferably those that result in the formation of chemically stable or chemically feasible compounds. The term "chemically stable", as used herein, refers to compounds that are not substantially altered when subjected to conditions to allow for their production, detection, and, in certain embodiments, their recovery, purification, and use for one or more of the purposes disclosed herein.

The terms "optionally substituted", "optionally substituted alkyl," "optionally substituted alkenyl," "optionally substituted alkynyl", "optionally substituted carbocyclic," "optionally substituted aryl", "optionally substituted heteroaryl," "optionally substituted heterocyclic," and any other optionally substituted group as used herein, refer to groups that are substituted or unsubstituted by independent replacement of one, two, or three or more of the hydrogen atoms thereon with substituents including, but not limited to F, Cl, Br, I, OH, $CO_2H$, protected alkoxy, oxo, thiooxo, $NO_2$, CN, $CF_3$, $NH_2$, protected amino, NHalkyl, NHalkenyl, NHalkynyl, NHcycloalkyl, NHaryl, NHheteroaryl, NHheterocyclic, dialkylamino, diarylamino, diheteroarylamino, O-alkyl, O-alkenyl, O-alkynyl, O-cycloalkyl, O-aryl, O-heteroaryl, O-haloalkyl, O-heterocyclic, C(O)alkyl, C(O)alkenyl, C(O)alkynyl, C(O)cycloalkyl, C(O)aryl, C(O)heteroaryl, C(O)heterocycloalkyl, $CO_2$alkyl, $CO_2$alkenyl, $CO_2$alkynyl, $CO_2$cycloalkyl, $CO_2$aryl, $CO_2$heteroaryl, $CO_2$heterocycloalkyl, OC(O)alkyl, OC(O)alkenyl, OC(O)alkynyl, OC(O)cycloalkyl, OC(O)aryl, OC(O)heteroaryl, OC(O)heterocycloalkyl, C(O)$NH_2$, C(O)NHalkyl, C(O)NHalkenyl, C(O)NHalkynyl, C(O)NHcycloalkyl, C(O)NHaryl, C(O)NHheteroaryl, C(O)NHheterocycloalkyl, $OCO_2$alkyl, $OCO_2$alkenyl, $OCO_2$alkynyl, $OCO_2$cycloalkyl, $OCO_2$aryl, $OCO_2$heteroaryl, $OCO_2$heterocycloalkyl, OC(O)$NH_2$, OC(O)NHalkyl, OC(O)NHalkenyl, OC(O)NHalkynyl, OC(O)NHcycloalkyl, OC(O)NHaryl, OC(O)NHheteroaryl, OC(O)NHheterocycloalkyl, NHC(O)alkyl, NHC(O)alkenyl, NHC(O)alkynyl, NHC(O)cycloalkyl, NHC(O)aryl, NHC(O)heteroaryl, NHC(O)heterocycloalkyl, $NHCO_2$alkyl, $NHCO_2$alkenyl, $NHCO_2$alkynyl, $NHCO_2$cycloalkyl, $NHCO_2$aryl, $NHCO_2$heteroaryl, $NHCO_2$heterocycloalkyl, NHC(O)$NH_2$, NHC(O)NHalkyl, NHC(O)NHalkenyl, NHC(O)NHalkenyl, NHC(O)NHcycloalkyl, NHC(O)NHaryl, NHC(O)NHheteroaryl, NHC(O)NHheterocycloalkyl, NHC(S)$NH_2$, NHC(S)NHalkyl, NHC(S)NHalkenyl, NHC(S)NHalkynyl, NHC(S)NHcycloalkyl, NHC(S)NHaryl, NHC(S)NHheteroaryl, NHC(S)NHheterocycloalkyl, NHC(NH)$NH_2$, NHC(NH)NHalkyl, NHC(NH)NHalkenyl, NHC(NH)NHalkenyl, NHC(NH)NHcycloalkyl, NHC(NH)NHaryl, NHC(NH)NHheteroaryl, NHC(NH)NHheterocycloalkyl, NHC(NH)alkyl, NHC(NH)alkenyl, NHC(NH)alkenyl, NHC(NH)cycloalkyl, NHC(NH)aryl, NHC(NH)heteroaryl, NHC(NH)heterocycloalkyl, C(NH)NHalkyl, C(NH)NHalkenyl, C(NH)NHalkynyl, C(NH)NHcycloalkyl, C(NH)NHaryl, C(NH)NHheteroaryl, C(NH)NHheterocycloalkyl, S(O)alkyl, S(O)alkenyl, S(O)alkynyl, S(O)cycloalkyl, S(O)aryl, S(O)$_2$alkyl, S(O)$_2$alkenyl, S(O)

$_2$alkynyl, S(O)$_2$cycloalkyl, S(O)$_2$aryl, S(O)heteroaryl, S(O)heterocycloalkyl, SO$_2$NH$_2$, SO$_2$NHalkyl, SO$_2$NHalkenyl, SO$_2$NHalkynyl, SO$_2$NHcycloalkyl, SO$_2$NHaryl, SO$_2$NHheteroaryl, SO$_2$NHheterocycloalkyl, NHSO$_2$alkyl, NHSO$_2$alkenyl, NHSO$_2$alkynyl, NHSO$_2$cycloalkyl, NHSO$_2$aryl, NHSO$_2$heteroaryl, NHSO$_2$heterocycloalkyl, CH$_2$NH$_2$, CH$_2$SO$_2$CH$_3$, alkyl, alkenyl, alkynyl, aryl, arylalkyl, heteroaryl, heteroarylalkyl, heterocycloalkyl, cycloalkyl, carbocyclic, heterocyclic, polyalkoxyalkyl, polyalkoxy, methoxymethoxy, methoxyethoxy, SH, S-alkyl, S-alkenyl, S-alkynyl, S-cycloalkyl, S-aryl, S-heteroaryl, S-heterocycloalkyl, or methylthiomethyl.

In certain embodiments, suitable monovalent substituents on a substitutable carbon atom of an "optionally substituted" group are independently halogen; (CH$_2$)$_{0-4}$R$^\circ$; (CH$_2$)$_{0-4}$OR$^\circ$; O(CH$_2$)$_{0-4}$C(O)OR$^\circ$; (CH$_2$)$_{0-4}$CH(OR$^\circ$)$_2$; (CH$_2$)$_{0-4}$SR$^\circ$; (CH$_2$)$_{0-4}$Ph, which may be substituted with R$^\circ$; (CH$_2$)$_{0-4}$O(CH$_2$)$_{0-4}$Ph which may be substituted with R$^\circ$; —CH=CHPh, which may be substituted with R$^\circ$; NO$_2$; CN; N$_3$; (CH$_2$)$_{0-4}$N(R$^\circ$)$_2$; (CH$_2$)$_{0-4}$N(R$^\circ$)C(O)R$^\circ$; N(R$^\circ$)C(S)R$^\circ$; (CH$_2$)$_{0-4}$N(R$^\circ$)C(O)NR$^\circ$$_2$; N(R$^\circ$)C(S)NR$^\circ$$_2$; (CH$_2$)$_{0-4}$N(R$^\circ$)C(O)OR$^\circ$; N(R$^\circ$)N(R$^\circ$)C(O)R$^\circ$; N(R$^\circ$)N(R$^\circ$)C(O)NR$^\circ$$_2$; N(R$^\circ$)N(R$^\circ$)C(O)OR$^\circ$; (CH$_2$)$_{0-4}$C(O)R$^\circ$; C(S)R$^\circ$; (CH$_2$)$_{0-4}$C(O)OR$^\circ$; (CH$_2$)$_{0-4}$C(O)SR$^\circ$; (CH$_2$)$_{0-4}$C(O)OSiR$^\circ$$_3$; (CH$_2$)$_{0-4}$OC(O)R$^\circ$; OC(O)(CH$_2$)$_{0-4}$SR—, SC(S)SR$^\circ$; (CH$_2$)$_{0-4}$SC(O)R$^\circ$; (CH$_2$)$_{0-4}$C(O)NR$^\circ$$_2$; C(S)NR$^\circ$$_2$; C(S)SR$^\circ$; SC(S)SR$^\circ$, (CH$_2$)$_{0-4}$OC(O)NR$^\circ$$_2$; C(O)N(OR$^\circ$)R$^\circ$; C(O)C(O)R$^\circ$; C(O)CH$_2$C(O)R$^\circ$; C(NOR$^\circ$)R$^\circ$; (CH$_2$)$_{0-4}$SSR$^\circ$; (CH$_2$)$_{0-4}$S(O)$_2$R$^\circ$; (CH$_2$)$_{0-4}$(O)$_2$OR$^\circ$; (CH$_2$)$_{0-4}$OS(O)$_2$ R$^\circ$; S(O)$_2$NR$^\circ$$_2$; (CH$_2$)$_{0-4}$S(O)R$^\circ$; N(R$^\circ$)S(O)$_2$NR$^\circ$$_2$; N(R$^\circ$)S(O)$_2$R$^\circ$; N(OR$^\circ$)R$^\circ$; C(NH)NR$^\circ$$_2$; P(O)$_2$R$^\circ$; P(O)R$^\circ$$_2$; OP(O)R$^\circ$$_2$; OP(O)(OR$^\circ$)$_2$; SiR$^\circ$$_3$; (straight or branched C$_{1-4}$alkylene)O—N(R$^\circ$)$_2$; or (straight or branched C$_{1-4}$alkylene)C(O)O—N(R$^\circ$)$_2$, wherein each R$^\circ$ may be substituted as defined below and is independently hydrogen, C$_{1-6}$aliphatic, CH$_2$Ph, O(CH$_2$)$_{0-1}$Ph, or a 5-6-membered saturated, partially unsaturated, or aromatic ring having 0-4 heteroatoms independently selected from nitrogen, oxygen, or sulfur, or, notwithstanding the definition above, two independent occurrences of R$^\circ$, taken together with their intervening atom(s), may form a 3 to 12 membered saturated, partially unsaturated, or aryl mono- or bicyclic ring having 0 to 4 heteroatoms independently selected from nitrogen, oxygen, or sulfur, which may be substituted as defined below.

Examples of monovalent substituents on R$^\circ$ (or the ring formed by taking two independent occurrences of R$^\circ$ together with their intervening atoms), are independently halogen, —(CH$_2$)$_{0-2}$R*, -(haloR*), —(CH$_2$)$_{0-2}$OH, —(CH$_2$)$_{0-2}$OR*, —(CH$_2$)$_{0-2}$CH(OR*)$_2$, —O(haloR'), —CN, —N$_3$, —(CH$_2$)$_{0-2}$C(O)R*, —(CH$_2$)$_{0-2}$C(O)OH, —(CH$_2$)$_{0-2}$C(O)OR*, —(CH$_2$)$_{0-2}$SR*, —(CH$_2$)$_{0-2}$SH, —(CH$_2$)$_{0-2}$NH$_2$, —(CH$_2$)$_{0-2}$NHR*, —(CH$_2$)$_{0-2}$NR*$_2$, —NO$_2$, —SiR*$_3$, —OSiR*$_3$, —C(O)SR*—(C$_{1-4}$straight or branched alkylene)C(O)OR*, or —SSR*, wherein each R* is unsubstituted or where preceded by "halo" is substituted only with one or more halogens, and is independently selected from C$_{1-4}$ aliphatic, —CH$_2$Ph, —O(CH$_2$)$_{0-1}$Ph, or a 5-6-membered saturated, partially unsaturated, or aryl ring having 0-4 heteroatoms independently selected from nitrogen, oxygen, or sulfur. Suitable divalent substituents on a saturated carbon atom of R$^\circ$ include =O and =S.

Examples of divalent substituents on a saturated carbon atom of an "optionally substituted" group include the following: =O, =S, =NNR*$_2$, =NNHC(O)R*, =NNHC(O)OR*, =NNHS(O)$_2$R*, =NR*, =NOR*, —O(C(R*$_2$))$_{2-30}$—, or —S(C(R*$_2$))$_{2-3}$S—, wherein each independent occurrence of R* is selected from hydrogen, C$_{1-6}$ aliphatic which may be substituted as defined below, or an unsubstituted 5-6-membered saturated, partially unsaturated, or aryl ring having 0-4 heteroatoms independently selected from nitrogen, oxygen, or sulfur. Suitable divalent substituents that are bound to vicinal substitutable carbons of an "optionally substituted" group include: —O(CR$_2$)$_{2-30}$—, wherein each independent occurrence of R is selected from hydrogen, C$_{1-6}$ aliphatic which may be substituted as defined below, or an unsubstituted 5-6-membered saturated, partially unsaturated, or aryl ring having 0-4 heteroatoms independently selected from nitrogen, oxygen, or sulfur.

Examplary substituents on the aliphatic group of R* include halogen, —R*, -(haloR*), —OH, —OR*, —O(haloR'), —CN, —C(O)OH, —C(O)OR*, —NH$_2$, —NHR*, —NR*$_2$, or —NO$_2$, wherein each R* is unsubstituted or where preceded by "halo" is substituted only with one or more halogens, and is independently C$_{1-4}$ aliphatic, —CH$_2$Ph, —O(CH$_2$)$_{0-1}$Ph, or a 5-6-membered saturated, partially unsaturated, or aryl ring having 0-4 heteroatoms independently selected from nitrogen, oxygen, or sulfur.

The expression "pharmaceutically acceptable salt" refers to those salts of the compounds formed by the process of the present description which are, within the scope of sound medical judgment, suitable for use in contact with the tissues of humans and lower animals without undue toxicity, irritation, allergic response and the like, and are commensurate with a reasonable benefit/risk ratio. Pharmaceutically acceptable salts are well known in the art. For example, S. M. Berge, et al. describes pharmaceutically acceptable salts in detail in *J. Pharmaceutical Sciences,* 66: 1-19 (1977). The salts can be prepared in situ during the final isolation and purification of the compounds of the present description, or separately by reacting a free base function of the compound with a suitable organic or inorganic acid (acid addition salts) or by reacting an acidic function of the compound with a suitable organic or inorganic base (base-addition salts). Examples of pharmaceutically acceptable salts include, but are not limited to, nontoxic acid addition salts, or salts of an amino group formed with inorganic acids such as hydrochloric acid, hydrobromic acid, phosphoric acid, sulfuric acid and perchloric acid or with organic acids such as acetic acid, maleic acid, tartaric acid, citric acid, succinic acid or malonic acid or by using other methods used in the art such as ion exchange. Other pharmaceutically acceptable salts include, but are not limited to, adipate, alginate, ascorbate, aspartate, benzenesulfonate, benzoate, bisulfate, borate, butyrate, camphorate, camphorsulfonate, citrate, cyclopentanepropionate, digluconate, dodecylsulfate, ethanesulfonate, formate, fumarate, glucoheptonate, glycerophosphate, gluconate, hemisulfate, heptanoate, hexanoate, hydroiodide, 2-hydroxy-ethanesulfonate, lactobionate, lactate, laurate, lauryl sulfate, malate, maleate, malonate, methanesulfonate, 2-naphthalenesulfonate, nicotinate, nitrate, oleate, oxalate, palmitate, pamoate, pectinate, persulfate, 3-phenylpropionate, phosphate, picrate, pivalate, propionate, stearate, succinate, sulfate, tartrate, thiocyanate, p-toluenesulfonate, undecanoate, valerate salts, and the like. Representative base addition alkali or alkaline earth metal salts include sodium, lithium, potassium, calcium, or magnesium salts, and the like. Further pharmaceutically acceptable salts include, when appropriate, nontoxic ammonium, quaternary ammonium, and amine cations formed using counterions such as halide, hydroxide, carboxylate, sulfate, phosphate, nitrate, sulfonate and aryl sulfonate.

The term "solvate" refers to a physical association of one of the present compounds with one or more solvent molecules. This physical association includes hydrogen bonding. In certain instances, the solvate will be capable of isolation, for example when one or more solvent molecules are incorporated in the crystal lattice of a crystalline solid. "Solvate" encompasses both solution-phase and isolable solvates. Exemplary solvates include, without limitation, hydrates, hemihydrates, ethanolates, hemiethanolates, n-propanolates, iso-propanolates, 1-butanolates, 2-butanolate, and solvates of other physiologically acceptable solvents, such as the Clas 3 solvents described in the *International Conference on Harmonization (ICH), Guide for Industry, Q3C Impurities: Residual Solvents* (1997). The compounds as herein described also include each of their solvates and mixtures thereof.

As used herein, the term "pharmaceutically acceptable ester" refers to esters of the compounds formed by the process of the present description which hydrolyze in vivo and include those that break down readily in the human body to leave the parent compound or a salt thereof. Suitable ester groups include, for example, those derived from pharmaceutically acceptable aliphatic carboxylic acids, particularly alkanoic, alkenoic, cycloalkanoic and alkanedioic acids, in which each alkyl or alkenyl moiety advantageously has not more than 6 carbon atoms. Examples of particular esters include, but are not limited to, formates, acetates, propionates, butyrates, acrylates and ethylsuccinates.

The expression "pharmaceutically acceptable prodrugs" as used herein refers to those prodrugs of the compounds formed by the process of the present description which are, within the scope of sound medical judgment, suitable for use in contact with the tissues of humans and lower animals with undue toxicity, irritation, allergic response, and the like, commensurate with a reasonable benefit/risk ratio, and effective for their intended use. "Prodrug", as used herein means a compound which is convertible in vivo by metabolic means (e.g. by hydrolysis) to afford any compound delineated by the formulae of the instant description. Various forms of prodrugs are known in the art, for example, as discussed in Bundgaard, (ed.), *Design of Prodrugs*, Elsevier (1985); Widder, et al. (ed.), *Methods in Enzymology*, vol. 4, Academic Press (1985); Krogsgaard-Larsen, et al., (ed). "*Design and Application of Prodrugs, Textbook of Drug Design and Development*", Chapter 5, 113-191 (1991); Bundgaard, et al., *Journal of Drug Deliver Reviews*, 8:1-38 (1992); Bundgaard, *J. of Pharmaceutical Sciences*, 77:285 et seq. (1988); Higuchi and Stella (eds.) *Prodrugs as Novel Drug Delivery Systems*, American Chemical Society (1975); and Bernard Testa & Joachim Mayer, "*Hydrolysis In Drug And Prodrug Metabolism: Chemistry, Biochemistry And Enzymology*", John Wiley and Sons, Ltd. (2002).

Combinations of substituents and variables envisioned by the present description are only those that result in the formation of stable compounds. The term "stable", as used herein, refers to compounds which possess stability sufficient to allow manufacture and which maintains the integrity of the compound for a sufficient period of time to be useful for the purposes detailed herein (e.g., therapeutic or prophylactic administration to a subject).

ii. Compounds

The compounds of the present application may be prepared by conventional chemical synthesis, such as exemplified in the general scheme and in Examples 1 to 73. As can be appreciated by the skilled artisan, further methods of synthesizing the compounds of the formulae herein will be evident to those of ordinary skill in the art. Additionally, the various synthetic steps may be performed in an alternate sequence or order to give the desired compounds. In addition, the solvents, temperatures, reaction durations, etc. delineated herein are for purposes of illustration only and one of ordinary skill in the art will recognize that variation of the reaction conditions can produce the desired products of the present description. Synthetic chemistry transformations and/or protecting group methodologies (protection and deprotection) useful in synthesizing the compounds described herein are known in the art and include, for example, those such as described in R. Larock, *Comprehensive Organic Transformations*, VCH Publishers (1989); T. W. Greene and P. G. M. Wuts, *Protective Groups in Organic Synthesis*, 2d. Ed., John Wiley and Sons (1991); L. Fieser and M. Fieser, *Fieser and Fieser's Reagents for Organic Synthesis*, John Wiley and Sons (1994); and L. Paquette, ed., *Encyclopedia of Reagents for Organic Synthesis*, John Wiley and Sons (1995), and subsequent editions thereof. The synthesized compounds can be separated from a reaction mixture and further purified by standard methods such as column chromatography, high pressure liquid chromatography, or recrystallization.

The compounds of the present description may be modified by appending various functionalities via any synthetic means delineated herein to enhance selective biological properties. Such modifications are known in the art and include those which increase biological penetration into a given biological system (e.g., blood, lymphatic system, central nervous system), increase oral availability, increase solubility to allow administration by injection, alter metabolism and alter rate of excretion.

The recitation of a listing of chemical groups in any definition of a variable herein includes definitions of that variable as any single group or combination of listed groups. The recitation of an embodiment for a variable herein includes that embodiment as any single embodiment or in combination with any other embodiments or portions thereof. The recitation of an embodiment herein includes that embodiment as any single embodiment or in combination with any other embodiments or portions thereof. As such, the following embodiments are present alone or in combination if applicable:

The present application provides aryl-substituted dihydroquinolinone compounds of general Formula (I), as well as their pharmaceutically acceptable salts, solvates, esters or prodrugs thereof:

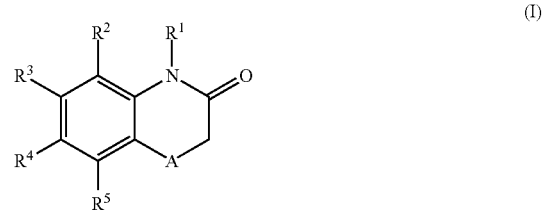

(I)

wherein:
A is —CH$_2$— or oxygen;
R$^1$ is hydrogen or C$_1$-C$_6$ alkyl;
R$^2$ and R$^5$ independently represent hydrogen, halogen, —CH$_3$, —C(R$^a$)(R$^b$)(R$^c$), —N(R$^d$)(R$^e$) or —O(R$^f$),
wherein
R$^a$ is hydrogen or C$_1$-C$_6$ alkyl;
R$^b$ is hydrogen, hydroxyl or C$_1$-C$_6$ alkyl;
R$^c$ is C$_3$-C$_6$ cycloalkyl, C$_6$-C$_{10}$ aryl, 3-7 membered heterocycloalkyl, 5-10 membered heteroaryl, (C$_3$-C$_6$ cycloalkyl)C$_1$-C$_6$ alkyl, (3-7 membered heterocycloalkyl)C$_1$-C$_6$ alkyl, (C$_6$-C$_{10}$ aryl)C$_1$-C$_6$ alkyl or (5-10 membered heteroaryl)C$_1$-C$_6$ alkyl, —O(R$^g$) or —N(R$^g$)(R$^h$);

R$^d$ is hydrogen or C$_1$-C$_6$ alkyl;

R$^e$ is C$_1$-C$_6$ alkyl, C$_3$-C$_6$ cycloalkyl, C$_6$-C$_{10}$ aryl, 3-7 membered heterocycloalkyl, 5-10 membered heteroaryl, (C$_3$-C$_6$ cycloalkyl)C$_1$-C$_6$ alkyl, (3-7 membered heterocycloalkyl)C$_1$-C$_6$ alkyl, (C$_6$-C$_{10}$ aryl) C$_1$-C$_6$ alkyl, (5-10 membered heteroaryl)C$_1$-C$_6$ alkyl, keto(C$_6$-C$_{10}$ aryl) or keto(5-10 membered heteroaryl);

R$^f$ is C$_1$-C$_6$ alkyl, C$_3$-C$_6$ cycloalkyl, 3-7 membered heterocycloalkyl, C$_6$-C$_{10}$ aryl, 5-10 membered heteroaryl, (C$_3$-C$_6$ cycloalkyl)C$_1$-C$_6$ alkyl, (3-7 membered heterocycloalkyl)C$_1$-C$_6$ alkyl, (C$_6$-C$_{10}$ aryl) C$_1$-C$_6$ alkyl or (5-10 membered heteroaryl)C$_1$-C$_6$ alkyl;

R$^g$ is C$_1$-C$_6$ alkyl, C$_3$-C$_6$ cycloalkyl, C$_6$-C$_{10}$ aryl, 3-7 membered heterocycloalkyl, 5-10 membered heteroaryl, (C$_3$-C$_6$ cycloalkyl)C$_1$-C$_6$ alkyl, (3-7 membered heterocycloalkyl)C$_1$-C$_6$ alkyl, (C$_6$-C$_{10}$ aryl) C$_1$-C$_6$ alkyl or (5-10 membered heteroaryl)C$_1$-C$_6$ alkyl;

R$^h$ is hydrogen, C$_1$-C$_4$ alkyl, —C(O)(R$^6$); —C(O)NH$_2$, —C(O)NH(R$^6$) or —C(O)N(R$^6$)(R$^{6'}$); one of R$^3$ and R$^4$ represents a group of formula (II), provided that when R$^3$ is a group of formula (II), then R$^4$ has the same definition than R$^2$ and R$^5$, and when R$^4$ is a group of formula (II), then R$^3$ has the same definition than R$^2$ and R$^5$;

the group of formula (II) has the following structure:

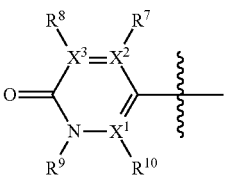

(II)

wherein:

X$^1$, X$^2$ and X$^3$ are each independently N or C, wherein when X$^1$, X$^2$ or X$^3$ is N, then the R$^7$, R$^8$ or R$^{10}$ attached thereto is absent, provided that at least two of X$^1$, X$^2$ and X$^3$ is C;

R$^7$ and R$^{10}$ are each independently hydrogen, halogen (such as F, Cl), CN, linear or branched C$_1$-C$_6$alkyl, C$_3$-C$_6$cycloalkyl, OR$^6$, SR$^6$, NHR$^6$, N(R$^6$)(R$^{6'}$), NHC(O)R$^6$ or N(R$^6$)C(O)R$^{6'}$;

R$^8$ is halogen (such as F, Cl), CN, linear or branched C$_1$-C$_6$alkyl, C$_3$-C$_6$cycloalkyl, OR$^6$, SR$^6$, NHR$^6$, N(R$^6$)(R$^{6'}$), NHC(O)R$^6$ or N(R$^6$)C(O)R$^{6'}$;

R$^6$ and R$^{6'}$, which are the same or different, represent a C$_1$-C$_6$ alkyl group;

R$^9$ is a C$_1$-C$_3$alkyl or C$_3$-C$_5$cycloalkyl group;

each alkyl group is linear or branched and optionally substituted, and each of cycloalkyl, aryl, heterocycloalkyl and heteroaryl is optionally substituted; and when R$^3$ is the group of formula (II), one of R$^2$, R$^4$ and R$^5$ is —C(R$^a$)(R$^b$)(R$^c$), —N(R$^d$)(R$^e$) or —O(R$^f$) and the other two of R$^2$, R$^4$ and R$^5$ are independently hydrogen, halogen or —CH$_3$; or when R$^4$ is the group of formula (II), one of R$^2$, R$^3$ and R$^5$ is —C(R$^a$)(R$^b$)(R$^c$), —N(R$^d$) (R$^e$) or —O(R$^f$) and the other two of R$^2$, R$^3$ and R$^5$ are independently hydrogen, halogen or —CH$_3$.

In one embodiment, when a substituent in Formula (I) comprises an alkyl group, this group can be unsubstituted or substituted with 1 to 3 groups being halogen, CN, alkoxy or haloalkoxy. In another embodiment, when a substituent in Formula (I) comprises a cycloalkyl, aryl, heterocycloalkyl and/or heteroaryl group, such group can be unsubstituted or substituted by 1 to 3 groups being halogen, CN, alkyl, haloalkyl, alkoxy or haloalkoxy.

According to one embodiment, A is a methylene (—CH$_2$—). According to another embodiment, A is an oxygen atom.

In yet another embodiment, the group R$^1$ in Formula (I) represents a hydrogen or a methyl group.

In another embodiment, R$^2$, R$^3$, R$^4$ or R$^5$ represent a group —C(R$^a$)(R$^b$)(R$^c$), —C(R$^a$)(R$^b$)O(R$^g$), —C(R$^a$)(R$^b$)N(R$^g$) (R$^h$), —N(R$^d$)(R$^e$) or —O(R$^f$) wherein:

R$^a$ is H;

R$^b$ is H or methyl;

R$^c$ is a group benzyl, cyclobutyl, cyclopentyl, cyclohexyl, phenyl, thienyl, furanyl, pyrrolyl, imidazolyl, pyrazolyl, triazolyl, tetrazolyl, oxazolyl, isoxazolyl, oxadiazolyl, thiazolyl, isothiazolyl, thiadiazolyl, pyridyl, pyridazinyl, pyrimidinyl, pyrazinyl, indolizinyl, purinyl, naphthyridinyl, pteridinyl, [1,3]dioxolane, pyrrolidinyl, pyrazolinyl, pyrazolidinyl, imidazolinyl, imidazolidinyl, piperidinyl, piperazinyl, oxazolidinyl, isoxazolidinyl, morpholinyl, thiazolidinyl, isothiazolidinyl, tetrahydrofuryl or tetrahydropyranyl, each group R$^c$ being optionally substituted by 1 to 3 groups being halogen, CN, alkyl, haloalkyl, alkoxy or haloalkoxy;

R$^d$ is hydrogen or methyl;

R$^e$ is a group cyclobutyl, cyclopentyl, cyclohexyl, phenyl, thienyl, furanyl, pyrrolyl, imidazolyl, pyrazolyl, triazolyl, tetrazolyl, oxazolyl, isoxazolyl, oxadiazolyl, thiazolyl, isothiazolyl, thiadiazolyl, pyridyl, pyridazinyl, pyrimidinyl, pyrazinyl, indolizinyl, purinyl, naphthyridinyl, pteridinyl, [1,3]dioxolane, pyrrolidinyl, pyrazolinyl, pyrazolidinyl, imidazolinyl, imidazolidinyl, piperidinyl, piperazinyl, oxazolidinyl, isoxazolidinyl, morpholinyl, thiazolidinyl, isothiazolidinyl, tetrahydrofuryl, or tetrahydropyranyl, each of these groups being optionally substituted by 1 to 3 groups being halogen, CN, alkyl, haloalkyl, alkoxy or haloalkoxy, or R$^e$ is a group —CH(R$^h$)(C$_3$-C$_6$ aryl) or —CH(R$^h$)(5-10 membered heteroaryl);

R$^f$ is C$_3$-C$_6$ cycloalkyl, C$_6$-C$_{10}$ aryl, 3-10 membered heterocycloalkyl, 5-10 membered heteroaryl, —CH(R$^h$) (C$_3$-C$_6$ cycloalkyl), —CH(R$^h$)(C$_3$-C$_6$ aryl), —CH(R$^h$) (3-7 membered heterocycloalkyl) or —CH(R$^h$)(5-10 membered heteroaryl);

R$^g$ is a group methyl, ethyl, propyl, cyclobutyl, cyclopentyl, cyclohexyl, phenyl, thienyl, furanyl, pyrrolyl, imidazolyl, pyrazolyl, triazolyl, tetrazolyl, oxazolyl, isoxazolyl, oxadiazolyl, thiazolyl, isothiazolyl, thiadiazolyl, pyridyl, pyridazinyl, pyrimidinyl, pyrazinyl, indolizinyl, purinyl, naphthyridinyl, pteridinyl, [1,3]dioxolane, pyrrolidinyl, pyrazolinyl, pyrazolidinyl, imidazolinyl, imidazolidinyl, piperidinyl, piperazinyl, oxazolidinyl, isoxazolidinyl, morpholinyl, thiazolidinyl, isothiazolidinyl, tetrahydrofuryl or tetrahydropyranyl, each group R$^g$ being optionally substituted by 1 to 3 groups being halogen, CN, alkyl, haloalkyl, alkoxy or haloalkoxy;

$R^h$ is hydrogen, linear or branched $C_1$-$C_4$ alkyl or —(CO)$R^6$ with $R^6$ being a $C_1$-$C_3$ alkyl group; and wherein each of cycloalkyl, heterocycloalkyl, aryl and heteroaryl is optionally substituted by 1 to 3 groups being halogen, CN, alkyl, haloalkyl, alkoxy or haloalkoxy.

In another embodiment, $R^2$, $R^3$, $R^4$ or $R^5$ represent a group —C($R^a$)($R^b$)($R^c$), —C($R^a$)($R^b$)O($R^g$), —C($R^a$)($R^b$)N($R^g$)($R^h$), —N($R^d$)($R^e$) or —O($R^f$) wherein:

$R^a$ is H;

$R^b$ is H or methyl;

$R^c$ is a group phenyl, benzyl, piperidinyl, tetrahydropyranyl or pyridyl;

$R^d$ is hydrogen or methyl;

$R^e$ is cyclohexyl, phenyl, benzyl, pyridyl, tetrahydropyranyl, —CH$_2$(pyridyl) or —CH(CH$_3$)(pyridyl);

$R^f$ is phenyl, cyclobutyl, cyclopentyl, cyclohexyl, benzyl, —CH$_2$(pyridyl), —CH(CH$_3$)(pyridyl), —CH$_2$(pyrazinyl), —CH$_2$(pyrimidinyl), —CH$_2$(tetrahydropyranyl), —CH$_2$(cyclopentyl), —CH$_2$(cyclohexyl), —CH$_2$(oxazolyl) or —CH$_2$(thiazolyl);

$R^g$ is ethyl, phenyl, cyclobutyl, cyclopentyl, cyclohexyl or tetrahydropyranyl;

$R^h$ is hydrogen, methyl or acetyl;

wherein each of $R^c$, $R^e$, $R^f$ and $R^g$ is optionally substituted by a 1 to 3 groups being halogen, CN, $C_1$-$C_6$ alkyl or $C_1$-$C_6$ alkoxy.

In yet another embodiment, $R^2$, $R^5$, and $R^3$ and $R^4$ when they do not represent a group of formula (II), can be, without being limited to, one of the following groups:

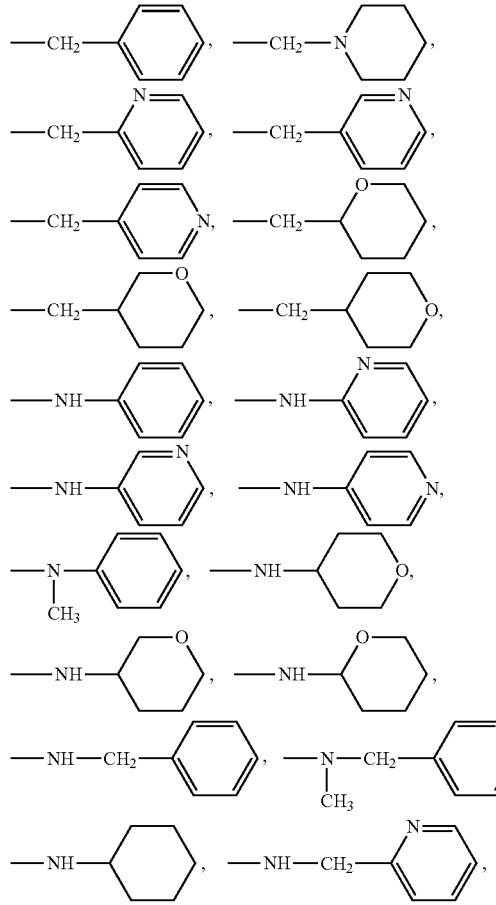

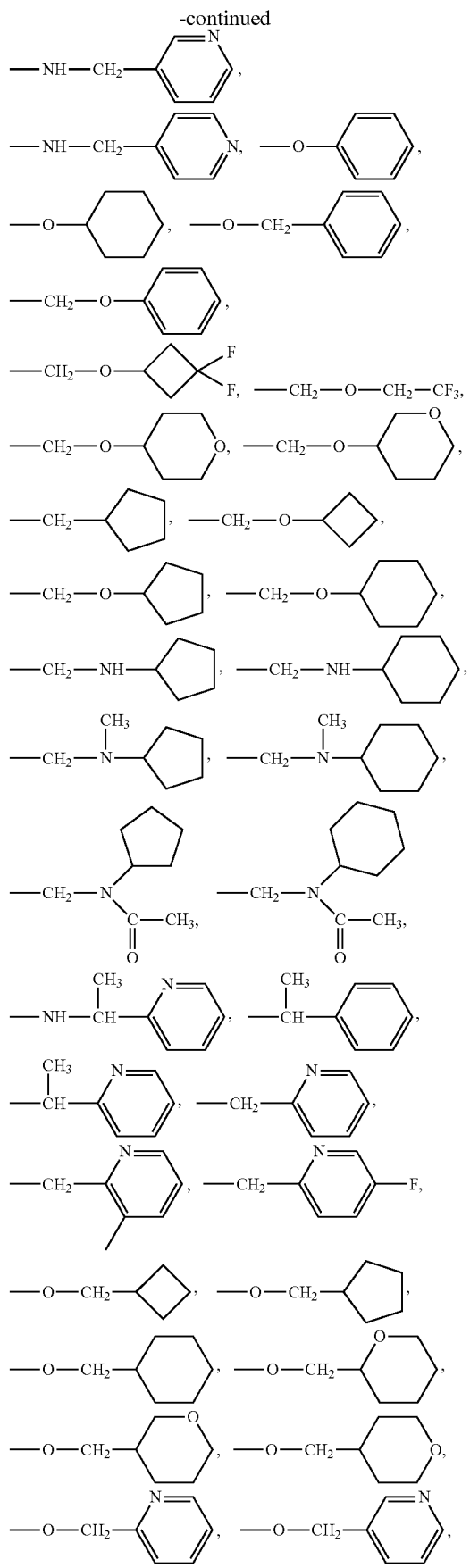

In particular embodiments, $R^2$, $R^5$, and $R^3$ and $R^4$ when they do not represent a group of formula (II), can be one of the following groups:

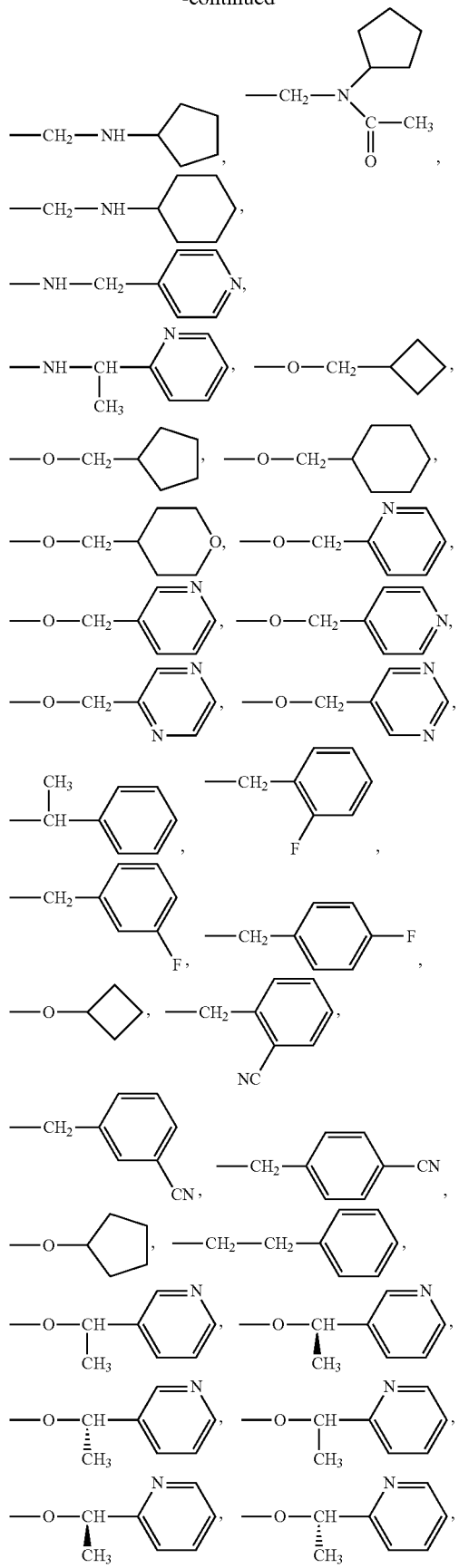
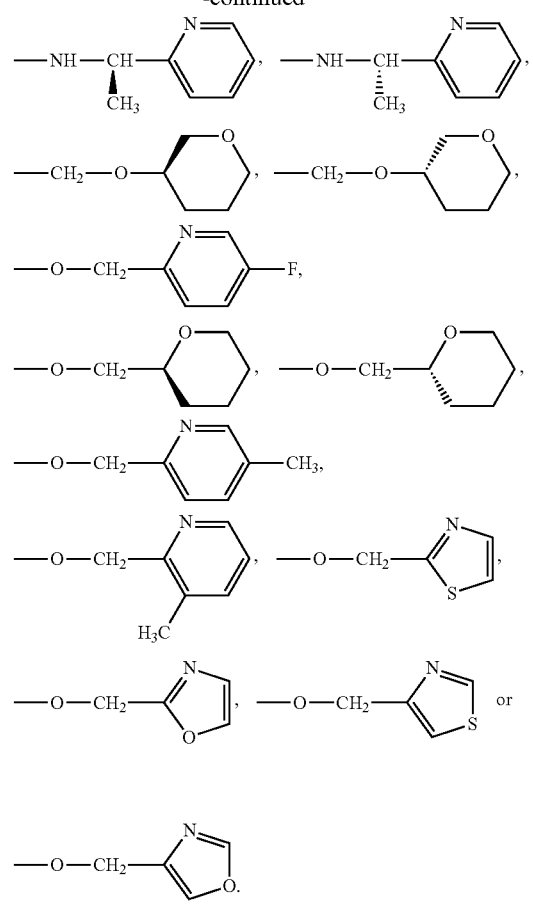

According to another embodiment, in Formula (II), the groups $X^1$, $X^2$ and $X^3$ are all carbon atoms. In another embodiment, $X^1$ is a nitrogen atom and $R^{10}$ is absent, and $X^2$ and $X^3$ are carbon atoms. For instance, the group of Formula (II) may be defined as a group of Formula (IIa):

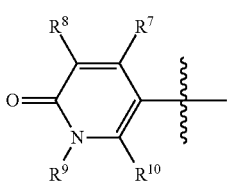

(IIa)

wherein $R^7$, $R^8$, $R^9$ and $R^{10}$ are as herein defined.

In one embodiment, $R^9$ is an unsubstituted $C_1$-$C_3$alkyl or $C_3$-$C_5$cycloalkyl group, such as a methyl, ethyl, n-propyl, isopropyl or cyclopropyl group. For instance, $R^9$ is a methyl group. Alternatively, $R^9$ can be a fluorine-substituted $C_1$-$C_3$alkyl or $C_3$-$C_5$cyclolkyl group, such as trifluoromethyl or difluorocyclopropyl. In another embodiment, $R^7$ and $R^{10}$ are each hydrogen atoms and $R^8$ is selected from Cl, CN, $NHR^6$ and a substituted or unsubstituted $C_1$-$C_6$alkyl or $C_3$-$C_6$cycloalkyl group.

Another embodiment relates to compounds of Formula (III), and pharmaceutically acceptable salts, solvates, esters or prodrugs thereof:

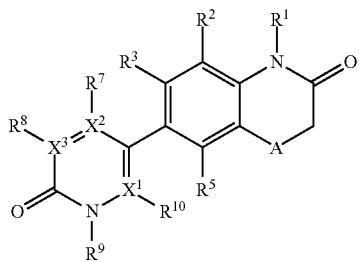

(III)

wherein A, R$^1$, R$^2$, R$^5$, R$^7$, R$^8$, R$^9$ and R$^{10}$ are as herein defined with respect to any of the applicable embodiments.

In one embodiment, the groups X$^1$, X$^2$ and X$^3$ are all carbon atoms. In another embodiment, X$^1$ is a nitrogen atom and R$^{10}$ is absent, and X$^2$ and X$^3$ are carbon atoms.

According to another embodiment, the application also relates to compounds of Formula (IIIa), and pharmaceutically acceptable salts, solvates, esters or prodrugs thereof:

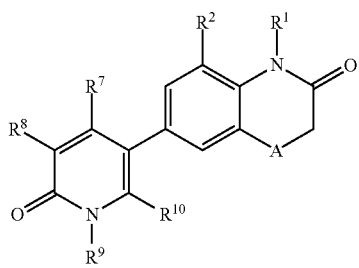

(IIIa)

wherein A, R$^1$, R$^2$ R$^7$, R$^8$, R$^9$ and R$^{10}$ are as herein defined with respect to any of the applicable embodiments.

In one embodiment, Formula (IIIa) is such that R$^1$ is hydrogen or methyl.

In another embodiment, the present application relates to compounds of Formula (IIIb), and pharmaceutically acceptable salts, solvates, esters or prodrugs thereof:

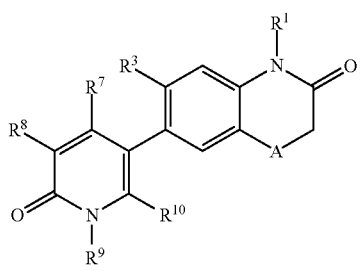

(IIIb)

wherein A, R$^1$, R$^3$, R$^7$, R$^8$, R$^9$ and R$^{10}$ are as herein defined with respect to any of the applicable embodiments.

In one embodiment, Formula (IIIb) is such that R$^1$ is hydrogen or methyl.

Another embodiment of the application relates to compounds of Formula (IIIc), and pharmaceutically acceptable salts, solvates, esters or prodrugs thereof:

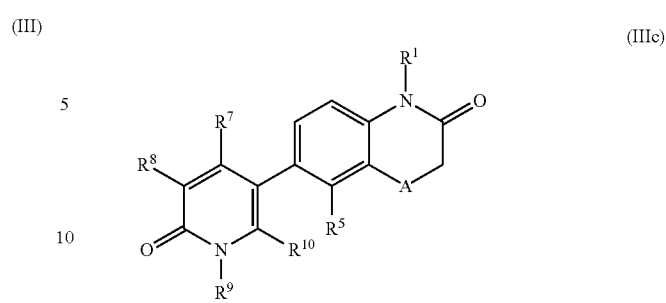

(IIIc)

wherein A, R$^1$, R$^5$, R$^7$, R$^8$, R$^9$ and R$^{10}$ are as defined herein.

In one embodiment, Formula (IIIc) is such that R$^1$ is hydrogen or methyl.

According to one embodiment, the application relates to compounds of Formulae (IIIa), (IIIb) or (IIIc) as herein defined, wherein R$^9$ is an unsubstituted C$_1$-C$_3$alkyl or C$_3$-C$_5$cycloalkyl group, or R$^9$ is a fluorine-substituted C$_1$-C$_3$alkyl or C$_3$-C$_5$cycloalkyl group. For instance, R$^9$ is selected from methyl, trifluoromethyl, ethyl, n-propyl, isopropyl and cyclopropyl. In one embodiment, R$^9$ is a methyl group.

In another embodiment, the application relates to compounds of Formulae (IIIa), (IIIb) or (IIIc), wherein R$^7$ and R$^{10}$ are each hydrogen atoms and R$^8$ is selected from Cl, CN, NHR$^6$ and a substituted or unsubstituted C$_1$-C$_6$alkyl or C$_3$-C$_6$cycloalkyl group. In a further embodiment, R$^8$ and R$^9$ are each independently a methyl, ethyl, isopropyl, fluoromethyl, difluoromethyl, trifluoromethyl, cyclopropyl, or difluorocyclopropyl group.

According to another embodiment, the application also relates to compounds of Formula (IIId), and pharmaceutically acceptable salts, solvates, esters or prodrugs thereof:

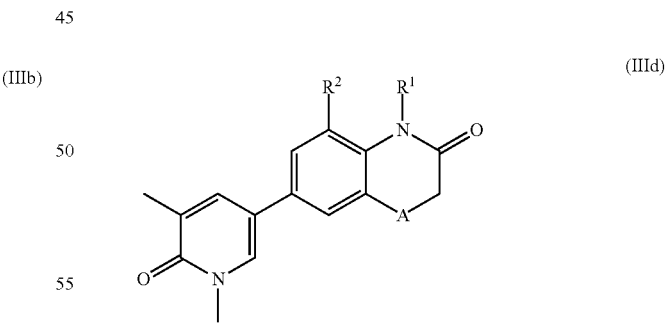

(IIId)

wherein A, R$^1$ and R$^2$ are as defined herein with respect to any applicable embodiments.

In one embodiment, Formula (IIId) is such that R$^1$ is hydrogen or methyl.

According to another embodiment, the application also relates to compounds of Formula (IIIe), and pharmaceutically acceptable salts, solvates, esters or prodrugs thereof:

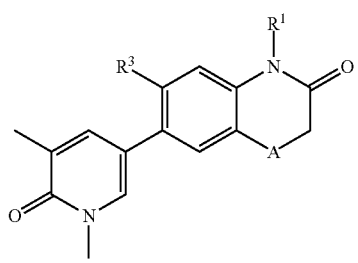

(IIIe)

wherein A, $R^1$ and $R^3$ are as defined herein with respect to any applicable embodiments.

In one embodiment, Formula (IIIe) is such that $R^1$ is hydrogen or methyl.

According to another embodiment, the application also relates to compounds of Formula (IIIf), and pharmaceutically acceptable salts, solvates, esters or prodrugs thereof:

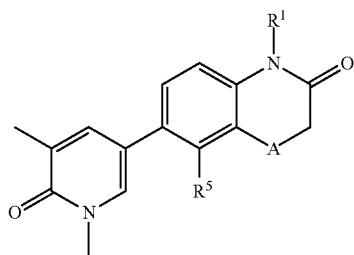

(IIIf)

wherein A, $R^1$ and $R^5$ are as defined herein with respect to any applicable embodiments.

In one embodiment, Formula (IIIf) is such that $R^1$ is hydrogen or methyl.

According to another embodiment, the application also relates to compounds of Formula (IV), and pharmaceutically acceptable salts, solvates, esters or prodrugs thereof:

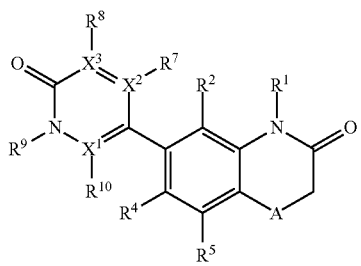

(IV)

wherein A, $R^1$, $R^2$, $R^4$, $R^5$, $R^7$, $R^8$, $R^9$, $R^{10}$, $X^1$, $X^2$ and $X^3$ are as defined herein.

In one embodiment, the groups $X^1$, $X^2$ and $X^3$ are all carbon atoms. In another embodiment, $X^1$ is a nitrogen atom and $R^{10}$ is absent, and $X^2$ and $X^3$ are carbon atoms.

According to another embodiment, the application also relates to compounds of Formula (IVa), and pharmaceutically acceptable salts, solvates, esters or prodrugs thereof:

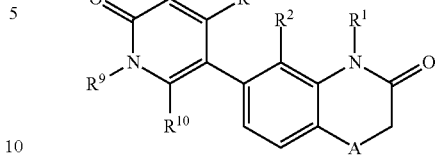

(IVa)

wherein A, $R^1$, $R^2$ $R^7$, $R^8$, $R^9$ and $R^{10}$ are as herein defined with respect to any of the applicable embodiments.

In one embodiment, Formula (IVa) is such that $R^1$ is hydrogen or methyl.

In another embodiment, the present application relates to compounds of Formula (IVb), and pharmaceutically acceptable salts, solvates, esters or prodrugs thereof:

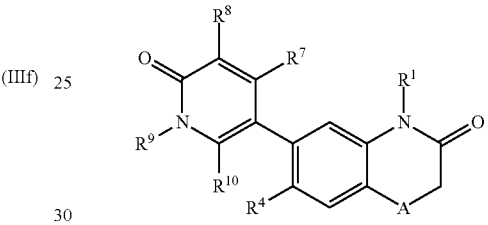

(IVb)

wherein A, $R^1$, $R^4$, $R^7$, $R^8$, $R^9$ and $R^{10}$ are as herein defined with respect to any of the applicable embodiments.

In one embodiment, Formula (IVb) is such that $R^1$ is hydrogen or methyl.

Another embodiment of the application relates to compounds of Formula (IVc), and pharmaceutically acceptable salts, solvates, esters or prodrugs thereof:

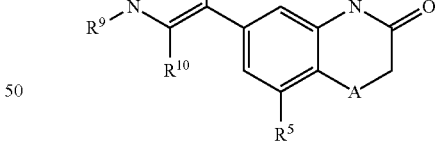

(IVc)

wherein A, $R^1$, $R^5$, $R^7$, $R^8$, $R^9$ and $R^{10}$ are as defined herein.

In one embodiment, Formula (IVc) is such that $R^1$ is hydrogen or methyl.

According to one embodiment, the application relates to compounds of Formulae (IVa), (IVb) or (IVc) as herein defined, wherein $R^9$ is an unsubstituted $C_1$-$C_3$alkyl or $C_3$-$C_5$cycloalkyl group, or $R^9$ is a fluorine-substituted $C_1$-$C_3$alkyl or $C_3$-$C_5$cycloalkyl group. For instance, $R^9$ is selected from methyl, trifluoromethyl, ethyl, n-propyl, isopropyl and cyclopropyl. In one embodiment, $R^9$ is a methyl group.

In another embodiment, the application relates to compounds of Formulae (IVa), (IVb) or (IVc), wherein $R^7$ and $R^{10}$ are each hydrogen atoms and $R^8$ is selected from Cl, CN, $NHR^6$ and a substituted or unsubstituted $C_1$-$C_6$alkyl or $C_3$-$C_6$cycloalkyl group. In a further embodiment, $R^8$ and $R^9$ are each independently a methyl, ethyl, isopropyl, fluoromethyl, difluoromethyl, trifluoromethyl, cyclopropyl, or difluorocyclopropyl group.

According to another embodiment, the application also relates to compounds of Formula (IVd), and pharmaceutically acceptable salts, solvates, esters or prodrugs thereof:

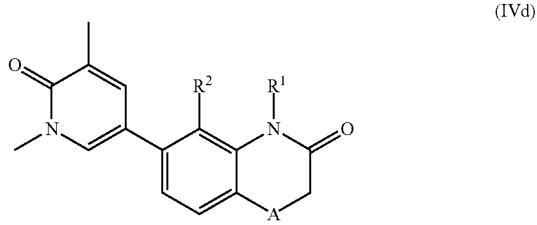

(IVd)

wherein A, $R^1$ and $R^2$ are as defined herein with respect to any applicable embodiments.

In one embodiment, Formula (IVd) is such that $R^1$ is hydrogen or methyl.

According to another embodiment, the application also relates to compounds of Formula (IVe), and pharmaceutically acceptable salts, solvates, esters or prodrugs thereof:

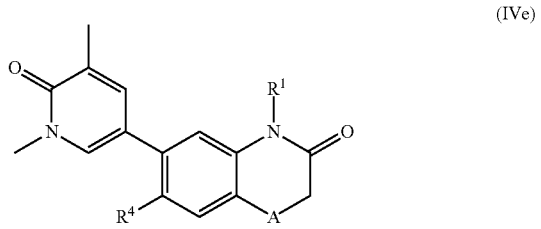

(IVe)

wherein A, $R^1$ and $R^4$ are as defined herein with respect to any applicable embodiments.

In one embodiment, Formula (IVe) is such that $R^1$ is hydrogen or methyl.

According to another embodiment, the application also relates to compounds of Formula (IVf), and pharmaceutically acceptable salts, solvates, esters or prodrugs thereof:

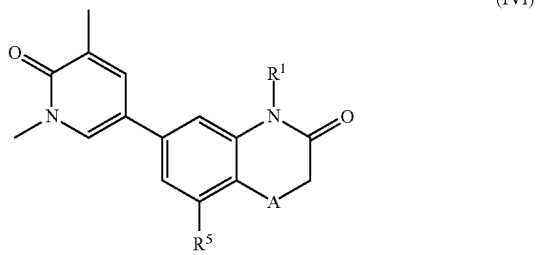

(IVf)

wherein A, $R^1$ and $R^5$ are as defined herein with respect to any applicable embodiments.

In one embodiment, Formula (IVf) is such that $R^1$ is hydrogen or methyl.

In a further embodiment, this application relates to a compound selected from Compounds 1 to 101 as defined in Table 1 below, or a pharmaceutically acceptable salt, solvate, or prodrug thereof. In yet another embodiment, this application relates to a compound selected from Compounds 1-29, 30-32, 34, 38, 39, 44, 46, 47, 48a, 48b, 52, 53, 54a, 54b, 55a, 55b, 57, 58, 61, 62, 67-73, 74a, 74b, 75-91, 92a, 92b and 93-101 as defined in Table 1 below, or a pharmaceutically acceptable salt, solvate, or prodrug thereof.

TABLE 1

Compounds 1 to 101

Compound 1

Compound 2

Compound 3

Compound 4

TABLE 1-continued
Compounds 1 to 101
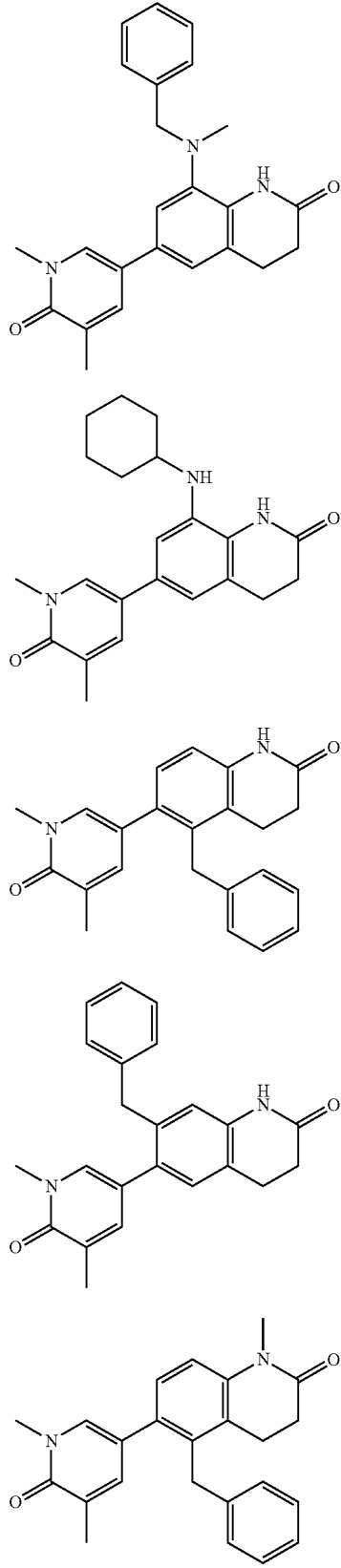
Compound 5
Compound 6
Compound 7
Compound 8
Compound 9
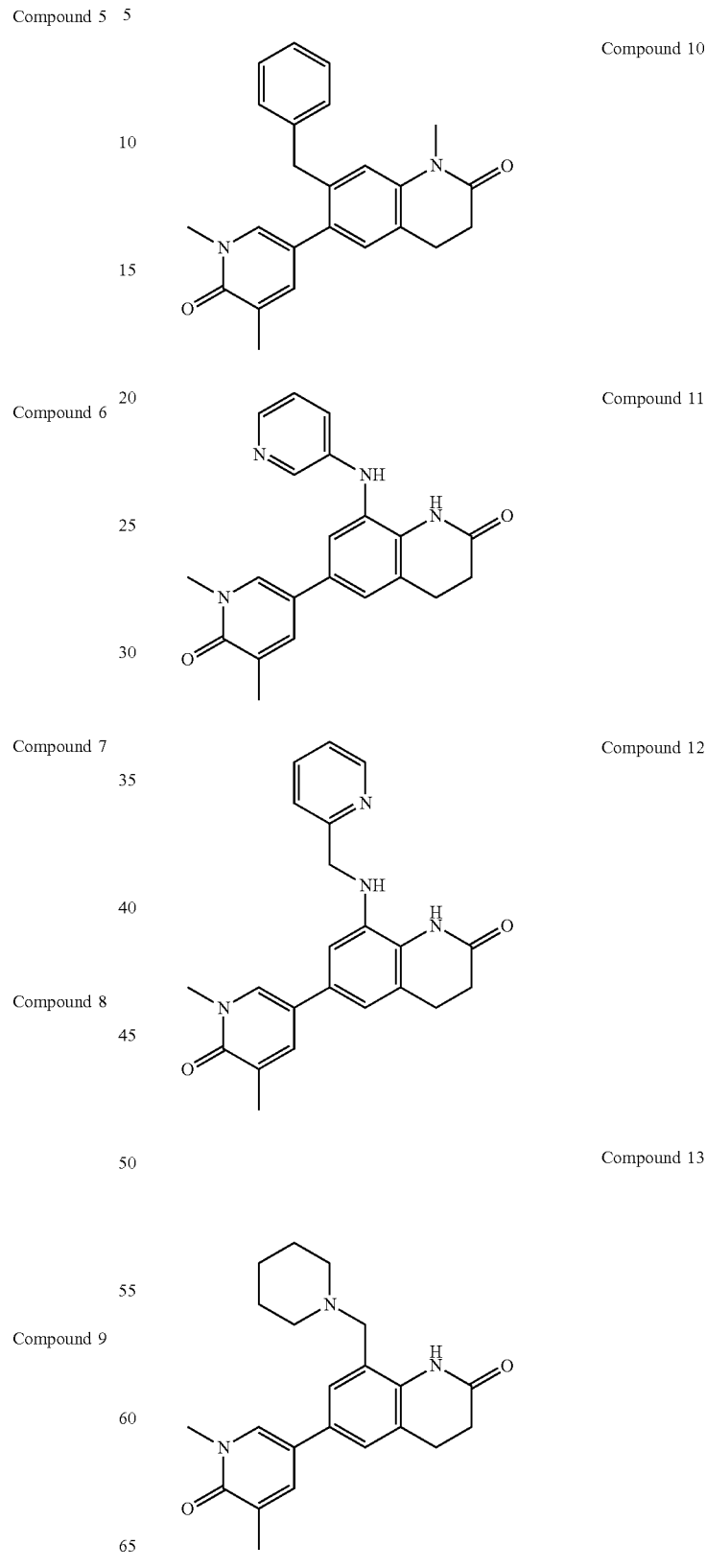
Compound 10
Compound 11
Compound 12
Compound 13

TABLE 1-continued
Compounds 1 to 101
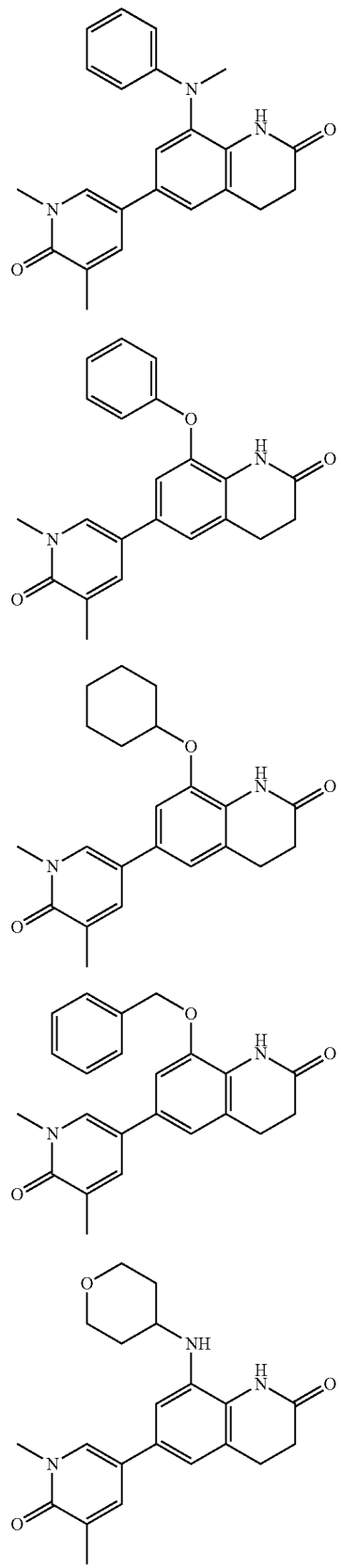
Compound 14
Compound 15
Compound 16
Compound 17
Compound 18
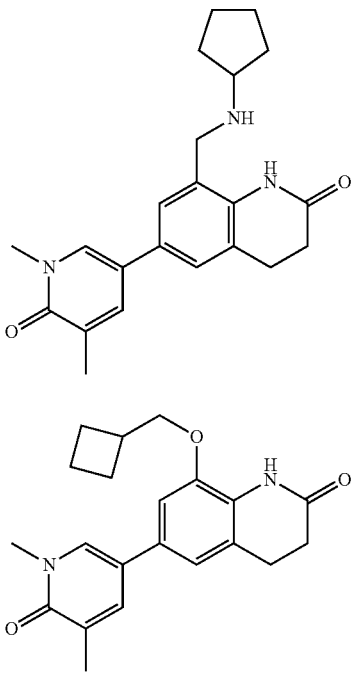
Compound 19
Compound 20
Compound 21
Compounds 22 and 23
(Compounds 22 and 23 are enantiomers, but absolute stereochemistry is unknown)

TABLE 1-continued
Compounds 1 to 101
Compound 24
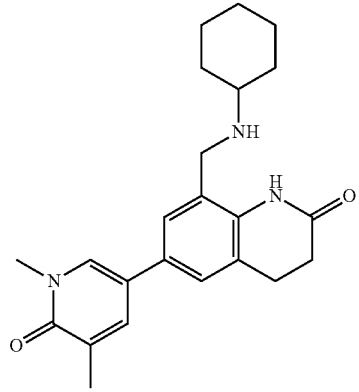 [SMILES: Cc1cc(-c2cc3c(c(CNC4CCCCC4)c2)NC(=O)CC3)cn(C)c1=O]
Compound 25
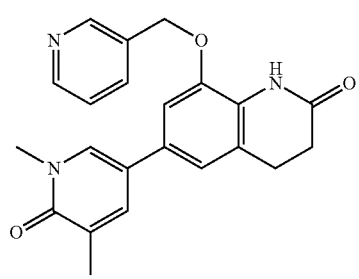 [SMILES: Cc1cc(-c2cc3c(c(OCc4cccnc4)c2)NC(=O)CC3)cn(C)c1=O]
Compound 26
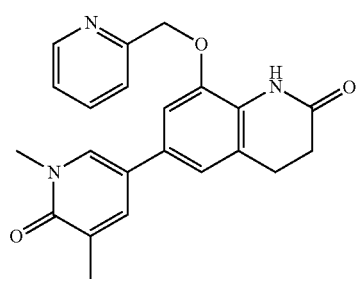 [SMILES: Cc1cc(-c2cc3c(c(OCc4ccccn4)c2)NC(=O)CC3)cn(C)c1=O]
Compound 27
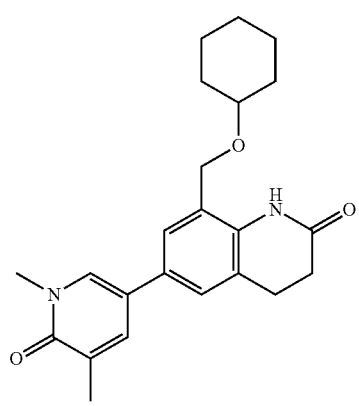 [SMILES: Cc1cc(-c2cc3c(c(COC4CCCCC4)c2)NC(=O)CC3)cn(C)c1=O]
Compound 28
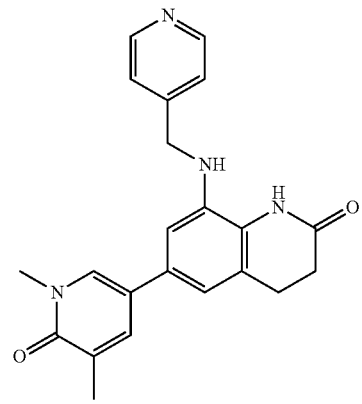 [SMILES: Cc1cc(-c2cc3c(c(NCc4ccncc4)c2)NC(=O)CC3)cn(C)c1=O]
Compound 29
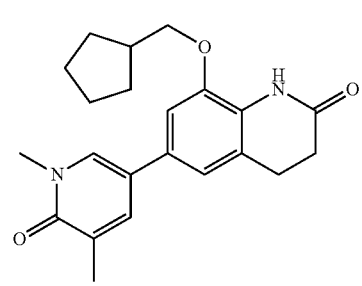 [SMILES: Cc1cc(-c2cc3c(c(OCC4CCCC4)c2)NC(=O)CC3)cn(C)c1=O]
Compound 30
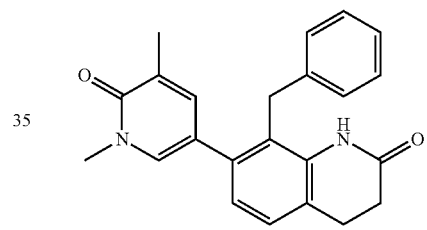
Compound 31
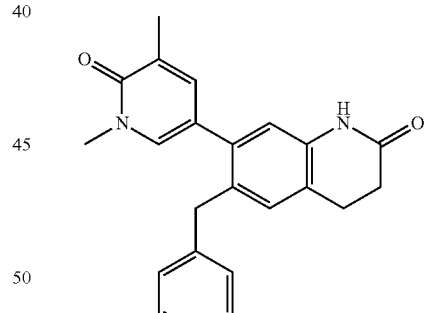
Compound 32
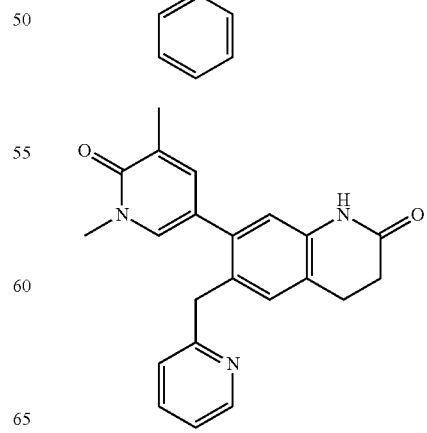

TABLE 1-continued
Compounds 1 to 101
Compound 33
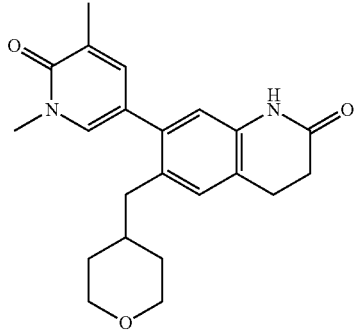 [SMILES: Cc1cc(-c2cc3c(cc2CC2CCOCC2)CCC(=O)N3)cn(C)c1=O]
Compound 34
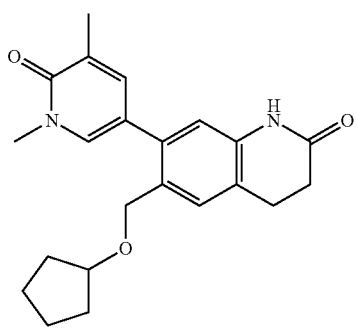 [SMILES: Cc1cc(-c2cc3c(cc2COC2CCCC2)CCC(=O)N3)cn(C)c1=O]
Compound 35
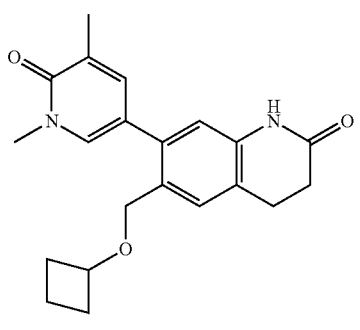 [SMILES: Cc1cc(-c2cc3c(cc2COC2CCC2)CCC(=O)N3)cn(C)c1=O]
Compound 36
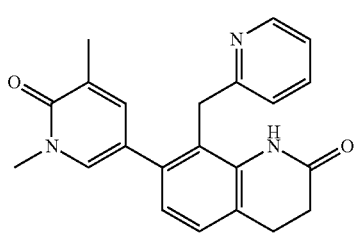 [SMILES: Cc1cc(-c2ccc3c(c2Cc2ccccn2)NC(=O)CC3)cn(C)c1=O]
Compound 37
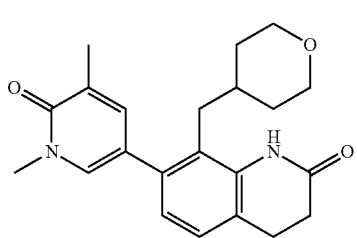 [SMILES: Cc1cc(-c2ccc3c(c2CC2CCOCC2)NC(=O)CC3)cn(C)c1=O]
TABLE 1-continued
Compounds 1 to 101
Compound 38
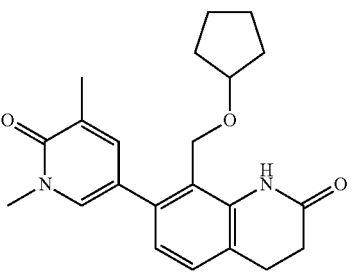 [SMILES: Cc1cc(-c2ccc3c(c2COC2CCCC2)NC(=O)CC3)cn(C)c1=O]
Compound 39
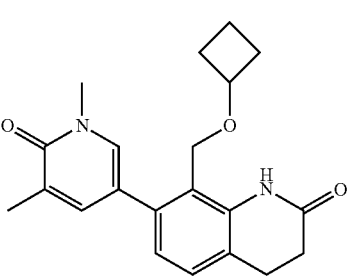 [SMILES: Cc1cc(-c2ccc3c(c2COC2CCC2)NC(=O)CC3)cn(C)c1=O]
Compound 40
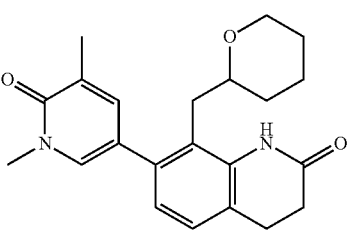 [SMILES: Cc1cc(-c2ccc3c(c2CC2CCCCO2)NC(=O)CC3)cn(C)c1=O]
Compound 41
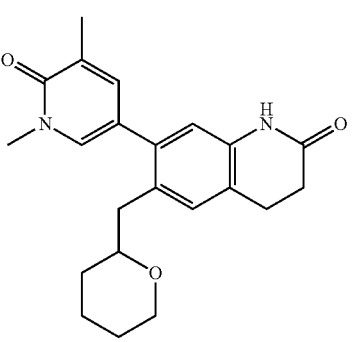 [SMILES: Cc1cc(-c2cc3c(cc2CC2CCCCO2)CCC(=O)N3)cn(C)c1=O]
Compound 42
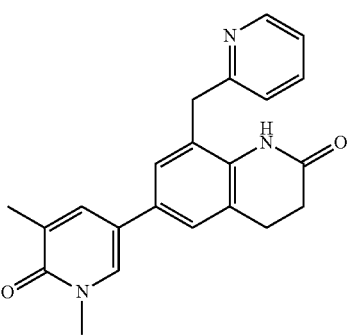 [SMILES: Cc1cc(-c2cc3c(c(Cc4ccccn4)c2)NC(=O)CC3)cn(C)c1=O]

TABLE 1-continued
Compounds 1 to 101
Compound 43
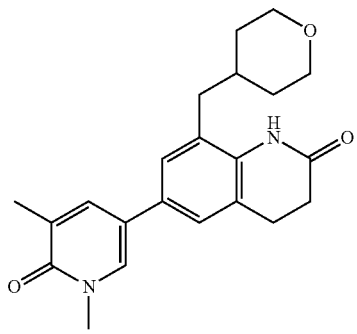 [SMILES: Cc1cc(-c2cc3c(c(CC4CCOCC4)c2)NC(=O)CC3)cn(C)c1=O]
Compound 44
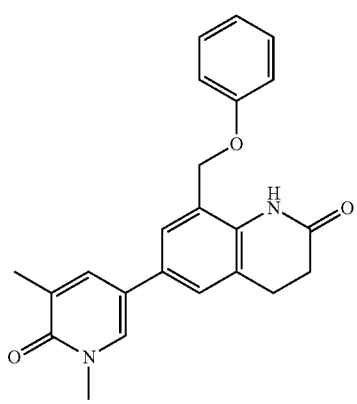 [SMILES: Cc1cc(-c2cc3c(c(COc4ccccc4)c2)NC(=O)CC3)cn(C)c1=O]
Compound 45
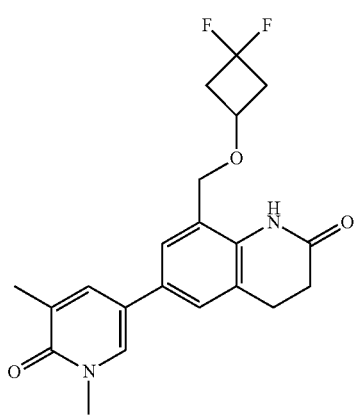 [SMILES: Cc1cc(-c2cc3c(c(COC4CC(F)(F)C4)c2)NC(=O)CC3)cn(C)c1=O]
Compound 46
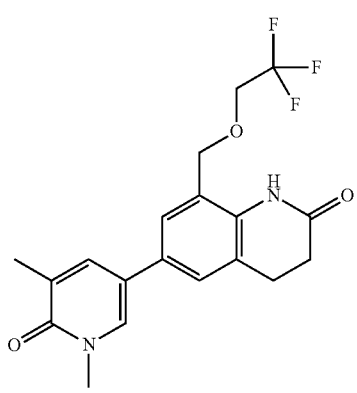 [SMILES: Cc1cc(-c2cc3c(c(COCC(F)(F)F)c2)NC(=O)CC3)cn(C)c1=O]
Compound 47
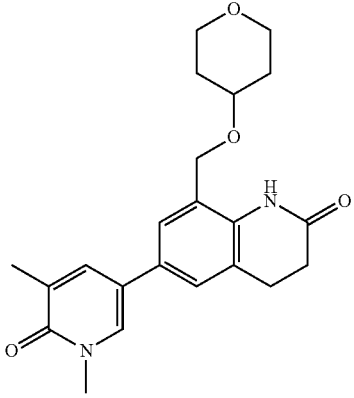 [SMILES: Cc1cc(-c2cc3c(c(COC4CCOCC4)c2)NC(=O)CC3)cn(C)c1=O]
Compounds 48a and 48b
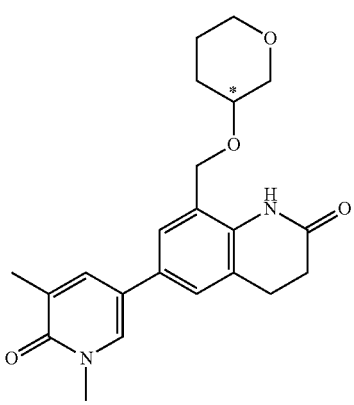 [SMILES: Cc1cc(-c2cc3c(c(COC4CCCOC4)c2)NC(=O)CC3)cn(C)c1=O]
(Compounds 48a and 48b are enantiomers, but absolute stereochemistry is unknown)
Compound 49
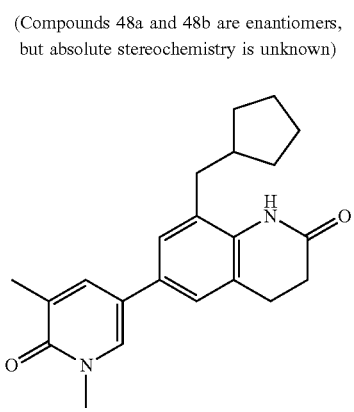
Compound 50
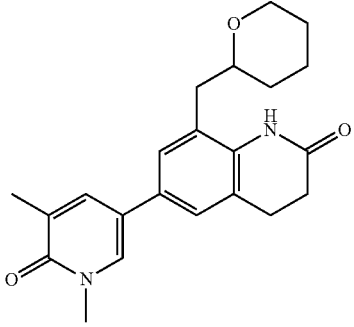 [SMILES: Cc1cc(-c2cc3c(c(CC4CCCCO4)c2)NC(=O)CC3)cn(C)c1=O]

TABLE 1-continued
Compounds 1 to 101
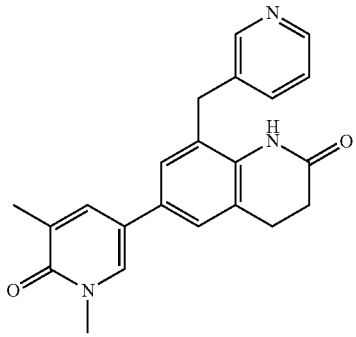 [SMILES: Cc1cc(-c2cc3c(c(Cc4cccnc4)c2)NC(=O)CC3)cn(C)c1=O]
Compound 51
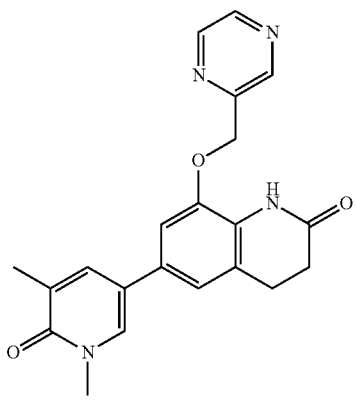 [SMILES: Cc1cc(-c2cc3c(c(OCc4cnccn4)c2)NC(=O)CC3)cn(C)c1=O]
Compound 52
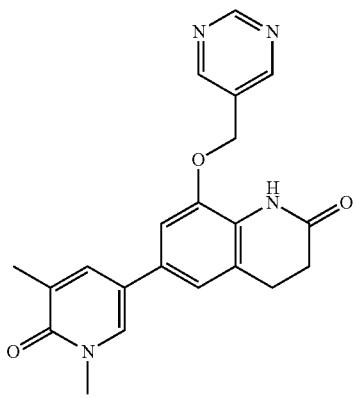 [SMILES: Cc1cc(-c2cc3c(c(OCc4cncnc4)c2)NC(=O)CC3)cn(C)c1=O]
Compound 53
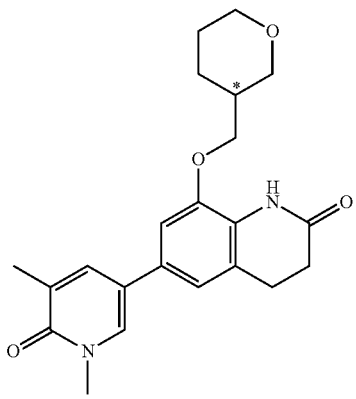 [SMILES: Cc1cc(-c2cc3c(c(OCC4CCCOC4)c2)NC(=O)CC3)cn(C)c1=O]
Compounds 54a and 54b
(Compounds 54a and 54b are enantiomers, but absolute stereochemistry is unknown)
TABLE 1-continued
Compounds 1 to 101
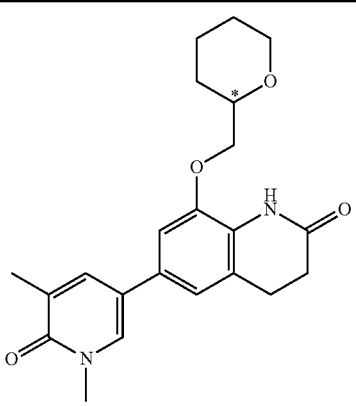
Compounds 55a and 55b
(Compounds 55a and 55b are enantiomers, but absolute stereochemistry is unknown)
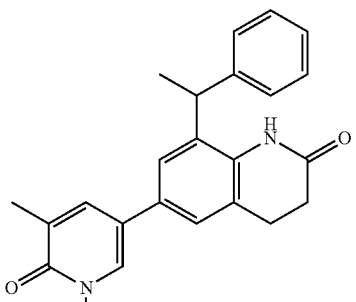
Compound 56
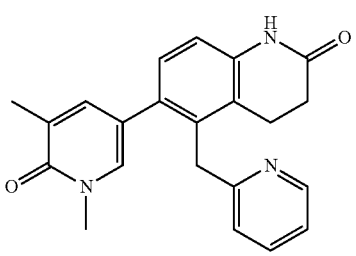 [SMILES: Cc1cc(-c2ccc3c(c2Cc2ccccn2)CCC(=O)N3)cn(C)c1=O]
Compound 57
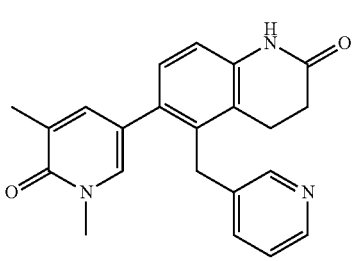 [SMILES: Cc1cc(-c2ccc3c(c2Cc2cccnc2)CCC(=O)N3)cn(C)c1=O]
Compound 58
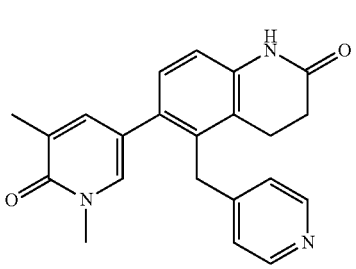 [SMILES: Cc1cc(-c2ccc3c(c2Cc2ccncc2)CCC(=O)N3)cn(C)c1=O]
Compound 59

TABLE 1-continued
Compounds 1 to 101
Compound 60
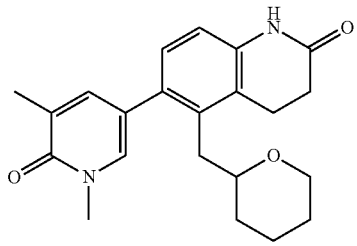 [SMILES: Cc1cc(-c2ccc3c(c2CC2CCCCO2)CCC(=O)N3)cn(C)c1=O]
Compound 61
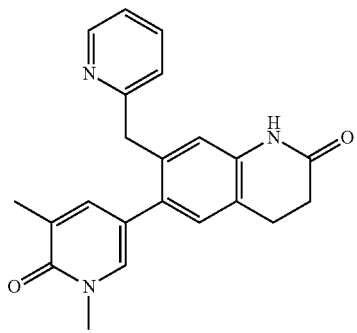 [SMILES: Cc1cc(-c2cc3c(cc2Cc2ccccn2)NC(=O)CC3)cn(C)c1=O]
Compound 62
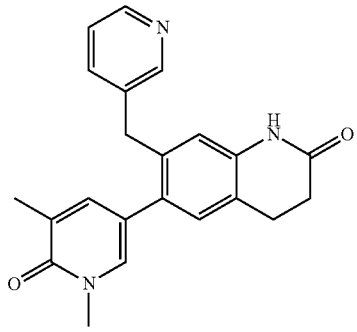 [SMILES: Cc1cc(-c2cc3c(cc2Cc2cccnc2)NC(=O)CC3)cn(C)c1=O]
Compound 63
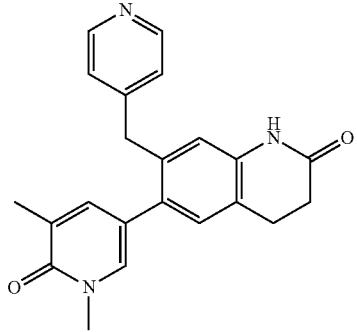 [SMILES: Cc1cc(-c2cc3c(cc2Cc2ccncc2)NC(=O)CC3)cn(C)c1=O]
Compound 64
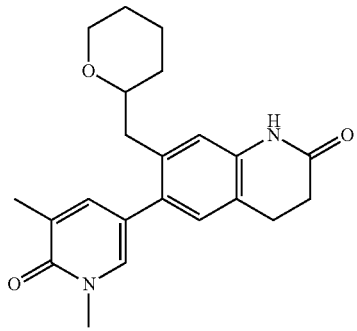 [SMILES: Cc1cc(-c2cc3c(cc2CC2CCCCO2)NC(=O)CC3)cn(C)c1=O]
Compound 65
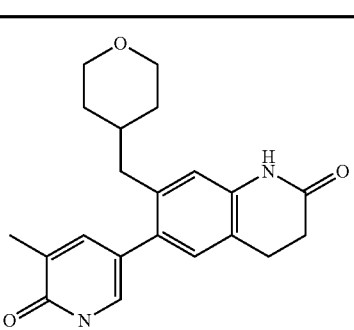
Compound 66
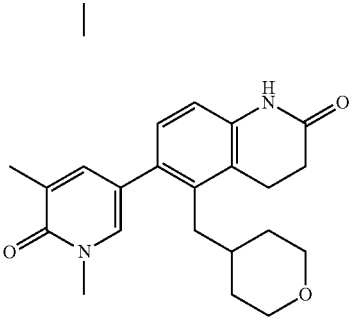
Compound 67
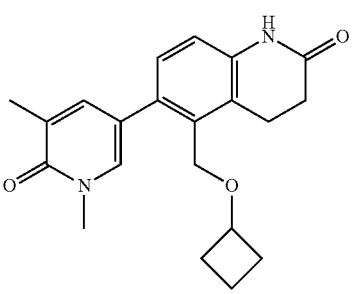 [SMILES: Cc1cc(-c2ccc3c(c2COC2CCC2)CCC(=O)N3)cn(C)c1=O]
Compound 68
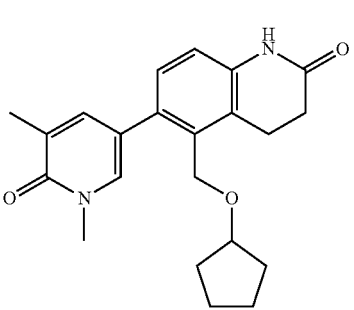 [SMILES: Cc1cc(-c2ccc3c(c2COC2CCCC2)CCC(=O)N3)cn(C)c1=O]
Compound 69
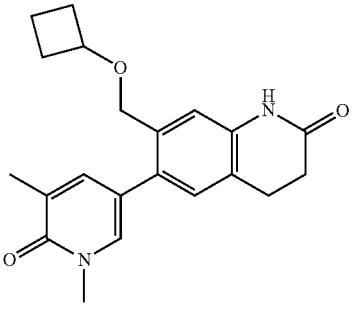 [SMILES: Cc1cc(-c2cc3c(cc2COC2CCC2)NC(=O)CC3)cn(C)c1=O]

TABLE 1-continued
Compounds 1 to 101
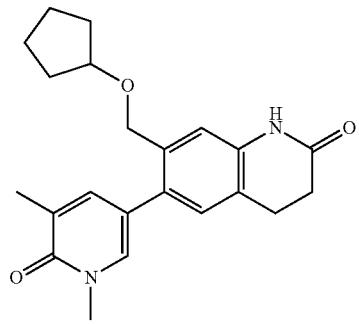 [SMILES: Cc1cc(-c2cc3c(cc2COC2CCCC2)NC(=O)CC3)cn(C)c1=O]
Compound 70
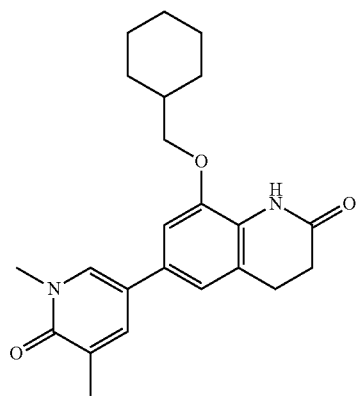 [SMILES: Cc1cc(-c2cc3c(c(OCC4CCCCC4)c2)NC(=O)CC3)cn(C)c1=O]
Compound 71
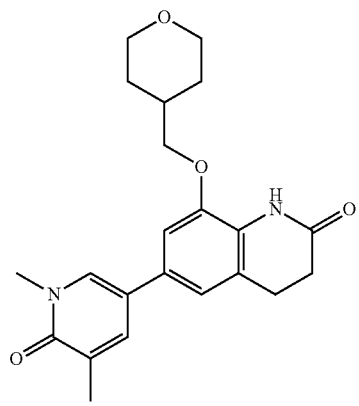 [SMILES: Cc1cc(-c2cc3c(c(OCC4CCOCC4)c2)NC(=O)CC3)cn(C)c1=O]
Compound 72
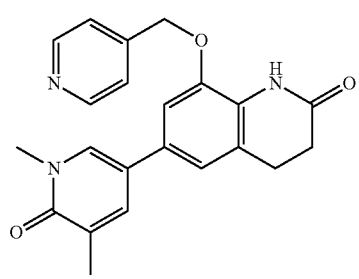 [SMILES: Cc1cc(-c2cc3c(c(OCc4ccncc4)c2)NC(=O)CC3)cn(C)c1=O]
Compound 73
TABLE 1-continued
Compounds 1 to 101
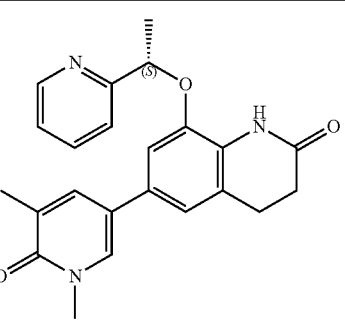
Compound 74a
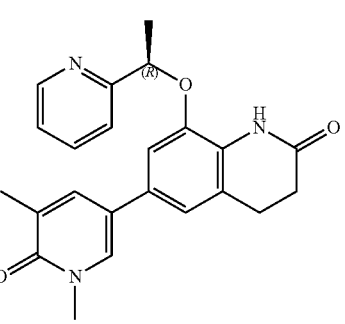
Compound 74b
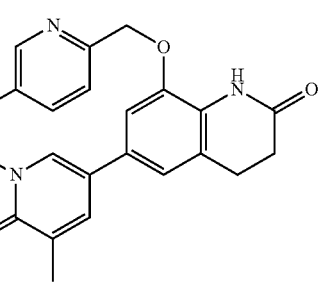
Compound 75
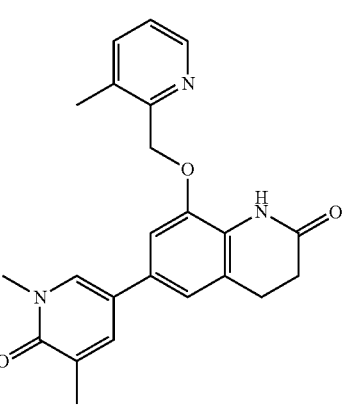
Compound 76

TABLE 1-continued
Compounds 1 to 101
Compound 77
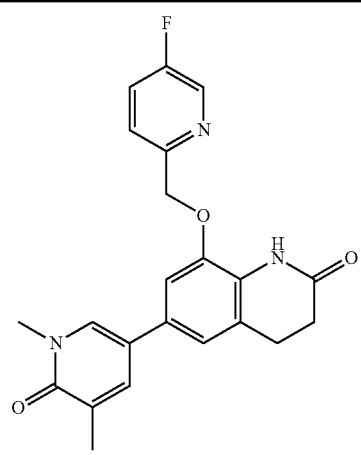
Compound 78
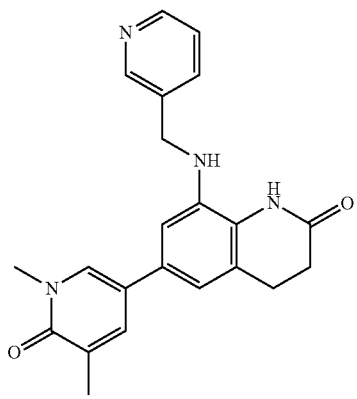 [SMILES: Cc1cc(-c2cc3c(c(NCc4cccnc4)c2)NC(=O)CC3)cn(C)c1=O]
Compound 79
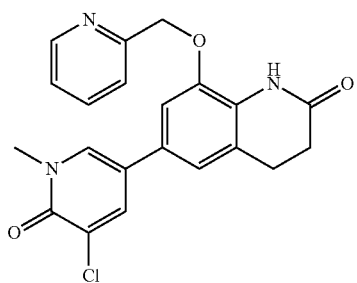 [SMILES: Cn1cc(-c2cc3c(c(OCc4ccccn4)c2)NC(=O)CC3)cc(Cl)c1=O]
Compound 80
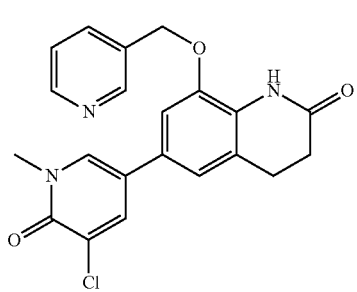 [SMILES: Cn1cc(-c2cc3c(c(OCc4cccnc4)c2)NC(=O)CC3)cc(Cl)c1=O]
TABLE 1-continued
Compounds 1 to 101
Compound 81
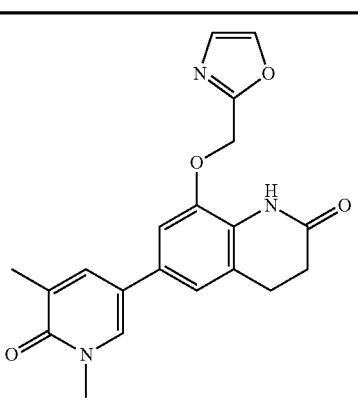
Compound 82
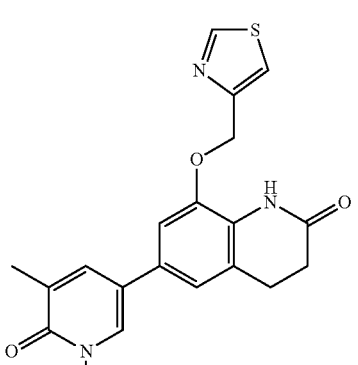
Compound 83
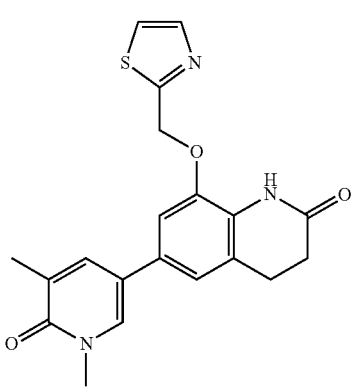
Compound 84
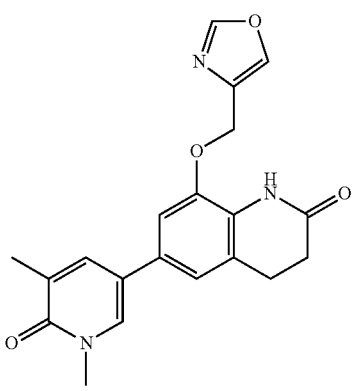 [SMILES: Cc1cc(-c2cc3c(c(OCc4cscn4)c2)NC(=O)CC3)cn(C)c1=O]

TABLE 1-continued
Compounds 1 to 101
Compound 85
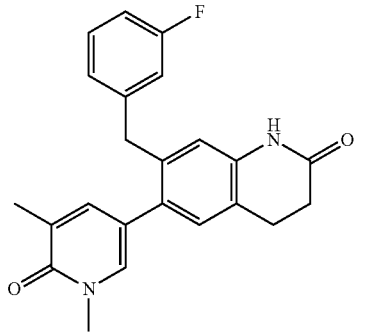 [SMILES: Cc1cc(-c2cc3c(cc2Cc2cccc(F)c2)NC(=O)CC3)cn(C)c1=O]
Compound 86
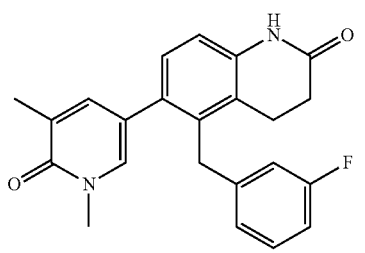 [SMILES: Cc1cc(-c2ccc3c(c2Cc2cccc(F)c2)CCC(=O)N3)cn(C)c1=O]
Compound 87
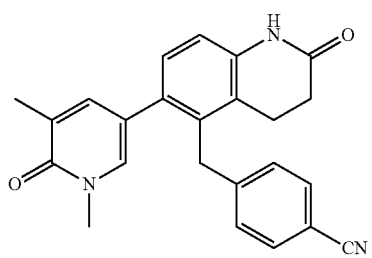 [SMILES: Cc1cc(-c2ccc3c(c2Cc2ccc(C#N)cc2)CCC(=O)N3)cn(C)c1=O]
Compound 88
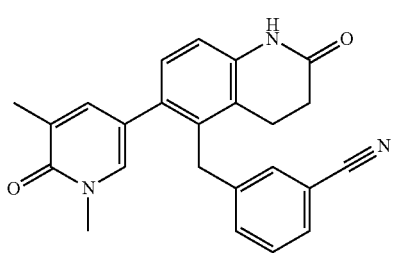 [SMILES: Cc1cc(-c2ccc3c(c2Cc2cccc(C#N)c2)CCC(=O)N3)cn(C)c1=O]
Compound 89
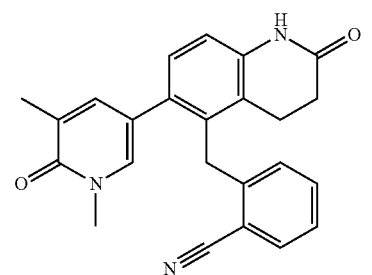 [SMILES: Cc1cc(-c2ccc3c(c2Cc2ccccc2C#N)CCC(=O)N3)cn(C)c1=O]
Compound 90
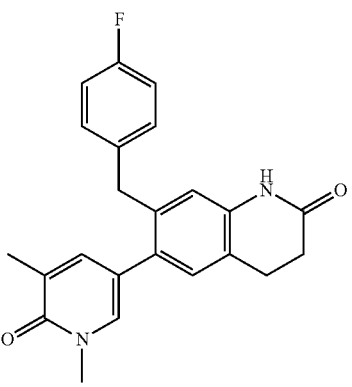 [SMILES: Cc1cc(-c2cc3c(cc2Cc2ccc(F)cc2)NC(=O)CC3)cn(C)c1=O]
Compound 91
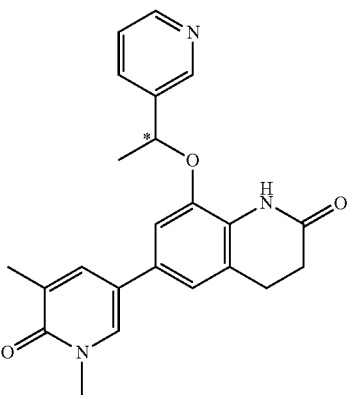 [SMILES: Cc1cc(-c2cc3c(c(OC(C)c4cccnc4)c2)NC(=O)CC3)cn(C)c1=O]
Compounds 92a and 92b
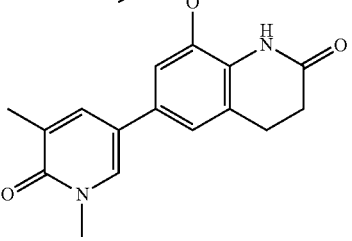
(Compounds 92a and 92b are enantiomers, but absolute stereochemistry is unknown)
Compound 93
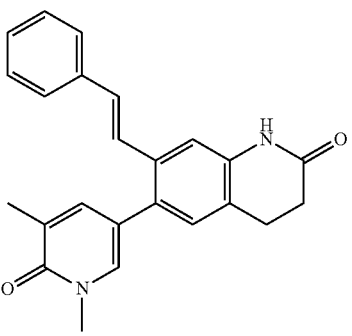 [SMILES: Cc1cc(-c2cc3c(cc2/C=C/c2ccccc2)NC(=O)CC3)cn(C)c1=O]

TABLE 1-continued
Compounds 1 to 101
Compound 94
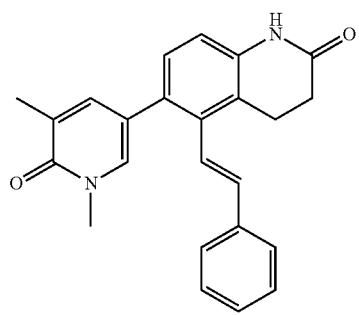 [SMILES: Cc1cc(-c2ccc3c(c2/C=C/c2ccccc2)CCC(=O)N3)cn(C)c1=O]
Compound 95
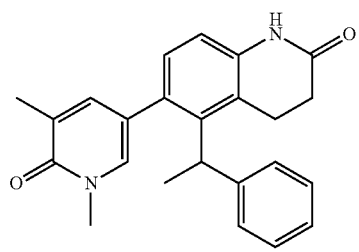 [SMILES: Cc1cc(-c2ccc3c(c2C(C)c2ccccc2)CCC(=O)N3)cn(C)c1=O]
Compound 96
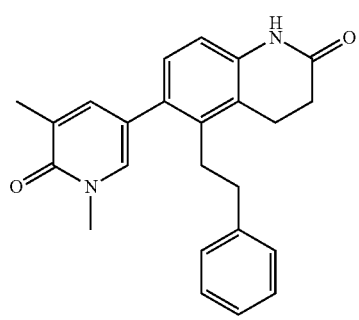 [SMILES: Cc1cc(-c2ccc3c(c2CCc2ccccc2)CCC(=O)N3)cn(C)c1=O]
Compound 97
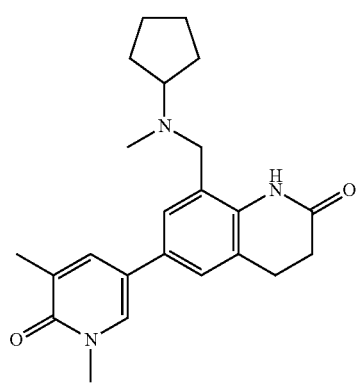 [SMILES: Cc1cc(-c2cc3c(c(CN(C)C4CCCC4)c2)NC(=O)CC3)cn(C)c1=O]
Compound 98
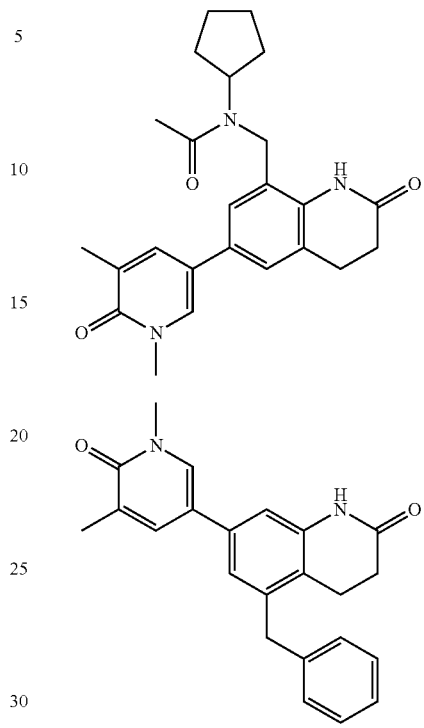
Compound 99
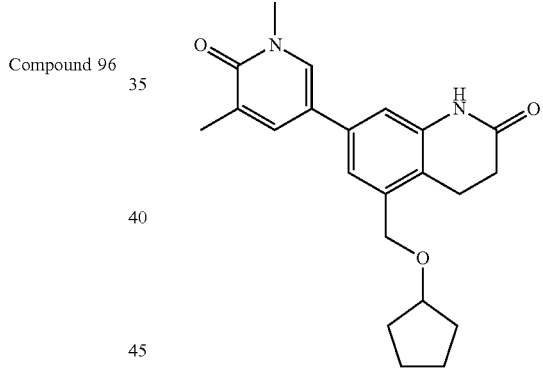
Compound 100
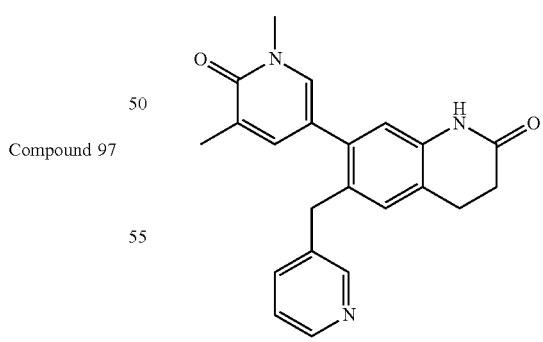
Compound 101
iii. Methods, Uses, Formulations and Administration
As used herein, the term "effective amount" means that amount of a drug or pharmaceutical agent that will elicit the biological or medical response of a tissue, system, animal or human that is being sought, for instance, by a researcher or clinician. Furthermore, the term "therapeutically effective amount" means any amount which, as compared to a corresponding subject who has not received such amount, results in treatment, healing, prevention, or amelioration of a disease, disorder, or side effect, or a decrease in the rate of advancement of a disease or disorder. The term also includes within its scope amounts effective to enhance normal physiological function.

As used herein, the terms "treatment," "treat," and "treating" refer to reversing, alleviating, delaying the onset of, or inhibiting the progress of a disease or disorder, or one or more symptoms thereof, as described herein. In some embodiments, treatment may be administered after one or more symptoms have developed. In other embodiments, treatment may be administered in the absence of symptoms. For example, treatment may be administered to a susceptible individual prior to the onset of symptoms (e.g., in light of a history of symptoms and/or in light of genetic or other susceptibility factors). Treatment may also be continued after symptoms have resolved, for example to prevent or delay their recurrence.

As used herein, the term "bromodomain inhibitor" denotes a compound which inhibits the binding of a bromodomain with its cognate acetylated proteins. In one embodiment the bromodomain inhibitor is a compound which inhibits the binding of a bromodomain to acetylated lysine residues. In a further embodiment the bromodomain inhibitor is a compound which inhibits the binding of a bromodomain to acetylated lysine residues on histones, particularly histones H3 and H4.

In a particular embodiment the bromodomain inhibitor is a compound that inhibits the binding of BET family bromodomains to acetylated lysine residues (hereafter referred to as a "BET family bromodomain inhibitor"). The BET family of bromodomain containing proteins comprises 4 proteins (BRD2, BRD3, BRD4 and BRD-t) which contain tandem bromodomains capable of binding to two acetylated lysine residues in close proximity, increasing the specificity of the interaction.

As used herein, the term "inhibitor" is defined as a compound that binds to and/or inhibits the target bromodomain-containing protein (such as a BET protein, e.g., BRD2, BRD3, BRD4, and/or BRDT) with measurable affinity.

The terms "measurable affinity" and "measurably inhibit," as used herein, means a measurable change in activity of at least one bromodomain-containing protein between a sample comprising a provided compound, or composition thereof, and at least one histone methyltransferase, and an equivalent sample comprising at least one bromodomain-containing protein, in the absence of said compound, or composition thereof.

The term "patient or subject" as used herein refers to a mammal. A subject therefore refers to, for example, dogs, cats, horses, cows, pigs, guinea pigs, and the like. Preferably the subject is a human. When the subject is a human, the subject may be either a patient or a healthy human.

In some embodiments, the disease or condition can be an auto-immune disorder, an inflammatory disorder, a dermal disorder, or cancer. In some optional embodiments, the disease or condition can be an auto-immune disorder. In some other optional embodiments, the disease or condition can be an inflammatory disorder. In further optional embodiments, the inflammatory disorder can be rheumatoid arthritis, irritable bowel syndrome, or psoriasis.

In some other optional embodiments, the disease or condition can be cancer. In further optional embodiments, the cancer can be brain cancer, pancreatic cancer, breast cancer, lung cancer, or prostate cancer. In further optional embodiments, the cancer can be brain cancer. In further optional embodiments, the brain cancer is glioblastoma multiforme.

In some embodiments, the cancer is selected from the group consisting of: brain (gliomas), glioblastomas, leukemias, lymphomas, Bannayan-Zonana syndrome, Cowden disease, Lhermitte-Duclos disease, breast, inflammatory breast cancer, Wilm's tumor, Ewing's sarcoma, Rhabdomyosarcoma, ependymoma, medulloblastoma, colon, gastric, bladder, head and neck, kidney, lung, liver, melanoma, renal, ovarian, pancreatic, prostate, sarcoma, osteosarcoma, giant cell tumor of bone and thyroid.

In some embodiments, the disorder can be a proliferative disorder, inflammatory disease, sepsis, autoimmune disease, or viral infection. In some optional embodiments, the proliferative disorder can be cancer.

The term "proliferative disorder" refers to cells having the capacity for autonomous growth, i.e., an abnormal state of condition characterized by rapidly proliferating cell growth which generally forms a distinct mass that show partial or total lack of structural organization and functional coordination with normal tissue.

The terms "neoplasm", "neoplastic disorder", "neoplasia" "cancer," and "tumor" are meant to encompass hematopoietic neoplasms (e.g. lymphomas or leukemias) as well as solid neoplasms (e.g. sarcomas or carcinomas), including all types of pre-cancerous and cancerous growths, or oncogenic processes, metastatic tissues or malignantly transformed cells, tissues, or organs, irrespective of histopathologic type or stage of invasiveness. Hematopoietic neoplasms are malignant tumors affecting hematopoietic structures (structures pertaining to the formation of blood cells) and components of the immune system, including leukemias (related to leukocytes (white blood cells) and their precursors in the blood and bone marrow) arising from myeloid, lymphoid or erythroid lineages, and lymphomas (related to lymphocytes). Solid neoplasms include sarcomas, which are malignant neoplasms that originate from connective tissues such as muscle, cartilage, blood vessels, fibrous tissue, fat or bone. Solid neoplasms also include carcinomas, which are malignant neoplasms arising from epithelial structures, including external epithelia (e.g., skin and linings of the gastrointestinal tract, lungs, and cervix), and internal epithelia that line various glands (e.g., breast, pancreas, thyroid). Examples of neoplasms include leukemia, and hepatocellular cancers, sarcoma, vascular endothelial cancers, breast cancers, central nervous system cancers (e.g. astrocytoma, gliosarcoma, neuroblastoma, oligodendroglioma and glioblastoma), prostate cancers, lung and bronchus cancers, larynx cancers, esophagus cancers, colon cancers, colorectal cancers, gastro-intestinal cancers, melanomas, ovarian and endometrial cancer, renal and bladder cancer, liver cancer, endocrine cancer (e.g. thyroid), and pancreatic cancer.

In some aspects, examples of cancers treated using the compounds and methods described herein include, but are not limited to, acinic cell carcinoma, acoustic neuroma, acral lentiginous melanoma, acrospiroma, acute eosinophilic leukemia, acute erythroid leukemia, acute lymphoblastic leukemia, acute lymphocytic leukemia, acute megakaryoblastic leukemia, acute monocytic leukemia, acute myelogenous leukemia, acute myelognous leukemia, acute promyelocytic leukemia, adrenal cancer, adenocarcinoma, adenoid cystic carcinoma, adenoma, adenomatoid odontogenic tumor, adenosquamous carcinoma, adipose tissue neoplasm, adrenal cancer, adrenocortical carcinoma, adult T-cell leukemia/lymphoma, aggressive NK-cell leukemia, AIDS-related lymphoma, alveolar rhabdomyosarcoma, alveolar soft part sarcoma, ameloblastic fibroma, anaplastic large cell lymphoma, anaplastic thyroid cancer, angioimmunoblastic T-cell lymphoma, angiomyolipoma, angiosarcoma, astrocytoma, atypical teratoid rhabdoid tumor, Bannayan-Zonana syndrome, basal cell carcinoma, B-cell chronic lymphocytic leukemia, B-cell lymphoma, B-cell prolymphocytic leukemia, biliary tract cancer, bladder, bladder cancer, blastoma, bone cancer, brain (gliomas), brain cancer, breast, breast cancer, Brenner tumor, Brown tumor, Burkitt's lymphoma, carcinoma, carcinoma in situ, carcinosarcoma, cartilage tumor, cementoma, cervical cancer, chondroma, chordoma, choriocarcinoma, choroid plexus papilloma, chronic lymphocytic leukemia, clear-cell sarcoma of the kidney, colon, colorectal cancer, Cowden disease, craniopharyngioma, cutaneous T-cell lymphoma, Degos disease, desmoplastic small round cell tumor, diffuse large B-cell lymphoma, dysembryoplastic neuroepithelial tumor, dysgerminoma, embryonal carcinoma, endocrine gland neoplasm, endodermal sinus tumor, enteropathy-associated T-cell lymphoma, ependymoma, esophageal cancer, Ewing's sarcoma, fetus in fetu, fibroma, fibrosarcoma, follicular lymphoma, follicular thyroid cancer, gallbladder cancer, ganglioneuroma, gastric, gastric cancer, gastrointestinal cancer, germ cell tumor, gestational choriocarcinoma, giant cell fibroblastoma, giant cell tumor of bone and thyroid, giant cell tumor of the bone, glial tumor, glioblastoma multiforme, glioblastomas, glioma, gliomatosis cerebri, glucagonoma, gonadoblastoma, granulosa cell tumor, gynandroblastoma, hairy cell leukemia, head and neck, head and neck cancer, hemangioblastoma, hemangiopericytoma, hematological malignancy, hepatoblastoma, hepatosplenic T-cell lymphoma, Hodgkin's lymphoma, inflammatory breast cancer, intestinal cancer, invasive lobular carcinoma, kidney, kidney cancer, laryngeal cancer, lentigo maligna, lethal midline carcinoma, leukemia, leukemias, leydig cell tumor, Lhermitte-Duclos disease, liposarcoma, liver, liver cancer, lung, lung cancer, lymphangio sarcoma, lymphangioma, lymphoepithelioma, lymphoma, lymphomas, malignant fibrous histiocytoma, malignant peripheral nerve sheath tumor, malignant triton tumor, MALT lymphoma, mantle cell lymphoma, marginal zone B-cell lymphoma, mast cell leukemia, mediastinal germ cell tumor, medullary carcinoma of the breast, medullary thyroid cancer, medulloblastoma, melanoma, meningioma, merkel cell cancer, mesothelioma, metastatic urothelial carcinoma, mixed Mullerian tumor, mucinous tumor, multiple myeloma, muscle tissue neoplasm, mycosis fungoides, myeloid sarcoma, myxoid liposarcoma, myxoma, myxosarcoma, nasopharyngeal carcinoma, neurinoma, neuroblastoma, neurofibroma, neuroma, nodular melanoma, non-Hodgkin's lymphoma, non-small cell lung cancer, ocular cancer, oligoastrocytoma, oligodendroglioma, oncocytoma, optic nerve sheath meningioma, optic nerve tumor, oral cancer, osteosarcoma, ovarian, ovarian cancer, Pancoast tumor, pancreatic, pancreatic cancer, papillary thyroid cancer, paraganglioma, pharyngeal cancer, pinealoblastoma, pineocytoma, pituicytoma, pituitary adenoma, pituitary tumor, plasmacytoma, polyembryoma, precursor T-lymphoblastic lymphoma, primary central nervous system lymphoma, primary effusion lymphoma, primary peritoneal cancer, prostate, prostate cancer, pseudomyxoma peritonei, rectal cancer, renal, renal cell carcinoma, renal medullary carcinoma, retinoblastoma, rhabdomyoma, Rhabdomyosarcoma, Richter's transformation, sarcoma, Schwannomatosis, seminoma, Sertoli cell tumor, sex cord-gonadal stromal tumor, Sezary's disease, signet ring cell carcinoma, skin cancer, small blue round cell tumors, small cell carcinoma, small cell lung cancer, small intestine cancer, soft tissue sarcoma, somatostatinoma, soot wart, spinal tumor, splenic marginal zone lymphoma, squamous carcinoma, squamous cell carcinoma, stomach cancer, synovial sarcoma, T-cell lymphoma, testicular cancer, thecoma, throat cancer, thyroid cancer, transitional cell carcinoma, urachal cancer, urogenital cancer, urothelial carcinoma, uterine cancer, uveal melanoma, vaginal cancer, verrucous carcinoma, visual pathway glioma, vulvar cancer, Waldenstrom's macroglobulinemia, Warthin's tumor, and Wilm's tumor.

In some embodiments, the cancer can be adenocarcinoma, adult T-cell leukemia/lymphoma, bladder cancer, blastoma, bone cancer, breast cancer, brain cancer, carcinoma, myeloid sarcoma, cervical cancer, colorectal cancer, esophageal cancer, gastrointestinal cancer, glioblastoma multiforme, glioma, gallbladder cancer, gastric cancer, head and neck cancer, Hodgkin's lymphoma, non-Hodgkin's lymphoma, intestinal cancer, kidney cancer, laryngeal cancer, leukemia, lung cancer, lymphoma, liver cancer, small cell lung cancer, non-small cell lung cancer, mesothelioma, multiple myeloma, ocular cancer, optic nerve tumor, oral cancer, ovarian cancer, pituitary tumor, primary central nervous system lymphoma, prostate cancer, pancreatic cancer, pharyngeal cancer, renal cell carcinoma, rectal cancer, sarcoma, skin cancer, spinal tumor, small intestine cancer, stomach cancer, T-cell lymphoma, testicular cancer, thyroid cancer, throat cancer, urogenital cancer, urothelial carcinoma, uterine cancer, vaginal cancer, or Wilms' tumor. In some other embodiments, the cancer can be acute myelognous leukemia or Burkitt's lymphoma.

In some embodiments, the autoimmune and inflammatory diseases or conditions can involve an inflammatory response to infections with bacteria, viruses, fungi, parasites or their toxins, as well as viruses. In some other embodiments, the autoimmune and inflammatory diseases or conditions can be selected from the group consisting of acute lung injury, acute pancreatitis, acute renal failure, ARDS (adult respiratory distress syndrome), burns, coronavirus, encephalitis, endotoxaemia, fulminant hepatitis, herpes simplex, herpes zoster, Herxheimer reactions, malaria and SIRS associated with viral infections such as influenza, meningitis, multi-organ dysfunction syndrome, myelitis, post-surgical syndromes, sarcoidosis, sepsis, sepsis syndrome, septic shock, systemic inflammatory response syndrome (SIRS), toxic shock syndrome.

In some embodiments, the present description provides a method of treating other conditions. Such other conditions include, but are not limited to, acne, acute inflammatory responses (such as acute respiratory distress syndrome and ischemia/reperfusion injury, glioblastoma, Graves' disease, HIV, HPV, inflammatory disease, keloids and related scarring, lung cancer, meningitis (bacterial and viral), multiple sclerosis, neoplasm, neuroblastoma, pancreatic cancer, scleroderma, skin cancer, toxic shock, viral infections, viral infections and diseases.

In some embodiments, the present description provides a method of treating a benign proliferative disorder. Such benign proliferative disorders include, but are not limited to, benign soft tissue tumors, bone tumors, brain and spinal tumors, eyelid and orbital tumors, granuloma, lipoma, meningioma, multiple endocrine neoplasia, nasal polyps, pituitary tumors, prolactinoma, pseudotumor cerebri, seborrheic keratoses, stomach polyps, thyroid nodules, cystic neoplasms of the pancreas, hemangiomas, vocal cord nodules, polyps, and cysts, Castleman disease, chronic pilonidal disease, dermatofibroma, pilar cyst, prolactinoma, pseudotumor cerebri, pyogenic granuloma, and juvenile polyposis syndrome.

The present description further relates to a method for treating infectious and noninfectious inflammatory events and autoimmune and other inflammatory diseases by administration of an effective amount of a provided compound to a mammal, in particular a human in need of such treatment. Examples of autoimmune and inflammatory diseases, disorders, and syndromes treated using the compounds and methods described herein include inflammatory pelvic disease, urethritis, skin sunburn, sinusitis, pneumonitis, encephalitis, meningitis, myocarditis, nephritis, osteomyelitis, myositis, hepatitis, gastritis, enteritis, dermatitis, gingivitis, appendicitis, pancreatitis, cholecystitis, agammaglobulinemia, psoriasis, allergy, Crohn's disease, irritable bowel syndrome, ulcerative colitis, Sjogren's disease, tissue graft rejection, hyperacute rejection of transplanted organs, asthma, allergic rhinitis, chronic obstructive pulmonary disease (COPD), autoimmune polyglandular disease (also known as autoimmune polyglandular syndrome), autoimmune alopecia, pernicious anemia, glomerulonephritis, dermatomyositis, multiple sclerosis, scleroderma, vasculitis, autoimmune hemolytic and thrombocytopenic states, Goodpasture's syndrome, atherosclerosis, Addison's disease, Parkinson's disease, Alzheimer's disease, Type I diabetes, septic shock, systemic lupus erythematosus (SLE), rheumatoid arthritis, psoriatic arthritis, juvenile arthritis, osteoarthritis, chronic idiopathic thrombocytopenic purpura, Waldenstrom macroglobulinemia, myasthenia gravis, Hashimoto's thyroiditis, atopic dermatitis, degenerative joint disease, vitiligo, autoimmune hypopituitarism, Guillain-Barre syndrome, Behcet's disease, scleracierma, mycosis fungoides, acute inflammatory responses (such as acute respiratory distress syndrome and ischemia/reperfusion injury), and Graves' disease. Other examples of infectious and noninfectious inflammatory events, autoimmune and other inflammatory diseases include, but are not limited to, Addison's disease, agammaglobulinemia, allergic rhinitis, allergy, Alzheimer's disease, appendicitis, asthma, atherosclerosis, atopic dermatitis, autoimmune alopecia, autoimmune hemolytic and thrombocytopenic states, autoimmune hypopituitarism, autoimmune polyglandular disease (also known as autoimmune polyglandular syndrome), Behcet's disease, cholecystitis, chronic idiopathic thrombocytopenic purpura, chronic obstructive pulmonary disease (COPD), Crohn's disease, degenerative joint disease, dermatitis, dermatomyositis, encephalitis, enteritis, gastritis, gingivitis, glomerulonephritis, Goodpasture's syndrome, Guillain-Barre syndrome, Hashimoto's thyroiditis, hepatitis, hyperacute rejection of transplanted organs, inflammatory pelvic disease, irritable bowel syndrome, juvenile arthritis, meningitis, multiple sclerosis, myasthenia gravis, mycosis fungoides, myocarditis, myositis, nephritis, osteoarthritis, osteomyelitis, pancreatitis, Parkinson's disease, pernicious anemia, pneumonitis, psoriasis, psoriatic arthritis, rheumatoid arthritis, scleracierma, scleroderma, septic shock, sinusitis, Sjogren's disease, skin sunburn, systemic lupus erythematosus (SLE), tissue graft rejection, Type I diabetes, ulcerative colitis, urethritis, vasculitis, vitiligo, and Waldenstrom macroglobulinemia.

In some embodiments, the present description provides a method of treating systemic inflammatory response syndromes such as LPS-induced endotoxic shock and/or bacteria-induced sepsis by administration of an effective amount of a provided compound to a mammal, in particular a human in need of such treatment.

The present description further relates to a method for treating viral infections and diseases by administration of an effective amount of a provided compound to a mammal, in particular a human in need of such treatment. Examples of viral infections and diseases treated using the compounds and methods described herein include episome-based DNA viruses including, but not limited to, human papillomavirus, Herpesvirus, Epstein-Barr virus, human immunodeficiency virus, hepatis B virus, and hepatitis C virus.

The present description further relates to a method of treating a subject, such as a human, suffering from one of the abovementioned conditions, illnesses, disorders or diseases. The method comprises administering a therapeutically effective amount of one or more provided compounds, which function by inhibiting a bromodomain and, in general, by modulating gene expression, to induce various cellular effects, in particular induction or repression of gene expression, arresting cell proliferation, inducing cell differentiation and/or inducing apoptosis, to a subject in need of such treatment.

The present description further provides a therapeutic method of modulating protein methylation, gene expression, cell proliferation, cell differentiation and/or apoptosis in vivo in diseases mentioned above, in particular cancer, inflammatory disease, and/or viral disease comprising administering to a subject in need of such therapy a pharmacologically active and therapeutically effective amount of one or more provided compounds.

The present description further provides a method of regulating endogenous or heterologous promoter activity by contacting a cell with a provided compound.

In certain embodiments, the present description provides a method of treating a disorder (as described herein) in a subject, comprising administering to the subject identified as in need thereof, a compound of the present description. The identification of those patients who are in need of treatment for the disorders described above is well within the ability and knowledge of one skilled in the art. Certain of the methods for identification of patients which are at risk of developing the above disorders which can be treated by the subject method are appreciated in the medical arts, such as family history, and the presence of risk factors associated with the development of that disease state in the subject patient. A clinician skilled in the art can readily identify such candidate patients, by the use of, for example, clinical tests, physical examination and medical/family history.

A method of assessing the efficacy of a treatment in a subject includes determining the pre-treatment extent of a disorder by methods well known in the art (e.g., determining tumor size or screening for tumor markers where the cell proliferative disorder is cancer) and then administering a therapeutically effective amount of a compound of the present description, to the subject. After an appropriate period of time after the administration of the compound (e.g., 1 day, 1 week, 2 weeks, one month, six months), the extent of the disorder is determined again. The modulation (e.g., decrease) of the extent or invasiveness of the disorder indicates efficacy of the treatment. The extent or invasiveness of the disorder may be determined periodically throughout treatment. For example, the extent or invasiveness of the disorder may be checked every few hours, days or weeks to assess the further efficacy of the treatment. A decrease in extent or invasiveness of the disorder indicates that the treatment is efficacious. The method described may be used to screen or select patients that may benefit from treatment with a compound of the present description.

According to one aspect, there is provided a method for identifying compounds for use in treating autoimmune and inflammatory diseases or conditions which comprises the step of determining whether the compound inhibits the binding of a bromodomain with its cognate acetylated protein.

According to another embodiment, the description provides a method of inhibiting a bromodomain-containing protein (such as a BET protein, e.g., BRD2, BRD3, BRD4, and/or BRDT) using a composition comprising a compound of the present description or a pharmaceutically acceptable derivative thereof and a pharmaceutically acceptable carrier, adjuvant, or vehicle. The amount of a compound of the present description in a provided composition is such that is effective to measurably inhibit one or more bromodomain-containing proteins (such as a BET protein, e.g., BRD2, BRD3, BRD4, and/or BRDT), or a mutant thereof, in a biological sample or in a patient. In certain embodiments, the amount of compound in a provided composition is such that is effective to measurably inhibit one or more bromodomain-containing proteins (such as a BET protein, e.g., BRD2, BRD3, BRD4, and/or BRDT), or a mutant thereof, in a biological sample or in a patient. In certain embodiments, a provided composition is formulated for administration to a patient in need of such composition. In some embodiments, a provided composition is formulated for oral administration to a patient.

In some embodiments, the therapeutically effective amount of a compound as defined herein can be administered to a patient alone or admixed with a pharmaceutically acceptable carrier, adjuvant, or vehicle.

The expression "pharmaceutically acceptable carrier, adjuvant, or vehicle" and equivalent expressions, refer to a non-toxic carrier, adjuvant, or vehicle that does not destroy the pharmacological activity of the compound with which it is formulated. Pharmaceutically acceptable carriers, adjuvants or vehicles that may be used in the compositions of this disclosure include, but are not limited to, ion exchangers, alumina, aluminum stearate, lecithin, serum proteins, such as human serum albumin, buffer substances such as phosphates, glycine, sorbic acid, potassium sorbate, partial glyceride mixtures of saturated vegetable fatty acids, water, salts or electrolytes, such as protamine sulfate, disodium hydrogen phosphate, potassium hydrogen phosphate, sodium chloride, zinc salts, colloidal silica, magnesium trisilicate, polyvinyl pyrrolidone, cellulose-based substances, polyethylene glycol, sodium carboxymethylcellulose, polyacrylates, waxes, polyethylene-polyoxypropylene-block polymers, polyethylene glycol and wool fat.

A "pharmaceutically acceptable derivative" means any non-toxic salt, ester, salt of an ester, prodrug, salt of a prodrug, or other derivative of a compound of the present description that, upon administration to a recipient, is capable of providing, either directly or indirectly, a compound of the present description or an inhibitory active metabolite or residue thereof.

As used herein, the term "inhibitory active metabolite or residue thereof" means that a metabolite or residue thereof is also an inhibitor of one or more bromodomain-containing protein(s) (such as a BET protein, e.g., BRD2, BRD3, BRD4, and/or BRDT), or a mutant thereof.

Compositions described herein may be administered orally, parenterally, by inhalation spray, topically, rectally, nasally, buccally, vaginally or via an implanted reservoir. The term "parenteral" as used herein includes subcutaneous, intravenous, intramuscular, intraarticular, intrasynovial, intrasternal, intrathecal, intrahepatic, intralesional and intracranial injection or infusion techniques. Other modes of administration also include intradermal or transdermal administration.

Liquid dosage forms for oral administration include, but are not limited to, pharmaceutically acceptable emulsions, microemulsions, solutions, suspensions, syrups and elixirs. In addition to the active compounds, the liquid dosage forms may contain inert diluents commonly used in the art such as, for example, water or other solvents, solubilizing agents and emulsifiers such as ethyl alcohol, isopropyl alcohol, ethyl carbonate, ethyl acetate, benzyl alcohol, benzyl benzoate, propylene glycol, 1,3-butylene glycol, dimethylformamide, oils (in particular, cottonseed, groundnut, corn, germ, olive, castor, and sesame oils), glycerol, tetrahydrofurfuryl alcohol, polyethylene glycols and fatty acid esters of sorbitan, and mixtures thereof. Besides inert diluents, the oral compositions can also include adjuvants such as wetting agents, emulsifying and suspending agents, sweetening, flavoring, and perfuming agents.

Injectable preparations, for example, sterile injectable aqueous or oleaginous suspensions may be formulated according to the known art using suitable dispersing or wetting agents and suspending agents. The sterile injectable preparation may also be a sterile injectable solution, suspension or emulsion in a nontoxic parenterally acceptable diluent or solvent, for example, as a solution in 1,3-butanediol. Among the acceptable vehicles and solvents that may be employed are water, Ringer's solution, U.S.P. and isotonic sodium chloride solution. In addition, sterile, fixed oils are conventionally employed as a solvent or suspending medium. For this purpose any bland fixed oil can be employed including synthetic mono- or diglycerides. In addition, fatty acids such as oleic acid are used in the preparation of injectables.

Injectable formulations can be sterilized, for example, by filtration through a bacterial-retaining filter, or by incorporating sterilizing agents in the form of sterile solid compositions which can be dissolved or dispersed in sterile water or other sterile injectable medium prior to use.

In order to prolong the effect of a provided compound, it is often desirable to slow the absorption of the compound from subcutaneous or intramuscular injection. This may be accomplished by the use of a liquid suspension of crystalline or amorphous material with poor water solubility. The rate of absorption of the compound then depends upon its rate of dissolution that, in turn, may depend upon crystal size and crystalline form. Alternatively, delayed absorption of a parenterally administered compound form is accomplished by dissolving or suspending the compound in an oil vehicle. Injectable depot forms are made by forming microencapsule matrices of the compound in biodegradable polymers such as polylactide-polyglycolide. Depending upon the ratio of compound to polymer and the nature of the particular polymer employed, the rate of compound release can be controlled.

Examples of other biodegradable polymers include poly(orthoesters) and poly(anhydrides). Depot injectable formulations are also prepared by entrapping the compound in liposomes or microemulsions that are compatible with body tissues.

Compositions for rectal or vaginal administration are preferably suppositories which can be prepared by mixing the compounds of the present description with suitable non-irritating excipients or carriers such as cocoa butter, polyethylene glycol or a suppository wax which are solid at ambient temperature but liquid at body temperature and therefore melt in the rectum or vaginal cavity and release the active compound.

Solid dosage forms for oral administration include capsules, tablets, pills, powders, and granules. In such solid dosage forms, the active compound is mixed with at least one inert, pharmaceutically acceptable excipient or carrier such as sodium citrate or dicalcium phosphate and/or a) fillers or extenders such as starches, lactose, sucrose, glucose, mannitol, and silicic acid, b) binders such as, for example, carboxymethylcellulose, alginates, gelatin, polyvinylpyrrolidinone (PVP), sucrose, and acacia, c) humectants such as glycerol, d) disintegrating agents such as agar-agar, calcium carbonate, potato or tapioca starch, alginic acid, certain silicates, and sodium carbonate, e) solution retarding agents such as paraffin, f) absorption accelerators such as quaternary ammonium compounds, g) wetting agents such as, for example, cetyl alcohol and glycerol monostearate, h) absorbents such as kaolin and bentonite clay, and i) lubricants such as talc, calcium stearate, magnesium stearate, solid polyethylene glycols, sodium lauryl sulfate, and mixtures thereof. In the case of capsules, tablets and pills, the dosage form may also comprise buffering agents.

Solid compositions of a similar type may also be employed as fillers in soft and hard-filled gelatin capsules using such excipients as lactose or milk sugar as well as high molecular weight polyethylene glycols and the like. The solid dosage forms of tablets, dragees, capsules, pills, and granules can be prepared with coatings and shells such as enteric coatings and other coatings well known in the pharmaceutical formulating art. They may optionally contain opacifying agents and can also be of a composition that they release the active ingredient(s) only, or preferentially, in a certain part of the intestinal tract, optionally, in a delayed manner. Examples of embedding compositions that can be used include polymeric substances and waxes. Solid compositions of a similar type may also be employed as fillers in soft and hard-filled gelatin capsules using such excipients as lactose or milk sugar as well as high molecular weight polyethylene glycols and the like.

Provided compounds can also be in micro-encapsulated form with one or more excipients as noted above. The solid dosage forms of tablets, dragees, capsules, pills, and granules can be prepared with coatings and shells such as enteric coatings, release controlling coatings and other coatings well known in the pharmaceutical formulating art. In such solid dosage forms the active compound may be admixed with at least one inert diluent such as sucrose, lactose or starch. Such dosage forms may also comprise, as is normal practice, additional substances other than inert diluents, e.g., tableting lubricants and other tableting aids such a magnesium stearate and microcrystalline cellulose. In the case of capsules, tablets and pills, the dosage forms may also comprise buffering agents. They may optionally contain opacifying agents and can also be of a composition that they release the active ingredient(s) only, or preferentially, in a certain part of the intestinal tract, optionally, in a delayed manner. Examples of embedding compositions that can be used include polymeric substances and waxes.

Dosage forms for topical or transdermal administration of a compound of the present description include ointments, pastes, creams, lotions, gels, powders, solutions, sprays, inhalants or patches. The active component is admixed under sterile conditions with a pharmaceutically acceptable carrier and any needed preservatives or buffers as may be required. Ophthalmic formulation, ear drops, and eye drops are also contemplated as being within the scope of the present description. Additionally, the description contemplates the use of transdermal patches, which have the added advantage of providing controlled delivery of a compound to the body. Such dosage forms can be made by dissolving or dispensing the compound in the proper medium. Absorption enhancers can also be used to increase the flux of the compound across the skin. The rate can be controlled by either providing a rate controlling membrane or by dispersing the compound in a polymer matrix or gel.

Pharmaceutically acceptable compositions provided herein may also be administered by nasal aerosol or inhalation. Such compositions are prepared according to techniques well-known in the art of pharmaceutical formulation and may be prepared as solutions in saline, employing benzyl alcohol or other suitable preservatives, absorption promotors to enhance bioavailability, fluorocarbons, and/or other conventional solubilizing or dispersing agents.

Pharmaceutically acceptable compositions provided herein may be formulated for oral administration. Such formulations may be administered with or without food. In some embodiments, pharmaceutically acceptable compositions of this disclosure are administered without food. In other embodiments, pharmaceutically acceptable compositions of this disclosure are administered with food.

The amount of provided compounds that may be combined with carrier materials to produce a composition in a single dosage form will vary depending upon the patient to be treated and the particular mode of administration. Provided compositions may be formulate such that a dosage of between 0.01-100 mg/kg body weight/day of the inhibitor can be administered to a patient receiving these compositions.

It should also be understood that a specific dosage and treatment regimen for any particular patient will depend upon a variety of factors, including age, body weight, general health, sex, diet, time of administration, rate of excretion, drug combination, the judgment of the treating physician, and the severity of the particular disease being treated. The amount of a provided compound in the composition will also depend upon the particular compound in the composition.

Compounds or compositions described herein may be administered using any amount and any route of administration effective for treating or lessening the severity of the disorders or diseases as contemplated herein. The exact amount required will vary from subject to subject, depending on the species, age, and general condition of the subject, the severity of the infection, the particular agent, its mode of administration, and the like. Provided compounds are preferably formulated in unit dosage form for ease of administration and uniformity of dosage. The expression "unit dosage form" as used herein refers to a physically discrete unit of agent appropriate for the patient to be treated. It will be understood, however, that the total daily usage of the compounds and compositions of the present disclosure will be decided by the attending physician within the scope of sound medical judgment. The specific effective dose level for any particular patient or organism will depend upon a variety of factors including the disorder being treated and the severity of the disorder; the activity of the specific compound employed; the specific composition employed; the age, body weight, general health, sex and diet of the patient; the time of administration, route of administration, and rate of excretion of the specific compound employed; the duration of the treatment; drugs used in combination or coincidental with the specific compound employed, and like factors well known in the medical arts.

Pharmaceutically acceptable compositions of this disclosure can be administered to humans and other animals orally, rectally, parenterally, intracisternally, intravaginally, intraperitoneally, topically (as by powders, ointments, or drops), buccally, as an oral or nasal spray, or the like, depending on the severity of the infection being treated. In certain embodiments, provided compounds may be administered orally or parenterally at dosage levels of about 0.01 mg/kg to about 50 mg/kg and preferably from about 1 mg/kg to about 25 mg/kg, of subject body weight per day, one or more times a day, to obtain the desired therapeutic effect.

Compounds and compositions described herein are generally useful for the inhibition of activity of one or more proteins involved in epigenetic regulation. Thus, in some embodiments, the present description provides a method of inhibiting one or more proteins involved in epigenetic regulation, such as proteins containing acetyl-lysine recognition motifs, also known as bromodomains (e.g., BET proteins, such as BRD2, BRD3, BRD4, and/or BRDT), by administering a provided compound or composition.

Examples of proteins inhibited by the compounds and compositions described herein and against which the methods described herein are useful include bromodomain-containing proteins, such as BET proteins, such as BRD2, BRD3, BRD4, and/or BRDT, or an isoform or mutant thereof.

The activity of a provided compound, or composition thereof, as an inhibitor of a bromodomain-containing protein, such as a BET protein, such as BRD2, BRD3, BRD4, and/or BRDT, or an isoform or mutant thereof, may be assayed in vitro, in vivo, or in a cell line. In vitro assays include assays that determine inhibition of bromodomain-containing proteins, such as BET proteins, such as BRD2, BRD3, BRD4, and/or BRDT, or a mutant thereof. Alternatively, inhibitor binding may be determined by running a competition experiment where a provided compound is incubated with a bromodomain-containing protein, such as a BET protein, such as BRD2, BRD3, BRD4, and/or BRDT bound to known ligands, labeled or unlabeled. Detailed conditions for assaying a provided compound as an inhibitor of a bromodomain-containing protein, such as a BET protein, such as BRD2, BRD3, BRD4, and/or BRDT or a mutant thereof.

The present description provides for a method of treating a subject with a MYC-dependent cancer, comprising: identifying a subject in need of treatment; administering to the subject a BET inhibitor; determining at least one of MYC mRNA expression, MYC protein expression and tumor mass, and wherein following administration, there is a decrease in at least one of MYC mRNA expression, MYC protein expression and tumor mass, thereby treating the disease.

In one embodiment, the identification step comprises determining whether the subject has at least one of a MYC translocation, a genetic rearrangement of MYC, MYC amplification, MYC over-expression and at least one cellular function that facilitates cellular and/or tumor growth and is altered upon reduction of MYC mRNA or protein expression.

The present description also provides for a method of treating a subject with a MYC-dependent cancer, comprising: determining at least one of MYC mRNA expression, MYC protein expression and tumor mass; administering to the subject a BET inhibitor; and comparing at least one of MYC mRNA expression, MYC protein expression and tumor mass in the subject before and after administration of the BET inhibitor.

The present description also provides a method of treating a subject with a MYC-dependent cancer, comprising: administering to the subject a BET inhibitor that is identified as capable of decreasing at least one of MYC mRNA expression, MYC protein expression and tumor mass; and determining at least one of MYC mRNA expression, MYC protein expression and tumor mass; wherein following the administration, there is a decrease in at least one of MYC mRNA expression, MYC protein expression and tumor mass, thereby treating the disease.

The present description also provides for a method of treating a subject with a disease, comprising: administering a BET inhibitor that is identified as capable of decreasing at least one of MYC mRNA expression, MYC protein expression and tumor mass, wherein following the administration, there is a decrease in at least one of MYC mRNA expression, MYC protein expression and tumor mass, thereby treating the disease.

Acetylated histone recognition and bromodomain-containing proteins (such as BET proteins) have been implicated in proliferative disease. BRD4 knockout mice die shortly after implantation and are compromised in their ability to maintain an inner cell mass, and heterozygotes display pre- and postnatal growth defects associated with reduced proliferation rates. BRD4 regulates genes expressed during M/GI, including growth-associated genes, and remains bound to chromatin throughout the cell cycle (Dey, et al. (2009) *Mol. Biol. Cell* 20:4899-4909). BRD4 also physically associates with Mediator and P-TEFb (CDK9/cyclin TI) to facilitate transcriptional elongation (Yang, et al. (2005) *Oncogene* 24:1653-1662; Yang, et al. (2005) *Mol. Cell* 19:535-545). CDK9 is a validated target in chronic lymphocytic leukemia (CLL), and is linked to c-MYC-dependent transcription (Phelps, et al. *Blood* 113:2637-2645; Rahl, et al. (2010) *Cell* 141:432-445).

BRD4 is translocated to the NUT protein in patients with lethal midline carcinoma, an aggressive form of human squamous carcinoma (French, et al. (2001) *Am. J. Pathol.* 159:1987-1992; French, et al. (2003) *Cancer Res.* 63:304-307). In vitro analysis with RNAi supports a causal role for BRD4 in this recurrent t(15; 19) chromosomal translocation. Pharmacologic inhibition of the BRD4 bromodomains results in growth arrest/differentiation of BRD4-NUT cell lines in vitro and in vivo (Filippakopoulos, et al. "Selective Inhibition of BET Bromodomains," *Nature* (published online Sep. 24, 2010)).

Bromodomain-containing proteins (such as BET proteins) have also been implicated in inflammatory diseases. BET proteins {e.g., BRD2, BRD3, BRD4, and BRDT) regulate assembly of histone acetylation-dependent chromatin complexes that control inflammatory gene expression (Hargreaves, et al. (2009) *Cell* 138:129-145; LeRoy, et al. (2008) *Mol. Cell* 30:51-60; Jang, et al. (2005) *Mol. Cell* 19:523-534; Yang, et al. (2005) *Mol. Cell* 19:535-545). Key inflammatory genes (secondary response genes) are down-regulated upon bromodomain inhibition of the BET subfamily, and non-responsive genes (primary response genes) are poised for transcription. BET bromodomain inhibition protects against LPS-induced endotoxic shock and bacteria-induced sepsis in vivo (Nicodeme, et al. "Suppression of Inflammation by a Synthetic Histone Mimic," *Nature* (published online Nov. 10, 2010)).

Bromodomain-containing proteins (such as BET proteins) also play a role in viral disease. For example, BRD4 is implicated in human papilloma virus (HPV). In the primary phase of HPV infection of basal epithelia, the viral genome is maintained in an extra-chromosomal episome. In some strains of HPV, BRD4 binding to the HPV E2 protein functions to tether the viral genome to chromosomes. E2 is critical for both the repression of E6/E7 and the activation of HPV viral genes. Disruption of BRD4 or the BRD4-E2 interaction blocks E2-dependent gene activation. BRD4 also functions to tether other classes of viral genomes to host chromatin (e.g., Herpesvirus, Epstein-Barr virus).

In certain embodiments, a provided compound inhibits one or more of BRD2, BRD3, BRD4, BRDT, and/or another member of the bromodomain-containing proteins, or a mutant thereof. In some embodiments, a provided compound inhibits two or more of BRD2, BRD3, BRD4, BRDT, and/or another member of the bromodomain-containing proteins, or a mutant thereof. Provided compounds are inhibitors of one of more of the bromodomain-containing proteins, such as BRD2, BRD3, BRD4, and/or BRDT and are therefore useful for treating one or more disorders associated with activity of one or more of the bromodomain-containing proteins, such as BRD2, BRD3, BRD4, and/or BRDT. Thus, in certain embodiments, the present description provides a method for treating an bromodomain-containing protein-mediated disorder, such as a BET-mediated, a BRD2-mediated, a BRD3-mediated, a BRD4-mediated disorder, and/or a BRDT-mediated disorder comprising the step of inhibiting a bromodomain-containing protein, such as a BET protein, such as BRD2, BRD3, BRD4, and/or BRDT, or a mutant thereof, by administering to a patient in need thereof a provided compound, or a pharmaceutically acceptable composition thereof.

As used herein, the terms "bromodomain-containing protein-mediated", "BET-mediated", "BRD2-mediated", "BRD3-mediated", "BRD4-mediated", and/or "BRDT-mediated" disorders or conditions means any disease or other deleterious condition in which one or more of the bromodomain-containing proteins, such as BET proteins, such as BRD2, BRD3, BRD4 and/or BRDT, or a mutant thereof, are known to play a role.

In some embodiments, the BET family bromodomain can be BRD2, BRD3 or BRD4.

Accordingly, another embodiment of the present description relates to treating or lessening the severity of one or more diseases in which one or more of the bromodomain-containing proteins, such as BET proteins, such as BRD2, BRD3, BRD4, and/or BRDT, or a mutant thereof, are known to play a role.

Diseases and conditions treatable according to the methods of the present description include, but are not limited to, cancer and other proliferative disorders, inflammatory diseases, sepsis, autoimmune disease, and viral infection. Thus one aspect is a method of treating a subject having a disease, disorder, or symptom thereof the method including administration of a compound or composition herein to the subject. In one embodiment, a human patient is treated with a compound of the present description and a pharmaceutically acceptable carrier, adjuvant, or vehicle, wherein said compound is present in an amount to measurably inhibit bromodomain-containing protein activity (such as BET protein, e.g., BRD2, BRD3, BRD4, and/or BRDT) in the patient.

The present description further relates to the use of provided compounds for the production of pharmaceutical compositions which are employed for the treatment and/or prophylaxis and/or amelioration of the diseases, disorders, illnesses and/or conditions as mentioned herein.

The present description further relates to the use of provided compounds for the production of pharmaceutical compositions which are employed for the treatment and/or prophylaxis of diseases and/or disorders responsive or sensitive to the inhibition of bromodomain-containing proteins, particularly those diseases mentioned above, such as e.g. cancer, inflammatory disease, viral disease.

According to some embodiments, the present description relates to a method of inhibiting bromodomain-containing proteins in a biological sample comprising the step of contacting said biological sample with a provided compound, or a composition thereof.

According to some embodiments, the present description relates to a method of inhibiting a bromodomain-containing protein, such as a BET protein, such as BRD2, BRD3, BRD4 and/or BRDT, or a mutant thereof, activity in a biological sample comprising the step of contacting said biological sample with a provided compound, or a composition thereof.

The term "biological sample", as used herein, includes, without limitation, cell cultures or extracts thereof, biopsied material obtained from a mammal or extracts thereof, and blood, saliva, urine, feces, semen, tears, or other body fluids or extracts thereof.

Inhibition of activity of a protein, e.g., a bromodomain-containing protein such as a BET protein (e.g. BRD2, BRD3, BRD4 and/or BRDT), or a mutant thereof, in a biological sample is useful for a variety of purposes that are known to one of skill in the art. Examples of such purposes include, but are not limited to, blood transfusion, organ-transplantation, biological specimen storage, and biological assays.

According to another embodiment, the present description relates to a method of inhibiting activity of one or more bromodomain-containing protein, such as a BET protein, such as BRD2, BRD3, BRD4, and/or BRDT, or a mutant thereof, in a patient comprising the step of administering to said patient a provided compound, or a composition comprising said compound. In certain embodiments, the present description provides a method for treating a disorder mediated by one or more bromodomain-containing proteins, such as a BET protein, such as BRD2, BRD3, BRD4, and/or BRDT, or a mutant thereof, in a patient in need thereof, comprising the step of administering to said patient a provided compound or pharmaceutically acceptable composition thereof. Such disorders are described in detail herein.

Depending upon the particular condition, or disease, to be treated, additional therapeutic agents that are normally administered to treat that condition may also be present in the compositions of this disclosure or administered separately as a part of a dosage regimen. As used herein, additional therapeutic agents that are normally administered to treat a particular disease, or condition, are known as "appropriate for the disease, or condition, being treated."

In some embodiments, the composition of a compound or compounds described herein can be in combination with an additional therapeutic agent.

In some embodiments, the additional therapeutic agent is an epigenetic drug. As used herein, the term "epigenetic drug" refers to a therapeutic agent that targets an epigenetic regulator. Examples of epigenetic regulators include the histone lysine methyltransferases, histone arginine methyl transferases, histone demethylases, histone deacetylases, histone acetylases, and DNA methyltransferases. Histone deacetylase inhibitors include, but are not limited to, vorinostat.

Other therapies, chemotherapeutic agents, or other anti-proliferative agents may be combined with a provided compound to treat proliferative diseases and cancer. Examples of therapies or anticancer agents that may be used in combination with compounds herein described include surgery, radiotherapy (e.g., gamma-radiation, neutron beam radiotherapy, electron beam radiotherapy, proton therapy, brachytherapy, and systemic radioactive isotopes), endocrine therapy, a biologic response modifier (e.g., an interferon, an interleukin, tumor necrosis factor (TNF), hyperthermia and cryotherapy, an agent to attenuate any adverse effects (e.g., an antiemetic), and any other approved chemotherapeutic drug.

A provided compound may also be used to advantage in combination with one or more antiproliferative compounds. Such antiproliferative compounds include an aromatase inhibitor; an anti-estrogen; an anti-androgen; a gonadorelin agonist; a topoisomerase I inhibitor; a topoisomerase II inhibitor; a microtubule active agent; an alkylating agent; a retinoid, a carotenoid, or a tocopherol; a cyclooxygenase inhibitor; an MMP inhibitor; an mTOR inhibitor; an antimetabolite; a platin compound; a methionine aminopeptidase inhibitor; a bisphosphonate; an antiproliferative antibody; a heparanase inhibitor; an inhibitor of Ras oncogenic isoforms; a telomerase inhibitor; a proteasome inhibitor; a compound used in the treatment of hematologic malignancies; a Flt-3 inhibitor; an Hsp90 inhibitor; a kinesin spindle protein inhibitor; a MEK inhibitor; an antitumor antibiotic; a nitrosourea; a compound targeting/decreasing protein or lipid kinase activity, a compound targeting/decreasing protein or lipid phosphatase activity, or any further anti-angiogenic compound.

Exemplary aromatase inhibitors include steroids, such as atamestane, exemestane and formestane, and non-steroids, such as aminoglutethimide, rogletimide, pyridoglutethimide, trilostane, testolactone, ketoconazole, vorozole, fadrozole, anastrozole and letrozole.

Exemplary anti-estrogens include tamoxifen, fulvestrant, raloxifene and raloxifene hydrochloride. Anti-androgens include, but are not limited to, bicalutamide. Gonadorelin agonists include, but are not limited to, abarelix, goserelin and goserelin acetate.

Exemplary topoisomerase I inhibitors include topotecan, gimatecan, irinotecan, camptothecin and its analogues, 9-nitrocamptothecin and the macromolecular camptothecin conjugate PNU-166148. Topoisomerase II inhibitors include, but are not limited to, the anthracyclines such as doxorubicin, daunorubicin, epirubicin, idarubicin and nemorubicin, the anthraquinones mitoxantrone and losoxantrone, and the podophillotoxins etoposide and teniposide.

Exemplary microtubule active agents include microtubule stabilizing, microtubule destabilizing compounds and microtubulin polymerization inhibitors including, but not limited to taxanes, such as paclitaxel and docetaxel; vinca alkaloids, such as vinblastine or vinblastine sulfate, vincristine or vincristine sulfate, and vinorelbine; discodermolides; colchicine and epothilones and derivatives thereof.

Exemplary alkylating agents include cyclophosphamide, ifosfamide, melphalan or nitrosoureas such as carmustine and lomustine.

Exemplary cyclooxygenase inhibitors include Cox-2 inhibitors, 5-alkyl substituted 2-arylaminophenylacetic acid and derivatives, such as celecoxib, rofecoxib, etoricoxib, valdecoxib or a 5-alkyl-2-arylaminophenylacetic acid, such as lumiracoxib.

Exemplary matrix metalloproteinase inhibitors ("MMP inhibitors") include collagen peptidomimetic and non-peptidomimetic inhibitors, tetracycline derivatives, batimastat, marimastat, prinomastat, metastat, BMS-279251, BAY 12-9566, TAA211, MMI270B, and AAJ996.

Exemplary mTOR inhibitors include compounds that inhibit the mammalian target of rapamycin (mTOR) and possess antiproliferative activity such as sirolimus, everolimus, CCI-779, and ABT578.

Exemplary antimetabolites include 5-fluorouracil (5-FU), capecitabine, gemcitabine, DNA demethylating compounds, such as 5-azacytidine and decitabine, methotrexate and edatrexate, and folic acid antagonists such as pemetrexed.

Exemplary platin-containing compounds include carboplatin, cisplatin, nedaplatin, and oxaliplatin.

Exemplary methionine aminopeptidase inhibitors include bengamide or a derivative thereof and PPI-2458.

Exemplary bisphosphonates include etidronic acid, clodronic acid, tiludronic acid, pamidronic acid, alendronic acid, ibandronic acid, risedronic acid and zoledronic acid.

Exemplary antiproliferative antibodies include trastuzumab, trastuzumab-DMI, cetuximab, bevacizumab, rituximab, PR064553, and 2C4. The term "antibody" is meant to include intact monoclonal antibodies, polyclonal antibodies, multispecific antibodies formed from at least two intact antibodies, and antibody fragments, so long as they exhibit the desired biological activity.

Exemplary heparanase inhibitors include compounds that target, decrease or inhibit heparin sulfate degradation, such as PI-88 and OGT2115.

The term "an inhibitor of Ras oncogenic isoforms," such as H-Ras, K-Ras, or N-Ras, as used herein refers to a compound which targets, decreases, or inhibits the oncogenic activity of Ras; for example, a farnesyl transferase inhibitor such as L-744832, DK8G557, tipifarnib, and lonafarnib.

Exemplary telomerase inhibitors include compounds that target, decrease or inhibit the activity of telomerase, such as compounds which inhibit the telomerase receptor, such as telomestatin.

Exemplary proteasome inhibitors include compounds that target, decrease or inhibit the activity of the proteasome including, but not limited to, bortezomib.

The phrase "compounds used in the treatment of hematologic malignancies" as used herein includes FMS-like tyrosine kinase inhibitors, which are compounds targeting, decreasing or inhibiting the activity of FMS-like tyrosine kinase receptors (Flt-3R); interferon, 1-β-D-arabinofuransylcytosine (ara-c) and busulfan; and ALK inhibitors, which are compounds which target, decrease or inhibit anaplastic lymphoma kinase.

Exemplary Flt-3 inhibitors include PKC412, midostaurin, a staurosporine derivative, SU11248 and MLN518.

Exemplary HSP90 inhibitors include compounds targeting, decreasing or inhibiting the intrinsic ATPase activity of HSP90; degrading, targeting, decreasing or inhibiting the HSP90 client proteins via the ubiquitin proteosome pathway. Compounds targeting, decreasing or inhibiting the intrinsic ATPase activity of HSP90 are especially compounds, proteins or antibodies which inhibit the ATPase activity of HSP90, such as 17-allylamino, 17-demethoxygeldanamycin (17AAG), a geldanamycin derivative; other geldanamycin related compounds; radicicol and HDAC inhibitors.

The phrase "a compound targeting/decreasing a protein or lipid kinase activity; or a protein or lipid phosphatase activity; or any further anti-angiogenic compound" as used herein includes a protein tyrosine kinase and/or serine and/or threonine kinase inhibitor or lipid kinase inhibitor, such as a) a compound targeting, decreasing or inhibiting the activity of the platelet-derived growth factor-receptors (PDGFR), such as a compound which targets, decreases, or inhibits the activity of PDGFR, such as an N-phenyl-2-pyrimidine-amine derivatives, such as imatinib, SU101, SU6668 and GFB-111; b) a compound targeting, decreasing or inhibiting the activity of the fibroblast growth factor-receptors (FGFR); c) a compound targeting, decreasing or inhibiting the activity of the insulin-like growth factor receptor I (IGF-IR), such as a compound which targets, decreases, or inhibits the activity of IGF-IR; d) a compound targeting, decreasing or inhibiting the activity of the Trk receptor tyrosine kinase family, or ephrin B4 inhibitors; e) a compound targeting, decreasing or inhibiting the activity of the Axl receptor tyrosine kinase family; f) a compound targeting, decreasing or inhibiting the activity of the Ret receptor tyrosine kinase; g) a compound targeting, decreasing or inhibiting the activity of the Kit/SCFR receptor tyrosine kinase, such as imatinib; h) a compound targeting, decreasing or inhibiting the activity of the c-Kit receptor tyrosine kinases, such as imatinib; i) a compound targeting, decreasing or inhibiting the activity of members of the c-Abl family, their gene-fusion products (e.g. Bcr-Abl kinase) and mutants, such as an N-phenyl-2-pyrimidine-amine derivative, such as imatinib or nilotinib; PD180970; AG957; NSC 680410; PD173955; or dasatinib; j) a compound targeting, decreasing or inhibiting the activity of members of the protein kinase C (PKC) and Raf family of serine/threonine kinases, members of the MEK, SRC, JAK, FAK, PDK1, PKB/Akt, and Ras/MAPK family members, and/or members of the cyclin-dependent kinase family (CDK), such as a staurosporine derivative disclosed in U.S. Pat. No. 5,093,330, such as midostaurin; examples of further compounds include UCN-01, safingol, BAY 43-9006, bryostatin 1, perifosine; ilmofosine; RO 318220 and RO 320432; GO 6976; ISIS 3521; LY333531/LY379196; a isochinoline compound; a farnesyl transferase inhibitor; PD184352 or QAN697, or AT7519; k) a compound targeting, decreasing or inhibiting the activity of a protein-tyrosine kinase, such as imatinib mesylate or a tyrphostin such as Tyrphostin A23/RG-50810; AG 99; Tyrphostin AG 213; Tyrphostin AG 1748; Tyrphostin AG 490; Tyrphostin B44; Tyrphostin B44 (+) enantiomer; Tyrphostin AG 555; AG 494; Tyrphostin AG 556, AG957 and adaphostin (4-{[(2,5-dihydroxyphenyl) methyl] amino}-benzoic acid adamantyl ester; NSC 680410, adaphostin); l) a compound targeting, decreasing or inhibiting the activity of the epidermal growth factor family of receptor tyrosine kinases (EGFR, ErbB2, ErbB3, ErbB4 as homo- or heterodimers) and their mutants, such as CP 358774, ZD 1839, ZM 105180; trastuzumab, cetuximab, gefitinib, erlotinib, OSI-774, CI-1033, EKB-569, GW-2016, antibodies EI.I, E2.4, E2.5, E6.2, E6.4, E2.I I, E6.3 and E7.6.3, and 7H-pyrrolo-[2,3-d]pyrimidine derivatives; and m) a compound targeting, decreasing or inhibiting the activity of the c-Met receptor.

Exemplary compounds that target, decrease or inhibit the activity of a protein or lipid phosphatase include inhibitors of phosphatase 1, phosphatase 2A, or CDC25, such as okadaic acid or a derivative thereof.

Further anti-angiogenic compounds include compounds having another mechanism for their activity unrelated to protein or lipid kinase inhibition, e.g. thalidomide and TNP-470.

Additional exemplary chemotherapeutic compounds, one or more of which may be used in combination with provided compounds, include: daunorubicin, adriamycin, Ara-C, VP-16, teniposide, mitoxantrone, idarubicin, carboplatinum, PKC412, 6-mercaptopurine (6-MP), fludarabine phosphate, octreotide, SOM230, FTY720, 6-thioguanine, cladribine, 6-mercaptopurine, pentostatin, hydroxyurea, 2-hydroxy-IH-isoindole-I,3-dione derivatives, I-(4-chloroanilino)-4-(4-pyridylmethyl)phthalazine or a pharmaceutically acceptable salt thereof, I-(4-chloroanilino)-4-(4-pyridylmethyl)phthalazine succinate, angiostatin, endostatin, anthranilic acid amides, ZD4190, ZD6474, SU5416, SU6668, bevacizumab, rhuMAb, rhuFab, macugen; FLT-4 inhibitors, FLT-3 inhibitors, VEGFR-2 IgGI antibody, RPI 4610, bevacizumab, porfimer sodium, anecortave, triamcinolone, hydrocortisone, 11α-epihydrocotisol, cortexolone, 17α-hydroxyprogesterone, corticosterone, desoxycorticosterone, testosterone, estrone, dexamethasone, fluocinolone, a plant alkaloid, a hormonal compound and/or antagonist, a biological response modifier, such as a lymphokine or interferon, an antisense oligonucleotide or oligonucleotide derivative, shRNA or siRNA, or a miscellaneous compound or compound with other or unknown mechanism of action.

For a more comprehensive discussion of updated cancer therapies see: The Merck Manual, $17^{th}$Ed. 1999. See also the National Cancer Institute (CNI) website (www.nci.nih.gov) and the Food and Drug Administration (FDA) website for a list of the FDA approved oncology drugs.

Other examples of additional therapeutic agents, one or more of which a provided compound may also be combined with include: a treatment for Alzheimer's Disease such as donepezil and rivastigmine; a treatment for Parkinson's Disease such as L-DOPA/carbidopa, entacapone, ropinirole, pramipexole, bromocriptine, pergolide, trihexyphenidyl, and amantadine; an agent for treating multiple sclerosis (MS) such as beta interferon {e.g., Avonex® and Rebif®), glatiramer acetate, and mitoxantrone; a treatment for asthma such as albuterol and montelukast; an agent for treating schizophrenia such as zyprexa, risperdal, seroquel, and haloperidol; an anti-inflammatory agent such as a corticosteroid, a TNF blocker, IL-1 RA, azathioprine, cyclophosphamide, and sulfasalazine; an immunomodulatory agent, including immunosuppressive agents, such as cyclosporin, tacrolimus, rapamycin, mycophenolate mofetil, an interferon, a corticosteroid, cyclophosphamide, azathioprine, and sulfasalazine; a neurotrophic factor such as an acetylcholinesterase inhibitor, an MAO inhibitor, an interferon, an anti-convulsant, an ion channel blocker, riluzole, or an anti-Parkinson's agent; an agent for treating cardiovascular disease such as a beta-blocker, an ACE inhibitor, a diuretic, a nitrate, a calcium channel blocker, or a statin; an agent for treating liver disease such as a corticosteroid, cholestyramine, an interferon, and an anti-viral agent; an agent for treating blood disorders such as a corticosteroid, an anti-leukemic agent, or a growth factor; or an agent for treating immunodeficiency disorders such as gamma globulin.

The above-mentioned compounds, one or more of which can be used in combination with a provided compound, can be prepared and administered as described in the art.

Provided compounds can be administered alone or in combination with one or more other therapeutic compounds, possible combination therapy taking the form of fixed combinations or the administration of a provided compound and one or more other therapeutic compounds being staggered or given independently of one another, or the combined administration of fixed combinations and one or more other therapeutic compounds. Provided compounds can besides or in addition be administered especially for tumor therapy in combination with chemotherapy, radiotherapy, immunotherapy, phototherapy, surgical intervention, or a combination of these. Long-term therapy is equally possible as is adjuvant therapy in the context of other treatment strategies, as described above. Other possible treatments are therapy to maintain the patient's status after tumor regression, or even chemopreventive therapy, for example in patients at risk.

Such additional agents may be administered separately from a composition containing a provided compound, as part of a multiple dosage regimen. Alternatively, those agents may be part of a single dosage form, mixed together with a provided compound in a single composition. If administered as part of a multiple dosage regimen, the two active agents may be submitted simultaneously, sequentially or within a period of time from one another normally within five hours from one another.

Upon improvement of a subject's condition, a maintenance dose of a compound, composition or combination of the present description may be administered, if necessary. Subsequently, the dosage or frequency of administration, or both, may be reduced, as a function of the symptoms, to a level at which the improved condition is retained when the symptoms have been alleviated to the desired level, treatment should cease. The subject may, however, require intermittent treatment on a long-term basis upon any recurrence of disease symptoms.

It will be understood, however, that the total daily usage of the compounds and compositions of the present description will be decided by the attending physician within the scope of sound medical judgment. The specific inhibitory dose for any particular patient will depend upon a variety of factors including the disorder being treated and the severity of the disorder; the activity of the specific compound employed; the specific composition employed; the age, body weight, general health, sex and diet of the patient; the time of administration, route of administration, and rate of excretion of the specific compound employed; the duration of the treatment; drugs used in combination or coincidental with the specific compound employed; and like factors well known in the medical arts.

The total daily inhibitory dose of the compounds of the present description administered to a subject in single or in divided doses can be in amounts, for example, from 0.01 to 50 mg/kg body weight or more usually from 0.1 to 25 mg/kg body weight. Single dose compositions may contain such amounts or submultiples thereof to make up the daily dose. In one embodiment, treatment regimens according to the present description comprise administration to a patient in need of such treatment from about 10 mg to about 1000 mg of the compound(s) of the present description per day in single or multiple doses.

As used herein, the term "combination," "combined," and related terms refers to the simultaneous or sequential administration of therapeutic agents in accordance with the present description. For example, a provided compound may be administered with another therapeutic agent simultaneously or sequentially in separate unit dosage forms or together in a single unit dosage form. Accordingly, an embodiment of the present description provides a single unit dosage form comprising a provided compound, an additional therapeutic agent, and a pharmaceutically acceptable carrier, adjuvant, or vehicle for use in the methods of the present description.

The amount of both, a provided compound and additional therapeutic agent (in those compositions which comprise an additional therapeutic agent as described above) that may be combined with the carrier materials to produce a single dosage form will vary depending upon the host treated and the particular mode of administration. Preferably, compositions should be formulated such that a dosage of between 0.01-100 mg/kg body weight/day of a provided compound can be administered.

In those compositions which comprise an additional therapeutic agent, that additional therapeutic agent and the provided compound may act synergistically. Therefore, the amount of additional therapeutic agent in such compositions will be less than that required in a monotherapy utilizing only that therapeutic agent. In such compositions a dosage of between 0.01-1,000 g/kg body weight/day of the additional therapeutic agent can be administered.

The amount of additional therapeutic agent present in the compositions of this disclosure will be no more than the amount that would normally be administered in a composition comprising that therapeutic agent as the only active agent. Preferably the amount of additional therapeutic agent in the presently disclosed compositions will range from about 50% to 100% of the amount normally present in a composition comprising that agent as the only therapeutically active agent.

Provided compounds, or pharmaceutical compositions thereof, may also be incorporated into compositions for coating an implantable medical device, such as prostheses, artificial valves, vascular grafts, stents and catheters. Vascular stents, for example, have been used to overcome restenosis (re-narrowing of the vessel wall after injury). However, patients using stents or other implantable devices risk clot formation or platelet activation. These unwanted effects may be prevented or mitigated by pre-coating the device with a pharmaceutically acceptable composition comprising a provided compound. Implantable devices coated with a compound of the present description are another embodiment of the present description.

In another aspect, the present description provides a method of method of synthesizing a compound of any of the formulae herein. Another embodiment is a method of making a compound of any of the formulae herein using any one, or combination of, reactions delineated herein. The method can include the use of one or more intermediates or chemical reagents delineated herein.

The recitation of a listing of chemical groups in any definition of a variable herein includes definitions of that variable as any single group or combination of listed groups. The recitation of an embodiment for a variable herein includes that embodiment as any single embodiment or in combination with any other embodiments or portions thereof. The recitation of an embodiment herein includes that embodiment as any single embodiment or in combination with any other embodiments or portions thereof.

Examples

The Examples set forth herein below provide syntheses and experimental results obtained for certain exemplary compounds. Unless otherwise indicated, all numbers expressing quantities of ingredients, reaction conditions, concentrations, properties, stabilities, and so forth used in the specification and claims are to be understood as being modified in all instances by the term "about." At the very least, each numerical parameter should at least be construed in light of the number of reported significant digits and by applying ordinary rounding techniques. Accordingly, unless indicated to the contrary, the numerical parameters set forth in the present specification and attached claims are approximations that may vary depending upon the properties sought to be obtained. Notwithstanding that the numerical ranges and parameters setting forth the broad scope of the embodiments are approximations, the numerical values set forth in the specific examples are reported as precisely as possible. Any numerical value, however, inherently contain certain errors resulting from variations in experiments, testing measurements, statistical analyses and such.

The following is to be construed as merely illustrative, and not limitations of the preceding disclosure in any way whatsoever. Those skilled in the art will promptly recognize appropriate variations from the procedures both as to reactants and as to reaction conditions and techniques. In some cases, starting materials or intermediates may be commercially available. Commercial material may be generally available from known sources, for example, Sigma-Aldrich, Bachem, Lancaster, Alfa Aesar, etc.

Chemical Synthesis of Exemplary Compounds

General:

All temperatures are in degrees Celsius (° C.) and are uncorrected. Reagent grade chemicals and anhydrous solvent were purchased from commercial sources and unless otherwise mentioned, were used without further purification. The names of the products were determined using the naming software included in the Contour Software AB electronic lab notebook iLabber version 4.11.3075.18678. Flash chromatography was performed on Teledyne Isco instruments using pre-packaged disposable $SiO_2$ stationary phase columns with eluent flow rate range of 5 to 300 mL/min, UV detection (254 and 280 nm). HPLC purifications were performed on a Gilson HPLC with a Phenomenex Gemini™ column, C18, 150:30 mm, 5 micron, eluting at 40 mL/min with mixtures of MeOH and water containing 0.1% $(NH_4)_2CO_3$ (high pH), or mixtures of MeCN and water containing 0.1% formic acid (low pH). Chiral isomer separation was performed on a Minigram Semi-Prep SFC from Mettler-Toledo. The analytical HPLC chromatograms were performed using an Agilent 1100 series instrument. The mass spectra were recorded with a Waters Micromass ZQ detector at 120° C. The mass spectrometer was equipped with an electrospray ion source (ESI) operated in a positive ion mode and was set to scan between m/z 150-750 with a scan time of 0.3 s. Products and intermediates were analyzed by HPLC/MS on a X-Bridge $C_{18}$, (3.5 μM, 2.10×30 mm) using a high pH buffer gradient of 5% to 95% of MeOH in $H_2O$ (0.03% $(NH_4)_2CO_3$/0.375% $NH_4OH$) over 4.5 min at 1 mL/min for a 6 min run. The $^1H$ NMR spectra were recorded on a Bruker UltraShield™ 500 MHz/54 mm instrument (BZH 43/500/70B, D221/54-3209) or on Bruker UltraShield™ Avance 400 MHz/5 mm (BBFO Probe). The chemical shifts are reported in part-per-million from a tetramethylsilane standard.

As used herein, the following abbreviations may have the following meanings:

| Abbreviation | Term |
| --- | --- |
| ACN | Acetonitrile |
| AcOH | Acetic acid |
| $AlCl_3$ | Aluminium Chloride |
| $CDCl_3$ | Deuterated chloroform |
| $Cs_2CO_3$ | Cesium carbonate |
| DCE | Dichloroethane |
| DCM | Dichloromethane |
| DIPEA | N,N-Diisopropylethylamine |
| DME | 1,2-dimethoxyethane |
| DMF | N,N-dimethyl formamide |
| DMSO | Dimethylsulfoxide |
| EtOAc | Ethyl acetate |
| h | Hour(s) |
| HCl | hydrochloric acid |
| $HNO_3$ | Nitric acid |
| $H_2SO_4$ | Sulfuric acid |
| HPLC | High-performance liquid chromatography |
| IPA | Isopropyl alcohol |
| $K_2CO_3$ | Potassium carbonate |
| $K_3PO_4$ | Tripotassium phosphate |
| MeI | Methyl Iodide |
| MS (ESI) | Electrospray Ionization Mass Spectrum |
| min | Minute(s) |
| MeCN | Acetonitrile |
| MeOH | Methanol |
| $MgSO_4$ | Magnesium sulfate |
| $N_2$ | Nitrogen |
| $NaBH_4$ | Sodium borohydride |
| $NaBH(OAc)_3$ | Sodium triacetoxyborohydride |
| $NaHCO_3$ | Sodium bicarbonate |
| $Na_2CO_3$ | Sodium carbonate |
| $Na_2SO_4$ | Sodium sulfate |
| NaH | Sodium hydride |
| $NH_4OH$ | Ammonium hydroxide |
| NMR | Nuclear magnetic resonance |
| $P(Cy)_3$ | Tricyclohexylphosphine |
| $Pd(OAc)_2$ | Palladium acetate |
| $Pd(PPh_3)_4$ | Tetrakis(triphenylphosphine)palladium(0) |
| $Pd_2(dba)_3$ | Tris(dibenzylideneacetone)dipalladium(0) |
| $PdCl_2(dppf)•DCM$ or $PdCl_2(dppf)•CH_2Cl_2$ | [1,1'-Bis(diphenylphosphino)ferrocene]dichloropalladium(II), complex with dichloromethane |
| $Pd(t-Bu_3P)_2$ | Bis(tri-tert-butylphosphine)palladium(0) |
| $PPh_3$ | Triphenylphosphine |
| rt | room temperature |
| SFC | Supercritical fluid chromatography |
| THF | Tetrahydrofuran |
| X-phos | 2-Dicyclohexylphosphino-2',4',6'-triisopropylbiphenyl |
| TFA | Trifluoroacetic acid |
| TEA | Triethylamine |

General Scheme: Preparation of Dihydroquinolinone Approach 1:

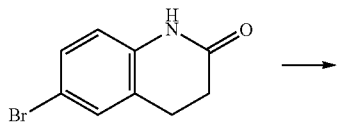

77 78
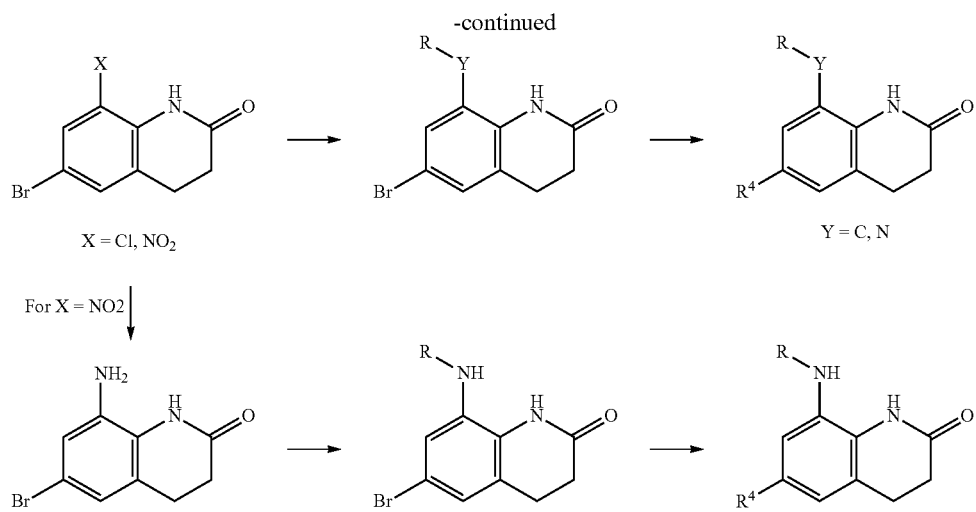
Approach 2:
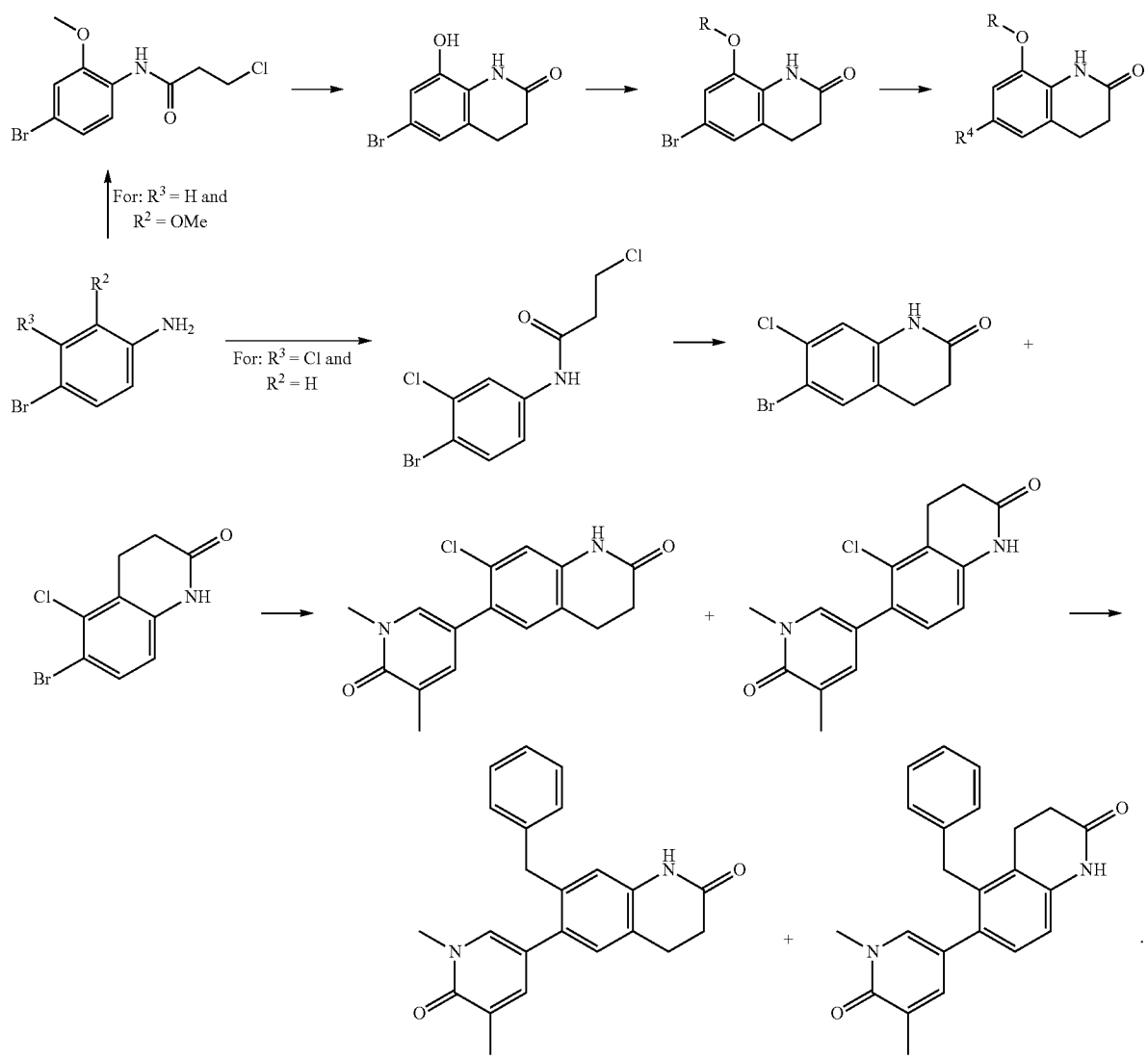

Intermediate 1: 8-chloro-6-(1,5-dimethyl-6-oxo-3-pyridyl)-3,4-dihydro-1H-quinolin-2-one

Step 1: Preparation of 6-bromo-8-chloro-3,4-dihydro-1H-quinolin-2-one

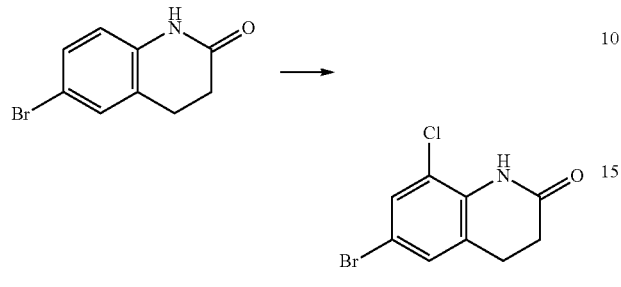

NCS (443 mg, 3.318 mmol) was added to a solution of 6-bromo-3,4-dihydro-1H-quinolin-2-one (500 mg, 2.21 mmol) in DMF (10 mL) at 80° C. and the solution was stirred at 80° C. for 30 min. To the mixture was added ice-cold water and solid was recuperated by filtration then dried to provide title compound (392 mg, 68%). $^1$H NMR (500 MHz, CDCl$_3$) δ 7.74 (s, 1H), 7.41 (d, J=2.1 Hz, 1H), 7.24 (dd, J=2.0, 0.8 Hz, 1H), 3.02-2.96 (m, 2H), 2.67-2.62 (m, 2H). MS (ESI) [M+H]$^+$ 260.2.

Step 2: Preparation of 8-chloro-6-(1,5-dimethyl-6-oxo-3-pyridyl)-3,4-dihydro-1H-quinolin-2-one

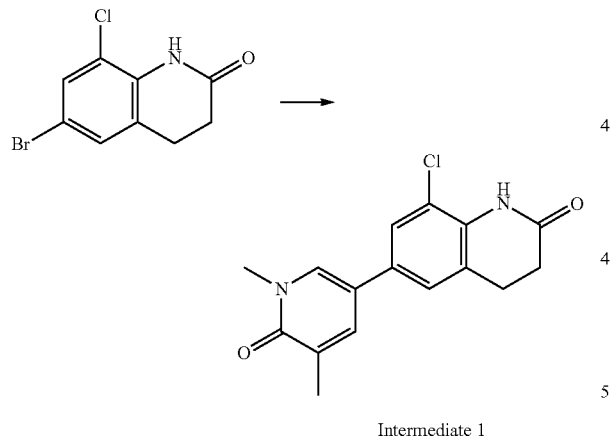

Intermediate 1

Pd(PPh$_3$)$_4$ (39 mg, 0.034 mmol) was added to a degassed solution of 6-bromo-8-chloro-3,4-dihydro-1H-quinolin-2-one (88 mg, 0.338 mmol), 1,3-dimethyl-5-(4,4,5,5-tetramethyl-1,3,2-dioxaborolan-2-yl)pyridin-2-one (prepared using procedure described in US20130053362, 100 mg, 0.405 mmol), and Cs$_2$CO$_3$ (220 mg, 0.676 mmol) in DME (4 mL) and water (0.4 mL). The resulting mixture was heated to 80° C. for 20 h and then cooled to rt. The mixture was diluted with saturated NaHCO$_3$ (20 mL) and EtOAc (20 mL), and the aqueous phase was extracted with EtOAc (3×20 mL). The combined organic phases were dried over Na$_2$SO$_4$, filtered, and evaporated under reduced pressure. The material was purified by flash chromatography on silica gel using a mixture of EtOAc in hexane as eluent to provide title compound (84 mg, 82%). $^1$H NMR (500 MHz, CDCl$_3$) δ 7.81 (s, 1H), 7.43 (dd, J=2.6, 1.2 Hz, 1H), 7.34 (d, J=2.3 Hz, 1H), 7.30 (d, J=2.0 Hz, 1H), 7.13 (d, J=1.2 Hz, 1H), 3.62 (s, 3H), 3.07-3.01 (m, 2H), 2.71-2.65 (m, 2H), 2.23 (s, 3H). MS (ESI) [M+H]$^+$ 303.2.

Intermediate 2: 8-amino-6-(1,5-dimethyl-6-oxo-3-pyridyl)-3,4-dihydro-1H-quinolin-2-one

Step 1: Preparation of 6-bromo-8-nitro-3,4-dihydro-1H-quinolin-2-one

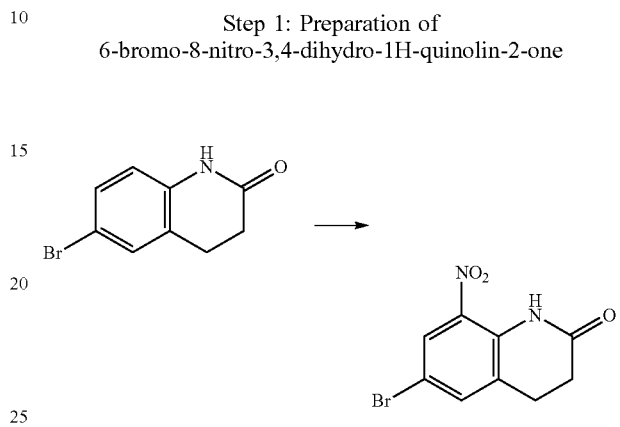

70% HNO$_3$ (0.31 mL, 4.87 mmol) was added dropwise to a solution of 6-bromo-3,4-dihydro-1H-quinolin-2-one (1.0 g, 4.42 mmol) in H$_2$SO$_4$ (6 mL) at 0° C. The reaction mixture was warmed to rt and stirred for 30 min. The mixture was poured into ice water (40 mL) and the solid was collected by filtration, rinsed with water, and dried under vacuum. The material was purified by flash chromatography on silica gel using a mixture of EtOAc in hexane as eluent to provide title compound (1.03 g, 86%). MS (ESI) [M+H]$^+$ 271.0.

Step 2: Preparation of 6-(1,5-dimethyl-6-oxo-3-pyridyl)-8-nitro-3,4-dihydro-1H-quinolin-2-one

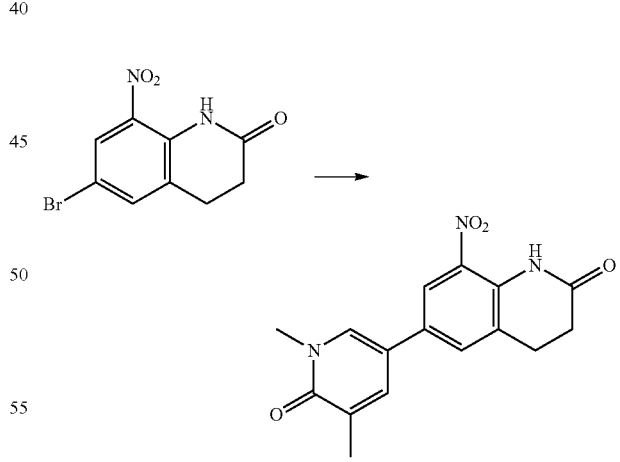

Pd(PPh$_3$)$_4$ (387 mg, 0.34 mmol) was added to a degassed solution of 6-bromo-8-nitro-3,4-dihydro-1H-quinolin-2-one (908 mg, 3.35 mmol), 1,3-dimethyl-5-(4,4,5,5-tetramethyl-1,3,2-dioxaborolan-2-yl)pyridin-2-one (prepared using procedure described in US20130053362, 1.09 g, 4.36 mmol), and Cs$_2$CO$_3$ (2.73 g, 8.37 mmol) in DME (40 mL) and water (4 mL) under N$_2$. The reaction mixture was heated to 80° C. for 3 h and then cooled to rt. To the mixture, saturated NaHCO$_3$ (50 mL) was added followed by EtOAc (50 mL), and the aqueous phase was extracted with EtOAc (3×50 mL). The combined organic phases were dried over MgSO$_4$, filtered, and evaporated under reduced pressure. The material was purified by flash chromatography on silica gel using a mixture of EtOAc in hexane as eluent to provide title compound as a solid (674 mg, 64%). MS (ESI) [M+H]$^+$ 313.3.

Step 3: Preparation of 8-amino-6-(1,5-dimethyl-6-oxo-3-pyridyl)-3,4-dihydro-1H-quinolin-2-one

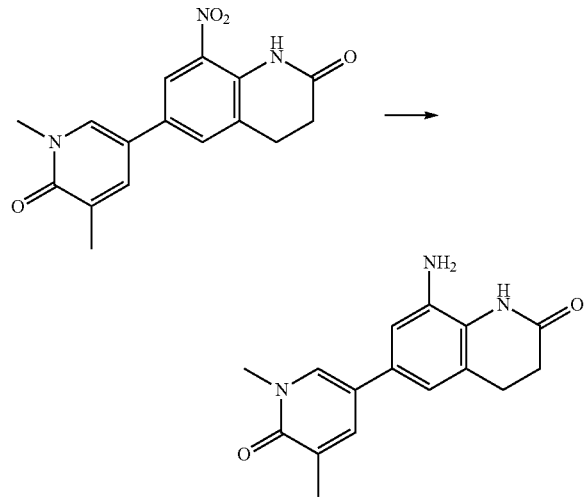

Intermediate 2

To a solution of 6-(1,5-dimethyl-6-oxo-3-pyridyl)-8-nitro-3,4-dihydro-1H-quinolin-2-one (674 mg, 2.15 mmol) in a mixture AcOH (10 mL) and water (1 mL), zinc powder (703 mg, 10.76 mmol) was added at rt and the suspension was stirred for 20 min. The mixture was diluted with EtOAc (10 mL) and filtered over Celite™. The filtrate was washed with saturated NaHCO$_3$ (30 mL) and brine (30 mL) then dried over Na$_2$SO$_4$, filtered, and evaporated under reduced pressure to provide title compound (451 mg, 74%), which was used in the next step without further purification. MS (ESI) [M+H]$^+$ 284.2.

Intermediate 3:
6-bromo-8-hydroxy-3,4-dihydroquinolin-2(1H)-one

Step 1: Preparation of
N-(4-bromo-2-methoxyphenyl)-3-chloropropanamide

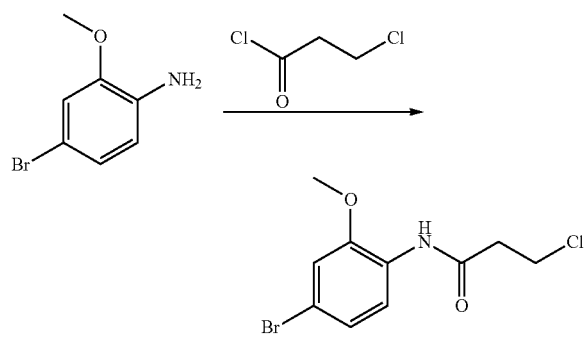

To stirred a solution of 4-bromo-2-methoxyaniline (10 g, 49.49 mmol) and K$_2$CO$_3$ (10.24 g, 74.22 mmol) in a mixture of acetone (20 mL) and water (40 mL) was added dropwise 3-chloro propanyl chloride (6.28 mL, 61.87 mmol) at 0° C. and the reaction mixture was stirred for 5 min at same temperature. The mixture was then transferred into ice water (1 L) and stirred for 30 min and the resulting solid was recuperated by filtration to afford title compound (10 g, 69%). $^1$H NMR (400 MHz, DMSO) δ ppm 9.41 (s, 1H), 7.92 (d, J=8.4 Hz, 1H), 7.23 (d, J=2 Hz, 1H), 7.11-7.09 (dd, J=8.2 Hz, 1H), 3.86-3.83 (m, 5H), 2.93 (t, J=6.4 Hz, 2H).

Step 2: Preparation of
6-bromo-8-hydroxy-3,4-dihydroquinolin-2(1H)-one

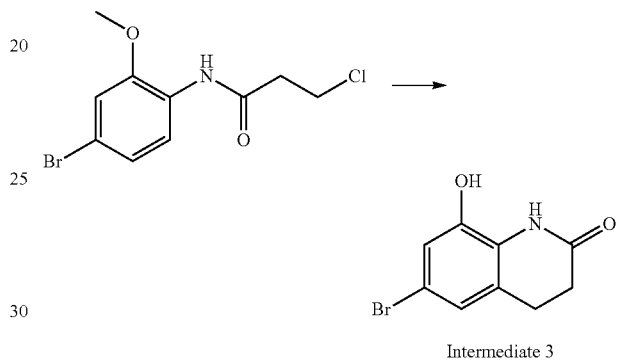

Intermediate 3

To an N-(4-bromo-2-methoxyphenyl)-3-chloropropanamide (8 g, 31.68 mmol) was added fine powder of AlCl$_3$ (21.12 g, 158.41 mmol) at rt and the mixture was heated at 140° C. for 5 h. After completion of reaction, the reaction mixture was transferred into 12% HCl solution (400 mL) and the aqueous phase was extracted with EtOAc (3×500 mL). The combined organic layers were washed with water (500 mL), dried over Na$_2$SO$_4$, filtered and evaporated under reduced pressure. The material was purified by flash chromatography on silica gel using a mixture 2% methanol in DCM as eluent to afford product, which was then further triturated with n-pentane to afford title compound (1.6 g, 27%). $^1$H NMR (400 MHz, DMSO) δ ppm $^1$H NMR (400 MHz, DMSO) δ ppm 10.18 (bs, 1H) 9.00 (s, 1H), 6.85 (d, J=1.6 Hz, 1H), 6.82 (d, J=1.6 Hz, 1H), 2.83 (t, J=7.2 Hz, 2H), 2.42 (t, J=6 Hz, 2H). MS (ESI) [M+H]$^+$ 163.7.

Example 1: 8-benzyl-6-(1,5-dimethyl-6-oxo-3-pyridyl)-3,4-dihydro-1H-quinolin-2-one

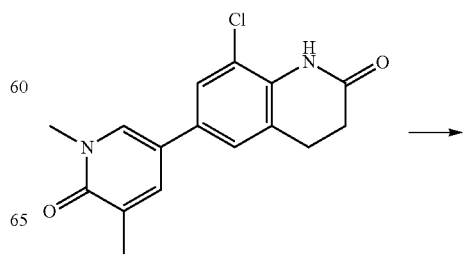

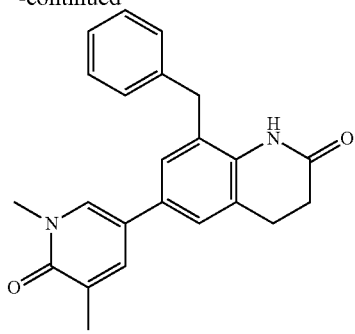

Compound 1

Pd(OAc)₂ (9.3 mg, 0.042 mmol) and P(Cy)₃ (117 mg, 0.083, 20% wt in toluene) were added to degassed DME (2 mL) and the solution was stirred at rt for 10 min. The mixture was then added to a solution of Intermediate 1 (84 mg, 0.277 mmol), 2-benzyl-4,4,5,5-tetramethyl-1,3,2-dioxaborolane (91 mg, 0.416 mmol), and Cs₂CO₃ (271 mg, 0.832 mmol) in DME (2 mL) and water (0.4 mL). The resulting mixture was heated to 90° C. for 20 h and then cooled to rt. The mixture was diluted with saturated NaHCO₃ (30 mL) and EtOAc (30 mL), and the aqueous phase was extracted with EtOAc (3×30 mL). The combined organic phases were dried over Na₂SO₄, filtered, and evaporated under reduced pressure. The material was purified by flash chromatography on silica gel using a mixture of EtOAc in hexane as eluent, and followed by preparative HPLC to provide Compound 1 (20 mg, 20%). $^1$H NMR (500 MHz, CDCl₃) δ 7.46 (d, J=1.3 Hz, 1H), 7.40 (s, 1H), 7.33 (d, J=2.7 Hz, 1H), 7.30 (d, J=7.6 Hz, 2H), 7.24 (t, J=7.4 Hz, 1H), 7.17-7.13 (m, 3H), 7.11 (d, J=1.6 Hz, 1H), 3.99 (s, 2H), 3.61 (s, 3H), 3.03-2.94 (m, 2H), 2.64-2.54 (m, 2H), 2.22 (s, 3H). MS (ESI) [M+H]⁺ 359.2.

Example 2: 8-benzyl-6-(1,5-dimethyl-6-oxo-3-pyridyl)-1-methyl-3,4-dihydroquinolin-2-one Compound 2

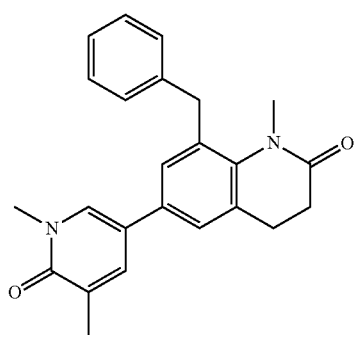

To a solution of 8-benzyl-6-(1,5-dimethyl-6-oxo-3-pyridyl)-3,4-dihydro-1H-quinolin-2-one (Compound 1, 25 mg, 0.071 mmol) in DMF (1 mL), NaH (4 mg, 0.093 mmol, 60% in oil) was added at 0° C. The mixture was stirred for 10 min, MeI (6 μL, 0.093 mmol) was added at 0° C. and then the reaction mixture was warmed slowly to rt. After 1 h, water (5 mL) was added and the aqueous phase was extracted with EtOAc (3×20 mL). The organic phase was then washed with brine (20 mL), dried over Na₂SO₄, filtered and evaporated under reduced pressure. The material was purified by preparative HPLC to provide Compound 2 (17 mg, 66%). $^1$H NMR (500 MHz, CDCl₃) δ 7.41 (dd, J=2.5, 1.1 Hz, 1H), 7.32-7.27 (m, 3H), 7.24-7.19 (m, 1H), 7.14-7.10 (m, 3H), 7.04 (d, J=2.2 Hz, 1H), 4.09 (s, 2H), 3.59 (s, 3H), 3.29 (s, 3H), 2.88 (dd, J=8.0, 5.6 Hz, 2H), 2.63-2.54 (m, 2H), 2.19 (s, 3H). MS (ESI) [M+H]⁺ 373.2.

Example 3: 8-anilino-6-(1,5-dimethyl-6-oxo-3-pyridyl)-3,4-dihydro-1H-quinolin-2-one Compound 3

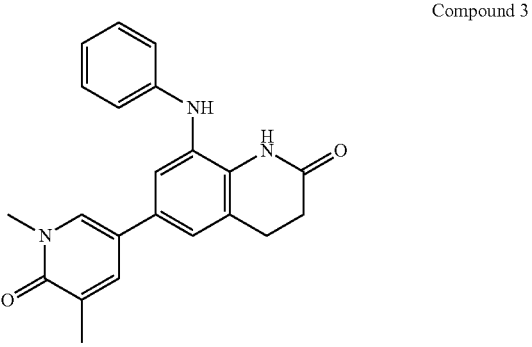

Intermediate 1 (30 mg, 0.099 mmol), Pd₂(dba)₃ (4.5 mg, 0.005 mmol), XPhos (9.5 mg, 0.020 mmol), K₂CO₃ (27 mg, 0.198 mmol) were added into an oven dried sealed tube under N₂. Aniline (14 μL, 0.149 mmol) and 1,4-dioxane (1 mL) were added to the reaction mixture, which was then heated at 90° C. for 21 h. The resulting reaction mixture was filtered through Celite™, washed with EtOAc and the filtrate was evaporated under reduced pressure. The material was purified by flash column chromatography on silica gel (dry pack) using a mixture of EtOAc in hexane as eluent, and followed by preparative HPLC to provide Compound 3 (7.7 mg, 22%). $^1$H NMR (500 MHz, CDCl₃) δ 8.43 (s, 1H), 7.42 (dd, J=2.5, 1.1 Hz, 1H), 7.30 (d, J=2.4 Hz, 1H), 7.25-7.20 (m, 2H), 7.19 (d, J=1.8 Hz, 1H), 7.02 (d, J=1.2 Hz, 1H), 6.89 (t, J=7.4 Hz, 1H), 6.80 (dd, J=8.5, 0.9 Hz, 2H), 5.66 (s, 1H), 3.59 (s, 3H), 3.08-3.01 (m, 2H), 2.67 (dd, J=8.4, 6.7 Hz, 2H), 2.20 (s, 3H). MS (ESI) [M+H]⁺ 360.2.

Example 4: 8-(benzylamino)-6-(1,5-dimethyl-6-oxo-3-pyridyl)-3,4-dihydro-1H-quinolin-2-one

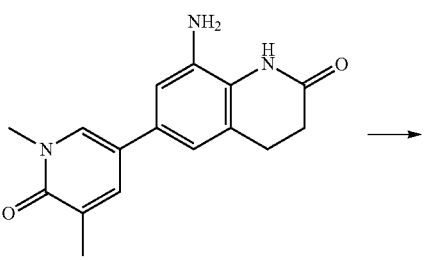

-continued

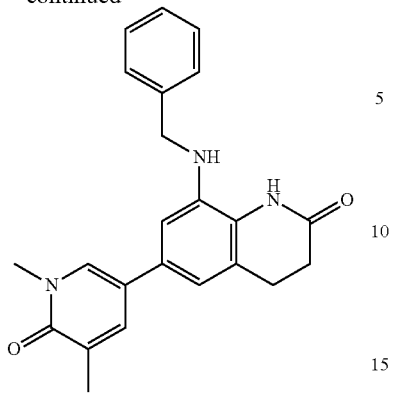

Compound 4

A mixture of AcOH (22 µL, 0.388 mmol), benzaldehyde (40 µL, 0.388 mmol), and Intermediate 2 (100 mg, 0.353 mmol) in DCE (4 mL) was stirred at rt for 20 h. To the mixture, saturated NaHCO$_3$ (5 mL) was added and the aqueous layer was extracted with DCM (3×5 mL). The combined organic layers were washed with brine, dried and evaporated under reduced pressure. The residue was diluted in MeOH (2 mL) and NaBH$_4$ (13 mg, 0.353 mmol) was added to the mixture which was stirred at rt for 1 h. Saturated NaHCO$_3$ (20 mL) and EtOAc (30 mL) were then added and the aqueous phase was extracted with EtOAc (3×30 mL). The combined organic phases were dried over Na$_2$SO$_4$, filtered and evaporated under reduced pressure. The material was purified by flash chromatography on silica gel using a mixture of EtOAc in hexane as eluent to provide title compound (54 mg). 27 mg of compound was further purified by preparative HPLC to provide Compound 4 (15.9 mg, 24%). $^1$H NMR (500 MHz, CDCl$_3$) δ 8.53 (s, 1H), 7.45-7.35 (m, 5H), 7.36-7.28 (m, 1H), 7.22 (d, J=2.4 Hz, 1H), 6.69 (s, 1H), 6.65 (s, 1H), 4.37 (s, 2H), 3.59 (s, 3H), 3.02-2.86 (m, 2H), 2.61-2.49 (m, 2H), 2.21 (s, 3H), —NH not visible. MS (ESI) [M+H]$^+$ 374.2.

Example 5: 8-[benzyl(methyl)amino]-6-(1,5-dimethyl-6-oxo-3-pyridyl)-3,4-dihydro-1H-quinolin-2-one

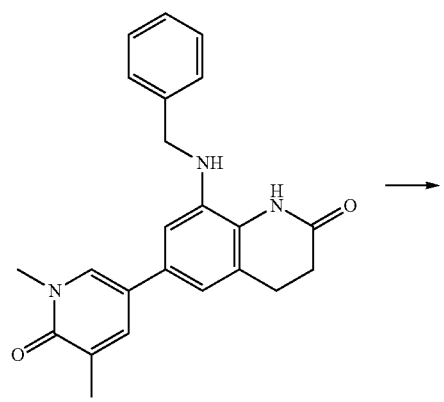

-continued

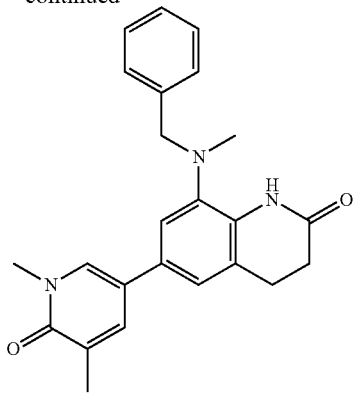

Compound 5

A mixture of AcOH (5 µL, 0.080 mmol), aqueous formaldehyde (27 µL, 0.361 mmol, 37%), NaBH(OAc)$_3$ (46 mg, 0.217 mmol) and 8-(benzylamino)-6-(1,5-dimethyl-6-oxo-3-pyridyl)-3,4-dihydro-1H-quinolin-2-one (Compound 4, 27 mg, 0.072 mmol) in DCE (1 mL) was stirred at rt for 1 h. Saturated NaHCO$_3$ (10 mL) and DCM (10 mL) were added to the reaction mixture and the aqueous phase was extracted with DCM (3×10 mL). The combined organic phases were dried over Na$_2$SO$_4$, filtered and evaporated under reduced pressure. The material was purified by flash chromatography on silica gel using a mixture of EtOAc in hexane as eluent, followed by preparative HPLC to provide Compound 5 (16 mg, 57%). $^1$H NMR (500 MHz, CDCl$_3$) δ 8.17 (s, 1H), 7.41 (dd, J=2.5, 1.2 Hz, 1H), 7.35-7.30 (m, 2H), 7.30-7.26 (m, 4H), 7.03 (d, J=1.9 Hz, 1H), 6.98 (d, J=1.1 Hz, 1H), 4.02 (s, 2H), 3.63 (s, 3H), 3.03-2.95 (m, 2H), 2.64 (dd, J=8.4, 6.8 Hz, 2H), 2.60 (s, 3H), 2.23 (s, 3H). MS (ESI) [M+H]$^+$ 388.2.

Example 6: 8-(cyclohexylamino)-6-(1,5-dimethyl-6-oxo-3-pyridyl)-3,4-dihydro-1H-quinolin-2-one

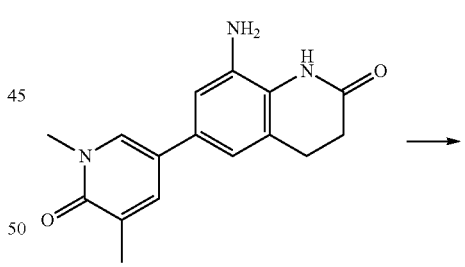

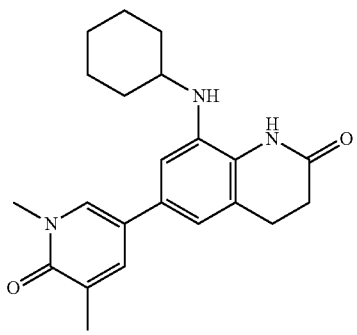

Compound 6

A mixture of AcOH (9 μL, 0.155 mmol), cyclohexanone (16 μL, 0.155 mmol), NaBH(OAc)₃ (59.8 mg, 0.282 mmol) and Intermediate 2 (40 mg, 0.141 mmol) in DCE (2 mL) was stirred at rt for 2 h. The reaction mixture was quenched with saturated NaHCO₃ (20 mL) and the aqueous layer was extracted with DCM (3×20 mL). The combined organic layers were washed with brine, dried over MgSO₄, filtered and evaporated under reduced pressure. The material was purified by flash chromatography on silica gel using a mixture of EtOAc in hexane as eluent, followed by preparative HPLC to provide Compound 6 (20.2 mg, 39%). ¹H NMR (500 MHz, CDCl₃) δ 9.46 (s, 1H), 7.44 (dd, J=2.5, 1.1 Hz, 1H), 7.31 (s, 1H), 6.59 (d, J=3.0 Hz, 2H), 4.10 (s, 1H), 3.63 (s, 3H), 3.31 (s, 1H), 2.95 (s, 2H), 2.63 (d, J=7.7 Hz, 2H), 2.23 (s, 3H), 2.11-2.02 (m, 2H), 1.86-1.78 (m, 2H), 1.71-1.64 (m, 1H), 1.47-1.21 (m, 5H). MS (ESI) [M+H]⁺: 366.1.

Example 7: 5-benzyl-6-(1,5-dimethyl-6-oxo-3-pyridyl)-3,4-dihydro-1H-quinolin-2-one and 7-benzyl-6-(1,5-dimethyl-6-oxo-3-pyridyl)-3,4-dihydro-1H-quinolin-2-one

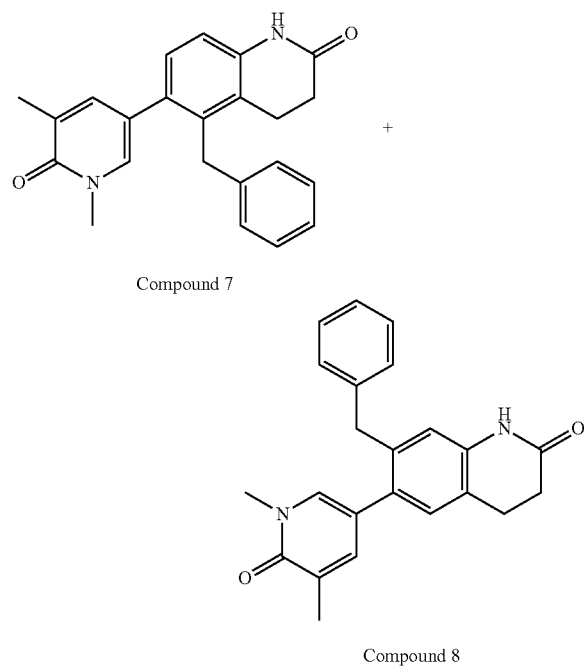

Step 1: Preparation of N-(4-bromo-3-chloro-phenyl)-3-chloro-propanamide 3-chloropropanoyl chloride (0.698 mL, 7.265 mmol) was added dropwise to a solution of 4-bromo-3-chloro-aniline (1.0 g, 4.843 mmol) and pyridine (0.586 mL, 7.265 mmol) in DCE (10 mL) at 10° C. and the reaction mixture was stirred at rt for 2 h. The solution was washed with water (10 mL) and then 2N HCl (10 mL). The organic layer was dried over Na₂SO₄, filtered and concentrated under reduced pressure to provide title compound, which was used in the next step without further purification. ¹H NMR (500 MHz, CDCl₃) δ 7.78 (d, J=2.4 Hz, 1H), 7.54 (d, J=8.7 Hz, 1H), 7.39 (s, 1H), 7.29-7.26 (m, 1H), 3.87 (t, J=6.3 Hz, 2H), 2.82 (t, J=6.3 Hz, 2H). MS (ESI) [M+H]⁺ 296.0.

Step 2: Preparation of 6-bromo-7-chloro-3,4-dihydro-1H-quinolin-2-one and 6-bromo-5-chloro-3,4-dihydro-1H-quinolin-2-one

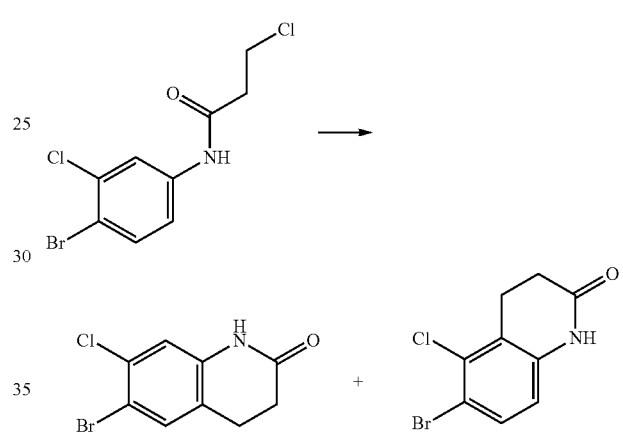

A vacuum-dried flask was charged with N-(4-bromo-3-chloro-phenyl)-3-chloro-propanamide (4.843 mmol) and AlCl₃ (969 mg, 7.265 mmol) and the mixture was heated to 130° C. for 20 h. The mixture was cooled to rt, and ice-water was added slowly. The aqueous phase was extracted with EtOAc (3×50 mL). The combined organic phases were washed with water (50 mL) and brine (50 mL), dried over Na₂SO₄, filtered and concentrated under reduced pressure. The material was purified by flash chromatography on silica gel using a mixture of EtOAc in hexane to provide title compound as a 2:1 mixture of isomer (534 mg, 42%). MS (ESI) [M+H]⁺ 262.0.

Step 3: preparation of 7-chloro-6-(1,5-dimethyl-6-oxo-3-pyridyl)-3,4-dihydro-1H-quinolin-2-one

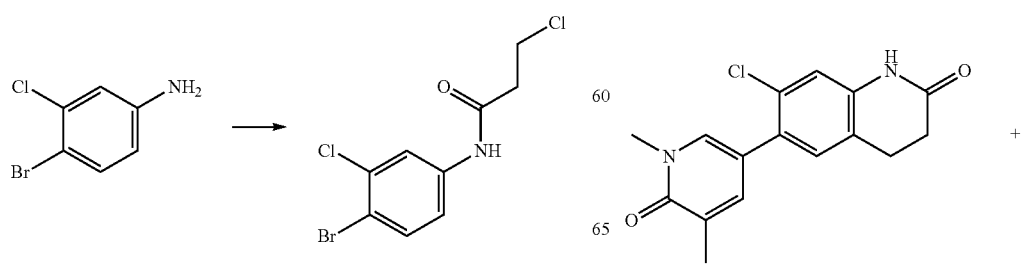

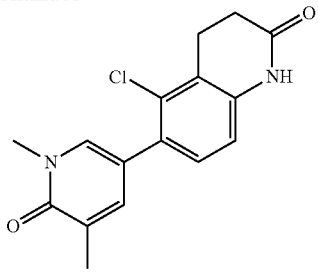

Pd(PPh₃)₄ (88 mg, 0.077 mmol) was added to a degassed solution of 6-bromo-7-chloro-3,4-dihydro-1H-quinolin-2-one and 6-bromo-5-chloro-3,4-dihydro-1H-quinolin-2-one (200 mg, 0.768 mmol), 1,3-dimethyl-5-(4,4,5,5-tetramethyl-1,3,2-dioxaborolan-2-yl)pyridin-2-one (prepared using procedure described in US20130053362, 229 mg, 0.921 mmol), Cs₂CO₃ (500 mg, 1.54 mmol) in DME (10 mL) and water (1 mL). The resulting mixture was heated to 80° C. for 3 h and then cooled to rt. The mixture was diluted with saturated NaHCO₃ (50 mL) and EtOAc (50 mL), and the aqueous phase was extracted with EtOAc (3×50 mL). The combined organic phases were dried over Na₂SO₄, filtered, and concentrated under reduced pressure. The product was purified by flash chromatography on silica gel using a mixture of hexanes and EtOAc as eluent to provide title compound as an inseparable mixture (162 mg). MS (ESI) [M+H]⁺ 303.3.

Step 4: preparation of 5-benzyl-6-(1,5-dimethyl-6-oxo-3-pyridyl)-3,4-dihydro-1H-quinolin-2-one and 7-benzyl-6-(1, 5-dimethyl-6-oxo-3-pyridyl)-3,4-dihydro-1H-quinolin-2-one

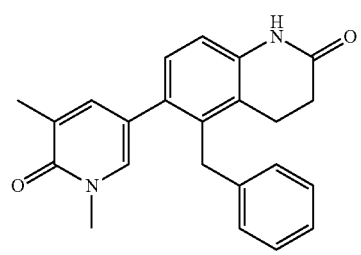

Compound 7

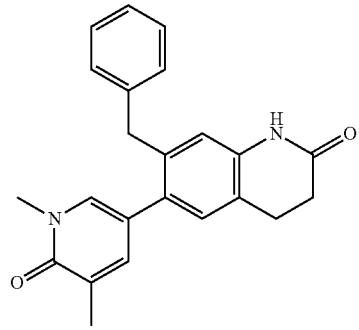

Compound 8

Pd(OAc)₂ (18 mg, 0.080 mmol) and P(Cy)₃ (225 mg, 0.161, 20% wt in toluene) were added to degassed DME (3 mL) and the solution was stirred at rt for 10 min. The mixture was then added to a solution of 7-chloro-6-(1,5-dimethyl-6-oxo-3-pyridyl)-3,4-dihydro-1H-quinolin-2-one and 5-chloro-6-(1,5-dimethyl-6-oxo-3-pyridyl)-3,4-dihydro-1H-quinolin-2-one (162 mg, 0.54 mmol), 2-benzyl-4,4,5,5-tetramethyl-1,3,2-dioxaborolane (175 mg, 0.803 mmol), Cs₂CO₃ (523 mg, 1.61 mmol) in DME (5 mL) and water (0.8 mL). The resulting mixture was heated to 90° C. for 16 h and then cooled to rt. The mixture was diluted with saturated NaHCO₃ (50 mL) and EtOAc (50 mL), and the aqueous phase was extracted with EtOAc (3×50 mL). The combined organic phases were dried over Na₂SO₄, filtered, and concentrated under reduced pressure. The material was purified by flash chromatography on silica gel using a mixture of EtOAc in hexane as eluent to provide a mixture of title compounds. The regioisomers were separated using SFC (IA 10×250 mm, 5 um isocratic 25% IPA+0.1% NH₄OH, 10 mL/min 100 bar) to afford Compound 7 (7.8 mg) and Compound 8 (4.6 mg).

Compound 7: Retention time=13.81: ¹H NMR (500 MHz, CDCl3) δ 8.26 (s, 1H), 7.29-7.24 (m, 2H), 7.20 (t, J=7.3 Hz, 1H), 7.08 (d, J=8.1 Hz, 1H), 7.02 (dd, J=2.4, 1.1 Hz, 1H), 6.93 (d, J=7.2 Hz, 2H), 6.80 (d, J=2.3 Hz, 1H), 6.77 (d, J=8.1 Hz, 1H), 4.01 (s, 2H), 3.39 (s, 3H), 2.90-2.83 (m, 2H), 2.57 (dd, J=8.4, 6.6 Hz, 2H), 2.07 (s, 3H). MS (ESI) [M+H]⁺ 359.2.

Compound 8: Retention time=16.18: ¹H NMR (500 MHz, CDCl₃) δ 8.11 (s, 1H), 7.24 (t, J=7.4 Hz, 2H), 7.18 (t, J=7.3 Hz, 1H), 7.08-7.02 (m, 1H), 7.00-6.95 (m, 3H), 6.77 (d, J=2.2 Hz, 1H), 6.66 (s, 1H), 3.88 (s, 2H), 3.43 (s, 3H), 2.96 (t, J=7.5 Hz, 2H), 2.66 (dd, J=8.3, 6.8 Hz, 2H), 2.12 (s, 3H). MS (ESI) [M+H]⁺ 359.2.

Example 8: 5-benzyl-6-(1,5-dimethyl-6-oxo-3-pyridyl)-1-methyl-3,4-dihydroquinolin-2-one and 7-benzyl-6-(1,5-dimethyl-6-oxo-3-pyridyl)-1-methyl-3,4-dihydroquinolin-2-one

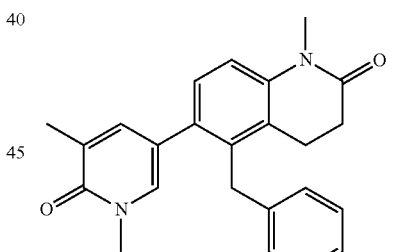

Compound 9

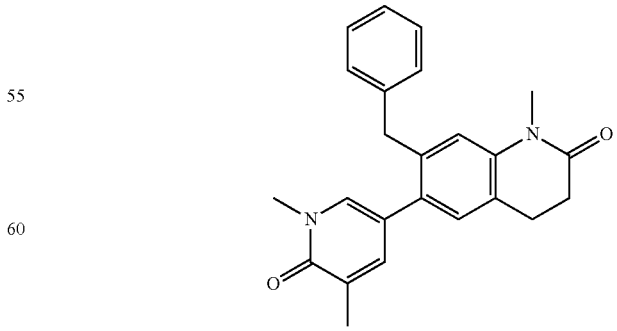

Compound 10

To a mixture of Compound 7 and Compound 8 (54 mg, 0.151 mmol) in DMF (1 mL), NaH (8 mg, 0.196 mmol, 60% in oil) was added at 0° C. The mixture was stirred for 10 min, then MeI (12 µL, 0.196 mmol) was added at 0° C. and the reaction mixture was warmed up slowly to rt. After 1 h, water (5 mL) was added and the aqueous phase was extracted with EtOAc (3×20 mL). The combined organic phases were then washed with brine (20 mL), dried over $Na_2SO_4$, filtered and concentrated under reduced pressure. The material was purified by Semi-Preparative SFC (ChiralCel™ OJ 10×250 mm, 5 um isocratic 20% MeOH+0.1% $NH_4OH$, 10 mL/min 100 Bar) to provide Compound 9 (6 mg, 11%) and Compound 10 (4.4 mg, 8%).

Compound 9: retention time=4.78: $^1$H NMR (500 MHz, $CDCl_3$) δ 7.29-7.24 (m, 2H), 7.18 (dd, J=21.7, 7.6 Hz, 2H), 7.03 (s, 1H), 6.98 (d, J=8.5 Hz, 1H), 6.92 (d, J=7.3 Hz, 2H), 6.81 (s, 1H), 4.02 (s, 2H), 3.40 (s, J=6.6 Hz, 3H), 3.39-3.37 (m, 3H), 2.79 (d, J=7.4 Hz, 2H), 2.57 (d, J=7.4 Hz, 2H), 2.07 (s, 3H). MS (ESI) [M+H]$^+$ 373.2.

Compound 10: retention time=7.71: $^1$H NMR (500 MHz, $CDCl_3$) δ 7.26-7.16 (m, 3H), 7.06 (s, 1H), 6.99 (s, 3H), 6.86 (s, 1H), 6.78 (s, 1H), 3.93 (s, 2H), 3.43 (s, 3H), 3.33 (s, 3H), 2.90 (t, J=6.7 Hz, 2H), 2.68 (t, J=6.9 Hz, 2H), 2.13 (s, 3H). MS (ESI) [M+H]$^+$: 373.2.

Example 9: 6-(1,5-dimethyl-6-oxo-3-pyridyl)-8-(3-pyridylamino)-3,4-dihydro-1H-quinolin-2-one

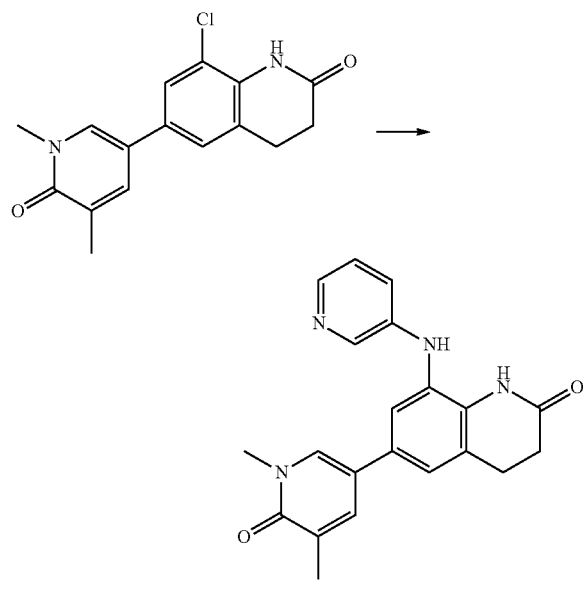

Compound 11

Intermediate 1 (20 mg, 0.066 mmol), $Pd_2(dba)_3$ (12 mg, 0.013 mmol), X-phos (25 mg, 0.053 mmol), $K_2CO_3$ (36 mg, 0.264 mmol), pyridin-3-amine (19 mg, 0.198 mmol) and 1,4-dioxane (1 mL) were added into an oven dried sealed tube under $N_2$. The resulting mixture was heated to 80° C. for 16 h. The mixture was filtered through Celite™, washed with EtOAc and the filtrate was evaporated under reduced pressure. The material was purified by flash column chromatography on silica gel using a mixture of EtOAc in hexane as eluent, followed by preparative HPLC to provide Compound 11 (3.9 mg). $^1$H NMR (500 MHz, $CDCl_3$) δ 8.73 (s, 1H), 8.27 (s, 1H), 8.14 (d, J=4.0 Hz, 1H), 7.41 (s, 1H), 7.31 (d, J=2.2 Hz, 1H), 7.17 (s, 1H), 7.17-7.08 (m, 2H), 7.05 (s, 1H), 5.90 (s, 1H), 3.61 (s, 3H), 3.05 (t, J=7.5 Hz, 2H), 2.73-2.65 (m, 2H), 2.20 (s, 3H). MS (ESI) [M+H]$^+$: 361.2.

Example 10: 6-(1,5-dimethyl-6-oxo-3-pyridyl)-8-(2-pyridylmethylamino)-3,4-dihydro-1H-quinolin-2-one

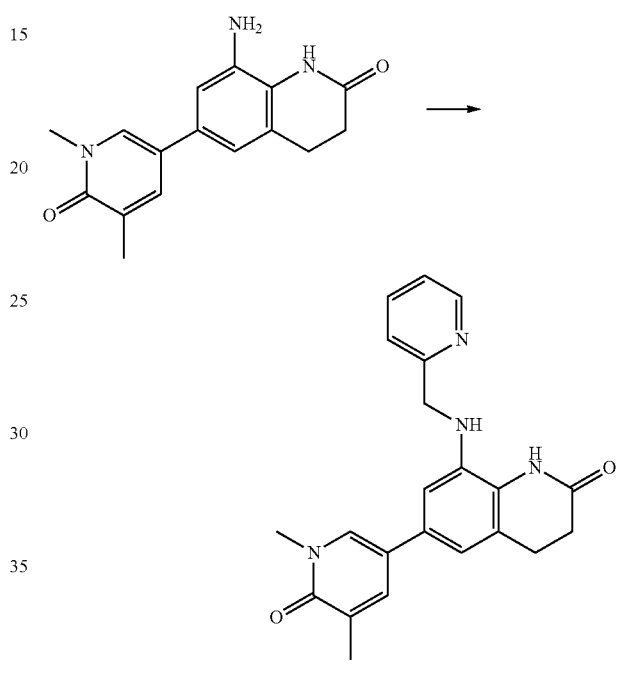

Compound 12

A mixture of AcOH (9 µL, 0.155 mmol), 2-pyridinecarboxaldehyde (15 µL, 0.155 mmol), and Intermediate 2 (40 mg, 0.141 mmol) in DCE (1 mL) was stirred at rt for 2 h. To the mixture was added saturated $NaHCO_3$ (5 mL) and the aqueous phase was extracted with DCM (3×5 mL). The combined organic layers were washed with brine, dried over $MgSO_4$, filtered and evaporated under reduced pressure. The residue was then dissolved in MeOH (2 mL), $NaBH_4$ (16 mg, 0.424 mmol) was added and the reaction mixture was stirred at rt for 1 h. To the mixture, saturated $NaHCO_3$ (10 mL) and EtOAc (10 mL) were added and the aqueous phase was extracted with EtOAc (3×10 mL). The organic phase was dried over $Na_2SO_4$, filtered and concentrated under reduced pressure. The material was purified by flash chromatography on silica gel using a mixture of EtOAc in hexane to provide Compound 12 (11 mg, 22%). $^1$H NMR (500 MHz, DMSO) δ 9.52 (s, 1H), 8.56 (d, J=4.2 Hz, 1H), 7.76 (td, J=7.7, 1.8 Hz, 1H), 7.74 (d, J=2.4 Hz, 1H), 7.48 (s, 1H), 7.41 (d, J=7.8 Hz, 1H), 7.27 (dd, J=7.0, 5.3 Hz, 1H), 6.67 (s, 1H), 6.57 (d, J=1.5 Hz, 1H), 6.04 (t, J=5.6 Hz, 1H), 4.49 (d, J=5.5 Hz, 2H), 3.47 (s, 3H), 2.88-2.79 (m, 2H), 2.47-2.41 (m, 2H), 2.03 (s, 3H). MS (ESI) [M+H]$^+$: 375.2.

Example 11: 6-(1,5-dimethyl-6-oxo-3-pyridyl)-8-(1-piperidylmethyl)-3,4-dihydro-1H-quinolin-2-one

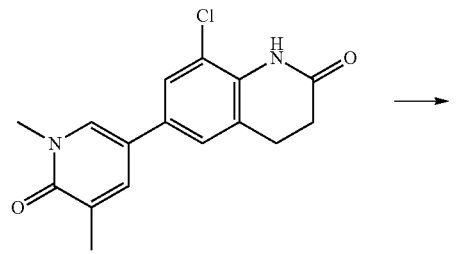

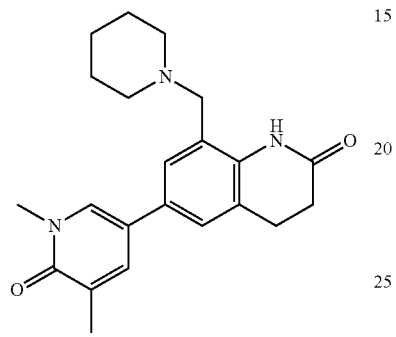

Compound 13

Intermediate 1 (40 mg, 0.132 mmol), Pd(OAc)$_2$ (5.9 mg, 0.026 mmol), X-phos (25 mg, 0.053 mmol), Cs$_2$CO$_3$ (129 mg, 0.396 mmol), potassium (piperidin-1-yl) methyltrifluoroborate (30 mg, 0.145 mmol) and THF/H$_2$O (10:1, 2 mL) were added into an oven dried sealed tube under N$_2$. The resulting mixture was heated to 80° C. for 18 h. The mixture was filtered through Celite™, washed with EtOAc and the filtrate was evaporated under reduced pressure. The material was purified by flash column chromatography on silica gel using a mixture of EtOAc in hexane as eluent, followed by preparative HPLC to provide Compound 13 (22 mg, 46%). $^1$H NMR (500 MHz, CDCl$_3$) δ 10.44 (s, 1H), 7.44 (d, J=1.2 Hz, 1H), 7.31 (d, J=2.3 Hz, 1H), 7.10 (s, 1H), 6.98 (s, 1H), 3.61 (s, 3H), 3.55 (s, 2H), 3.01-2.94 (m, 2H), 2.64-2.57 (m, 2H), 2.38 (s, 4H), 2.21 (s, 3H), 1.67-1.56 (m, 4H), 1.46 (s, 2H). MS (ESI) [M+H]$^+$: 366.2.

Example 12: 6-(1,5-dimethyl-6-oxo-3-pyridyl)-8-(N-methylanilino)-3,4-dihydro-1H-quinolin-2-one

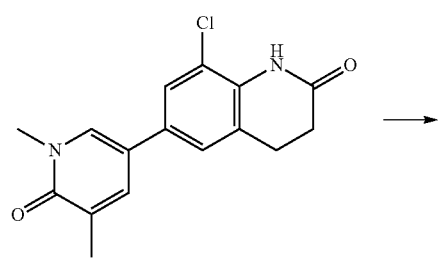

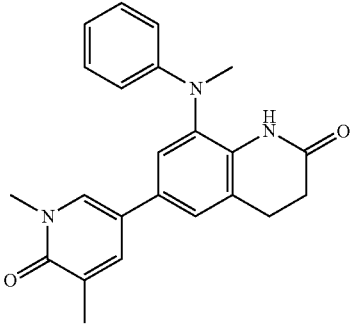

Compound 14

Intermediate 1 (40 mg, 0.132 mmol), Pd$_2$(dba$_3$) (24 mg, 0.026 mmol), X-phos (50 mg, 0.106 mmol), K$_2$CO$_3$ (73 mg, 0.528 mmol), N-methylaniline (43 µL, 0.396 mmol) and 1,4-dioxane (1 mL) were added into an oven dried sealed tube under N$_2$. The resulting mixture was heated to 80° C. for 20 h. The mixture was filtered through Celite™, washed with EtOAc and the filtrate was evaporated under reduced pressure. The material was purified by flash column chromatography on silica gel using a mixture of EtOAc in hexane as eluent, followed by preparative HPLC to provide Compound 14 (12.6 mg, 26%). $^1$H NMR (500 MHz, CDCl$_3$) δ 7.75 (s, 1H), 7.41 (dd, J=2.6, 1.1 Hz, 1H), 7.30 (d, J=2.3, 1H), 7.24-7.19 (m, 2H), 7.16 (d, J=1.2 Hz, 1H), 7.07 (d, J=2.0 Hz, 1H), 6.86-6.81 (m, 1H), 6.67-6.61 (m, 2H), 3.59 (s, 3H), 3.22 (s, 3H), 3.13-3.04 (m, 2H), 2.69 (dd, J=8.3, 6.9 Hz, 2H), 2.20 (s, 3H). MS (ESI) [M+H]$^+$ 374.2.

Example 13: 6-(1,5-dimethyl-6-oxo-1,6-dihydro-pyridin-3-yl)-8-phenoxy-3,4-dihydroquinolin-2(1H)-one Compound 15

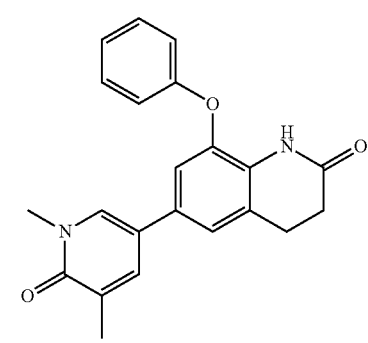

Step 1: Preparation of 6-bromo-8-phenoxy-3,4-dihydroquinolin-2(1H)-one

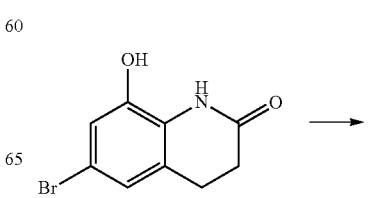

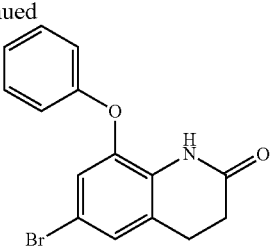

An oven dried vial was charged with copper (I) iodide (0.01 g, 0.054 mmol), K$_2$CO$_3$ (0.15 g, 1.079 mmol) and Intermediate 3 (0.26 g, 1.079 mmol). The vial was evacuated and back filled with argon. The evacuation and backfill sequence was repeated two additional times at rt.

Bromobenzene (0.17 g, 1.079 mmol) was added, followed by DMSO (5 mL) under a flow of argon. The vial was evacuated and back filled with argon. The vial was placed in a pre-heated oil bath at 140° C. and the reaction mixture was stirred vigorously for 16 h at 140° C. The mixture was then cooled to rt, water (50 mL) was added and the aqueous layer was extracted with EtOAc (3×30 mL). The combined organic layers were washed with brine (30 mL), dried over Na$_2$SO$_4$, filtered and evaporated under reduced pressure. The material was purified by flash chromatography on silica gel using a mixture of 0.5 to 2% methanol in DCM as eluent to afford title compound (0.25 g, 40%). MS (ESI) [M+H]$^+$ 318.4.

Step 2: Preparation of 6-(1,5-dimethyl-6-oxo-1,6-dihydropyridin-3-yl)-8-phenoxy-3,4-dihydroquinolin-2(1H)-one

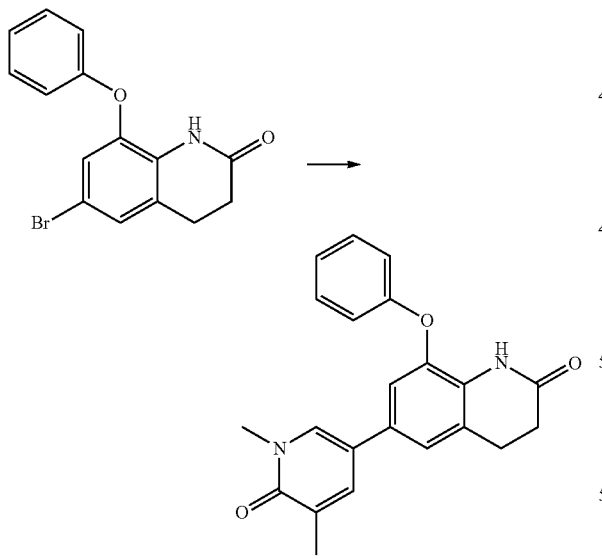

Compound 15

A stirred solution of 6-bromo-8-phenoxy-3,4-dihydroquinolin-2(1H)-one (0.15 g, 0.47 mmol) and 1,3-dimethyl-5-(4,4,5,5-tetramethyl-1,3,2-dioxaborolan-2-yl)pyridin-2 (1H)-one (0.18 g, 0.71 mmol, prepared using procedure described in US20130053362) in 1,4-dioxane (5 mL) was purged with N$_2$ for 20 min. A solution of Na$_2$SO$_4$ (0.15 g, 1.42 mmol) in water (0.5 mL) was then added to the reaction mixture which was further purged with N$_2$ for 20 min. Pd(PPh$_3$)$_4$(0.03 g, 0.024 mmol) was then added and the resulting mixture was heated at 90° C. for 4 h. Water (100 mL) was then added to the mixture and the aqueous layer was extracted with EtOAc (3×30 mL). The combined organic layers were washed with brine (30 mL), dried over Na$_2$SO$_4$, filtered and evaporated under reduced pressure. The material was purified by flash chromatography on silica gel using a mixture of 2% methanol in DCM as eluent, followed by preparative HPLC purification to afford Compound 15 (26 mg, 15%). $^1$H NMR (400 MHz, DMSO) δ 7.84 (d, J=2 Hz, 1H), 7.61 (s, 1H), 7.31 (t, J=7.6 Hz, 2H), 7.21-7.13 (m, 3H) 6.98 (s, 1H), 6.72 (d, J=2 Hz, 1H), 3.49 (s, 3H), 2.95 (t, J=6 Hz, 2H), 2.61 (t, J=6.4 Hz, 2H), 2.06 (s, 3H), —NH not visible. MS (ESI) [M+H]$^+$ 361.6.

Example 14: 8-(cyclohexyloxy)-6-(1,5-dimethyl-6-oxo-1,6-dihydropyridin-3-yl)-3,4-dihydroquinolin-2(1H)-one

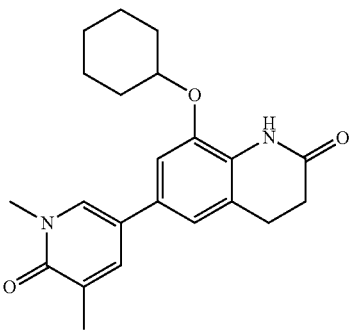

Compound 16

Step 1: Preparation of 6-bromo-8-(cyclohexyloxy)-3,4-dihydroquinolin-2(1H)-one

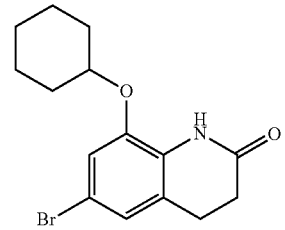

An oven dried vial was charged with copper (I) iodide (0.02 g, 0.10 mmol), K$_2$CO$_3$ (0.29 g, 2.07 mmol) and Intermediate 3 (0.5 g, 2.07 mmol). The vial was evacuated and back filled with argon and the sequence was repeated two additional times at rt. 1-bromo cyclohexane (0.34 g, 2.07 mmol) was then added, followed by DMSO (5 mL) under argon. The vial was evacuated and back filled with argon and the resulting mixture was placed in a preheated oil bath at 140° C. The reaction mixture was stirred vigorously for 16 h at 140° C. The mixture was then cooled to rt, water (130 mL) was added and the aqueous layer was extracted with EtOAc (3×40 mL). The combined organic layers were washed with brine (30 mL), dried over Na$_2$SO$_4$, filtered and evaporated under reduced pressure. The material was purified by flash chromatography on silica gel using a mixture of 0.5 to 2% methanol in DCM as eluent to afford title compound (0.13 g, 19%). MS (ESI) [M+H]$^+$ 324.5.

Step 2: Preparation of 8-(cyclohexyloxy)-6-(1,5-dimethyl-6-oxo-1,6-dihydropyridin-3-yl)-3,4-dihydroquinolin-2(1H)-one

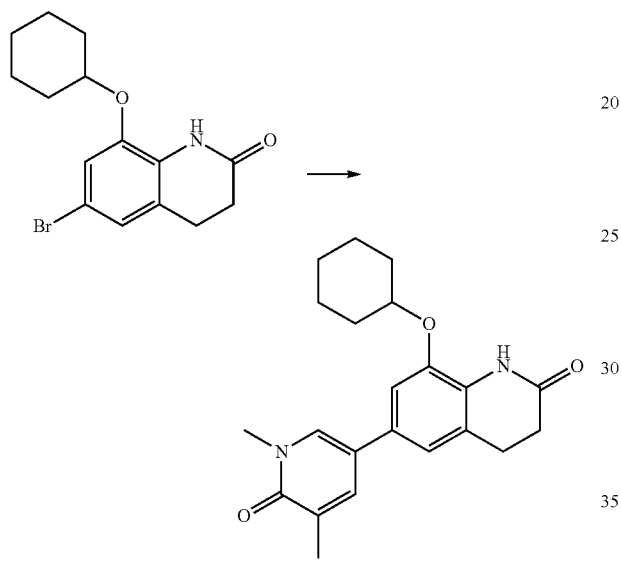

Compound 16

A stirred solution of 6-bromo-8-(cyclohexyloxy)-3,4-dihydroquinolin-2(1H)-one (0.13 g, 0.40 mmol) and 1,3-dimethyl-5-(4,4,5,5-tetramethyl-1,3,2-dioxaborolan-2-yl)pyridin-2(1H)-one (0.15 g, 0.60 mmol, prepared using procedure described in US20130053362) in 1,4-dioxane (5 mL) was purged with N$_2$ for 20 min. A solution of Na$_2$CO$_3$ (0.13 g, 1.20 mmol) in water (0.5 mL) was added and the mixture was further purged with $_{N2}$ for 20 min. Pd(PPh$_3$)$_4$ (0.023 g, 0.02 mmol) was then added and the resulting mixture was heated at 90° C. for 16 h. Water (100 mL) was added to the mixture and the aqueous layer was extracted with EtOAc (3×30 mL). The combined organic layers were washed with brine (30 mL), dried over Na$_2$SO$_4$, filtered and evaporated under reduced pressure. The material was purified by flash chromatography on silica gel using a mixture of 2% methanol in DCM as eluent, followed by preparative HPLC to afford Compound 16 (16 mg, 11%). $^1$H NMR (400 MHz, DMSO) δ 8.86 (s, 1H), 7.92 (s, 1H), 7.71 (s, 1H), 7.07 (s, 1H), 6.99 (s, 1H), 4.51-4.46 (m, 1H), 3.50 (s, 3H), 2.91 (t, J=7.4, 2H), 2.47 (t, J=7.2, 2H), 2.08 (d, J=4.8, 3H), 1.91-1.88 (m, 2H), 1.75-1.73 (m, 2H), 1.58-1.57 (m, 2H), 1.40-1.23 (m, 4H). MS (ESI) [M+H]$^+$ 367.6.

Example 15: 8-(benzyloxy)-6-(1,5-dimethyl-6-oxo-1,6-dihydropyridin-3-yl)-3,4-dihydroquinolin-2(1H)-one

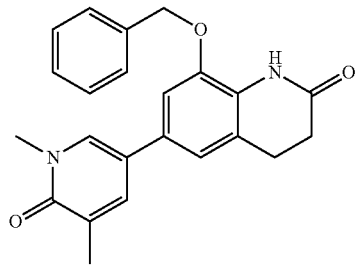

Compound 17

Step 1: Preparation of 8-(benzyloxy)-6-bromo-3,4-dihydroquinolin-2(1H)-one

Intermediate 3 (0.2 g, 0.83 mmol) was added to a suspension of K$_2$CO$_3$ (0.23 g, 1.66 mmol) in DMF (6 mL) and the mixture was stirred at rt for 15 min. Then, benzyl bromide (0.21 g, 1.24 mmol) was added dropwise and the mixture stirred at rt for 6 h. After that time, water (100 mL) was added and the aqueous extracted with EtOAc (3×30 mL). The combined organic layers was washed with brine (30 mL), dried over Na$_2$SO$_4$, filtered and evaporated under reduced pressure. The material was purified by flash chromatography on silica gel using 30% EtOAc in hexane as eluent to afford title compound (0.18 g, 66%). MS (ESI) [M+H]$^+$ 332.5.

Step 2: Preparation of 8-(benzyloxy)-6-(1,5-dimethyl-6-oxo-1,6-dihydropyridin-3-yl)-3,4-dihydroquinolin-2(1H)-one

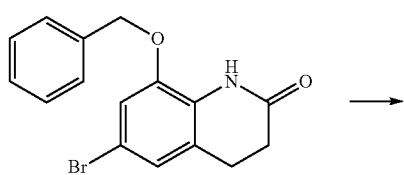

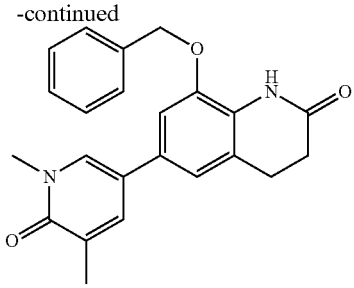

Compound 17

A stirred solution of 8-(benzyloxy)-6-bromo-3,4-dihydroquinolin-2(1H)-one (0.18 g, 0.54 mmol) and 1,3-dimethyl-5-(4,4,5,5-tetramethyl-1,3,2-dioxaborolan-2-yl)pyridin-2(1H)-one (0.20 g, 0.81 mmol, prepared using procedure described in US20130053362) in 1,4-dioxane (5 mL) was purged with $N_2$ for 20 min. A solution of $Na_2CO_3$ (0.17 g, 1.62 mmol) in water (0.5 mL) was added to the mixture, which was further purged with $N_2$ for 20 min. $Pd(PPh_3)_4$ (0.03 g, 0.03 mmol) was added and the resulting mixture was heated at 90° C. for 4 h. After that time, water (30 mL) was added to the mixture and the aqueous layer extracted with EtOAc (3×30 mL). The combined organic layers were washed with brine (30 mL), dried over $Na_2SO_4$, filtered and evaporated under reduced pressure. The material was purified by flash chromatography on silica gel using a mixture of 0.5-1.8% methanol in DCM as eluent, followed by preparative HPLC to afford Compound 17 (48 mg, 24%). $^1$H NMR (400 MHz, DMSO) δ 9.11 (bs, 1H), 7.94 (d, J=2 Hz, 1H), 7.71 (s, 1H), 7.59 (d, J=7.2 Hz, 2H), 7.42-7.33 (m, 3H), 7.17 (s, 1H), 7.03 (s, 1H), 5.25 (s, 2H), 3.51 (s, 3H), 2.90 (t, J=7.4 Hz, 2H), 2.47 (t, J=7.2 Hz, 2H), 2.08 (s, 3H). MS (ESI) [M+H]$^+$ 375.52.

Example 16: 6-(1,5-dimethyl-6-oxo-3-pyridyl)-8-(tetrahydropyran-4-ylamino)-3,4-dihydro-1H-quinolin-2-one

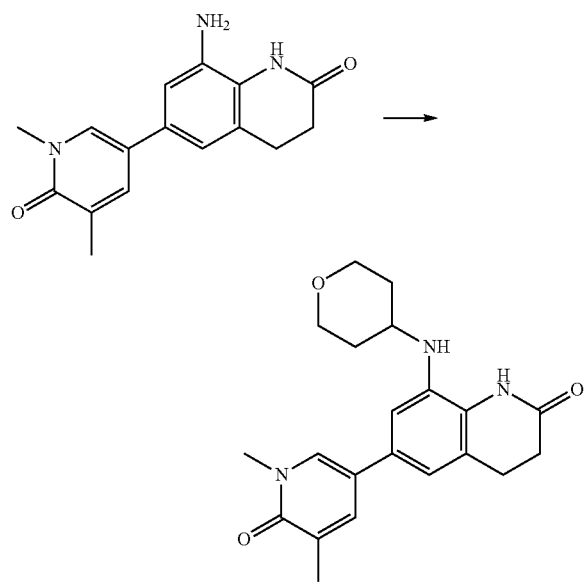

Compound 18

A mixture of AcOH (9 μL, 0.155 mmol), tetrahydro-4H-pyran-4-one (14 μL, 0.155 mmol), $NaBH(OAc)_3$ (59.8 mg, 0.282 mmol) and Intermediate 2 (40 mg, 0.141 mmol) in DCE (2 mL) was stirred at rt for 2 h. The reaction mixture was quenched with saturated $NaHCO_3$ (20 mL) and the aqueous layer was extracted with DCM (3×20 mL). The combined organic layers were washed with brine, dried over $MgSO_4$, filtered and evaporated under reduced pressure. The material was purified by flash chromatography on silica gel using a mixture of EtOAc in hexane as eluent, followed by preparative HPLC to provide Compound 18 (9 mg, 17%). $^1$H NMR (500 MHz, CDCl$_3$) δ 8.81 (s, 1H), 7.43 (dd, J=2.5, 1.1 Hz, 1H), 7.30 (d, J=2.3 Hz, 1H), 6.70 (s, 1H), 6.65 (s, 1H), 4.04 (dt, J=11.8, 3.7 Hz, 2H), 3.70 (s, 1H), 3.63 (s, 3H), 3.54 (td, J=11.6, 2.2 Hz, 2H), 3.53-3.47 (m, 1H), 3.02-2.94 (m, 2H), 2.68-2.62 (m, 2H), 2.23 (s, 3H), 2.03 (d, J=12.5 Hz, 2H), 1.62 (td, J=14.3, 4.3 Hz, 2H). MS (ESI) [M+H]$^+$ 368.2.

Example 17: 8-[(cyclopentylamino)methyl]-6-(1,5-dimethyl-6-oxo-3-pyridyl)-3,4-dihydro-1H-quinolin-2-one

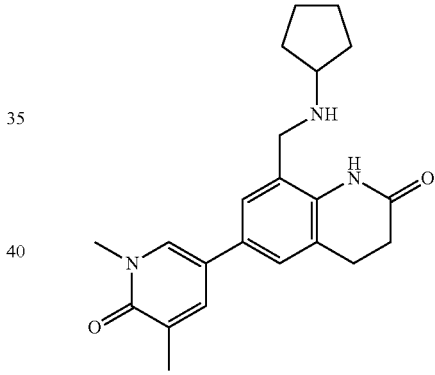

Compound 19

Intermediate 1 (40 mg, 0.132 mmol), $Pd(OAc)_2$ (5.9 mg, 0.026 mmol), X-phos (25 mg, 0.053 mmol), $Cs_2CO_3$ (129 mg, 0.396 mmol) and potassium (cyclopentylamino)methyltrifluoroborate (30 mg, 0.145 mmol) in a mixture of THF/$H_2O$ (10:1, 2 mL), were added into an oven dried sealed tube under $N_2$. The resulting reaction mixture was heated to 80° C. for 18 h. The mixture was filtered through Celite™, washed with EtOAc and the filtrate concentrated under reduced pressure. The material was purified by flash chromatography on silica gel using a mixture of EtOAc in hexane as eluent followed by preparative HPLC to provide Compound 19 (8 mg, 17%) as a solid. $^1$H NMR (500 MHz, CDCl$_3$) δ 10.31 (s, 1H), 7.45 (s, 1H), 7.34 (s, 1H), 7.11 (s, 1H), 7.05 (s, 1H), 3.91 (s, 2H), 3.62 (s, 3H), 3.16-3.06 (m, 1H), 2.98 (t, J=7.4 Hz, 2H), 2.67-2.56 (m, 2H), 2.22 (s, 3H), 1.87 (dd, J=11.9, 5.7 Hz, 2H), 1.77-1.64 (m, 2H), 1.63-1.49 (m, 2H), 1.49-1.37 (m, 2H), —NH not visible. MS (ESI) [M+H]$^+$ 366.2.

Example 18: 8-(cyclobutylmethoxy)-6-(1,5-dimethyl-6-oxo-1,6-dihydropyridin-3-yl)-3,4-dihydroquinolin-2(1H)-one

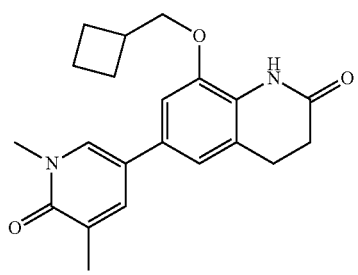

Compound 20

Step 1: Preparation of 6-bromo-8-(cyclobutylmethoxy)-3,4-dihydroquinolin-2(1H)-one

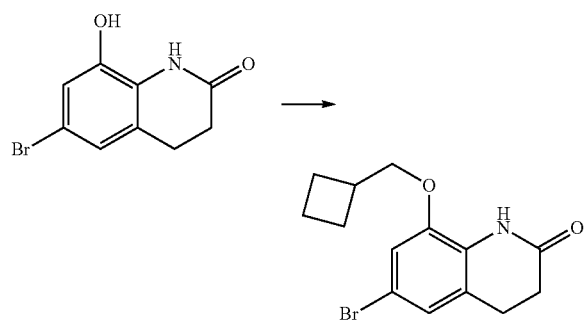

Intermediate 3 (0.3 g, 1.2448 mmol) was added to a suspension of K₂CO₃ (0.35 g, 2.4896 mmol) in DMF (2 mL) and the mixture as stirred at rt for 15 min. Then, (bromomethyl)cyclobutane (0.28 g, 1.8672 mmol) was added dropwise at rt and the resultant reaction mixture was heated at 60° C. for 6 h. After completion of reaction, the mixture was diluted with EtOAc (70 mL) and washed with water (2×30 mL) and brine solution (30 mL), dried over Na₂SO₄, filtered and evaporated under reduced pressure to afford a crude product, which was purified by silica gel column chromatography using a gradient of 30-40% EtOAc in hexane as eluent. The product fractions were combined and evaporated to dryness to give title compound (0.3 g, 78%) as a solid. MS (ESI) [M+H]⁺ 310.5.

Step 2: Preparation of 8-(cyclobutylmethoxy)-6-(1,5-dimethyl-6-oxo-1,6-dihydropyridin-3-yl)-3,4-dihydroquinolin-2(1H)-one

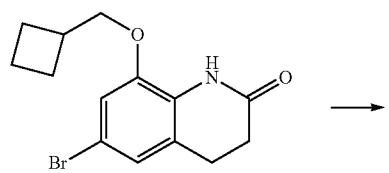

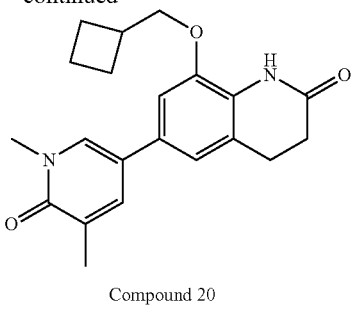

Compound 20

A stirred solution of 6-bromo-8-(cyclobutylmethoxy)-3,4-dihydroquinolin-2(1H)-one (0.30 g, 0.9707 mmol) and 1,3-dimethyl-5-(4,4,5,5-tetramethyl-1,3,2-dioxaborolan-2-yl)pyridin-2(1H)-one (0.32 g, 1.2619 mmol, prepared using procedure described in US20130053362) in 1,4-dioxane (6 mL) was purged with N₂ for 10 min, followed by addition of solution of Na₂CO₃ (0.31 g, 2.9121 mmol) in water (0.5 mL) and purging with N₂ for another 10 min. Pd(PPh₃)₄(0.056 g, 0.0485 mmol) was then added and the reaction mixture was heated at 90° C. for 4 h. The solvent was evaporated under vacuum and water (80 mL) was added. The product was extracted using EtOAc (3×40 mL). The combined organic layers were washed with brine solution (40 mL), dried over Na₂SO₄, filtered and evaporated under reduced pressure to afford a crude product, which was purified by flash chromatography using a gradient of 1.5-2% methanol in DCM as eluent, followed by preparative HPLC using 30% acetonitrile in water containing 0.1% TFA as modifier to afford Compound 20 (0.039 g, 21%). ¹H NMR (400 MHz, MeOD) δ 7.84 (d, J=2 Hz, 1H), 7.77 (d, J=1.2 Hz, 1H), 7.04 (d, J=1.6 Hz, 1H), 7.00 (s, 1H), 4.14 (d, J=6.8 Hz, 2H), 3.67 (s, 3H), 3.02 (t, J=8 Hz, 2H), 2.90-2.86 (m, 1H), 2.62 (t, J=6 Hz, 2H), 2.24-2.18 (m, 5H), 2.01-1.92 (m, 4H), —NH not visible. (ESI) [M+H]⁺ 353.6.

Example 19: 8-(cyclopentoxymethyl)-6-(1,5-dimethyl-6-oxo-3-pyridyl)-3,4-dihydro-1H-quinolin-2-one

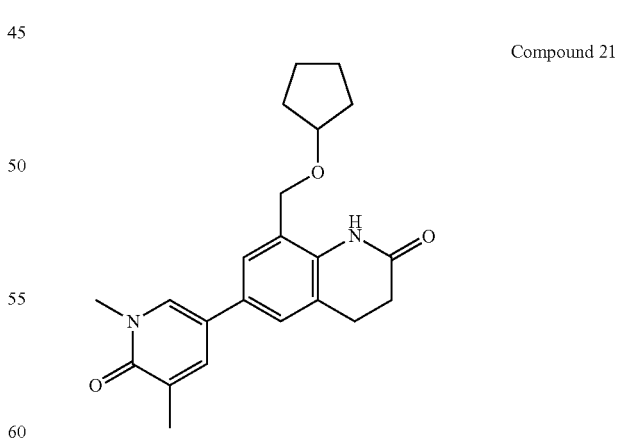

Compound 21

Intermediate 1 (45 mg, 0.149 mmol), Pd(OAc)₂ (6.7 mg, 0.030 mmol), X-phos (28 mg, 0.059 mmol), Cs₂CO₃ (145 mg, 0.446 mmol) and potassium cyclopentoxymethyl-trifluoroborate (70 mg, 0.340 mmol) in a mixture THF/H₂O (10:1, 3 mL) were added into an oven dried sealed tube under N₂. The resulting reaction mixture was heated to 80°

C. for 3 days. The mixture was filtered through Celite™, washed with EtOAc and the filtrate was concentrated under reduced pressure. The material was purified by flash chromatography on silica gel using a mixture of EtOAc in hexane as eluent and followed by preparative HPLC to afford Compound 21 (9 mg, 17%) as a solid. $^1$H NMR (500 MHz, CDCl$_3$) δ 8.52 (s, 1H), 7.38 (dd, J=2.6, 1.2 Hz, 1H), 7.25 (d, J=2.3 Hz, 1H), 7.09 (d, J=1.5 Hz, 1H), 6.99 (d, J=2.0 Hz, 1H), 4.47 (s, 2H), 3.99-3.91 (m, 1H), 3.55 (s, 3H), 2.96-2.90 (m, 2H), 2.61-2.51 (m, 2H), 2.15 (s, 3H), 1.76-1.62 (m, 6H), 1.53-1.46 (m, 2H). MS (ESI) [M+H]$^+$ 367.2.

Example 20: 6-(1,5-dimethyl-6-oxo-3-pyridyl)-8-[1-(2-pyridyl)ethylamino]-3,4-dihydro-1H-quinolin-2-one Compounds 22 and 23

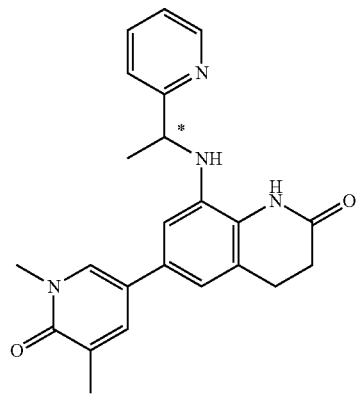

A mixture of AcOH (14 μL, 0.241 mmol), 2-acetylpyridine (27 μL, 0.241 mmol) and Intermediate 2 (62 mg, 0.219 mmol) in DCE (2 mL) was stirred at rt for 1 h. NaBH(OAc)$_3$ (231 mg, 1.094 mmol) was then added and the reaction mixture was stirred for 18 h at rt. Saturated NaHCO$_3$ (20 mL) was then added to the mixture and the aqueous layer was extracted with DCM (3×20 mL). The combined organic layers were washed with brine, dried over Na$_2$SO$_4$, filtered and concentrated under reduced pressure. The material was purified by flash chromatography on silica gel using a mixture of EtOAc in hexane as eluent, followed by SFC purification (ID 10×250 mm, 5 um isocratic 55% IPA+0.1% NH$_4$OH, 10 mL/min 100 Bar) to afford Compound 22 (6.5 mg) and Compound 23 (6.3 mg) as solids.

Compound 22: Retention time: 6.47 min. $^1$H NMR (500 MHz, CDCl$_3$) δ 9.67 (s, 1H), 8.63-8.57 (m, 1H), 7.65 (td, J=7.7, 1.8 Hz, 1H), 7.41 (d, J=7.9 Hz, 1H), 7.25 (dd, J=2.5, 1.1 Hz, 1H), 7.18 (ddd, J=7.4, 4.9, 1.1 Hz, 1H), 7.11 (d, J=2.3 Hz, 1H), 6.58 (s, 1H), 6.45 (d, J=1.7 Hz, 1H), 5.01 (s, 1H), 4.69 (s, 1H), 3.56 (s, 3H), 2.98-2.91 (m, 2H), 2.64 (dd, J=8.9, 6.4 Hz, 2H), 2.17 (s, 3H), 1.66 (d, J=6.8 Hz, 3H). MS (ESI) [M+H]$^+$ 389.2.

Compound 23: Retention time: 8.76 min. $^1$H NMR (500 MHz, CDCl$_3$) δ 9.74 (s, 1H), 8.65-8.56 (m, 1H), 7.65 (td, J=7.7, 1.7 Hz, 1H), 7.42 (d, J=7.9 Hz, 1H), 7.26-7.24 (m, 1H), 7.18 (ddd, J=7.4, 4.9, 1.0 Hz, 1H), 7.11 (d, J=2.4 Hz, 1H), 6.58 (s, 1H), 6.45 (d, J=1.7 Hz, 1H), 5.05 (d, J=5.0 Hz, 1H), 4.74-4.65 (m, 1H), 3.56 (s, 3H), 2.99-2.91 (m, 2H), 2.64 (dd, J=8.8, 6.4 Hz, 2H), 2.16 (s, 3H), 1.66 (d, J=6.8 Hz, 3H). MS (ESI) [M+H]$^+$ 389.2.

Example 21: 8-[(cyclohexylamino)methyl]-6-(1,5-dimethyl-6-oxo-3-pyridyl)-3,4-dihydro-1H-quinolin-2-one

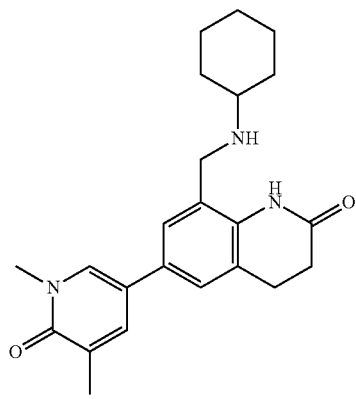

Intermediate 1 (40 mg, 0.132 mmol), Pd(OAc)$_2$ (5.9 mg, 0.026 mmol), X-phos (25 mg, 0.053 mmol), Cs$_2$CO$_3$ (129 mg, 0.396 mmol) and potassium (cyclohexylamino)methyltrifluoroborate (37 mg, 0.169 mmol) in a mixture THF/H$_2$O (10:1, 2 mL) were added into an oven dried sealed tube under N$_2$. The resulting reaction mixture was heated at 80° C. for 20 h. The mixture was filtered through Celite™, washed with EtOAc and the filtrate was concentrated under reduced pressure. The material was purified by flash chromatography on silica gel using a mixture of EtOAc in hexane as eluent and followed by preparative HPLC to afford Compound 24 (11 mg, 23%) as a solid. $^1$H NMR (500 MHz, CDCl$_3$) δ 10.43 (s, 1H), 7.45 (d, J=1.3 Hz, 1H), 7.34 (s, 1H), 7.11 (s, 1H), 7.04 (s, 1H), 3.95 (s, 2H), 3.61 (s, 3H), 3.01-2.94 (m, 2H), 2.61 (dd, J=8.3, 6.7 Hz, 2H), 2.49 (t, J=9.7 Hz, 1H), 2.21 (s, 3H), 1.96 (d, J=11.5 Hz, 2H), 1.77-1.67 (m, 2H), 1.60 (d, J=11.1 Hz, 1H), 1.30-1.10 (m, 6H). MS (ESI) [M+H]$^+$ 366.2.

Example 22: 6-(1,5-dimethyl-6-oxo-1,6-dihydro-pyridin-3-yl)-8-(pyridin-3-ylmethoxy)-3,4-dihydro-quinolin-2(1H)-one

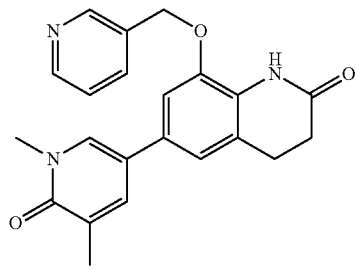

Step 1: Preparation of 6-bromo-8-(pyridin-3-yl-methoxy)-3,4-dihydroquinolin-2(1H)-one

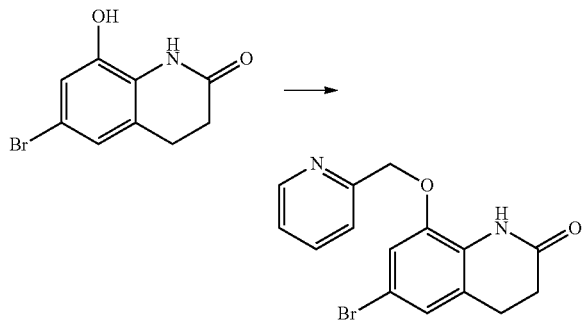

Intermediate 3 (0.3 g, 1.2448 mmol) was added to a suspension of K$_2$CO$_3$ (0.35 g, 2.4896 mmol) in DMF (3 mL) and the mixture was stirred at rt for 15 min. 3-(bromomethyl)pyridine hydrobromide (0.47 g, 1.8672 mmol) was then added at rt and the resultant reaction mixture was heated at 60° C. for 6 h. After completion of reaction, the mixture was diluted with EtOAc (70 mL) and washed with water (2×30 mL) and brine solution (30 mL), dried over anhydrous Na$_2$SO$_4$, filtered and evaporated to afford a crude product, which was purified by silica gel column chromatography and the product was eluted in 1.5-2% MeOH in DCM as gradient. The product fractions were collected and evaporated to afford title compound (0.3 g, 73%) as a solid MS (ESI) [M+H]$^+$ 335.44.

Step 2: Preparation of of 6-(1,5-dimethyl-6-oxo-1,6-dihydropyridin-3-yl)-8-(pyridin-3-ylmethoxy)-3,4-dihydroquinolin-2(1H)-one

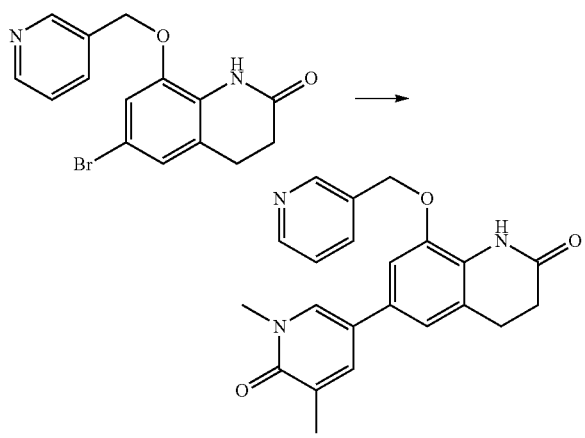

Compound 25

A stirred solution of 6-bromo-8-(pyridin-3-ylmethoxy)-3,4-dihydroquinolin-2(1H)-one (0.30 g, 0.903 mmol) and 1,3-dimethyl-5-(4,4,5,5-tetramethyl-1,3,2-dioxaborolan-2-yl)pyridin-2(1H)-one (0.30 g, 1.1739 mmol, prepared using procedure described in US20130053362) in 1,4-dioxane (5 mL) was purged with N$_2$ for 10 min followed by addition of a solution of sodium carbonate (0.29 g, 2.709 mmol) in water (0.5 mL) and purging with N$_2$ for another 10 min. Then, Pd(PPh$_3$)$_4$(0.052 g, 0.0451 mmol) was added and the reaction mixture was heated at 90° C. for 4 h. The solvent was evaporated under vacuum and water (60 mL) was added. The product was then extracted using EtOAc (40 mL×3). The combined organic layers were washed with brine solution (30 mL), dried over anhydrous Na$_2$SO$_4$, filtered and evaporated to afford a crude product. The crude product was purified by flash chromatography using a gradient of 2.5-3% methanol in DCM as eluent, followed by preparative HPLC purification using 3-12% acetonitrile in water containing 0.1% formic acid as modifier to afford Compound 25 (0.035 g, 11%) as a solid. $^1$H NMR (400 MHz, DMSO) δ 9.34 (s, 1H), 8.80 (d, J=2.4 Hz, 1H), 8.55 (dd, J=1.2 Hz and 1.6 Hz, 1H), 8.03 (d, J=7.6 Hz, 1H), 7.95 (d, J=2 Hz, 1H], 7.74 (s, 1H), 7.44 (dd, J=4.4 Hz and 5.2 Hz, 1H), 7.22 (d, J=1.6 Hz, 1H), 7.05 (s, 1H), 5.28 (s, 2H), 3.52 (s, 3H), 2.90 (t, J=7.2 Hz, 2H), 2.50 (m, 2H), 2.08 (s 3H). MS (ESI) [M+H]$^+$ 376.52.

Example 23: 6-(1,5-dimethyl-6-oxo-1,6-dihydro-pyridin-3-yl)-8-(pyridin-2-ylmethoxy)-3,4-dihydro-quinolin-2(1H)-one

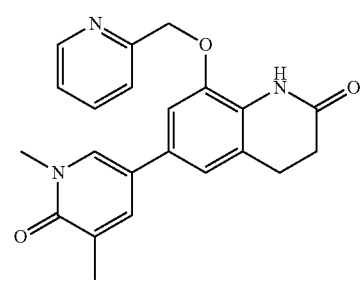

Compound 26

Step 1: Preparation of 6-bromo-8-(pyridin-2-yl-methoxy)-3,4-dihydroquinolin-2(1H)-one

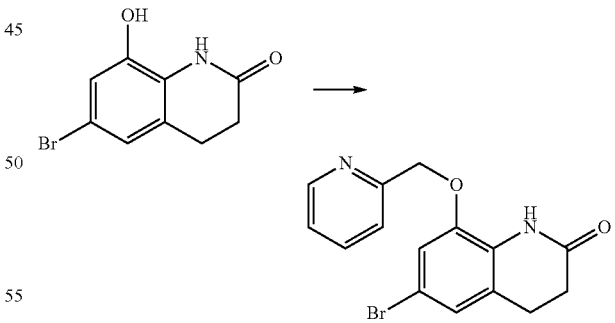

Intermediate 3 (0.3 g, 1.2448 mmol) was added to a suspension of K$_2$CO$_3$ (0.35 g, 2.4896 mmol) in DMF (3 mL) and the mixture was stirred at rt for 15 min. 2-(bromomethyl)pyridine hydrobromide (0.47 g, 1.8672 mmol) was then added at rt and the resultant reaction mixture was heated at 60° C. for 6 h. After completion of reaction, the mixture was diluted with EtOAc (70 mL) and washed with water (30 mL×2) and brine solution (30 mL), dried over anhydrous Na$_2$SO$_4$, filtered and evaporated to afford a crude product, which was purified by silica gel column chromatography using a gradient of 1.5-2% MeOH in DCM as eluent. The product fractions were collected and evaporated to afford title compound (0.3 g, 73%) as a solid. MS (ESI) [M+H]$^+$ 335.44.

Step 2: Preparation of 6-(1,5-dimethyl-6-oxo-1,6-dihydropyridin-3-yl)-8-(pyridin-2-ylmethoxy)-3,4-dihydroquinolin-2(1H)-one

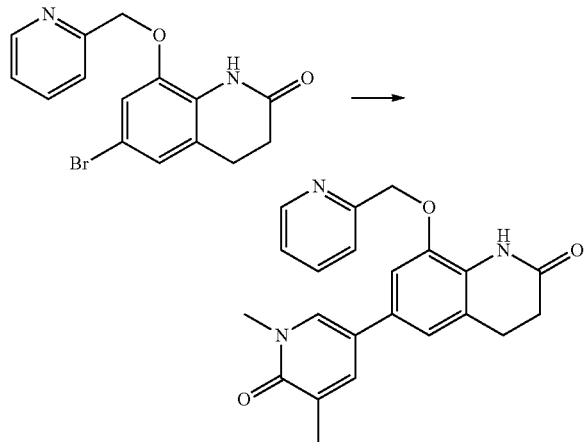

Compound 26

A stirred solution of 6-bromo-8-(pyridin-2-ylmethoxy)-3,4-dihydroquinolin-2(1H)-one (0.30 g, 0.903 mmol) and 1,3-dimethyl-5-(4,4,5,5-tetramethyl-1,3,2-dioxaborolan-2-yl)pyridin-2(1H)-one (0.30 g, 1.1739 mmol, prepared using procedure described in US20130053362) in 1,4-dioxane (5 mL) was purged with $N_2$ for 10 min followed by addition of a solution of sodium carbonate (0.29 g, 2.709 mmol) in water (0.5 mL) and purging with $N_2$ for another 10 min. Then, Pd(PPh$_3$)$_4$(0.052 g, 0.0451 mmol) was added and the reaction mixture was heated at 90° C. for 4 h. The solvent was evaporated under vacuum and water (60 mL) was added. The product was then extracted using EtOAc (40 mL×3). The combined organic layers were washed with brine solution (30 mL), dried over anhydrous Na$_2$SO$_4$, filtered and evaporated under reduced pressure to afford a crude product, which was purified by flash chromatography using a gradient of 3-4% methanol in DCM as eluent, followed by preparative HPLC purification using 2-24% acetonitrile in water containing 0.1% formic acid as modifier to afford Compound 26 (0.025 g, 8%) as a solid. $^1$H NMR (400 MHz, DMSO) δ 9.39 (bs, 1H), 8.59 (d, J=4 Hz, 1H), 7.97 (d, J=2.8 Hz, 1H), 7.88-7.84 (m, 1H), 7.84 (d, J=8 Hz, 1H), 7.72 (s, 1H), 7.36 (t, J=6 Hz, 1H), 7.20 (d, J=1.6 Hz, 1H), 7.06 (s, 1H), 5.31 (s, 2H), 3.50 (s, 3H), 2.92 (t, J=7.4 Hz, 2H), 2.50 (m, 2H), 2.07 (s 3H). MS (ESI) [M+H]$^+$ 376.52.

Example 24: 8-(cyclohexoxymethyl)-6-(1,5-dimethyl-6-oxo-3-pyridyl)-3,4-dihydro-1H-quinolin-2-one

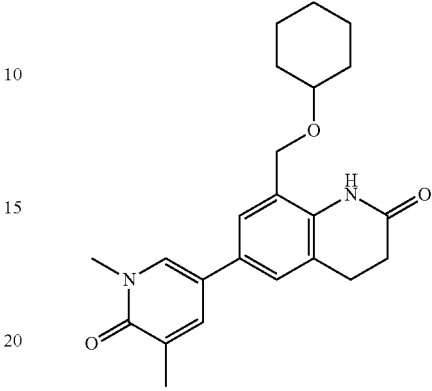

Compound 27

Intermediate 1 (40 mg, 0.132 mmol), Pd(OAc)$_2$ (5.9 mg, 0.026 mmol), X-phos (25 mg, 0.053 mmol), Cs$_2$CO$_3$ (129 mg, 0.396 mmol) and potassium cyclohexoxy-methyl(trifluoro)borate (54 mg, 0.245 mmol) in a mixture THF/H$_2$O (10:1, 2 mL) were added into an oven dried sealed tube under N$_2$. The resulting reaction mixture was heated at 80° C. for 2 days. Pd(OAc)$_2$ (5.9 mg, 0.026 mmol) and X-phos (25 mg, 0.053 mmol) were added and the reaction mixture was stirred at 80° C. for 24 h. The resulting mixture was filtered through Celite™, washed with EtOAc and the filtrate was concentrated under reduced pressure. The material was purified by flash chromatography on silica gel using a mixture of EtOAc in hexane as eluent, followed by preparative HPLC to afford Compound 27 (12 mg, 24%) as a solid. $^1$H NMR (500 MHz, CDCl$_3$) δ 8.68 (s, 1H), 7.45 (s, 1H), 7.32 (d, J=2.5 Hz, 1H), 7.15 (s, 1H), 7.06 (d, J=2.0 Hz, 1H), 4.62 (s, 2H), 3.62 (s, 3H), 3.46-3.34 (m, 1H), 3.05-2.97 (m, 2H), 2.68-2.60 (m, 2H), 2.22 (s, 3H), 2.02-1.92 (m, 2H), 1.84-1.72 (m, 2H), 1.46-1.35 (m, 2H), 1.33-1.23 (m, 4H). MS (ESI) [M+H]$^+$ 381.2.

Example 25: 6-(1,5-dimethyl-6-oxo-3-pyridyl)-8-(4-pyridylmethylamino)-3,4-dihydro-1H-quinolin-2-one

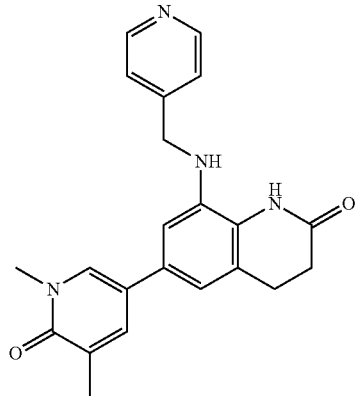

Compound 28

A mixture of AcOH (6 μL, 0.113 mmol), 4-pyridinecarboxaldehyde (11 μL, 0.113 mmol), NaBH(OAc)₃ (65 mg, 0.307 mmol) and Intermediate 2 (29 mg, 0.102 mmol) in DCE (2 mL) was stirred at rt for 4 h. Saturated NaHCO₃ (5 mL) was then added to the mixture and the aqueous layer was extracted with DCM (3×5 mL). The combined organic layers were washed with brine, dried over anhydrous Na₂SO₄, filtered and concentrated under reduced pressure. The residue was then dissolved in MeOH (2 mL), NaBH₄ (11 mg, 0.307 mmol) was added and the reaction mixture was stirred at rt for 20 h. Saturated NaHCO₃ (10 mL) and EtOAc (10 mL) were then added to the mixture and the aqueous phase was extracted with EtOAc (3×10 mL). The combined organic layers were dried over anhydrous Na₂SO₄, filtered and concentrated under reduced pressure. The material was purified by flash chromatography on silica gel using a mixture of EtOAc in hexane as eluent and followed by preparative HPLC to afford Compound 28 (3 mg, 8%) as a solid. ¹H NMR (500 MHz, CDCl₃) δ 9.72 (s, 1H), 8.53 (dd, J=4.4, 1.6 Hz, 2H), 7.30 (d, J=5.9 Hz, 2H), 7.26 (d, J=1.3 Hz, 1H), 7.11 (d, J=2.3 Hz, 1H), 6.57 (s, 1H), 6.37 (d, J=1.6 Hz, 1H), 4.95 (s, 1H), 4.39 (d, J=5.1 Hz, 2H), 3.51 (s, 3H), 2.92-2.83 (m, 2H), 2.48-2.41 (m, 2H), 2.12 (s, 3H). MS (ESI) [M+H]⁺ 375.1.

Example 26: 8-(cyclopentylmethoxy)-6-(1,5-dimethyl-6-oxo-1,6-dihydropyridin-3-yl)-3,4-dihydroquinolin-2(1H)-one Compound 29

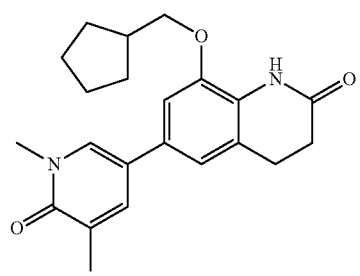

Step 1: Preparation of of 6-bromo-8-(cyclopentylmethoxy)-3,4-dihydroquinolin-2(1H)-one

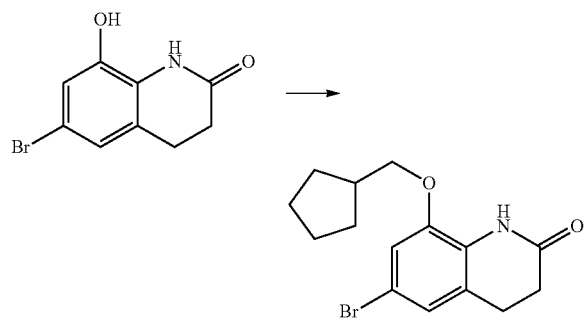

Intermediate 3 (0.3 g, 1.2448 mmol) was added to a suspension of K₂CO₃ (0.35 g, 2.4896 mmol) in DMF (6 mL) and the mixture was stirred at rt for 15 min. (bromomethyl)cyclopentane (0.30 g, 1.8672 mmol) was then added dropwise at rt and the resultant reaction mixture was heated at 60° C. for 6 h. After completion of the reaction, the mixture was diluted with EtOAc (70 mL) and washed with water (3×30 mL) and brine solution (30 mL), dried over anhydrous Na₂SO₄, filtered and evaporated under reduced pressure to afford a crude product, which was then purified by silica gel column chromatography using a gradient of 30-40% EtOAc in hexane as eluent. The product fractions were then collected and evaporated to afford title compound (0.35 g, 77%) as a semi-solid]. MS (ESI) [M+H]⁺ 367.4.

Step 2: Preparation of 8-(cyclopentylmethoxy)-6-(1,5-dimethyl-6-oxo-1,6-dihydropyridin-3-yl)-3,4-dihydroquinolin-2(1H)-one

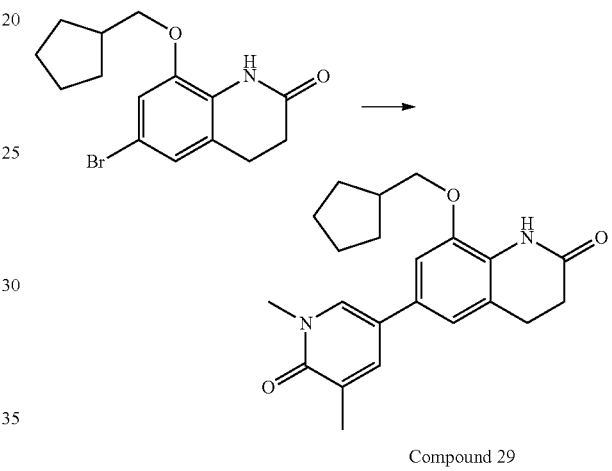

Compound 29

A stirred solution of 6-bromo-8-(cyclopentylmethoxy)-3,4-dihydroquinolin-2(1H)-one (0.35 g, 0.9557 mmol) and 1,3-dimethyl-5-(4,4,5,5-tetramethyl-1,3,2-dioxaborolan-2-yl)pyridin-2(1H)-one (0.31 g, 1.2424 mmol, prepared using procedure described in US20130053362) in 1,4-dioxane (6 mL) was purged with N₂ for 10 min, followed by addition of solution of sodium carbonate (0.31 g, 2.8671 mmol) in water (0.5 mL) and purging with nitrogen for another 10 min. Pd(PPh₃)₄(0.055 g, 0.0478 mmol) was then added and the reaction mixture was heated at 90° C. for 4 h. The solvent was evaporated under vacuum and water (70 mL) was added. The product was then extracted using EtOAc (40 mL×3). The combined organic layers were washed with brine solution (40 mL), dried over anhydrous Na₂SO₄, filtered and evaporated to afford a crude product, which was then purified by flash chromatography using a gradient of 1.5-2% methanol in DCM as eluent followed by preparative HPLC purification using 35 to 47% acetonitrile in water containing 0.1% formic acid as modifier to afford Compound 29 (0.076 g, 20%) as a solid. ¹H NMR (400 MHz, DMSO) δ 8.92 (s, 1H), 7.95 (d, J=2.4 Hz, 1H), 7.74 (d, J=1.2 Hz, 1H), 7.03 (d, J=1.6 Hz, 1H), 7.00 (s, 1H), 3.95 (d, J=7.2 Hz, 2H), 3.51 (s, 3H), 2.90 (t, J=6.8 Hz, 2H), 2.48 (m, 3H), 2.42-2.35 (m, 1H), 2.07 (s, 2H), 1.88-1.81 (m, 2H), 1.64-1.53 (m, 4H) 1.38-1.32 (m, 2H). MS (ESI) [M+H]⁺ 367.56.

Example 27: 8-benzyl-7-(1,5-dimethyl-6-oxo-1,6-dihydropyridin-3-yl)-3,4-dihydroquinolin-2(1H)-one Compound 30

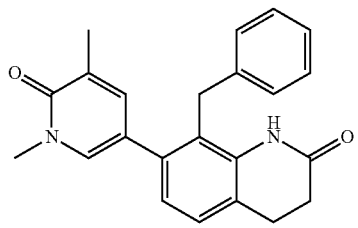

Step 1: Preparation of N-(2-bromo-3-chlorophenyl)-3-chloropropanamide

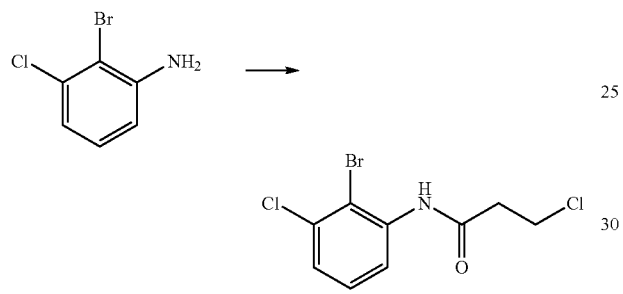

To a stirred solution of 2-bromo-3-chloroaniline (2.0 g, 10.00 mmol) and K$_2$CO$_3$ (2.0 g, 15.00 mmol) in a mixture of acetone (20 mL) and water (40 mL), 3-chloropropanoyl chloride (1.5 g, 12.0 mmol) was added dropwise at 0° C. and the reaction mixture was allowed to stir for 1 h at same temperature. After completion of reaction, the mixture was transferred into ice water (500 mL) and solid was filtered off to afford title compound (1.9 g, 65%) as a solid. MS (ESI) [M+H]$^+$ 298.49.

Step 2: Preparation of 8-bromo-7-chloro-3,4-dihydroquinolin-2(1H)-one

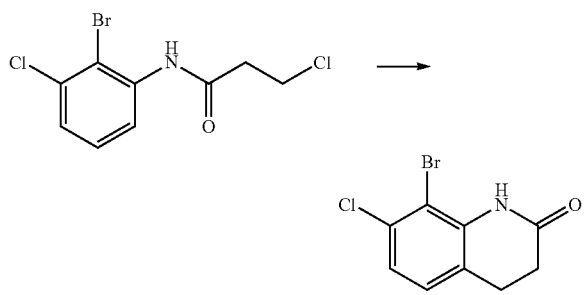

To N-(2-bromo-3-chlorophenyl)-3-chloropropanamide (1.9 g, 6.40 mmol) was added fine powder of AlCl$_3$ (2.56 g, 19.00 mmol) at rt and the mixture was heated under stirring at 140° C. for 5 h. After completion of reaction, the mixture was transferred into 12% HCl solution in water (40 mL) and extracted with EtOAc (50 mL×3). The combined EtOAc layers were washed with water (50 mL) and brine (50 mL), dried over anhydrous Na$_2$SO$_4$, filtered and evaporated to provide a crude product, which was purified by silica gel column chromatography using 20% EtOAc in hexane as eluent to afford title compound (1.0 g, 51%) as a solid. MS (ESI) [M+H]$^+$ 262.1.

Step 3: Preparation of 8-benzyl-7-chloro-3,4-dihydroquinolin-2(1H)-one

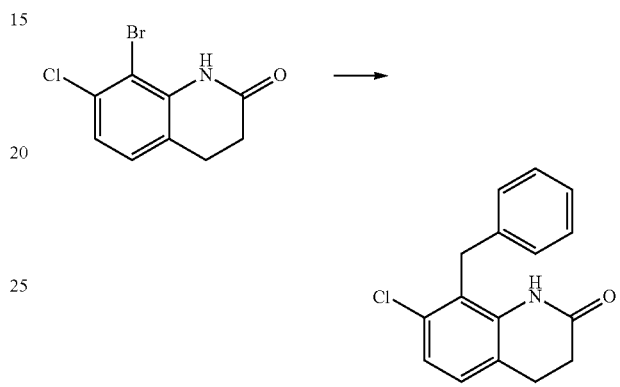

A stirred solution of 8-bromo-7-chloro-3,4-dihydroquinolin-2(1H)-one (0.25 g, 0.96 mmol) and 2-benzyl-4,4,5,5-tetramethyl-1,3,2-dioxaborolane (0.215 g, 1.15 mmol) in 1,4-dioxane (5 mL) was purged with N$_2$ for 10 min followed by addition of a solution of cesium carbonate (0.938 g, 2.88 mmol) in water (0.5 mL) and purging with N$_2$ for another 10 min. PdCl$_2$(dppf).DCM (0.039 g, 0.048 mmol) was added and the reaction mixture was heated at 90° C. for 12 h. After completion of the reaction, the solvent was evaporated under vacuum and the product was extracted using EtOAc (30 mL×3). The combined organic layers were washed with water (20 mL), brine (20 mL), dried over anhydrous Na$_2$SO$_4$, filtered and evaporated to afford a crude product, which was purified by silica gel column chromatography using 30% EtOAc in hexane as eluent to afford title compound (0.225 g, 74%) as a solid. MS (ESI) [M+H]$^+$ 272.23

Step 4: Preparation of 8-benzyl-7-(1,5-dimethyl-6-oxo-1,6-dihydropyridin-3-yl)-3,4-dihydroquinolin-2(1H)-one

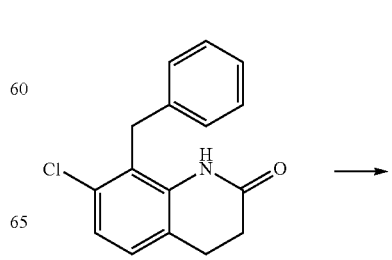

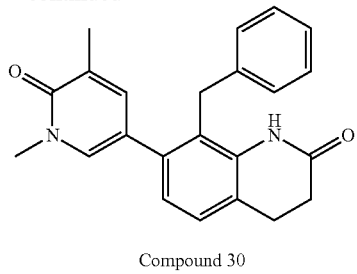

Compound 30

A stirred solution of 8-benzyl-7-chloro-3,4-dihydroquinolin-2(1H)-one (0.225 g, 0.83 mmol) and 1,3-dimethyl-5-(4,4,5,5-tetramethyl-1,3,2-dioxaborolan-2-yl)pyridin-2(1H)-one (0.25 g, 0.99 mmol, prepared using procedure described in US20130053362) in 1,4-dioxane (4 mL) was purged with N₂ for 10 min. A solution of potassium phosphate (0.527 g, 2.49 mmol) in water (0.4 mL) was then added and the mixture was further purged with N₂ for 10 min. Pd(t-Bu₃P)₂ (0.021 g, 0.041 mmol) was added and the reaction mixture was heated at 90° C. for 10 h. After completion of the reaction, the solvent was evaporated under vacuum and the product was extracted using EtOAc (20 mL×3). The combined organic layers were washed with water (20 mL), brine (20 mL), dried over anhydrous Na₂SO₄, filtered and evaporated to afford a crude product, which was purified by silica gel column chromatography using 4% methanol in DCM as eluent to afford Compound 30 (0.024 g, 8%) as a solid. ¹H NMR (400 MHz, DMSO) δ ppm 9.37 (s, 1H), 7.29 (d, J=2 Hz, 1H), 7.23-7.11 (m, 4H), 7.01 (d, J=1.2 Hz, 1H), 6.90 (d, J=7.2 Hz, 2H), 6.85 (d, J=7.6 Hz, 1H), 4.07 (s, 2H), 3.36 (s, 3H), 2.91 (t, J=14.8 Hz, 2H), 2.43 (t, J=14.8 Hz, 2H), 1.90 (s, 3H). MS (ESI) [M+H]⁺ 359.34.

Example 28: 6-benzyl-7-(1,5-dimethyl-6-oxo-1,6-dihydropyridin-3-yl)-3,4-dihydro-quinolin-2(1H)-one

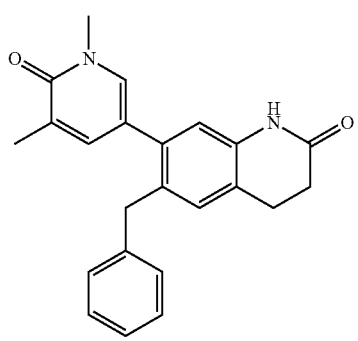 [SMILES: Cc1cc(-c2cc3c(cc2Cc2cccnc2)CCC(=O)N3)cn(C)c1=O]

Compound 31

Step 1: Preparation of 6-benzyl-7-chloro-3,4-dihydroquinolin-2(1H)-one

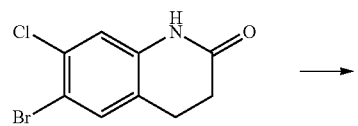

A stirred solution of 6-bromo-7-chloro-3,4-dihydroquinolin-2(1H)-one (0.25 g, 0.9654 mmol, prepared according to step 2 of Example 7) and 2-benzyl-4,4,5,5-tetramethyl-1,3,2-dioxaborolane (0.32 g, 1.4482 mmol) in 1,4-dioxane (2 mL) was purged with N₂ for 10 min. A solution of sodium carbonate (0.31 g, 2.8962 mmol) in water (0.3 mL) was added and the mixture was further purged with N₂ for 10 min. PdCl₂(dppf).DCM (0.04 g, 0.0483 mmol) was then added and the reaction mixture was microwave irradiated at 150° C. for 30 min. After completion of reaction, the solvent was evaporated and water (80 mL) was added. The product was extracted using EtOAc (40 mL×3). The combined organic layers were washed with brine solution (50 mL), dried over anhydrous Na₂SO₄, filtered and evaporated to afford a crude product, which was purified by flash chromatography using a gradient of 30-50% EtOAc in hexane as eluent. The pure product fractions were collected and evaporated to afford title compound (0.18 g, 48%) as a solid. MS (ESI) [M+H]⁺ 272.7.

Step 2: Preparation of 6-benzyl-7-(1,5-dimethyl-6-oxo-1,6-dihydropyridin-3-yl)-3,4-dihydroquinolin-2(1H)-one

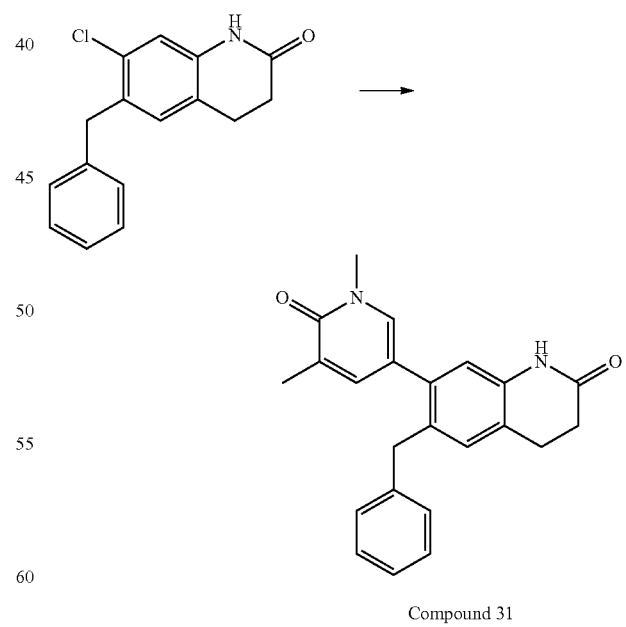

Compound 31

A stirred solution of 6-benzyl-7-chloro-3,4-dihydroquinolin-2(1H)-one (0.18 g, 0.6640 mmol) and 1,3-dimethyl-5-(4,4,5,5-tetramethyl-1,3,2-dioxaborolan-2-yl)pyridin-2(1H)-one (0.25 g, 0.9960 mmol, prepared using procedure described in US20130053362) in 1,4-dioxane (5 mL) was purged with $N_2$ for 10 min. A solution of $K_3PO_4$ (0.42 g, 1.9920 mmol) in water (0.5 mL) was then added and the mixture was further purged with $N_2$ for 10 min. Pd(t-$Bu_3$P)$_2$ (0.017 g, 0.0332 mmol) was added and the reaction mixture was microwave irradiated at 90° C. for 30 min. The solvent was evaporated and water (80 mL) was added. The product was extracted using EtOAc (40 mL×3). The combined organic layers were washed with brine solution (50 mL), dried over anhydrous $Na_2SO_4$, filtered and evaporated to afford a crude product, which was purified by silica gel column chromatography using a gradient of 1.5-2% methanol in DCM as eluent. The pure product fractions were collected and evaporated to afford Compound 31 (0.03 g, 13%) as a solid. $^1$H NMR (400 MHz, DMSO) δ; 10.09 (s, 1H), 7.36 (d, J=2 Hz, 1H), 7.22 (t, J=7 Hz, 2H), 7.16-7.12 (m, 2H), 7.04 (s, 1H), 6.98 (d, J=6.8 Hz, 2H), 6.66 (s, 1H), 3.84 (s, 2H), 3.40 (s, 3H), 2.84 (t, J=7.2 Hz, 2H), 2.44 (t, J=7.4 Hz, 2H), 1.97 (s, 3H). MS (ESI) [M+H]$^+$ 359.6.

Example 29: of 7-(1,5-dimethyl-6-oxo-1,6-dihydropyridin-3-yl)-6-(pyridin-2-ylmethyl)-3,4-dihydroquinolin-2(1H)-one

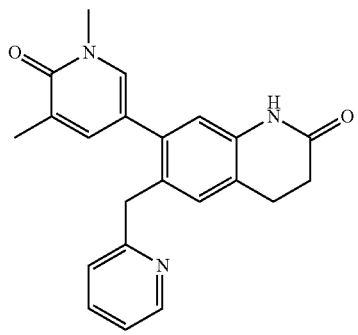

Compound 32

Step 1: Preparation of 7-chloro-6-(pyridin-2-ylmethyl)-3,4-dihydroquinolin-2(1H)-one

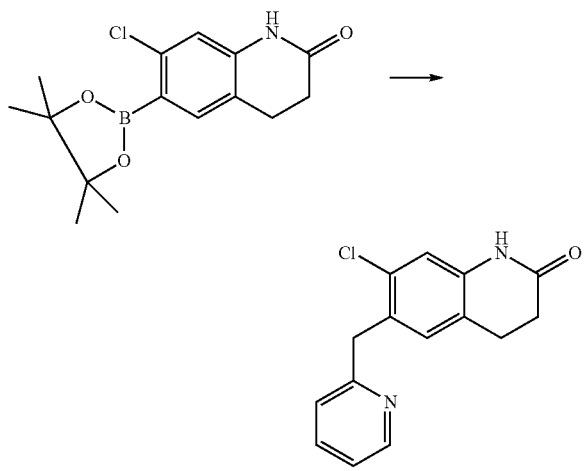

A stirred solution of 7-chloro-6-(4,4,5,5-tetramethyl-1,3,2-dioxaborolan-2-yl)-3,4-dihydroquinolin-2(1H)-one (0.2 g, 0.65 mmol, prepared according to step 1 of Example 73) and 2-(bromomethyl)pyridine hydrobromide (0.24 g, 0.97 mmol) in 1,4-dioxane (4 mL) was purged with $N_2$ for 10 min. A solution of $Cs_2CO_3$ (0.63 g, 1.95 mmol) in water (1.5 mL) was then added and the mixture was further purged with $N_2$ for 10 min. PdCl$_2$(dppf).CH$_2$Cl$_2$ (0.027 g, 0.03 mmol) was added and the reaction mixture was heated at 100° C. for 3 h. The solvent was evaporated under vacuum and the product was extracted using EtOAc (10 mL×3). The combined organic layers were washed with water (20 mL) and brine solution (20 mL), dried over anhydrous $Na_2SO_4$, filtered and evaporated to afford a crude product, which was purified by flash chromatography using 3% methanol in DCM as eluent. The pure product fractions were collected and evaporated to afford title compound (0.06 g, 34%) as a solid. MS (ESI) [M+H]$^+$ 273.1.

Step 2: Preparation of 7-(1,5-dimethyl-6-oxo-1,6-dihydropyridin-3-yl)-6-(pyridin-2-ylmethyl)-3,4-dihydroquinolin-2(1H)-one

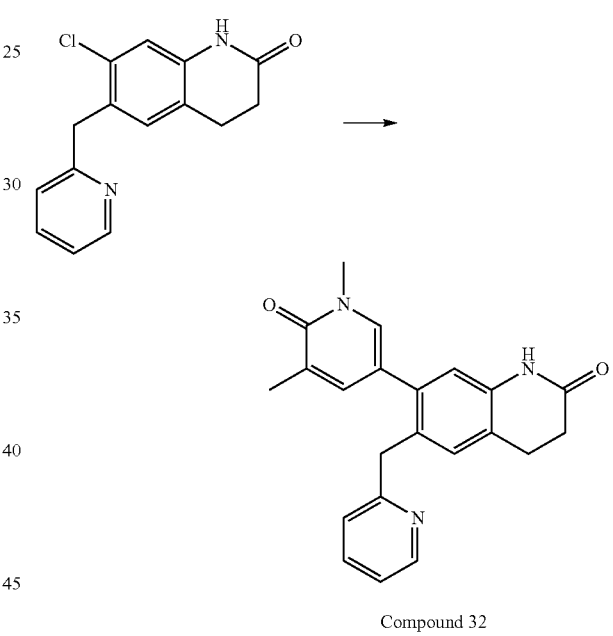

Compound 32

A stirred solution of 7-chloro-6-(pyridin-2-ylmethyl)-3,4-dihydroquinolin-2(1H)-one (0.06 g, 0.22 mmol) and 1,3-dimethyl-5-(4,4,5,5-tetramethyl-1,3,2-dioxaborolan-2-yl)pyridin-2(1H)-one (0.082 g, 0.33 mmol, prepared using procedure described in US20130053362) in 1,4-dioxane (1 mL) was purged with $N_2$ for 10 min. A solution of $K_3PO_4$ (0.14 g, 0.66 mmol) in water (0.5 mL) was then added and the mixture was further purged with $N_2$ for 10 min. Pd(t-$Bu_3$P)$_2$ (0.005 g, 0.01 mmol) was then added and the reaction mixture was heated at 150° C. in microwave for 8 h. The solvent was evaporated under vacuum and the product was extracted using EtOAc (10 mL×3). The combined organic layers were washed with water (15 mL) and brine solution (15 mL), dried over anhydrous $Na_2SO_4$, filtered and evaporated to afford a crude product, which was purified by flash chromatography using 5% methanol in DCM as eluent, followed by preparative HPLC purification using 35-70% IPA: Methanol (1:1) in n-hexane to afford Compound 32 (0.025 g, 32%) as a solid. $^1$H NMR (400

MHz, MeOD) δ ppm 8.38 (d, J=4.4 Hz, 1H), 7.69 (dt, J=7.6, 1.6 Hz, 1H), 7.31 (d, J=2.0 Hz, 1H), 7.23 (t, J=6.0 Hz, 1H), 7.17 (d, J=1.2 Hz, 1H), 7.16 (s, 1H), 7.05 (d, J=8.0 Hz, 1H), 6.74 (s, 1H), 4.10 (s, 2H), 3.54 (s, 3H), 2.98 (t, J=7.4 Hz, 2H), 2.60 (t, J=7.6 Hz, 2H), 2.07 (s, 3H), —NH was not visible. MS (ESI) [M+H]+ 360.3.

Example 30: 6-((cyclopentyloxy)methyl)-7-(1,5-dimethyl-6-oxo-1,6-dihydropyridin-3-yl)-3,4-dihydroquinolin-2(1H)-one Compound 34

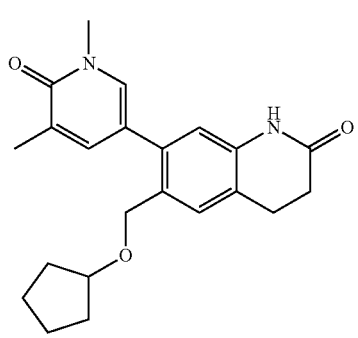

Step 1a: Preparation of N-(4-bromo-3-chlorophenyl)-3-chloropropanamide

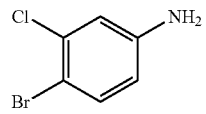 

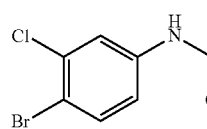

3-chloropropanoyl chloride (4.1 mL, 42.38 mmol) was added dropwise to stirred a solution of 4-bromo-3-chloroaniline (7 g, 206.47 mmol) and K₂CO₃ (7 g, 50.85 mmol) in a mixture of acetone (20 mL) and water (40 mL) at 5° C. and the reaction mixture was allowed to stir for 30 min at same temperature. Then, the reaction mixture was transferred into water (200 mL) and extracted with ethyl acetate (100 mL×3). The combined ethyl acetate layers were washed with water (200 mL), dried over anhydrous Na₂SO₄, filtered and evaporated under pressure to afford title compound (10 g, 99%) as an oil. MS (ESI) [M+H]+ 294, 296.

Step 1b: Preparation of 6-bromo-7-chloro-3,4-dihydroquinolin-2(1H)-one

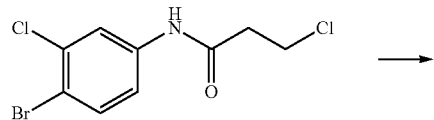

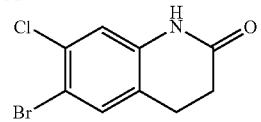

A fine powder of AlCl₃ (9 g, 67.34 mmol) was added at rt to N-(4-bromo-3-chlorophenyl)-3-chloropropanamide (10 g, 33.67 mmol) and the mixture was heated under stirring at 140° C. for 6 h. Then, the reaction mixture was carefully transferred into cold water (500 L) and extracted with ethyl acetate (200 mL×3). The combined ethyl acetate layers were washed with water (500 mL), dried over anhydrous Na₂SO₄, filtered and evaporated to afford a crude product, which was purified by silica gel column chromatography using 4% ethyl acetate in hexanes as eluent. The pure product fractions were collected and evaporated to afford title compound (1.7 g, 19%) as a solid. ¹H NMR (400 MHz, DMSO) δ ppm 10.27 (s, 1H) 7.59 (s, 1H), 7.02 (s, 1H), 2.88 (t, J=7.6 Hz, 2H), 2.45 (t, J=8 Hz, 2H, merge with DMSO). MS (ESI) [M+H]+ 259.98.

Step 2: Preparation of 7-chloro-6-((cyclopentyloxy)methyl)-3,4-dihydroquinolin-2(1H)-one

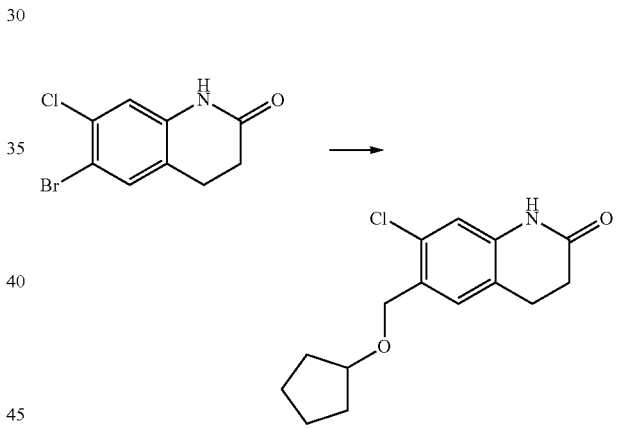

A stirred solution of 6-bromo-7-chloro-3,4-dihydroquinolin-2(1H)-one (0.5 g, 1.9 mmol) and potassium ((cyclopentyloxy)methyl)trifluoroborate (0.47 g, 2.3 mmol, prepared according to step 1a of Example 31) in dioxane (8 mL) was purged with N₂ for 10 min. A solution of Cs₂CO₃ (1.85 g, 5.7 mmol) in water (2 mL) was then added and the mixture was further purged with N₂ for 10 min. PdCl₂(dppf).DCM (0.077 g, 0.095 mmol) was then added and the reaction mixture was heated at 100° C. for 16 h. After completion of reaction, the mixture was diluted with EtOAc (100 mL), washed with water (100 mL) and brine solution (100 mL), dried over anhydrous Na₂SO₄, filtered and evaporated to afford a crude product, which was purified by silica gel column chromatography using a gradient of 10-100% EtOAc in hexane as eluent. The pure product fractions were collected and evaporated under reduced pressure to afford title compound (0.4 g, 79%) as a solid. MS (ESI) [M+H]+ 280.

119

Step 3: Preparation of 6-((cyclopentyloxy)methyl)-7-(1,5-dimethyl-6-oxo-1,6-dihydropyridin-3-yl)-3,4-dihydroquinolin-2(1H)-one

120

Example 31: 8-((cyclopentyloxy)methyl)-7-(1,5-dimethyl-6-oxo-1,6-dihydropyridin-3-yl)-3,4-dihydroquinolin-2(1H)-one

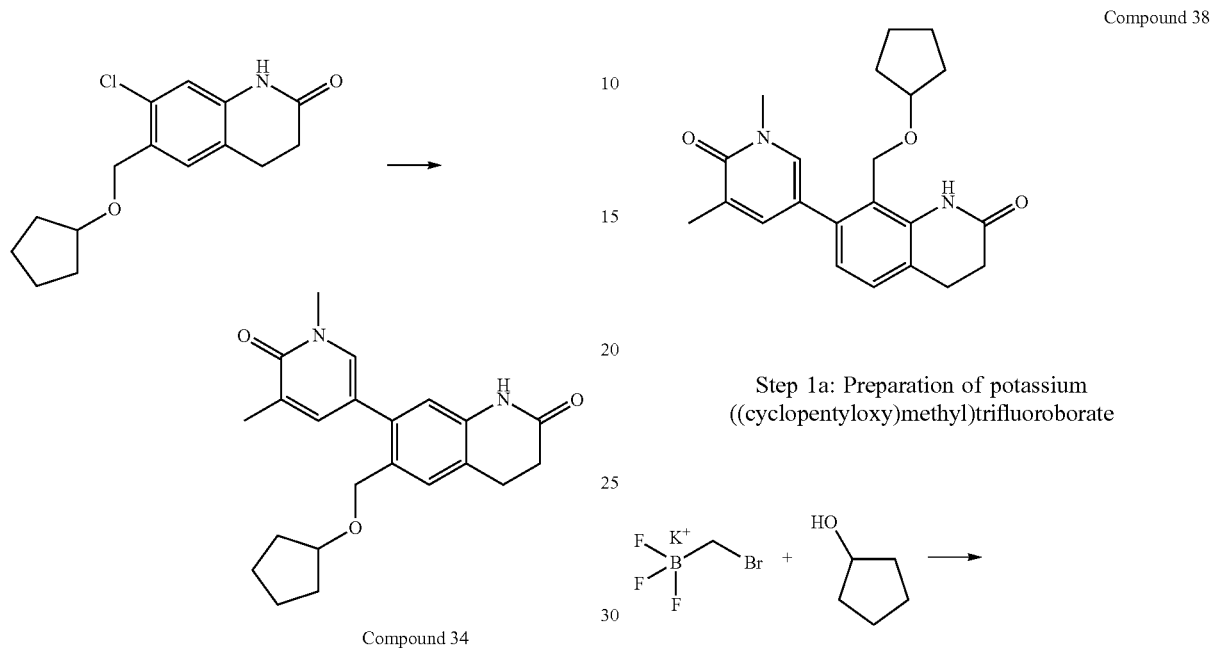

Compound 38

Compound 34

A stirred solution of 7-chloro-6-((cyclopentyloxy)methyl)-3,4-dihydroquinolin-2(1H)-one (0.4 g, 1.4 mmol) and 1,3-dimethyl-5-(4,4,5,5-tetramethyl-1,3,2-dioxaborolan-2-yl)pyridin-2(1H)-one (0.53 g, 2.1 mmol, prepared using procedure described in US20130053362) in 1,4-dioxane (8 mL) was purged with $N_2$ for 10 min. A solution of $K_3PO_4$ (0.89 g, 4.2 mmol) in water (2 mL) was then added and the mixture was further purged with $N_2$ for 10 min. $Pd(t-Bu_3P)_2$ (0.03 g, 0.07 mmol) was added and the reaction mixture was heated at 150° C. in microwave for 6 h. The solvent was evaporated under vacuum and the product was extracted using EtOAc (50 mL×3). The combined organic layers were washed with water (50 mL) and brine solution (50 mL), dried over anhydrous $Na_2SO_4$, filtered and evaporated to afford a crude product, which was purified by flash chromatography using a gradient of 2.5-3% methanol in DCM as eluent, followed by preparative HPLC purification using 35-40% acetonitrile in water containing 0.1% formic acid as modifier to afford Compound 34 (0.012 g, 2%) as a solid. $^1$H NMR (400 MHz, MeOD) δ 7.58 (s, 1H), 7.51 (s, 1H), 7.29 (s, 1H), 6.77 (s, 1H), 4.27 (s, 2H), 3.98-3.97 (m, 1H), 3.64 (s, 3H), 3.00 (t, J=14 Hz, 2H), 2.61 (t, J=14 Hz, 2H), 2.18 (s, 3H), 1.76-1.56 (m, 8H). MS (ESI) [M+H]$^+$ 367.3.

Step 1a: Preparation of potassium ((cyclopentyloxy)methyl)trifluoroborate

To a stirred solution of 60% NaH in mineral oil (0.54 g, 22.00 mmol) in THF (15 mL) was added cyclopentanol (1.94 g, 22.00 mmol) at 0° C. The mixture was stirred at 0° C. for 15 min and at rt for 30 min. Potassium(bromomethyl)trifluoroborate (1.5 g, 7.5 mmol) was added at 0° C. to the mixture which was then stirred at rt for 20 h. The mixture was then quenched with 4.5 M $KHF_2$ (15 mL) and the solution was stirred at rt for 30 min. The reaction mixture was evaporated under reduced pressure and dried under vacuum to obtain a crude compound. The crude compound was suspended in diethyl ether (20 mL) and filtered to remove organic impurities and the resulting solid was suspended in acetone (30 mL) and filtered to remove further inorganic impurities. The organic phase was then evaporated to afford title compound (1.0 g, 65%) as a solid. $^1$H NMR (400 MHz, DMSO) δ ppm 3.58-3.54 (m, 1H), 2.40 (dd, J=5.6 Hz and 5.2 Hz, 2H), 1.59-1.46 (m, 6H), 1.43-1.38 (m, 2H).

Step 1b: Preparation of 7-chloro-8-((cyclopentyloxy)methyl)-3,4-dihydroquinolin-2(1H)-one

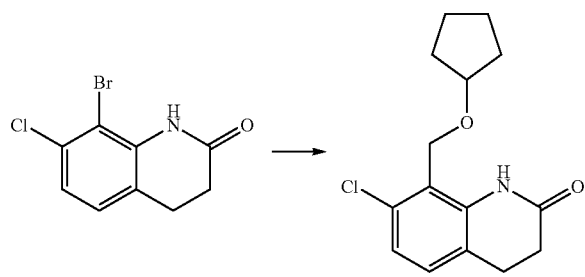 [SMILES: O=C1CCc2ccc(Cl)c(Br)c2N1 ; O=C1CCc2ccc(Cl)c(COC3CCCC3)c2N1]

A stirred solution of 8-bromo-7-chloro-3,4-dihydroquinolin-2(1H)-one (0.3 g, 1.15 mmol, prepared according to step 2 of Example 27) and potassium ((cyclopentyloxy)methyl)trifluoroborate (0.28 g, 1.38 mmol) in 1,4-dioxane (6 mL) was purged with $N_2$ for 10 min. A solution of cesium carbonate (1.1 g, 3.46 mmol) in water (0.5 mL) was then added and the mixture was further purged with $N_2$ for 10 min. PdCl$_2$(dppf).DCM (0.047 g, 0.057 mmol) was then added and the reaction mixture was heated at 90° C. for 12 h. After completion of the reaction, the solvent was evaporated under vacuum and the product was extracted using EtOAc (25 mL×3). The combined organic layers were washed with water (20 mL), brine (20 mL), dried over anhydrous Na$_2$SO$_4$, filtered and evaporated to afford a crude product, which was purified by silica gel column chromatography using 25% EtOAc in hexane as eluent to afford title compound (0.17 g, 43%) as a solid. MS (ESI) [M+H]$^+$ 280.2.

Step 2: Preparation of 8-((cyclopentyloxy)methyl)-7-(1,5-dimethyl-6-oxo-1,6-dihydropyridin-3-yl)-3,4-dihydroquinolin-2(1H)-one

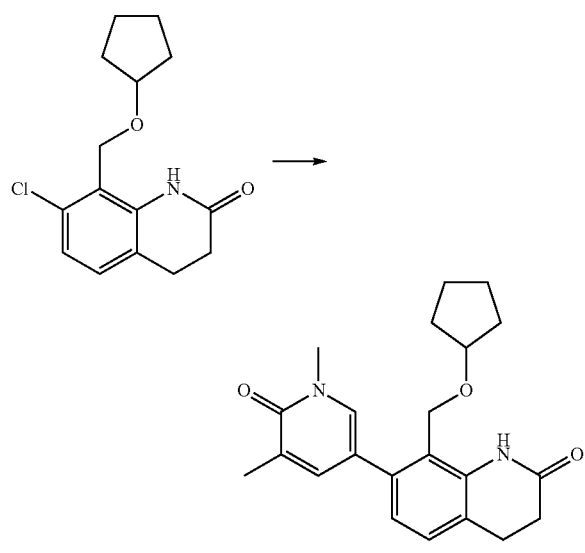

Compound 38

A stirred solution of 7-chloro-8-((cyclopentyloxy)methyl)-3,4-dihydroquinolin-2(1H)-one (0.17 g, 0.61 mmol) and 1,3-dimethyl-5-(4,4,5,5-tetramethyl-1,3,2-dioxaborolan-2-yl)pyridin-2(1H)-one (0.18 g, 0.73 mmol, prepared using procedure described in US20130053362) in 1,4-dioxane (4 mL) was purged with $N_2$ for 10 min. A solution of potassium phosphate (0.39 g, 1.83 mmol) in water (0.4 mL) was then added and the mixture was further purged with $N_2$ for 10 min. Pd(t-Bu$_3$P)$_2$ (0.016 g, 0.03 mmol) was then added and the reaction mixture was heated at 90° C. for 10 h. After completion of the reaction, the solvent was evaporated under vacuum and the product was extracted using EtOAc (20 mL×3). The combined organic layers were washed with water (20 mL), brine (20 mL), dried over anhydrous Na$_2$SO$_4$, filtered and evaporated to afford a crude product, which was purified by silica gel column chromatography using 3% methanol in DCM as eluent to afford Compound 38 (0.075 g, 33%) as a solid. $^1$H NMR (400 MHz, DMSO) δ ppm 8.90 (s, 1H), 7.53 (d, J=2 Hz, 1H), 7.28 (t, J=2.4 Hz, 1H), 7.20 (d, J=7.6 Hz, 1H), 6.85 (d, J=7.6 Hz, 1H), 4.37 (s, 2H), 3.99-3.98 (m, 1H), 3.47 (s, 3H), 2.92 (t, J=7.4 Hz, 2H), 2.50 (m, 2H), 2.04 (s, 3H), 1.61-1.50 (m, 8H). MS (ESI) [M+H]$^+$ 367.3.

Example 32: 8-(cyclobutoxymethyl)-7-(1,5-dimethyl-6-oxo-1,6-dihydropyridin-3-yl)-3,4-dihydroquinolin-2(1H)-one

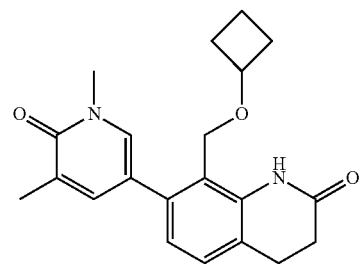

Compound 39

Step 1a: Preparation of potassium (cyclobutoxymethyl)trifluoroborate

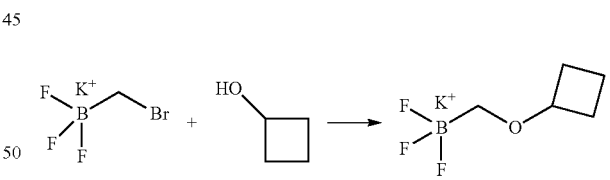

To a stirred solution of 60% NaH in paraffin (0.36 g, 15.00 mmol) in THF (10 mL) was added cyclobutanol (1.1 g, 15.00 mmol) at 0° C. The mixture was stirred for 15 min at 0° C. and at rt for 30 min. Potassium (bromomethyl)trifluoroborate (1.0 g, 5.00 mmol) was then added at 0° C. and the mixture further stirred at rt for 20 h. Then, the mixture was quenched with 4.5 M KHF$_2$ (10 mL) and the solution was stirred at rt for 30 min. The reaction mixture was then evaporated under reduced pressure and dried under vacuum to obtain a product which was suspended in diethyl ether (15 mL) and filtered to remove organic impurities. The resulting solid was suspended in acetone (20 mL) and filtered to remove further inorganic impurities. The organic phase was then evaporated to afford title compound (0.28 g, 29%) as a solid. $^1$H NMR (400 MHz, DMSO) δ ppm 3.65-3.58 (m, 1H), 2.38 (dd, J=5.6 and 5.2 Hz, 2H), 2.07-2.00 (m, 2H), 1.73-1.63 (m, 2H), 1.58-1.50 (m, 1H), 1.42-1.33 (m, 1H).

Step 1 b: Preparation of 7-chloro-8-(cyclobutoxymethyl)-3,4-dihydroquinolin-2(1H)-one

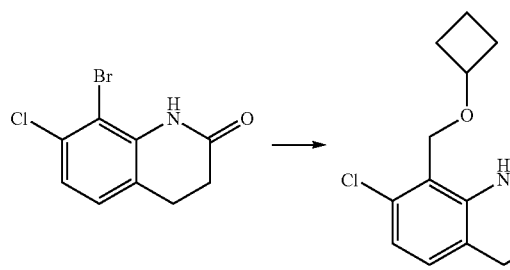

A stirred solution of 8-bromo-7-chloro-3,4-dihydroquinolin-2(1H)-one (0.15 g, 0.58 mmol, prepared according to step 2 of Example 27) and potassium (cyclobutoxymethyl)trifluoroborate (0.13 g, 0.69 mmol) in 1,4-dioxane (3 mL) was purged with N₂ for 10 min. A solution of cesium carbonate (0.57 g, 1.74 mmol) in water (0.3 mL) was then added and the mixture was further purged with N₂ for 10 min. PdCl₂(dppf).DCM (0.024 g, 0.029 mmol) was then added and the reaction mixture was heated at 90° C. for 10 h. After completion of the reaction, the solvent was evaporated under vacuum and the product was extracted using EtOAc (15 mL×3). The combined organic layers were washed with water (15 mL), brine (15 mL), dried over anhydrous Na₂SO₄, filtered and evaporated to afford a crude product, which was purified by silica gel column chromatography using 20% EtOAc in hexane as eluent to afford title compound (0.15 g, 36%) as a solid. MS (ESI) [M+H]⁺ 266.1.

Step 2: Preparation of 8-(cyclobutoxymethyl)-7-(1,5-dimethyl-6-oxo-1,6-dihydro-pyridin-3-yl)-3,4-dihydroquinolin-2(1H)-one

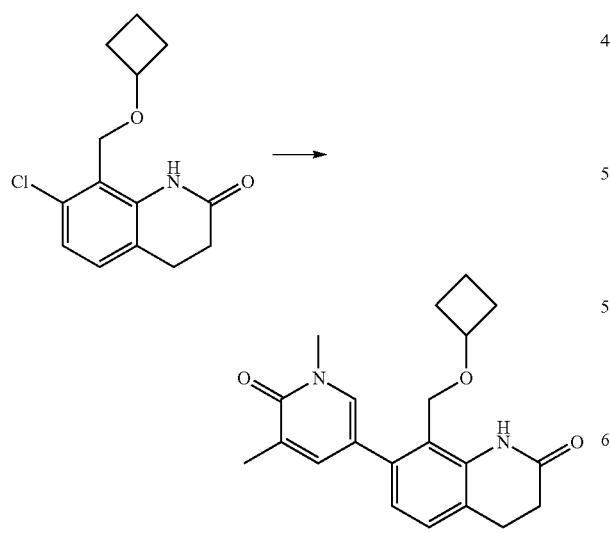

Compound 39

A stirred solution of 7-chloro-8-(cyclobutoxymethyl)-3,4-dihydroquinolin-2(1H)-one (0.15 g, 0.56 mmol) and 1,3-dimethyl-5-(4,4,5,5-tetramethyl-1,3,2-dioxaborolan-2-yl)pyridin-2(1H)-one (0.17 g, 0.68 mmol, prepared using procedure described in US20130053362) in 1,4-dioxane (3 mL) was purged with N₂ for 10 min. A solution of potassium phosphate (0.36 g, 1.70 mmol) in water (0.3 mL) was then added and the mixture was further purged with N₂ for 10 min. Pd(t-Bu₃P)₂ (0.015 g, 0.028 mmol) was then added and the reaction mixture was heated at 90° C. for 12 h. After completion of the reaction, the solvent was evaporated under vacuum and the product was extracted using EtOAc (20 mL×3). The combined organic layers were washed with water (20 mL), brine (20 mL), dried over anhydrous Na₂SO₄, filtered and evaporated to afford a crude product, which was purified by silica gel column chromatography using 3% methanol in DCM as eluent to afford Compound 39 (0.010 g, 13%) as a solid. ¹H NMR (400 MHz, MeOD) δ ppm 7.52 (d, J=2.4 Hz, 1H), 7.42 (d, J=1.6 Hz, 1H), 7.25 (d, J=7.6 Hz, 1H), 6.95 (d, J=7.6 Hz, 1H), 4.42 (s, 2H), 4.04 (q, J=14.4 Hz, 1H), 3.64 (s, 3H), 3.02 (t, J=14.8 Hz, 2H), 2.63 (t, J=14.8 Hz, 2H), 2.23-2.16 (m, 5H), 2.01-1.91 (m, 2H), 1.78-1.73 (m, 1H), 1.60-1.53 (m, 1H), —NH was not visible. MS (ESI) [M+H]⁺ 353.2.

Example 33: 6-(1,5-dimethyl-6-oxo-1,6-dihydropyridin-3-yl)-8-(phenoxymethyl)-3,4-dihydroquinolin-2(1H)-one

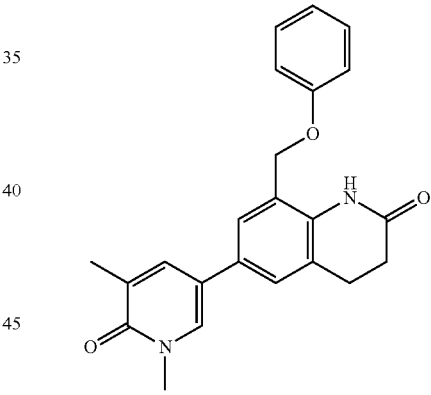

Compound 44

Step 1: Preparation of potassium trifluoro(phenoxymethyl)borate

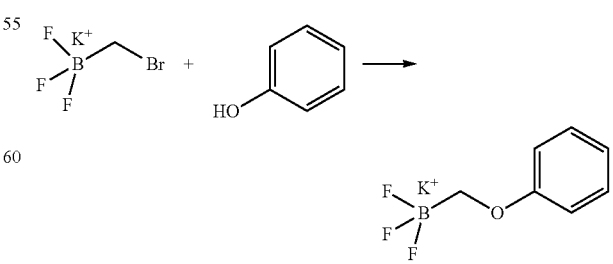

To a stirred solution of 60% NaH in paraffin (0.6 g, 14.9 mmol) in THF (6 mL) was added phenol (1.4 g, 14.9 mmol)

at 0° C. The mixture was stirred at 0° C. for 15 min and at rt for 30 min. Potassium (bromomethyl)trifluoroborate (1 g, 4.98 mmol) was then added at 0° C. and the mixture was stirred at rt for 20 h. The mixture was then quenched with 4.5 M KHF₂ (10 mL) and the solution was stirred at rt for 30 min. The reaction mixture was evaporated under reduced pressure and dried under vacuum to obtain a product, which was suspended in diethyl ether (10 mL) and filtered to remove organic impurities. The resulting solid was suspended in acetone (20 mL) and filtered to remove further inorganic impurities. The organic phase was then evaporated to afford title compound (0.6 g, 56%) as a solid. ¹H NMR (400 MHz, DMSO) δ ppm 7.21-7.16 (m, 2H), 6.84-6.82 (dd, J=0.8 and 0.9 Hz, 2H), 6.76 (t, J=7.2 Hz, 1H), 2.93 (q, J=5.2 Hz, 2H).

Step 2: Preparation of 6-(1,5-dimethyl-6-oxo-1,6-dihydropyridin-3-yl)-8-(phenoxy-methyl)-3,4-dihydroquinolin-2(1H)-one

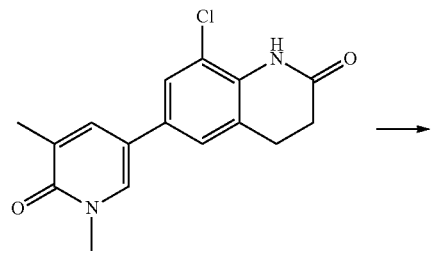

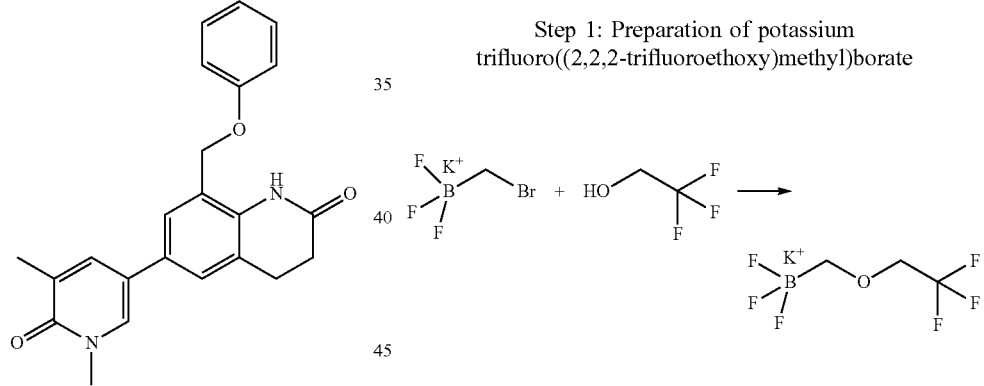

Compound 44

A stirred solution of Intermediate 1 (0.15 g, 0.49 mmol) and potassium trifluoro(phenoxymethyl)borate (0.22 g, 0.99 mmol) in THF (3 mL) was purged with N₂ for 10 min. A solution of Cs₂CO₃ (0.48 g, 1.47 mmol) in water (0.3 mL) was then added and the mixture was further purged with N₂ for 10 min. Pd(OAc)₂ (0.033 g, 0.15 mmol) and X-phos (0.12 g, 0.24 mmol) were then added and the reaction mixture was heated at 100° C. for 16 h. The reaction mixture was then diluted with EtOAc (100 mL), washed with water (100 mL) and brine solution (100 mL), dried over anhydrous Na₂SO₄, filtered and evaporated to afford a crude product, which was purified by preparative HPLC purification using 35-45% ACN: Water and using 0.1% formic acid as a modifier to afford Compound 44 (0.01 g, 6%) as a solid. ¹H NMR (400 MHz, DMSO) δ ppm 9.66 (s, 1H), 7.95 (d, J=2 Hz, 1H), 7.72 (s, 1H), 7.53 (d, J=1.6 Hz, 1H), 7.44 (s, 1H), 7.32 (t, J=7.6 Hz, 2H), 7.06 (d, J=8 Hz, 2H), 6.96 (t, J=7.2 Hz, 1H), 5.16 (s, 2H), 3.50 (s, 3H), 2.95 (t, J=7.2 Hz, 2H), 2.50 (t, merge with DMSO, 2H), 2.07 (s, 3H). MS (ESI) [M+H]⁺ 375.2.

Example 34: 6-(1,5-dimethyl-6-oxo-1,6-dihydro-pyridin-3-yl)-8-((2,2,2-trifluoro-ethoxy)methyl)-3,4-dihydroquinolin-2(1H)-one Compound 46

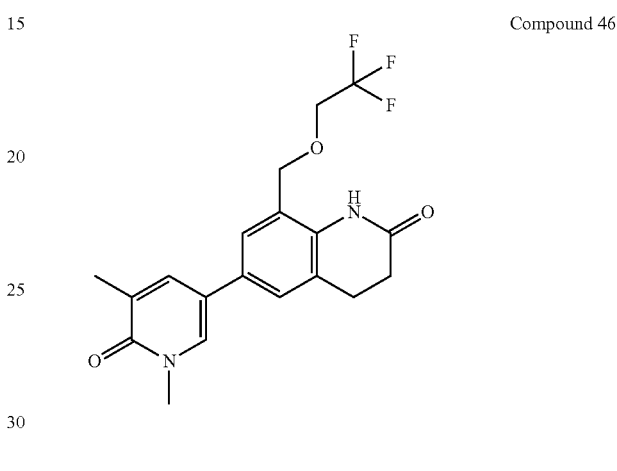

Step 1: Preparation of potassium trifluoro((2,2,2-trifluoroethoxy)methyl)borate

To a stirred solution of 60% NaH in paraffin (0.3 g, 7.47 mmol) in THF (5 mL) was added 2,2,2-trifluoroethan-1-ol (0.5 g, 2.49 mmol) at 0° C. The mixture was stirred at 0° C. for 15 min and at rt for 30 min. Potassium (bromomethyl)trifluoroborate (0.75 g, 7.47 mmol) was then added at 0° C. and the mixture was stirred at rt for 20 h. The reaction mixture was then quenched with 4.5 M KHF₂ (5 mL) and the solution was stirred at rt for 30 min. The mixture was then evaporated under reduced pressure and dried under vacuum. The crude product was suspended in diethyl ether (10 mL) and filtered to remove organic impurities. The resulting product was suspended in acetone (20 mL) and filtered to remove further inorganic impurities. The organic phase was then evaporated to afford title compound (0.5 g, 91%) as a solid. ¹H NMR (400 MHz, DMSO) δ ppm 3.75 (q, J=9.6 Hz, 2H), 2.71 (q, J=5.2 Hz, 2H).

Step 2: Preparation of 6-(1,5-dimethyl-6-oxo-1,6-dihydropyridin-3-yl)-8-((2,2,2-trifluoroethoxy)methyl)-3,4-dihydroquinolin-2(1H)-one

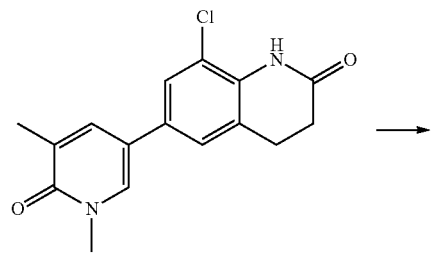

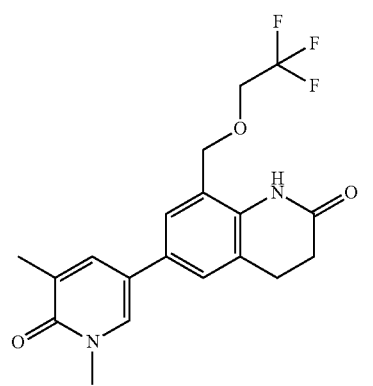

Compound 46

A stirred solution of Intermediate 1 (0.1 g, 0.33 mmol) and potassium trifluoro((2,2,2-trifluoroethoxy)methyl)borate (0.15 g, 0.66 mmol) in THF (3 mL) was purged with $N_2$ for 10 min. A solution of $Cs_2CO_3$ (0.32 g, 0.99 mmol) in water (0.3 mL) was then added and the mixture was further purged with $N_2$ for 10 min. Pd(OAc)$_2$ (0.023 g, 0.099 mmol) and X-phos (0.08 g, 0.165 mmol) were then added and the reaction mixture was heated at 100° C. for 16 h. The reaction mixture was then diluted with EtOAc (100 mL), washed with water (100 mL) and brine solution (100 mL), dried over anhydrous $Na_2SO_4$, filtered and evaporated to afford a crude product, which was purified by flash chromatography using 2% methanol in DCM as eluent. The pure product fractions were collected and evaporated to afford Compound 46 (0.056 g, 45%) as a solid. $^1$H NMR (400 MHz, DMSO) δ ppm 9.34 (s, 1H), 7.94 (s, 1H), 7.72 (s, 1H), 7.43 (s, 1H), 7.37 (s, 1H), 4.74 (s, 2H), 4.12 (t, J=9.8 Hz, 2H), 3.50 (s, 3H), 2.93 (t, J=7.2 Hz, 2H), 2.47 (s, 2H), 2.07 (s, 3H). MS (ESI) [M+H]$^+$ 381.5.

Example 35: 6-(1,5-dimethyl-6-oxo-1,6-dihydropyridin-3-yl)-8-(((tetrahydro-2H-pyran-4-yl)oxy)methyl)-3,4-dihydroquinolin-2(1H)-one

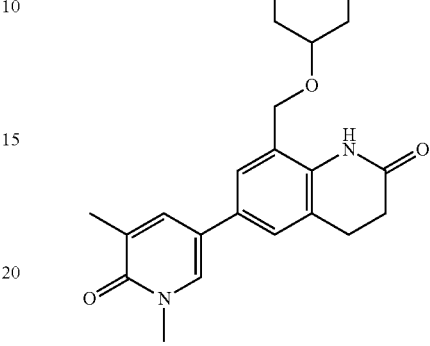

Compound 47

Step 1: Preparation of potassium trifluoro(((tetrahydro-2H-pyran-4-yl)oxy)methyl)borate

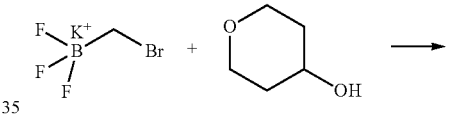

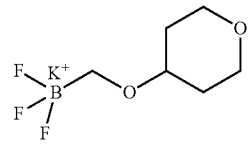

To a stirred solution of 60% NaH in paraffin (0.3 g, 7.47 mmol) in THF (2 mL) was added tetrahydro-2H-pyran-4-ol (0.5 g, 2.49 mmol) at 0° C. The mixture was stirred at 0° C. for 15 min and at rt for 30 min. Potassium (bromomethyl)trifluoroborate (0.77 g, 7.47 mmol) was then added at 0° C. and the mixture stirred at rt for 20 h. The reaction mixture was then quenched with 4.5 M KHF$_2$ (5 mL) and the solution was stirred at rt for 30 min. The mixture was evaporated under reduced pressure and dried under vacuum. The crude product was suspended in diethyl ether (10 mL) and filtered to remove organic impurities. The resulting solid was suspended in acetone (20 mL) and filtered to remove further inorganic impurities. The organic phase was then evaporated to afford title compound (0.28 g, 51%) as a solid. $^1$H NMR (400 MHz, DMSO) δ ppm 3.80-3.75 (m, 2H), 3.28-3.22 (m, 2H), 3.14-3.10 (m, 1H), 2.48-2.46 (m, 2H), 1.79 (d, J=12.8 Hz, 2H), 1.30-1.21 (m, 2H).

Step 2: Preparation of 6-(1,5-dimethyl-6-oxo-1,6-dihydropyridin-3-yl)-8-(((tetrahydro-2H-pyran-4-yl)oxy)methyl)-3,4-dihydroquinolin-2(1H)-one

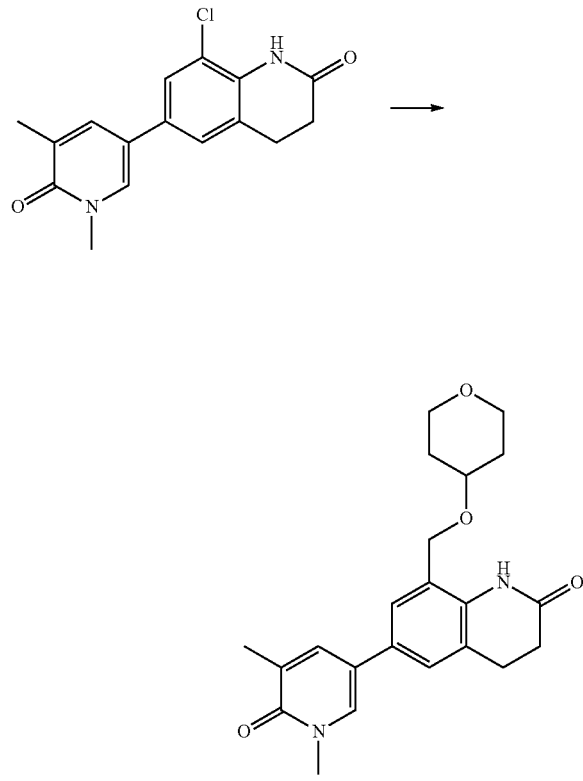

Compound 47

A stirred solution of Intermediate 1 (0.18 g, 0.59 mmol) and potassium trifluoro(((tetrahydro-2H-pyran-4-yl)oxy)methyl)borate (0.27 g, 1.19 mmol) in THF (3 mL) was purged with $N_2$ for 10 min. A solution of $Cs_2CO_3$ (0.58 g, 1.8 mmol) in water (1 mL) was then added and the mixture was further purged with $N_2$ for 10 min. $Pd(OAc)_2$ (0.04 g, 0.18 mmol) and X-phos (0.14 g, 0.29 mmol) were then added and the reaction mixture was heated at 100° C. for 16 h. After completion of reaction, the reaction mixture was diluted with EtOAc (100 mL), washed with water (100 mL) and brine solution (100 mL), dried over anhydrous $Na_2SO_4$, filtered and evaporated to afford a crude product, which was purified by preparative HPLC purification using 15-65% ACN: Water and 0.1% formic acid as a modifier to afford Compound 47 (0.034 g, 15%) as a solid. $^1$H NMR (400 MHz, DMSO) δ ppm 9.08 (s, 1H), 7.92 (s, 1H), 7.70 (s, 1H), 7.38 (s, 1H), 7.37 (s, 1H), 4.64 (s, 2H), 3.84-3.79 (m, 2H), 3.65-3.60 (m, 1H), 3.35-3.37 (m, 5H), 2.93 (t, J=6.8 Hz, 2H), 2.93 (t, J=6.8 Hz, 2H), 2.07 (s, 3H), 1.93-1.89 (m, 2H), 1.51-1.42 (m, 2H). MS (ESI) [M+H]$^+$ 383.5.

Example 36: 6-(1,5-dimethyl-6-oxo-1,6-dihydropyridin-3-yl)-8-(((tetrahydro-2H-pyran-3-yl)oxy)methyl)-3,4-dihydroquinolin-2(1H)-one Compounds 48a and 48b

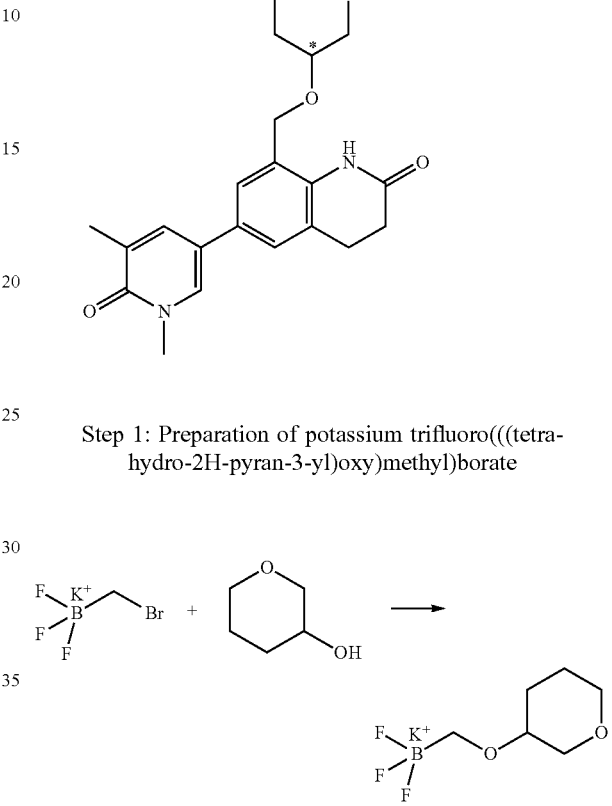

Step 1: Preparation of potassium trifluoro(((tetrahydro-2H-pyran-3-yl)oxy)methyl)borate To a stirred solution of 60% NaH in paraffin (0.51 g, 12.7 mmol) in THF (5 mL) was added tetrahydro-2H-pyran-3-ol (1.3 g, 12.7 mmol) at 0° C. The mixture was stirred at 0° C. for 15 min and at rt for 30 min. Potassium(bromomethyl)trifluoroborate (0.85 g, 4.23 mmol) was then added at 0° C. and the mixture was stirred at rt for 20 h. The reaction mixture was then quenched with 4.5 M $KHF_2$ solution (10 mL) and stirred at rt for 30 min. Then, the reaction mixture was evaporated under reduced pressure and dried under vacuum. The crude product was suspended in diethyl ether (10 mL) and filtered to remove organic impurities and the resulting solid was suspended in acetone (20 mL) and filtered to remove further inorganic impurities. The organic phase was then evaporated to afford title compound (0.8 g, 85%) as a solid. $^1$H NMR (400 MHz, DMSO) δ ppm 3.75 (d, J=9.2 Hz, 1H), 3.63-3.58 (m, 1H), 3.27-3.21 (m, 1H), 3.06-2.96 (m, 2H), 2.57 (m, 1H), 2.48-2.44 (m, merge with DMSO, 1H), 1.93-1.63 (m, 1H), 1.64-1.58 (m, 1H), 1.42-1.37 (m, 1H), 1.35-1.23 (m, 1H).

Step 2: Preparation of 6-(1,5-dimethyl-6-oxo-1,6-dihydropyridin-3-yl)-8-(((tetrahydro-2H-pyran-3-yl)oxy)methyl)-3,4-dihydroquinolin-2(1H)-one

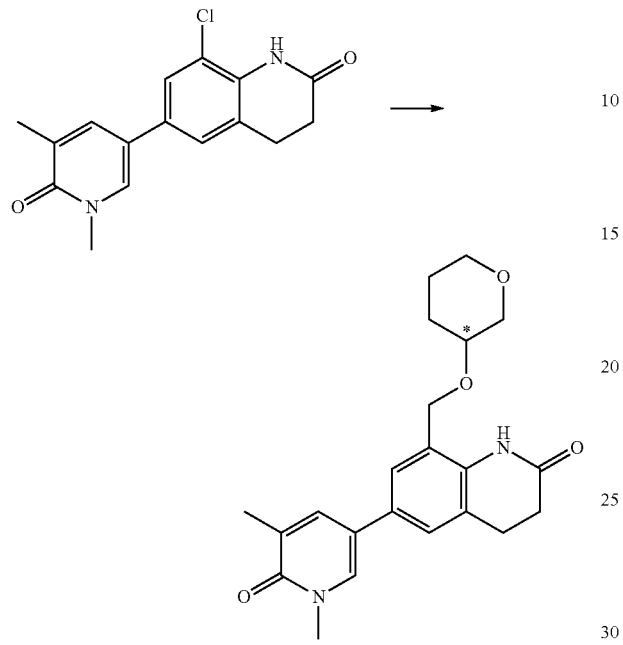

Compounds 48a and 48b

A stirred solution of Intermediate 1 (0.3 g, 0.99 mmol) and potassium trifluoro(((tetrahydro-2H-pyran-3-yl)oxy)methyl)borate (0.45 g, 1.98 mmol) in THF (5 mL) was purged with $N_2$ for 10 min. A solution of $Cs_2CO_3$ (0.97 g, 2.97 mmol) in water (0.5 mL) was then added and the mixture was further purged with $N_2$ for 10 min. Pd(OAc)$_2$ (0.033 g, 0.15 mmol) and X-phos (0.28 g, 0.59 mmol) were then added and the reaction mixture was heated at 100° C. for 16 h. Then, the reaction mixture was diluted with EtOAc (100 mL), washed with water (100 mL) and brine solution (100 mL), dried over anhydrous $Na_2SO_4$, filtered and evaporated to afford a crude product, which was purified by preparative HPLC purification using 40-85% ACN: Methanol and 0.1% formic acid as a modifier to afford Compounds 48a and 48b as a racemic mixture (0.2 g). 0.2 g of the racemic mixture was further purified by chiral preparative HPLC purification (Daicel Chiralpak™ IC column, 250*21 mm, 5 microns, column flow 10 ml/min) using 5% of IPA:Methanol:DCM (30:50:20) in n-hexane using 0.1% DEA as a modifier to afford chirally pure Compounds 48a and 48b as two solids (Compound 48a: 0.055 g; Compound 48b: 0.03 g).

Compound 48a: Retention time=12.14 min: $^1$H NMR (400 MHz, DMSO) δ ppm 9.09 (s, 1H), 7.93 (d, J=2.4 Hz, 1H), 7.70 (d, J=1.6 Hz, 1H), 7.39 (s, 1H), 7.36 (d, J=2 Hz, 1H), 4.61 (q, J=6.4 Hz, 2H), 3.73 (d, J=9.2 Hz, 1H), 3.72-3.56 (m, 1H), 3.50 (s, 3H), 3.49-3.38 (m, 3H), 2.93 (t, J=7.2 Hz, 2H), 2.48 (m, 2H), 2.07 (s, 3H), 1.96-1.91 (m, 1H), 1.75-1.70 (m, 1H), 1.58-1.54 (m, 1H), 1.46-1.40 (m, 1H). MS (ESI) [M+H]$^+$ 383.3.

Compound 48b: Retention time=13.81 min: $^1$H NMR (400 MHz, DMSO) δ ppm 9.09 (s, 1H), 7.93 (d, J=2.4 Hz, 1H), 7.70 (d, J=1.6 Hz, 1H), 7.39 (s, 1H), 7.36 (d, J=2 Hz, 1H), 4.61 (q, J=6.4 Hz, 2H), 3.73 (d, J=9.2 Hz, 1H), 3.72-3.56 (m, 1H), 3.50 (s, 3H), 3.49-3.38 (m, 3H), 2.93 (t, J=7.2 Hz, 2H), 2.48 (m, 2H), 2.07 (s, 3H), 1.96-1.91 (m, 1H), 1.76-1.70 (m, 1H), 1.58-1.53 (m, 1H), 1.46-1.39 (m, 1H). MS (ESI) [M+H]$^+$ 383.3.

Example 37: 6-(1,5-dimethyl-6-oxo-1,6-dihydropyridin-3-yl)-8-(pyrazin-2-ylmethoxy)-3,4-dihydroquinolin-2(1H)-one

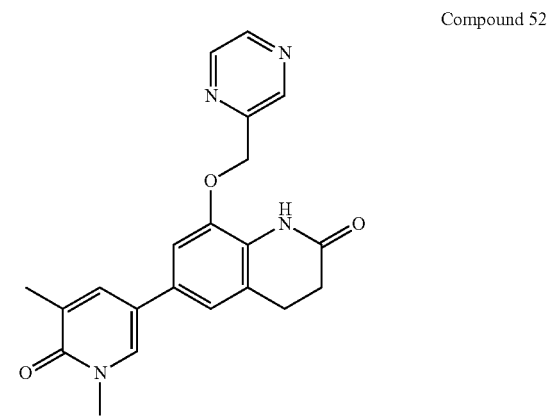 [SMILES: Cc1cc(-c2cc3c(c(OCc4cncnc4)c2)NC(=O)CC3)cn(C)c1=O]

Compound 52

Step 1: Preparation of 6-bromo-8-(pyrazin-2-ylmethoxy)-3,4-dihydroquinolin-2(1H)-one

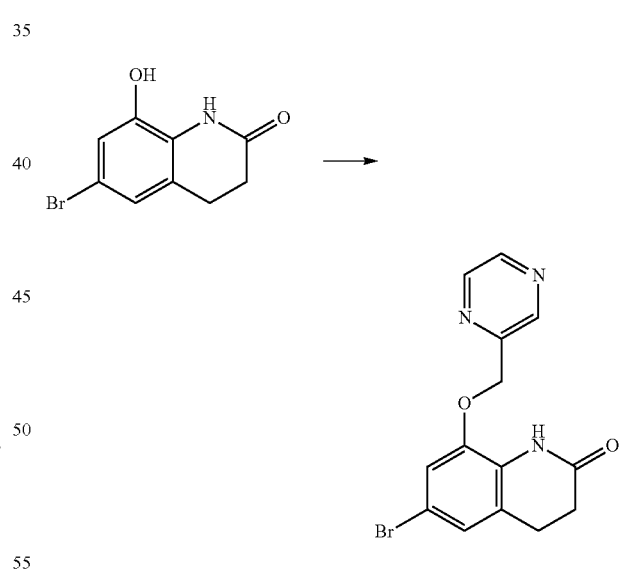

To a suspension of $K_2CO_3$ (0.43 g, 1.66 mmol) in DMF (3 mL), intermediate 3 (0.25 g, 1.03 mmol) was added and the mixture stirred at rt for 15 min. 2-(bromomethyl)pyrazine HBr salt (0.31 g, 1.24 mmol) was then added and the mixture stirred at 70° C. for 8 h. The mixture was then diluted with water (100 mL) and extracted with EtOAc (30 mL×3). The combined EtOAc layers were washed with brine (30 mL), dried over anhydrous $Na_2SO_4$, filtered and evaporated to afford title compound (0.29 g, 60%). MS (ESI) [M+H]$^+$ 334.09. The product was used in next step without further purification.

133

Step 2: Preparation of 6-(1,5-dimethyl-6-oxo-1,6-dihydropyridin-3-yl)-8-(pyrazin-2-ylmethoxy)-3,4-dihydroquinolin-2(1H)-one

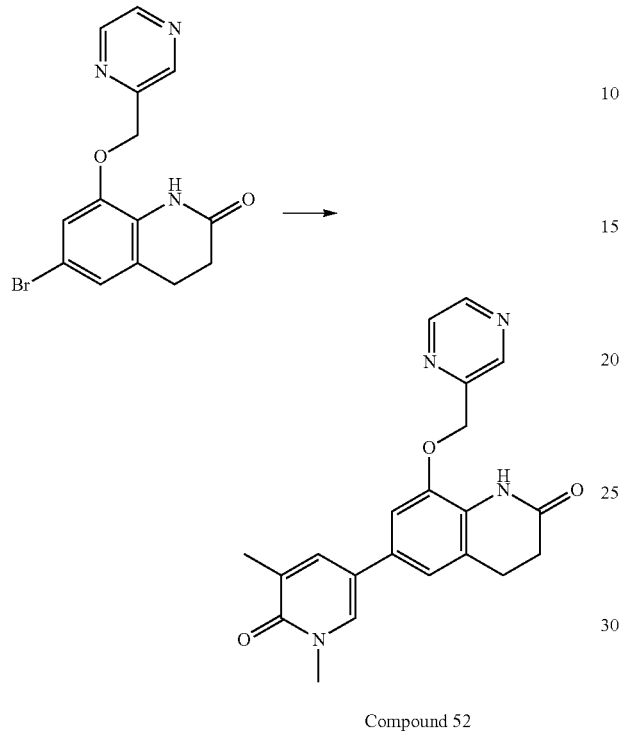

Compound 52

A stirred solution of 6-bromo-8-(pyrazin-2-ylmethoxy)-3,4-dihydroquinolin-2(1H)-one (0.21 g, 0.63 mmol) and 1,3-dimethyl-5-(4,4,5,5-tetramethyl-1,3,2-dioxaborolan-2-yl)pyridin-2(1H)-one (0.19 g, 0.75 mmol, prepared using procedure described in US20130053362) in 1,4-dioxane (3 mL) was purged with $N_2$ for 20 min. A solution of sodium carbonate (0.2 g, 1.89 mmol) in water (0.3 mL) was then added and the mixture was further purged with $N_2$ for 20 min. Pd(PPh$_3$)$_4$ (0.037 g, 0.031 mmol) was then added and the reaction mixture was heated at 90° C. for 6 h. Then, the reaction mixture was diluted with water (30 mL) and extracted with EtOAc (30 mL×3). The combined EtOAc layers were washed with brine (30 mL), dried over anhydrous Na$_2$SO$_4$, filtered and evaporated to afford a crude product, which was purified by silica gel column chromatography using a gradient of 3-5% methanol in DCM as eluent, followed by preparative HPLC purification using 20% acetonitrile in water containing 0.1% formic acid as modifier to afford Compound 52 (0.037 g, 16%) as a solid. $^1$H NMR (400 MHz, DMSO) δ 9.54 (s, 1H), 9.13 (s, 1H), 8.66 (d, J=5.6 Hz, 2H), 7.99 (d, J=2 Hz, 1H), 7.77 (s, 1H), 7.26 (s, 1H), 7.09 (s, 1H), 5.38 (s, 2H), 3.51 (s, 3H), 2.92 (t, J=7.2 Hz, 2H), 2.48 (m, 2H), 2.08 (s, 3H). MS (ESI) [M+H]$^+$ 377.29.

134

Example 38: 6-(1,5-dimethyl-6-oxo-1,6-dihydropyridin-3-yl)-8-(pyrimidin-5-ylmethoxy)-3,4-dihydroquinolin-2(1H)-one

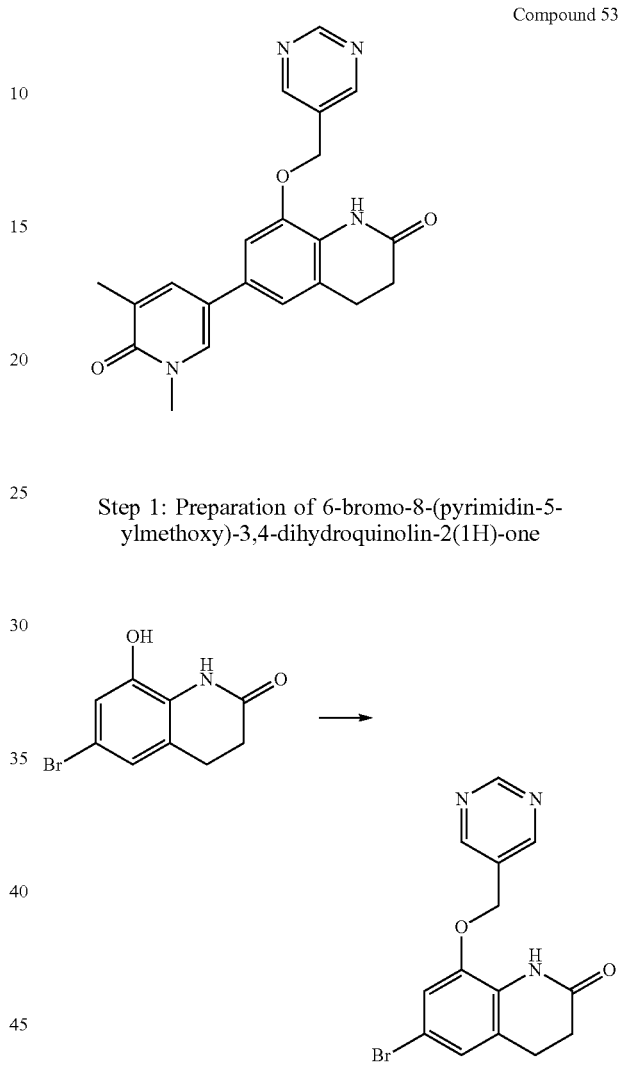

Compound 53

Step 1: Preparation of 6-bromo-8-(pyrimidin-5-ylmethoxy)-3,4-dihydroquinolin-2(1H)-one To a suspension of K$_2$CO$_3$ (0.35 g, 2.49 mmol) in DMF (4 mL), Intermediate 3 (0.2 g, 0.83 mmol) was added and the mixture stirred at rt for 15 min. Pyrimidin-5-ylmethyl methanesulfonate (0.31 g, 1.24 mmol) in DMF (1 mL) was then added dropwise and the reaction mixture was stirred at 50° C. for 16 h. After that time, the reaction mixture was diluted with water (100 mL) and extracted with EtOAc (30 mL×3). The combined EtOAc layers were washed with brine (30 mL), dried over anhydrous Na$_2$SO$_4$, filtered and evaporated to afford a crude product, which was purified by silica gel column chromatography using a gradient of 3-5% methanol in DCM as eluent. The product fractions were collected and evaporated to give title compound (0.23 g, 58%) as a solid. MS (ESI) [M+H]$^+$ 334.09.

135

Step 2: Preparation of 6-(1,5-dimethyl-6-oxo-1,6-dihydropyridin-3-yl)-8-(pyrimidin-5-ylmethoxy)-3,4-dihydroquinolin-2(1H)-one

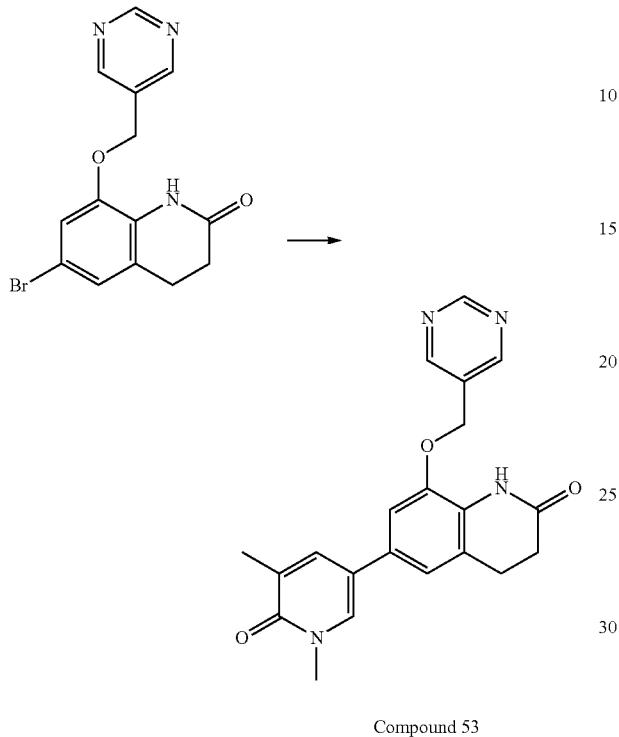

Compound 53

A stirred solution of 6-bromo-8-(pyrimidin-5-ylmethoxy)-3,4-dihydroquinolin-2(1H)-one (0.23 g, 0.69 mmol) and 1,3-dimethyl-5-(4,4,5,5-tetramethyl-1,3,2-dioxaborolan-2-yl)pyridin-2(1H)-one (0.21 g, 0.82 mmol, prepared using procedure described in US20130053362) in 1,4-dioxane (3 mL) was purged with N₂ for 20 min. A solution of sodium carbonate (0.22 g, 2.06 mmol) in water (0.3 mL) and was then added and the mixture was further purged with N₂ for 20 min. Pd(PPh₃)₄ (0.04 g, 0.034 mmol) was then added and the reaction mixture was heated at 90° C. for 16 h. After that time, the reaction mixture was diluted with water (30 mL) and extracted with EtOAc (30 mL×3). The combined EtOAc layers were washed with brine (30 mL), dried over anhydrous Na₂SO₄, filtered and evaporated to afford a crude product, which was purified by silica gel column chromatography using a gradient of 3-5% methanol in DCM as eluent, followed by preparative HPLC purification using 25% acetonitrile in water containing 0.1% formic acid as modifier to afford Compound 53 (0.021 g, 8%) as a solid. $^1$H NMR (400 MHz, DMSO) δ 9.57 (s, 1H), 9.18 (s, 1H), 9.06 (s, 2H), 7.97 (d, J=2.4 Hz, 1H), 7.76 (d, J=1.2 Hz, 1H), 7.24 (d, J=1.6 Hz, 1H), 7.08 (s, 1H), 5.29 (s, 2H), 3.52 (s, 3H), 2.91 (t, J=6.8 Hz, 2H), 2.46 (m, 2H), 2.09 (s, 3H). MS (ESI) [M+H]$^+$ 377.17.

136

Example 39: 6-(1,5-dimethyl-6-oxo-1,6-dihydropyridin-3-yl)-8-((tetrahydro-2H-pyran-3-yl)methoxy)-3,4-dihydroquinolin-2(1H)-one Compounds 54a and 54b

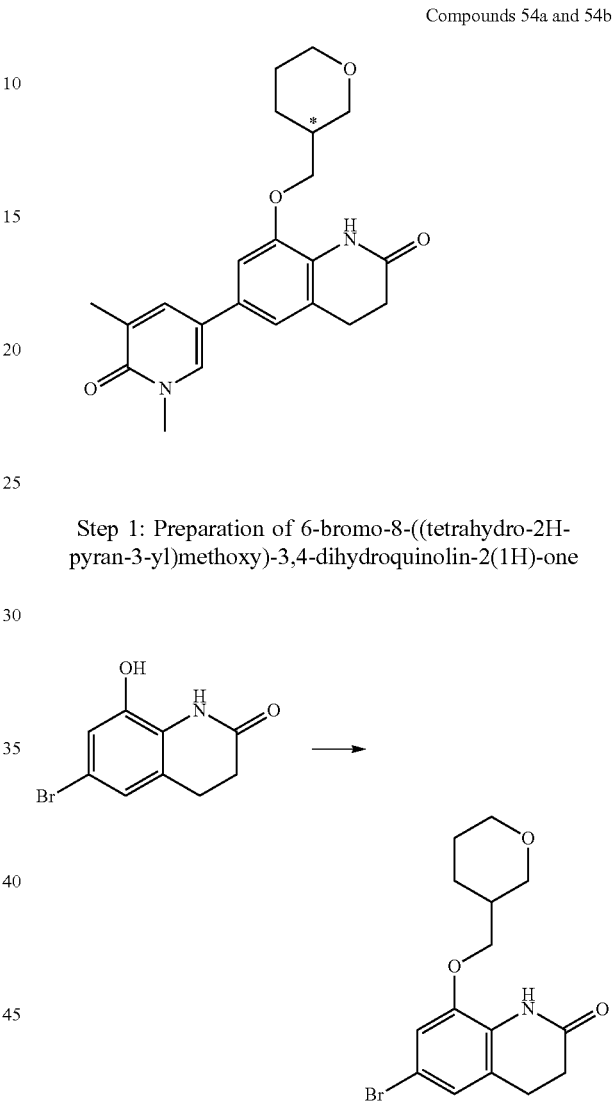

Step 1: Preparation of 6-bromo-8-((tetrahydro-2H-pyran-3-yl)methoxy)-3,4-dihydroquinolin-2(1H)-one To a suspension of K₂CO₃ (1.03 g, 7.4697 mmol) in DMF (6 mL) was added Intermediate 3 (0.6 g, 2.4899 mmol) and the mixture was stirred at rt for 15 min. 3-(bromomethyl)tetrahydro-2H-pyran (0.58 g, 3.2368 mmol) was then added at rt and the resultant reaction mixture was stirred at 60° C. for 6 h. Then, the reaction mixture was diluted with EtOAc (70 mL) and washed with water (30 mL×2) and brine solution (30 mL), dried over anhydrous Na₂SO₄, filtered and evaporated to afford a crude product, which was purified by silica gel column chromatography using a gradient of 20-40% EtOAc in hexane as eluent. The product fractions were collected and evaporated to afford title compound (0.35 g, 72%) as a solid. MS (ESI) [M+H]$^+$ 342.09. The product was used without further purification in the next step.

Step 2: Preparation of 6-(1,5-dimethyl-6-oxo-1,6-dihydropyridin-3-yl)-8-((tetrahydro-2H-pyran-3-yl)methoxy)-3,4-dihydroquinolin-2(1H)-one

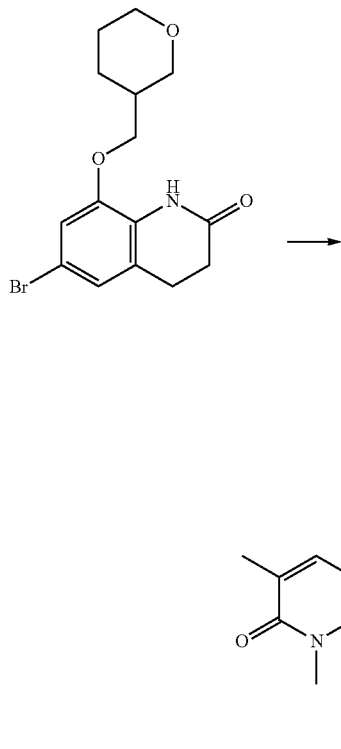

Compounds 54a and 54b

A stirred solution of 6-bromo-8-((tetrahydro-2H-pyran-3-yl)methoxy)-3,4-dihydroquinolin-2(1H)-one (0.6 g, 1.7690 mmol) and 1,3-dimethyl-5-(4,4,5,5-tetramethyl-1,3,2-dioxaborolan-2-yl)pyridin-2(1H)-one (0.57 g, 2.3007 mmol, prepared using procedure described in US20130053362) in 1,4-dioxane (10 mL) was purged with $N_2$ for 10 min. A solution of sodium carbonate (0.56 g, 5.3070 mmol) in water (1 mL) was then added and the mixture was further purged with $N_2$ for 10 min. Pd(PPh$_3$)$_4$(0.1 g, 0.0884 mmol) was then added and the reaction mixture was heated at 90° C. for 6 h. The solvent was evaporated under vacuum and water (60 mL) was added. The product was extracted using EtOAc (3×40 mL). The combined organic layers were washed with brine solution (30 mL), dried over anhydrous $Na_2SO_4$, filtered and evaporated to afford a crude product, which was purified by flash chromatography using a gradient of 1.8-2.2% methanol in DCM as eluent, followed by preparative HPLC purification using 28-35% acetonitrile in water containing 0.1% TFA as modifier to afford Compounds 54a and 54b as a racemic mixture (0.13 g, 19%). $^1$H NMR (400 MHz, DMSO) δ 9.29 (s, 1H), 7.95 (d, J=2.7 Hz, 1H), 7.74 (d, J=1.3 Hz, 1H), 7.05-6.98 (m, 2H), 4.05 (dd, J=10.9 and 3.7 Hz, 1H), 3.93 (d, J=6.6 Hz, 2H), 3.77-3.75 (m, 1H), 3.51 (s, 3H), 3.41-3.27 (m, 2H), 2.89 (t, J=7.2 Hz, 2H), 2.47 (t, J=7.2 Hz, 2H), 2.08 (s, 3H), 1.89-1.74 (m, 1H), 1.59-1.52 (m, 2H), 1.48-1.38 (m, 2H); MS (ESI) [M+H]$^+$ 383.3.

The isomers were then separated by SFC purification (AS 10×250 mm, 5 um Isocratic 35% MeOH, 10 mL/min 100 Bar) to provide Compound 54a (39.7 mg) and Compound 54b (36.7 mg).

Compound 54a: retention time: 7.80 min; $^1$H NMR (400 MHz, DMSO) δ 9.29 (s, 1H), 7.95 (d, J=2.7 Hz, 1H), 7.74 (d, J=1.3 Hz, 1H), 7.05-6.98 (m, 2H), 4.05 (dd, J=10.9 and 3.7 Hz, 1H), 3.93 (d, J=6.6 Hz, 2H), 3.77-3.75 (m, 1H), 3.51 (s, 3H), 3.41-3.27 (m, 2H), 2.89 (t, J=7.2 Hz, 2H), 2.47 (t, J=7.2 Hz, 2H), 2.08 (s, 3H), 1.89-1.74 (m, 1H), 1.59-1.52 (m, 2H), 1.48-1.38 (m, 2H). MS (ESI) [M+H]$^+$ 383.4.

Compound 54b: retention time: 10.34 min; $^1$H NMR (400 MHz, DMSO) δ 9.29 (s, 1H), 7.95 (d, J=2.7 Hz, 1H), 7.74 (d, J=1.3 Hz, 1H), 7.05-6.98 (m, 2H), 4.05 (dd, J=10.9 and 3.7 Hz, 1H), 3.93 (d, J=6.6 Hz, 2H), 3.77-3.75 (m, 1H), 3.51 (s, 3H), 3.41-3.27 (m, 2H), 2.89 (t, J=7.2 Hz, 2H), 2.47 (t, J=7.2 Hz, 2H), 2.08 (s, 3H), 1.89-1.74 (m, 1H), 1.59-1.52 (m, 2H), 1.48-1.38 (m, 2H). MS (ESI) [M+H]$^+$ 383.4.

Example 40: 6-(1,5-dimethyl-6-oxo-1,6-dihydropyridin-3-yl)-8-((tetrahydro-2H-pyran-2-yl)methoxy)-3,4-dihydroquinolin-2(1H)-one

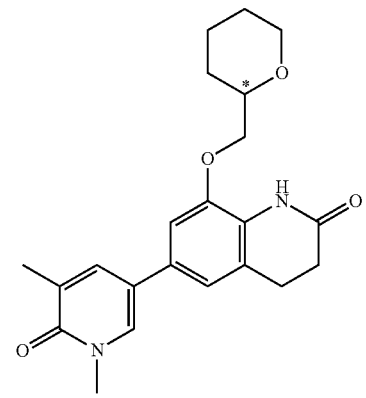

Compounds 55a and 55b

Step 1: Preparation of 6-bromo-8-((tetrahydro-2H-pyran-2-yl)methoxy)-3,4-dihydroquinolin-2(1H)-one

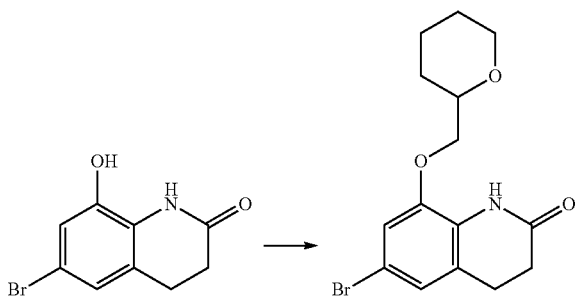 [SMILES: O=C1CCc2cc(Br)cc(O)c2N1 ; O=C1CCc2cc(Br)cc(OCC3CCCCO3)c2N1]

To a suspension of $K_2CO_3$ (0.86 g, 6.18 mmol) in DMF (5 mL), Intermediate 3 (0.5 g, 2.06 mmol) was added and the mixture stirred at rt for 15 min. 2-(bromomethyl)tetrahydro-2H-pyran (0.55 g, 3.09 mmol) was then added and the mixture stirred at 70° C. for 16 h. Then, the reaction mixture was diluted with water (100 mL) and extracted with EtOAc (50 mL×3). The combined EtOAc layers were washed with brine (30 mL), dried over anhydrous $Na_2SO_4$, filtered and evaporated to afford title compound (0.65 g, 58%) as a solid. MS (ESI) [M+H]$^+$ 342.14. The product was used in next step without further purification.

Step 2: Preparation of 6-(1,5-dimethyl-6-oxo-1,6-dihydropyridin-3-yl)-8-((tetrahydro-2H-pyran-2-yl)methoxy)-3,4-dihydroquinolin-2(1H)-one

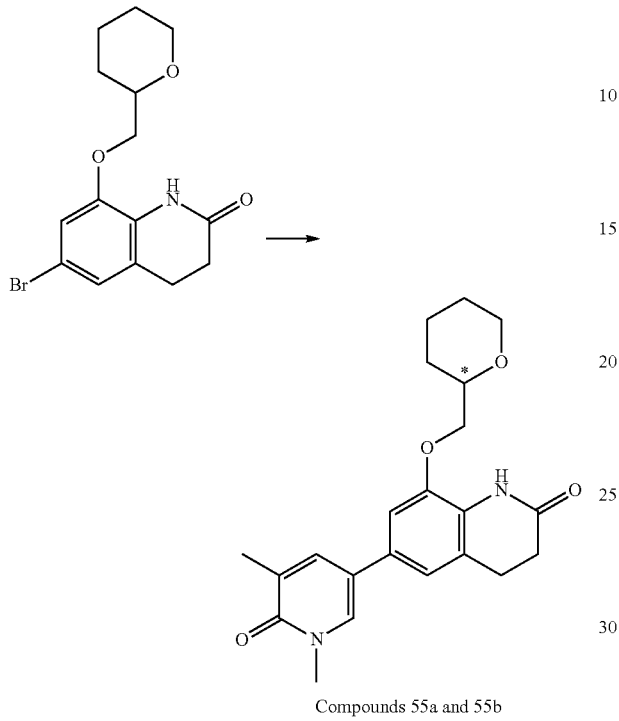

Compounds 55a and 55b

A stirred solution of 6-bromo-8-((tetrahydro-2H-pyran-2-yl)methoxy)-3,4-dihydroquinolin-2(1H)-one (0.65 g, 1.91 mmol) and 1,3-dimethyl-5-(4,4,5,5-tetramethyl-1,3,2-dioxaborolan-2-yl)pyridin-2(1H)-one (0.58 g, 2.29 mmol, prepared using procedure described in US20130053362) in 1,4-dioxane (5 mL) was purged with $N_2$ for 20 min. A solution of sodium carbonate (0.61 g, 5.73 mmol) in water (0.5 mL) was then added and the mixture was further purged with $N_2$ for 20 min. Pd(PPh$_3$)$_4$ (0.11 g, 0.095 mmol) was then added and the reaction mixture was heated at 90° C. for 3 h. After that time, the reaction mixture was diluted with water (50 mL) and extracted with EtOAc (50 mL×3). The combined EtOAc layers were washed with brine (50 mL), dried over anhydrous Na$_2$SO$_4$, filtered and evaporated to afford a crude product, which was purified by silica gel column chromatography using a gradient of 3-5% methanol in DCM as eluent, followed by preparative HPLC purification using 5-26% ACN in water and 0.1% formic acid as a modifier to afford 0.16 g of racemic 6-(1,5-dimethyl-6-oxo-1,6-dihydropyridin-3-yl)-8-((tetrahydro-2H-pyran-2-yl)methoxy)-3,4-dihydroquinolin-2(1H)-one. The racemic product was then purified by chiral preparative HPLC purification (Chiralcel™ OJ-H (250*21) mm, 5 u Column, flow 12.0 ml/min) using 20% IPA: Methanol (50:50%) in n-hexane to afford chirally pure Compounds 55a and 55b as solids. Compound 55a: 0.041 g Compound 55b: 0.033 g.

Compound 55a: Retention time=3.17 min: $^1$H NMR (400 MHz, DMSO) δ ppm 8.98 (s, 1H), 7.96 (d, J=2.4 Hz, 1H), 7.74 (d, J=1.6 Hz, 1H), 7.07 (s, 1H), 7.04 (s, 1H), 4.05-4.01 (m, 1H), 3.98-3.91 (m, 2H), 3.73 (t, J=4.8 Hz, 1H), 3.50 (s, 3H), 3.46-3.40 (m, 1H), 2.90 (t, J=7.2 Hz, 2H), 2.48 (m, 2H), 2.07 (s, 3H), 1.82-1.75 (m, 2H), 1.50 (s, 3H), 1.34-1.28 (m, 1H), MS (ESI) [M+H]$^+$: 383.29.

Compound 55b: Retention time=3.43 min: $^1$H NMR (400 MHz, DMSO) δ ppm 8.98 (s, 1H), 7.96 (d, J=2.4 Hz, 1H), 7.74 (s, 1H), 7.07 (s, 1H), 7.04 (s, 1H), 4.05-4.01 (m, 1H), 3.98-3.91 (m, 2H), 3.73 (t, J=4.8 Hz, 1H), 3.50 (s, 3H), 3.46-3.40 (m, 1H), 2.90 (t, J=7.2 Hz, 2H), 2.48 (m, 2H), 2.07 (s, 3H), 1.82-1.74 (m, 2H), 1.50 (s, 3H), 1.34-1.28 (m, 1H), MS (ESI) [M+H]$^+$: 383.34.

Example 41: 6-(1,5-dimethyl-6-oxo-1,6-dihydropyridin-3-yl)-5-(pyridin-2-ylmethyl)-3,4-dihydroquinolin-2(1H)-one

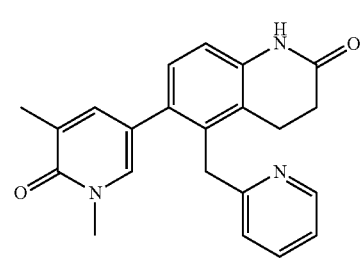

Compound 57

Step 1: Preparation of 6-chloro-5-(4,4,5,5-tetramethyl-1,3,2-dioxaborolan-2-yl)-3,4-dihydroquinolin-2(1H)-one See the procedure used in step 2 of Example 42.

Step 2: Preparation of 6-chloro-5-(pyridin-2-ylmethyl)-3,4-dihydroquinolin-2(1H)-one

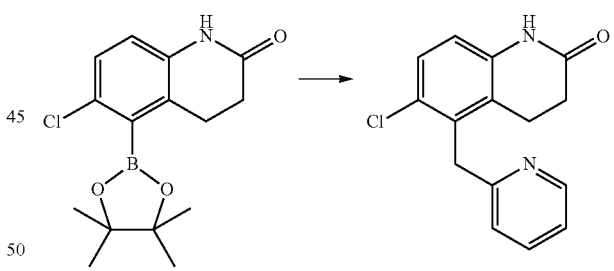

A stirred solution of 6-chloro-5-(4,4,5,5-tetramethyl-1,3,2-dioxaborolan-2-yl)-3,4-dihydroquinolin-2(1H)-one (0.3 g, 0.97 mmol) and 2-(bromomethyl)pyridine hydrobromide (0.37 g, 1.46 mmol) in 1,4-dioxane (6 mL) was purged with $N_2$ for 10 min. A solution of Cs$_2$CO$_3$ (0.95 g, 2.92 mmol) in water (2 mL) was then added and the mixture was further purged with $N_2$ for 10 min. PdCl$_2$(dppf).CH$_2$Cl$_2$ (0.04 g, 0.05 mmol) was then added and the reaction mixture was heated at 100° C. for 3 h. The solvent was evaporated under vacuum and the product was extracted using EtOAc (20 mL×3). The combined organic layers were washed with water (30 mL) and brine solution (30 mL), dried over anhydrous Na$_2$SO$_4$, filtered and evaporated to afford a crude product, which was purified by flash chromatography using 3% methanol in DCM as eluent. The pure product fractions were collected and evaporated to afford title compound (0.2 g, 75%) as a solid. MS (ESI) [M+H]+ 273.23.

Step 3: Preparation of 6-(1,5-dimethyl-6-oxo-1,6-dihydropyridin-3-yl)-5-(pyridin-2-ylmethyl)-3,4-dihydroquinolin-2(1H)-one

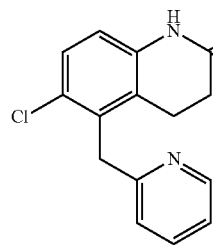

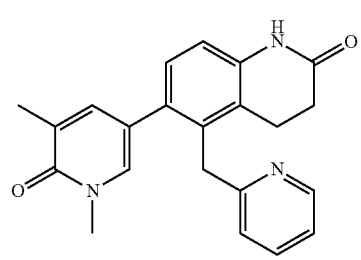

Compound 57

A stirred solution of 6-chloro-5-(pyridin-2-ylmethyl)-3,4-dihydroquinolin-2(1H)-one (0.2 g, 0.73 mmol) and 1,3-dimethyl-5-(4,4,5,5-tetramethyl-1,3,2-dioxaborolan-2-yl)pyridin-2(1H)-one (0.27 g, 1.10 mmol, prepared using procedure described in US20130053362) in 1,4-dioxane (4 mL) was purged with N$_2$ for 10 min. A solution of K$_3$PO$_4$ (0.46 g, 2.20 mmol) in water (1.5 mL) was then added and the mixture was further purged with N$_2$ for 10 min. Pd(t-Bu$_3$P)$_2$ (0.02 g, 0.03 mmol) was then added and the reaction mixture was heated at 150° C. in microwave for 8 h. The solvent was evaporated under vacuum and the product was extracted using EtOAc (10 mL×3). The combined organic layers were washed with water (15 mL) and brine solution (15 mL), dried over anhydrous Na$_2$SO$_4$, filtered and evaporated to afford a crude product, which was purified by flash chromatography using 4% methanol in DCM as eluent. The pure product fractions were evaporated to afford Compound 57 (0.09 g, 34%) as a solid. $^1$H NMR (400 MHz, MeOD) δ ppm 8.43 (d, J=4 Hz, 1H), 7.72 (dt, J=7.6, 1.6 Hz, 1H), 7.30 (d, J=1.2 Hz, 1H), 7.26 (t, J=6.2 Hz, 1H), 7.16 (d, J=1.2 Hz, 1H), 7.13 (d, J=8.0 Hz, 1H), 6.99 (d, J=8.0 Hz, 1H), 6.92 (d, J=8.0 Hz, 1H), 4.21 (s, 2H), 3.51 (s, 3H), 2.87 (t, J=7.6 Hz, 2H), 2.54 (t, J=7.6 Hz, 2H), 2.03 (s, 3H), —NH was not visible. MS (ESI) [M+H]+ 360.34.

Example 42: 6-(1,5-dimethyl-6-oxo-1,6-dihydropyridin-3-yl)-5-(pyridin-3-ylmethyl)-3,4-dihydroquinolin-2(1H)-one

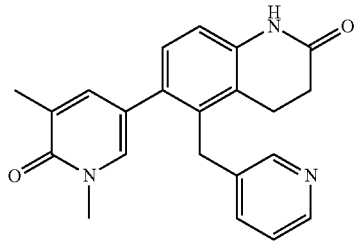

Compound 58

Step 1a: Preparation of N-(3-bromo-4-chlorophenyl)-3-chloropropanamide

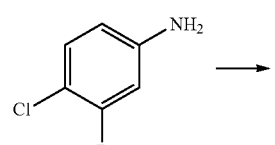

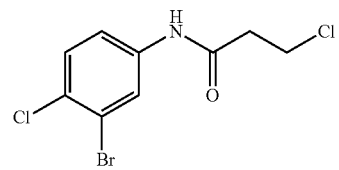

3-chloropropionyl chloride (5.8 mL, 60.54 mmol) was added to a stirred solution of 3-bromo-4-chloroaniline (10 g, 48.43 mmol) and K$_2$CO$_3$ (10 g, 72.65 mmol) in acetone: water (1:2, 75 mL) and the reaction mixture was stirred at 0° C. for 15 minutes. Then, the reaction mixture was poured in to water (100 mL) and extracted with ethyl acetate (100 mL×3). The combined organic layers were dried over anhydrous Na$_2$SO$_4$, filtered and evaporated to afford N-(3-bromo-4-chlorophenyl)-3-chloropropanamide (14 g, 98%) as a solid. $^1$H NMR (400 MHz, DMSO) δ ppm 10.35 (s, 1H), 8.14 (d, J=2.4 Hz, 1H), 7.58-7.51 (m, 2H), 3.87 (t, J=6.2 Hz, 2H), 2.83 (t, J=6.2 Hz, 2H). MS (ESI) [M+H]+ 298.1.

Step 1b: Preparation of Mixture of 7-bromo-6-chloro-3,4-dihydroquinolin-2(1H)-one and 5-bromo-6-chloro-3,4-dihydroquinolin-2(1H)-one

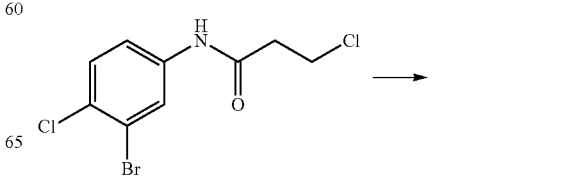

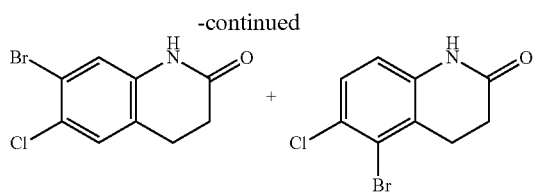

AlCl₃ (9.4 g, 70.71 mmol) was added to N-(3-bromo-4-chlorophenyl)-3-chloropropanamide (14 g, 47.14 mmol) and the mixture was heated at 140° C. for 20 h under nitrogen atmosphere. Then, the reaction mixture was poured in ice-cold water (300 mL) and extracted with ethyl acetate (200 mL×3). The combined organic layers were dried over anhydrous Na₂SO₄, filtered and evaporated under vacuum to afford a crude product which was further treated with ethyl acetate: hexane (1:1, 60 mL) and filtered under vacuum to afford a mixture of 7-bromo-6-chloro-3,4-dihydroquinolin-2(1H)-one and 5-bromo-6-chloro-3,4-dihydroquinolin-2(1H)-one (10 g, 81% yield) as a solid. ¹H NMR (400 MHz, DMSO) δ ppm 10.35 (s, 1H), 10.27 (s, 1H), 7.47 (s, 1H), 7.42 (d, J=8.8 Hz, 1H), 7.16 (s, 1H), 6.88 (d, J=8.4 Hz, 1H), 3.03 (t, J=7.8 Hz, 2H), 2.86 (t, J=7.4 Hz, 2H), 2.50 (t, J=8 Hz, 2H), 2.45 (t, J=8 Hz, 2H). MS (ESI) [M+H]⁺ 262.5.

Step 2: Preparation of 6-chloro-5-(4,4,5,5-tetramethyl-1,3,2-dioxaborolan-2-yl)-3,4-dihydroquinolin-2(1H)-one

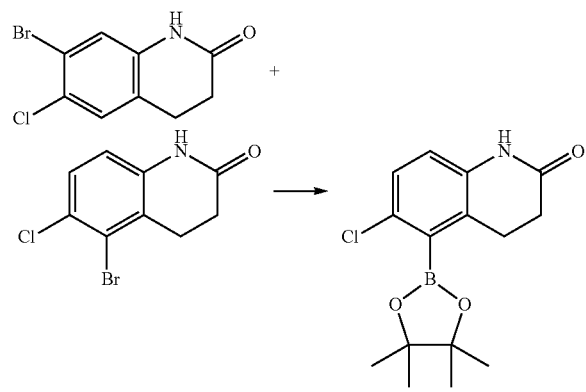

A stirred solution of mixture of 7-bromo-6-chloro-3,4-dihydroquinolin-2(1H)-one and 5-bromo-6-chloro-3,4-dihydroquinolin-2(1H)-one (1 g, 3.84 mmol) and potassium acetate (1.12 g, 11.52 mmol) in 1,4-dioxane (20 mL) was purged with N₂ for 15 min. 4,4,4',4',5,5,5',5'-octamethyl-2,2'-bi(1,3,2-dioxaborolane) (1.16 g, 5.76 mmol) was then added and the mixture was further purged with N₂ for 15 min. After that time, Pd(dppf)Cl₂.CH₂Cl₂ (0.16 g, 0.02 mmol) was added to the mixture, which was heated at 110° C. for 5 h. The reaction mixture was then filtered through Celite™ bed and washed with EtOAc (20 mL×3). The combined organic layers were evaporated under vacuum to get a crude product, which was purified by flash chromatography using 15% EtOAc in hexane as eluent. The pure product fractions were collected and evaporated to afford title compound (0.25 g, 21%) as a solid. ¹H NMR (400 MHz, DMSO) δ ppm 10.16 (s, 1H), 7.17 (d, J=8.4 Hz, 1H), 6.86 (d, J=8.8 Hz, 1H), 2.84 (t, J=7.4 Hz, 2H), 2.44 (t, J=7.4 Hz, 2H), 1.33 (s, 12H). MS (ESI) [M+H]⁺ 308.19.

Step 3: Preparation of 6-chloro-5-(pyridin-3-ylmethyl)-3,4-dihydroquinolin-2(1H)-one

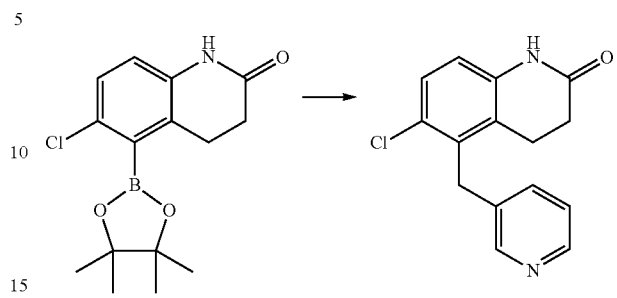

A stirred solution of 6-chloro-5-(4,4,5,5-tetramethyl-1,3,2-dioxaborolan-2-yl)-3,4-dihydroquinolin-2(1H)-one (0.25 g, 0.81 mmol) and 3-(bromomethyl)pyridine hydrobromide (0.21 g, 0.81 mmol) in 1,4-dioxane (5 mL) was purged with N₂ for 10 min. A solution of sodium carbonate (0.26 g, 2.43 mmol) in water (2 mL) was then added and the mixture was further purged with N₂ for 10 min. Pd(PPh₃)₄(0.047 g, 0.04 mmol) was then added and the reaction mixture was heated at 100° C. for 3 h. The solvent was evaporated under vacuum and the product was extracted using EtOAc (20 mL×3). The combined organic layers were washed with water (20 mL) and brine solution (20 mL), dried over anhydrous Na₂SO₄, filtered and evaporated to afford a crude product, which was purified by flash chromatography using 3% methanol in DCM as eluent. The pure product fractions were collected and evaporated to afford title compound (0.12 g, 54%) as a solid. ¹H NMR (400 MHz, DMSO) δ ppm 10.20 (s, 1H), 8.40-8.38 (m, 2H), 7.41 (d, J=8.0 Hz, 1H), 7.32-7.27 (m, 2H), 6.84 (d, J=8.8 Hz, 1H), 4.18 (s, 2H), 2.84 (t, J=7.6 Hz, 2H), 2.40 (t, J=7.4 Hz, 2H). MS (ESI) [M+H]⁺ 273.18.

Step 4: Preparation of 6-(1,5-dimethyl-6-oxo-1,6-dihydropyridin-3-yl)-5-(pyridin-3-ylmethyl)-3,4-dihydroquinolin-2(1H)-one

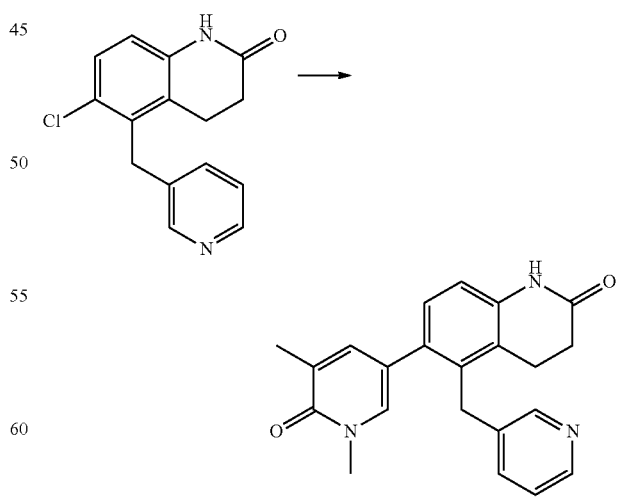

Compound 58

A stirred solution of 6-chloro-5-(pyridin-3-ylmethyl)-3,4-dihydroquinolin-2(1H)-one (0.12 g, 0.44 mmol) and 1,3- dimethyl-5-(4,4,5,5-tetramethyl-1,3,2-dioxaborolan-2-yl)pyridin-2(1H)-one (0.16 g, 0.0.66 mmol, prepared using procedure described in US20130053362) in 1,4-dioxane (3 mL) was purged with N₂ for 10 min. A solution of K₃PO₄ (0.28 g, 1.32 mmol) in water (1 mL) was then added and the mixture was further purged with N₂ for 10 min. Pd(t-Bu₃P)₂ (0.011 g, 0.02 mmol) was then added and the reaction mixture was heated at 150° C. in microwave for 90 min. The solvent was evaporated under vacuum and the product was extracted using EtOAc (15 mL×3). The combined organic layers were washed with water (15 mL) and brine solution (15 mL), dried over anhydrous Na₂SO₄, filtered and evaporated to afford a crude product, which was purified by flash chromatography using a gradient of 2-3% methanol in DCM as eluent. The pure product fractions were collected and evaporated under vacuum to afford Compound 58 (0.025 g, 16%) as a solid. ¹H NMR (400 MHz, MeOD) δ ppm 8.36 (d, J=3.6 Hz, 1H), 8.16 (s, 1H), 7.41 (d, J=8.0 Hz, 1H), 7.35-7.29 (m, 2H), 7.17 (d, J=0.8 Hz, 1H), 7.14 (d, J=8.0 Hz, 1H), 6.93 (d, J=8.4 Hz, 1H), 4.13 (s, 2H), 3.52 (s, 3H), 2.88 (t, J=7.4 Hz, 2H), 2.54 (t, J=7.6 Hz, 2H), 2.06 (s, 3H). MS (ESI) [M+H]⁺ 360.18.

Example 43: 6-(1,5-dimethyl-6-oxo-1,6-dihydropyridin-3-yl)-5-(pyridin-4-ylmethyl)-3,4-dihydroquinolin-2(1H)-one

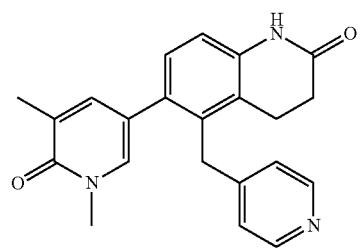

Compound 59

Step 1: Preparation of preparation of 6-chloro-5-(4,4,5,5-tetramethyl-1,3,2-dioxaborolan-2-yl)-3,4-dihydroquinolin-2(1H)-one See the procedure used in step 2 of Example 42.

Step 2: Preparation of 6-chloro-5-(pyridin-4-ylmethyl)-3,4-dihydroquinolin-2(1H)-one

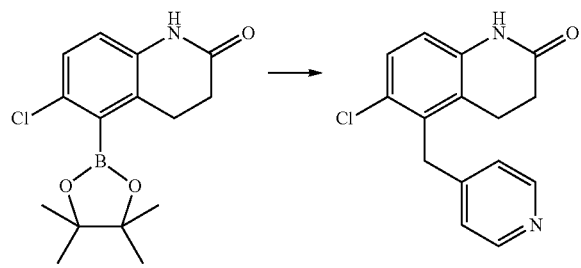 [SMILES: CC1(C)OB(c2c(Cl)ccc3c2CCC(=O)N3)OC1(C)C ; O=C1CCc2c(ccc(Cl)c2Cc2ccncc2)N1]

A stirred solution of 6-chloro-5-(4,4,5,5-tetramethyl-1,3,2-dioxaborolan-2-yl)-3,4-dihydro-quinolin-2(1H)-one (0.3 g, 0.97 mmol) and 4-(bromomethyl)pyridine hydrobromide (0.37 g, 1.46 mmol) in 1,4-dioxane (6 mL) was purged with N₂ for 10 min. A solution of Cs₂CO₃ (0.95 g, 2.92 mmol) in water (2 mL) was then added and the mixture was further purged with N₂ for 10 min. PdCl₂(dppf).CH₂Cl₂ (0.04 g, 0.05 mmol) was then added and the reaction mixture was heated at 100° C. for 3 h. The solvent was evaporated under vacuum and the product was extracted using EtOAc (20 mL×3). The combined organic layers were washed with water (30 mL) and brine solution (30 mL), dried over anhydrous Na₂SO₄, filtered and evaporated to afford a crude product, which was purified by flash chromatography using 3% methanol in DCM as eluent. The pure product fractions were collected and evaporated to afford title compound (0.2 g, 75%) as a solid. MS (ESI) [M+H]⁺ 273.23.

Step 3: Preparation of 6-(1,5-dimethyl-6-oxo-1,6-dihydropyridin-3-yl)-5-(pyridin-4-ylmethyl)-3,4-dihydroquinolin-2(1H)-one

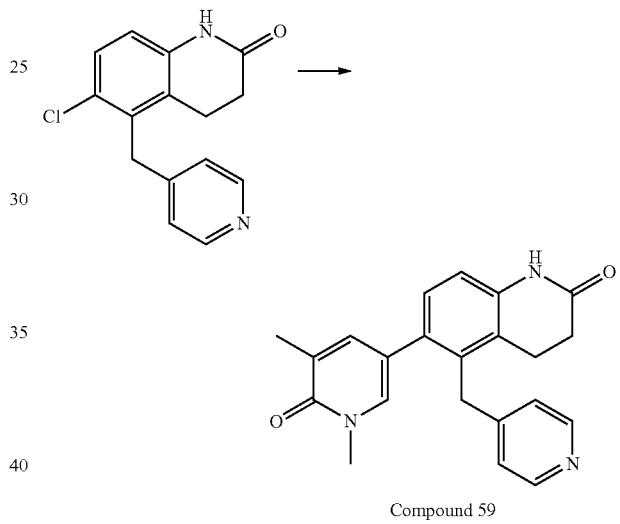

Compound 59

A stirred solution of 6-chloro-5-(pyridin-4-ylmethyl)-3,4-dihydroquinolin-2(1H)-one (0.2 g, 0.73 mmol) and 1,3-dimethyl-5-(4,4,5,5-tetramethyl-1,3,2-dioxaborolan-2-yl)pyridin-2(1H)-one (0.27 g, 1.10 mmol, prepared using procedure described in US20130053362) in 1,4-dioxane (4 mL) was purged with N₂ for 10 min. A solution of K₃PO₄ (0.46 g, 2.20 mmol) in water (1.5 mL) was then added and the mixture was further purged with N₂ for 10 min. Pd(t-But₃P)₂ (0.02 g, 0.03 mmol) was then added and the reaction mixture was heated at 150° C. in microwave for 8 h. The solvent was evaporated under vacuum and the product was extracted using EtOAc (10 mL×3). The combined organic layers were washed with water (15 mL) and brine solution (15 mL), dried over anhydrous Na₂SO₄, filtered and evaporated to afford a crude product, which was purified by flash chromatography using 4% methanol in DCM as eluent. The pure product fractions were evaporated to afford Compound 59 (0.09 g, 34%) as a solid. ¹H NMR (400 MHz, MeOD) δ ppm 8.39 (dd, J=1.6 and 4.4 Hz, 2H), 7.29 (d, J=2.0 Hz, 1H), 7.17 (d, J=1.6 Hz, 1H), 7.15 (d, J=8.4 Hz, 1H), 7.05 (d, J=6.4 Hz, 2H), 6.94 (d, J=8.4 Hz, 1H), 4.13 (s, 2H), 3.51 (s, 3H), 2.84 (t, J=7.6 Hz, 2H), 2.54 (t, J=7.6 Hz, 2H), 2.05 (s, 3H). MS (ESI) [M+H]⁺ 360.34.

Example 44: 6-(1,5-dimethyl-6-oxo-1,6-dihydropyridin-3-yl)-7-(pyridin-2-ylmethyl)-3,4-dihydroquinolin-2(1H)-one

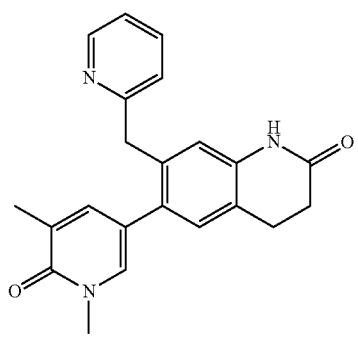

Compound 61

Step 1: Preparation of 6-chloro-7-(4,4,5,5-tetramethyl-1,3,2-dioxaborolan-2-yl)-3,4-dihydroquinolin-2(1H)-one See the procedure used in step 1 of Example 45.

Step 2: Preparation of 6-chloro-7-(pyridin-2-ylmethyl)-3,4-dihydroquinolin-2(1H)-one

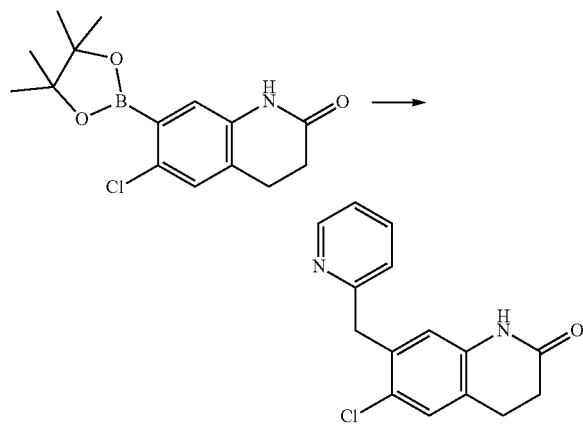

A stirred solution of 6-chloro-7-(4,4,5,5-tetramethyl-1,3,2-dioxaborolan-2-yl)-3,4-dihydroquinolin-2(1H)-one (0.3 g, 0.97 mmol) and 2-(bromomethyl)pyridine hydrobromide (0.37 g, 1.46 mmol) in 1,4-dioxane (6 mL) was purged with $N_2$ for 10 min. A solution of $Cs_2CO_3$ (0.95 g, 2.92 mmol) in water (2 mL) was then added and the mixture was further purged with $N_2$ for 10 min. $PdCl_2(dppf).CH_2Cl_2$ (0.04 g, 0.05 mmol) was then added and the reaction mixture was heated at 100° C. for 3 h. The solvent was evaporated under vacuum and the product was extracted using EtOAc (20 mL×3). The combined organic layers were washed with water (30 mL) and brine solution (30 mL), dried over anhydrous $Na_2SO_4$, filtered and evaporated to afford a crude product, which was purified by flash chromatography using 3% methanol in DCM as eluent. The pure product fractions were collected and evaporated to afford title compound (0.1 g, 37%) as an oil. MS (ESI) $[M+H]^+$ 273.23.

Step 3: Preparation of 6-(1,5-dimethyl-6-oxo-1,6-dihydropyridin-3-yl)-7-(pyridin-2-ylmethyl)-3,4-dihydroquinolin-2(1H)-one

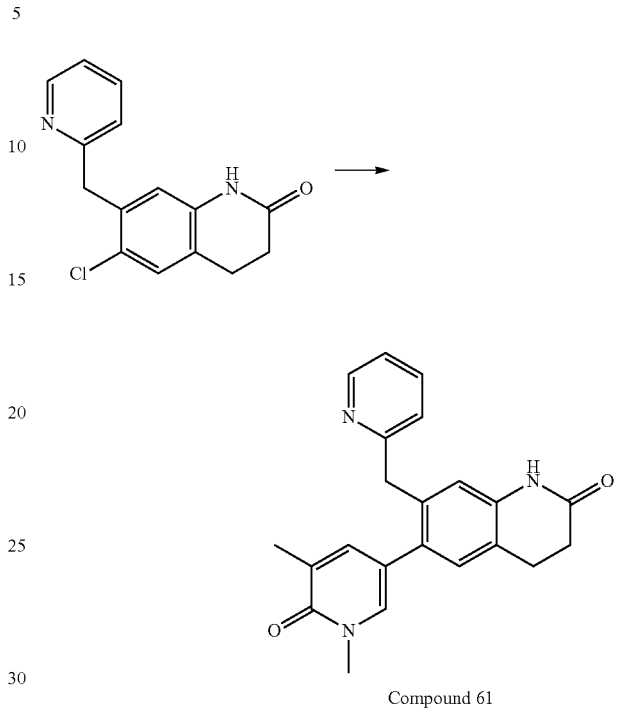

Compound 61

A stirred solution of 6-chloro-7-(pyridin-2-ylmethyl)-3,4-dihydroquinolin-2(1H)-one (0.1 g, 0.36 mmol) and 1,3-dimethyl-5-(4,4,5,5-tetramethyl-1,3,2-dioxaborolan-2-yl)pyridin-2(1H)-one (0.135 g, 0.55 mmol, prepared using procedure described in US20130053362) in 1,4-dioxane (2 mL) was purged with $N_2$ for 10 min. A solution of $K_3PO_4$ (0.23 g, 1.10 mmol) in water (0.7 mL) was then added and the mixture was further purged with $N_2$ for 10 min. Pd(t-$But_3P)_2$ (0.01 g, 0.02 mmol) was then added and the reaction mixture was heated at 150° C. in microwave for 8 h. The solvent was evaporated under vacuum and the product was extracted using EtOAc (10 mL×3). The combined organic layers were washed with water (10 mL) and brine solution (10 mL), dried over anhydrous $Na_2SO_4$, filtered and evaporated to afford a crude product, which was purified by flash chromatography using 5% methanol in DCM as eluent, followed by preparative HPLC purification using 5 to 37% acetonitrile in water to afford Compound 61 (0.025 g, 19%) as a solid. $^1H$ NMR (400 MHz, MeOD) δ ppm 8.46 (dd, J=0.8 and 5.2 Hz, 1H), 7.90 (dt, J=7.6 and 1.6 Hz, 1H), 7.41 (t, J=6.2 Hz, 1H), 7.34 (d, J=2.0 Hz, 1H), 7.23-7.20 (m, 2H), 7.10 (s, 1H), 6.81 (s, 1H), 4.20 (s, 2H), 3.55 (s, 3H), 2.98 (t, J=7.6 Hz, 2H), 2.60 (t, J=7.6 Hz, 2H), 2.08 (s, 3H), —NH was not visible. MS (ESI) $[M+H]^+$ 360.34.

Example 45: 6-(1,5-dimethyl-6-oxo-1,6-dihydropyridin-3-yl)-7-(pyridin-3-ylmethyl)-3,4-dihydroquinolin-2(1H)-one

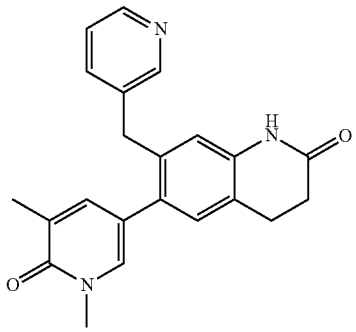

Compound 62

Step 1: Preparation of 6-chloro-7-(4,4,5,5-tetramethyl-1,3,2-dioxaborolan-2-yl)-3,4-dihydroquinolin-2(1H)-one

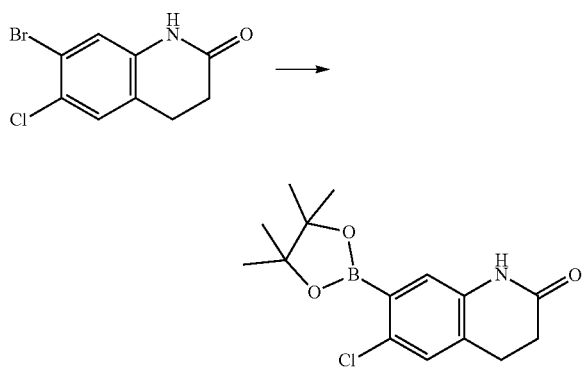 [SMILES: O=C1CCc2cc(Cl)c(Br)cc2N1 ; CC1(C)OB(c2cc3c(cc2Cl)CCC(=O)N3)OC1(C)C]

A stirred solution of 7-bromo-6-chloro-3,4-dihydroquinolin-2(1H)-one (0.8 g, 3.07 mmol) and potassium acetate (0.9 g, 9.21 mmol) in 1,4-dioxane (16 mL) was purged with $N_2$ for 15 min. 4,4,4',4',5,5,5',5'-octamethyl-2,2'-bi(1,3,2-dioxaborolane) (3.9 g, 15.35 mmol) was then added and the mixture was further purged with $N_2$ for 15 min. After that time, Pd(dppf)Cl$_2$·CH$_2$Cl$_2$ (0.13 g, 0.02 mmol) was added and the reaction mixture was stirred in microwave irradiation at 100° C. for 30 min. The reaction mixture was filtered through Celite™ bed and washed with EtOAc (20 mL×3). The combined organic layers were evaporated under vacuum to give the crude product which was purified by flash chromatography using 35% EtOAc in hexane as eluent. The pure product fractions were collected and evaporated to afford title compound (0.45 g, 47%) as a solid. MS (ESI) [M+H]$^+$ 226.28 (boronic acid).

Step 2: Preparation of 6-chloro-7-(pyridin-3-ylmethyl)-3,4-dihydroquinolin-2(1H)-one

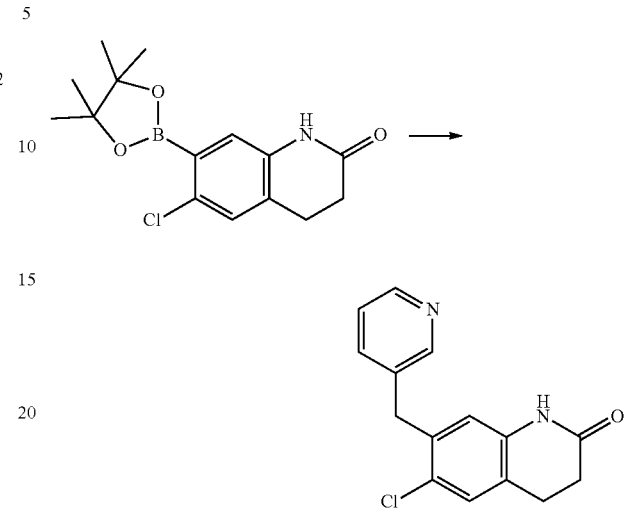

A stirred solution of 6-chloro-7-(4,4,5,5-tetramethyl-1,3,2-dioxaborolan-2-yl)-3,4-dihydroquinolin-2(1H)-one (0.45 g, 1.46 mmol) and 3-(bromomethyl)pyridine hydrobromide (0.55 g, 2.19 mmol) in 1,4-dioxane (9 mL) was purged with $N_2$ for 10 min. A solution of sodium carbonate (0.47 g, 4.38 mmol) in water (3 mL) was then added and the mixture was further purged with $N_2$ for 10 min. Pd(PPh$_3$)$_4$ (0.084 g, 0.07 mmol) was then added and the reaction mixture was heated at 100° C. for 3 h. The solvent was evaporated under vacuum and the product was extracted using EtOAc (20 mL×3). The combined organic layers were washed with water (20 mL) and brine solution (20 mL), dried over anhydrous Na$_2$SO$_4$, filtered and evaporated to afford a crude product, which was purified by flash chromatography using 3% methanol in DCM as eluent. The pure product fractions were collected and evaporated to afford title compound (0.2 g, 50%) as a solid. MS (ESI) [M+H]$^+$ 273.23.

Step 3: Preparation of 6-(1,5-dimethyl-6-oxo-1,6-dihydropyridin-3-yl)-7-(pyridin-3-ylmethyl)-3,4-dihydroquinolin-2(1H)-one

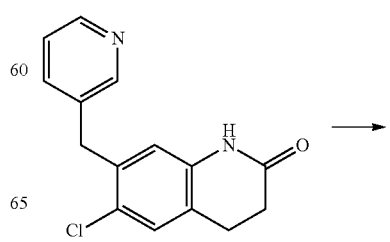

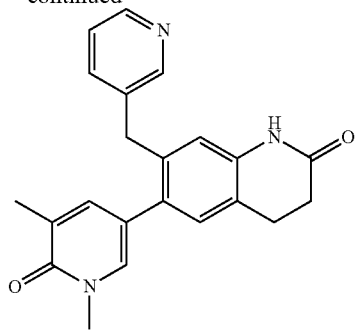

Compound 62

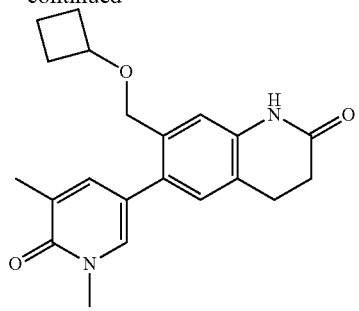

Compound 69

A stirred solution of 6-chloro-7-(pyridin-3-ylmethyl)-3,4-dihydroquinolin-2(1H)-one (0.2 g, 0.74 mmol) and 1,3-dimethyl-5-(4,4,5,5-tetramethyl-1,3,2-dioxaborolan-2-yl)pyridin-2(1H)-one (0.27 g, 1.10 mmol, prepared using procedure described in US20130053362) in 1,4-dioxane (4 mL) was purged with $N_2$ for 10 min. A solution of $K_3PO_4$ (0.46 g, 2.20 mmol) in water (1.5 mL) was then added and the mixture was further purged with $N_2$ for 10 min. Pd(t-But$_3$P)$_2$ (0.02 g, 0.03 mmol) was then added and the reaction mixture was heated at 150° C. in microwave for 8 h. The solvent was evaporated under vacuum and the product was extracted using EtOAc (15 mL×3). The combined organic layers were washed with water (15 mL) and brine solution (15 mL), dried over anhydrous $Na_2SO_4$, filtered and evaporated to afford a crude product, which was purified by flash chromatography using 6% methanol in DCM as eluent, followed by preparative HPLC purification using 12% acetonitrile in water and using formic acid as modifier to afford Compound 62 (0.04 g, 15%) as a solid. $^1$H NMR (400 MHz, MeOD) δ ppm 8.34 (dd, $J_1$=1.2 and 1.6 Hz, 1H), 8.16 (d, J=1.6 Hz, 1H), 7.46 (dd, J=1.6 and 5.2 Hz, 1H), 7.32-7.29 (m, 2H), 7.23 (dd, J=0.8 and 1.2 Hz, 1H), 7.08 (s, 1H), 6.82 (s, 1H), 4.01 (s, 2H), 3.55 (s, 3H), 2.98 (t, J=7.4 Hz, 2H), 2.60 (t, J=7.4 Hz, 2H), 2.11 (s, 3H), —NH was not visible. MS (ESI) [M+H]$^+$ 360.1.

Example 46: 5-(cyclobutoxymethyl)-6-(1,5-dimethyl-6-oxo-1,6-dihydropyridin-3-yl)-3,4-dihydroquinolin-2(1H)-one and 7-(cyclobutoxymethyl)-6-(1,5-dimethyl-6-oxo-1,6-dihydropyridin-3-yl)-3,4-dihydroquinolin-2(1H)-one

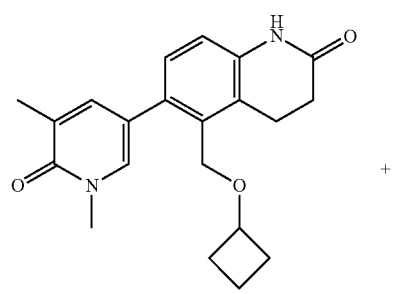

Compound 67

+

Step 1: Preparation of 6-chloro-5-(cyclobutoxymethyl)-3,4-dihydroquinolin-2(1H)-one and 6-chloro-7-(cyclobutoxymethyl)-3,4-dihydroquinolin-2(1H)-one

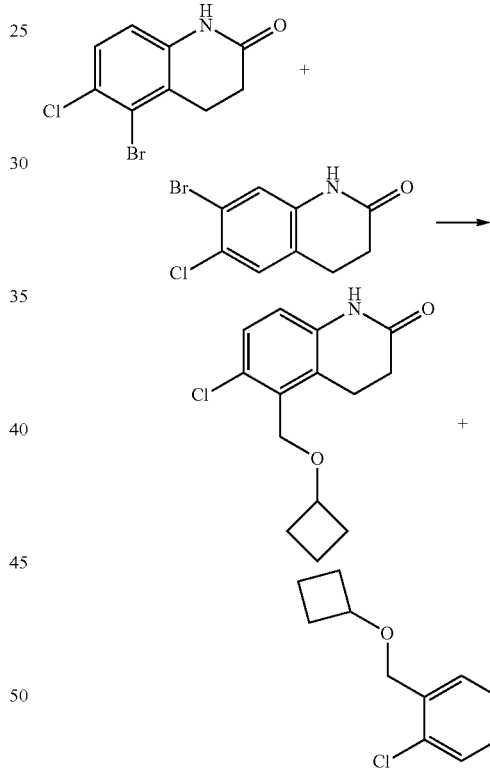

A stirred solution of 5-bromo-6-chloro-3,4-dihydroquinolin-2(1H)-one and 7-bromo-6-chloro-3,4-dihydroquinolin-2(1H)-one (0.3 g, 1.15 mmol, prepared as for Example 42) and potassium (cyclobutoxymethyl)trifluoroborate (0.28 g, 1.38 mmol) in 1,4-dioxane (6.0 mL) was purged with $N_2$ for 10 min. A solution of cesium carbonate (1.12 g, 3.46 mmol) in water (0.6 mL) was then added and the mixture was further purged with $N_2$ for 10 min. PdCl$_2$(dppf).DCM (0.075 g, 0.10 mmol) was then added and the reaction mixture was heated at 90° C. for 12 h. Then, the solvent was evaporated under vacuum and the product was extracted using EtOAc (30 mL×3). The combined organic layers were washed with water (30 mL), brine (30 mL), dried over anhydrous Na₂SO₄, filtered and evaporated to afford a crude product, which was purified by silica gel column chromatography using 25% EtOAc in hexane as eluent to afford a mixture of title compounds (0.27 g, 54%) as a solid. MS (ESI) [M+H]⁺ 266.2.

Step 2: Preparation of 5-(cyclobutoxymethyl)-6-(1,5-dimethyl-6-oxo-1,6-dihydropyridin-3-yl)-3,4-dihydroquinolin-2(1H)-one and 7-(cyclobutoxymethyl)-6-(1,5-dimethyl-6-oxo-1,6-dihydropyridin-3-yl)-3,4-dihydroquinolin-2(1H)-one

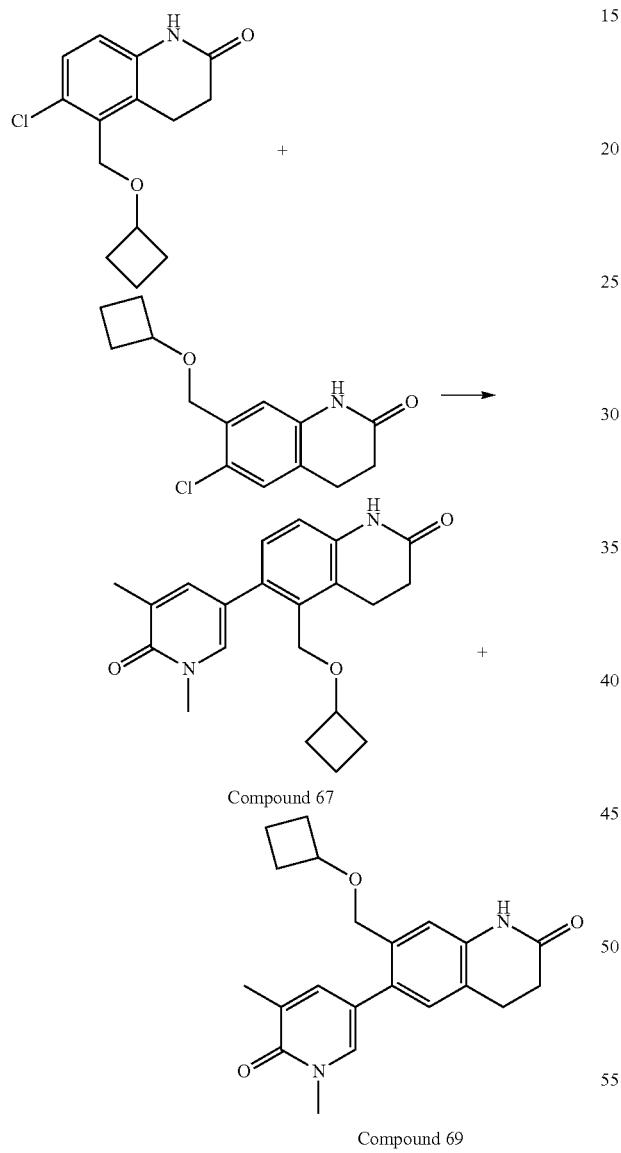

Compound 67

Compound 69

A stirred solution of 6-chloro-5-(cyclobutoxymethyl)-3,4-dihydroquinolin-2(1H)-one and 6-chloro-7-(cyclobutoxymethyl)-3,4-dihydroquinolin-2(1H)-one (0.27 g, 1.01 mmol) and 1,3-dimethyl-5-(4,4,5,5-tetramethyl-1,3,2-dioxaborolan-2-yl)pyridin-2(1H)-one (0.31 g, 1.22 mmol, prepared using procedure described in US20130053362) in 1,4-dioxane (6 mL) was purged with N₂ for 10 min. A solution of potassium phosphate (0.65 g, 3.05 mmol) in water (0.6 mL) was then added and the mixture was further purged with N₂ for 10 min. Pd(t-But₃P)₂ (0.052 g, 0.18 mmol) was then added and the reaction mixture was heated at 90° C. for 10 h. Then, the solvent was evaporated under vacuum and the product was extracted using EtOAc (25 mL×3). The combined organic layers were washed with water (30 mL), brine (30 mL), dried over anhydrous Na₂SO₄, filtered and evaporated to afford a crude product, which was purified by preparative HPLC purification using 10-42% Acetonitrile and using 0.1% NH₃ in water as a modifier to afford Compound 67 (7 mg g, 4%) and Compound 69 (6 mg, 4%).

Compound 67: ¹H NMR (400 MHz, MeOD) δ ppm 7.55 (d, J=2 Hz, 1H), 7.53 (d, J=1.2 Hz, 1H), 7.14 (d, J=8.4 Hz, 1H), 6.93 (d, J=8.4 Hz, 1H), 4.29 (s, 2H), 4.02 (t, J=14.4 Hz, 1H), 3.65 (s, 3H), 3.10 (t, J=15.2 Hz, 2H), 2.61 (t, J=15.2 Hz, 2H), 2.19 (s, 3H), 1.97-1.92 (m, 2H), 1.74 (d, J=10 Hz, 2H), 1.62-1.54 (m, 2H), —NH was not visible. MS (ESI) [M+H]⁺ 353.39.

Compound 69: ¹H NMR (400 MHz, MeOD) δ ppm 7.58 (d, J=2 Hz, 1H), 7.52 (s, 1H), 7.13 (s, 1H), 7.00 (s, 1H), 4.25 (s, 2H), 4.01 (t, J=14.8 Hz, 1H), 3.64 (s, 3H), 3.00 (t, J=15.2 Hz, 2H), 2.61 (t, J=15.2 Hz, 2H), 2.18 (s, 3H), 1.93-1.89 (m, 2H), 1.73-1.70 (m, 2H), 1.59-1.54 (m, 2H), —NH was not visible. MS (ESI) [M+H]⁺ 353.34.

Example 47: 5-((cyclopentyloxy)methyl)-6-(1,5-dimethyl-6-oxo-1,6-dihydropyridin-3-yl)-3,4-dihydroquinolin-2(1H)-one and 7-((cyclopentyloxy)methyl)-6-(1,5-dimethyl-6-oxo-1,6-dihydropyridin-3-yl)-3,4-dihydroquinolin-2(1H)-one

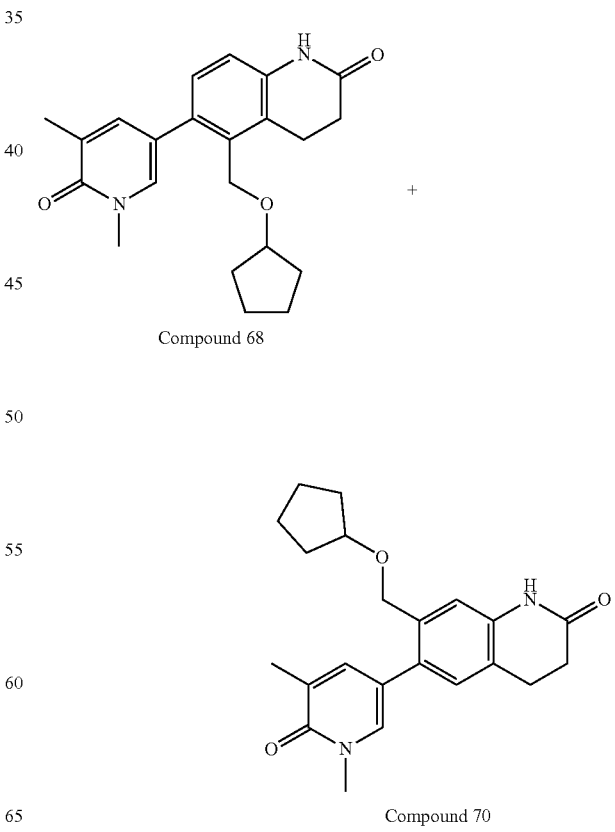

Compound 68

Compound 70

Step 1: Preparation of 6-chloro-5-((cyclopentyloxy)methyl)-3,4-dihydroquinolin-2(1H)-one and 6-chloro-7-((cyclopentyloxy)methyl)-3,4-dihydroquinolin-2(1H)-one Step 2: Preparation of 5-((cyclopentyloxy)methyl)-6-(1,5-dimethyl-6-oxo-1,6-dihydropyridin-3-yl)-3,4-dihydroquinolin-2(1H)-one and 7-((cyclopentyloxy)methyl)-6-(1,5-dimethyl-6-oxo-1,6-dihydropyridin-3-yl)-3,4-dihydroquinolin-2(1H)-one

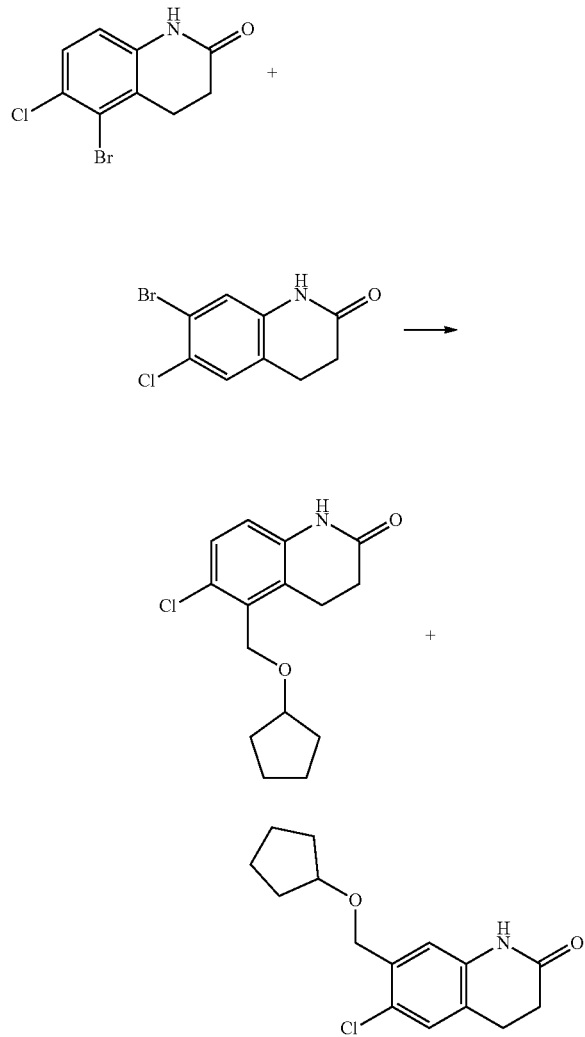

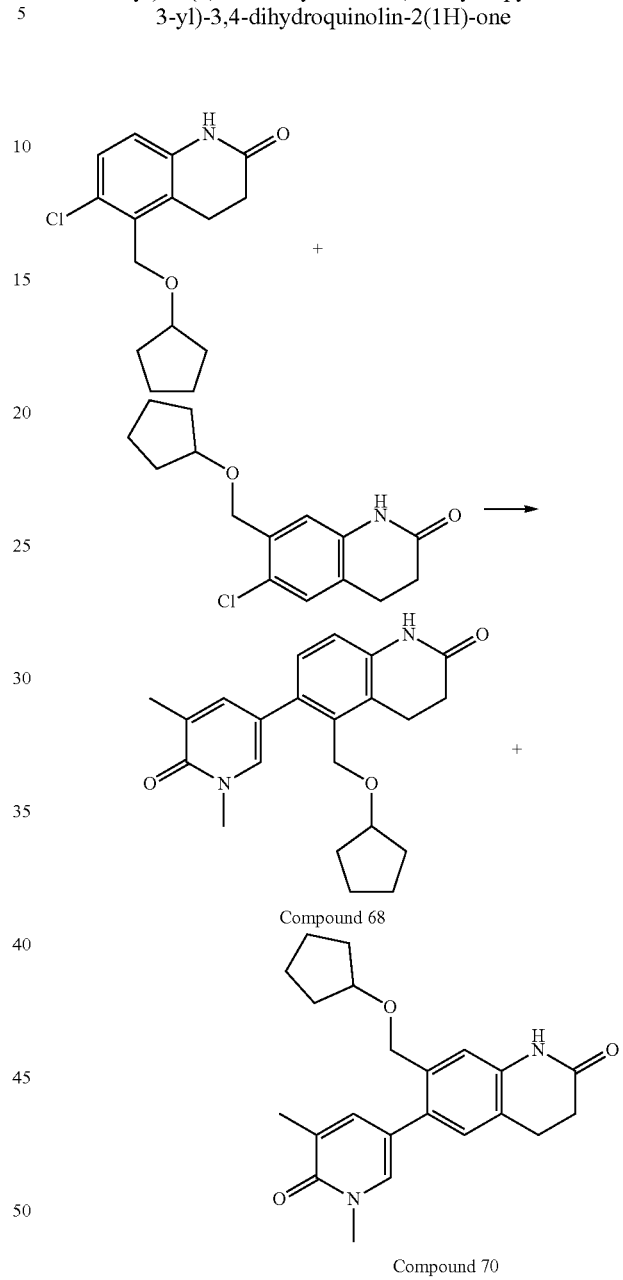

Compound 68

Compound 70

A stirred solution of 5-bromo-6-chloro-3,4-dihydroquinolin-2(1H)-one and 7-bromo-6-chloro-3,4-dihydroquinolin-2(1H)-one (0.6 g, 2.31 mmol, prepared as for Example 42) and potassium ((cyclopentyloxy)methyl)trifluoroborate (0.57 g, 2.77 mmol) in 1,4-dioxane (12 mL) was purged with $N_2$ for 10 min. A solution of cesium carbonate (2.25 g, 6.93 mmol) in water (1.2 mL) was then added and the mixture was further purged with $N_2$ for 10 min. $PdCl_2$(dppf).DCM (0.094 g, 0.12 mmol) was then added and the reaction mixture was heated at 90° C. for 12 h. Then, the solvent was evaporated under vacuum and the product was extracted using EtOAc (50 mL×3). The combined organic layers were washed with water (50 mL), brine (50 mL), dried over anhydrous $Na_2SO_4$, filtered and evaporated to afford a crude product, which was purified by silica gel column chromatography using 25% EtOAc in hexane as eluent to afford a mixture of title compounds (0.55 g, 54%). MS (ESI) $[M+H]^+$ 321.2.

A stirred solution of 6-chloro-5-((cyclopentyloxy)methyl)-3,4-dihydroquinolin-2(1H)-one and 6-chloro-7-((cyclopentyloxy)methyl)-3,4-dihydroquinolin-2(1H)-one (0.55 g, 2.00 mmol) and 1,3-dimethyl-5-(4,4,5,5-tetramethyl-1,3,2-dioxaborolan-2-yl)pyridin-2(1H)-one (0.59 g, 2.4 mmol, prepared using procedure described in US20130053362) in 1,4-dioxane (10 mL) was purged with $N_2$ for 10 min. A solution of potassium phosphate (1.27 g, 6.00 mmol) in water (1.0 mL) was then added and the mixture was further purged with $N_2$ for 10 min. $Pd(t-But_3P)_2$ (0.051 g, 0.0001 mmol) was then added and the reaction mixture was heated at 90° C. for 10 h. Then, the solvent was evaporated under vacuum and the product was extracted using EtOAc (30 mL×3). The combined organic layers were washed with water (30 mL), brine (30 mL), dried over anhydrous $Na_2SO_4$, filtered and evaporated to afford a crude product, which was purified by preparative HPLC purification using 5-27% acetonitrile and using 0.1% $NH_3$ in water as a modifier to afford Compound 68 (34 mg, 8%) and Compound 70 (20 mg, 8%).

Compound 68: $^1$H NMR (400 MHz, DMSO) δ ppm 10.12 (s, 1H), 7.52 (d, J=2 Hz, 1H), 7.35 (d, J=1.2 Hz, 1H), 7.06 (d, J=8.4 Hz, 1H), 6.86 (d, J=8 Hz, 1H), 4.20 (s, 2H), 3.92-3.91 (m, 1H), 3.47 (s, 3H), 2.95 (t, J=15.2 Hz, 2H), 2.46 (t, J=15.2 Hz, 2H), 2.04 (s, 3H), 1.67-1.50 (m, 8H). MS (ESI) [M+H]+ 367.2.

Compound 70: $^1$H NMR (400 MHz, DMSO) δ ppm 10.13 (s, 1H), 7.56 (d, J=2 Hz, 1H), 7.37 (s, 1H), 7.06 (s, 1H), 6.94 (s, 1H), 4.21 (s, 2H), 3.97-3.91 (m, 1H), 3.47 (s, 3H), 2.87 (t, J=14.8 Hz, 2H), 2.47 (m, 2H), 2.03 (s, 3H), 1.61-1.47 (m, 8H). MS (ESI) [M+H]+ 367.3.

Example 48: 8-(cyclohexylmethoxy)-6-(1,5-dimethyl-6-oxo-1,6-dihydropyridin-3-yl)-3,4-dihydroquinolin-2(1H)-one Compound 71

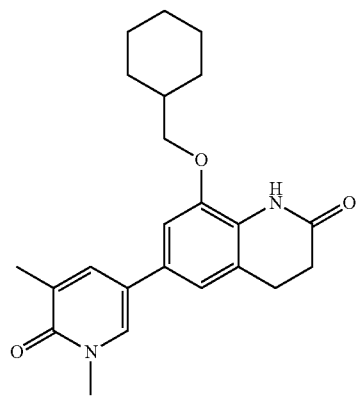

Step 1: Preparation of 6-bromo-8-(cyclohexylmethoxy)-3,4-dihydroquinolin-2(1H)-one

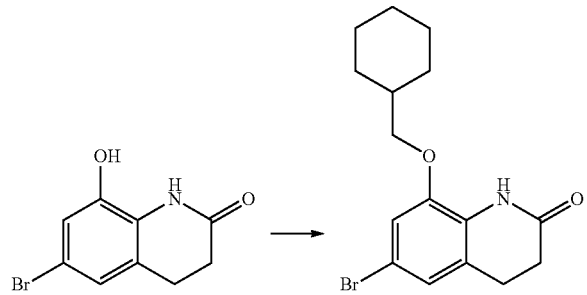 [SMILES: O=C1CCc2cc(Br)cc(O)c2N1 ; O=C1CCc2cc(Br)cc(OCC3CCCCC3)c2N1]

Intermediate 3 (0.3 g, 1.2448 mmol) was added to a suspension of $K_2CO_3$ (0.52 g, 3.7344 mmol) in DMF (3 mL) and the mixture was stirred at rt for 15 min. Bromomethylcyclohexane (0.26 g, 1.4938 mmol) was then added dropwise at rt and the resultant mixture was heated at 70° C. for 8 h. Then, the reaction mixture was diluted with EtOAc (60 mL) and washed with water (30 mL×2) and brine solution (30 mL), dried over anhydrous $Na_2SO_4$, filtered and evaporated to afford a crude product, which was purified by silica gel column chromatography using a gradient of 30-40% EtOAc in hexane as eluent. The product fractions were collected and evaporated to afford title compound (0.2 g, 48%) as an oil. MS (ESI) [M+H]+ 340.4.

Step 2: Preparation of 8-(cyclohexylmethoxy)-6-(1,5-dimethyl-6-oxo-1,6-dihydro-pyridin-3-yl)-3,4-dihydroquinolin-2(1H)-one

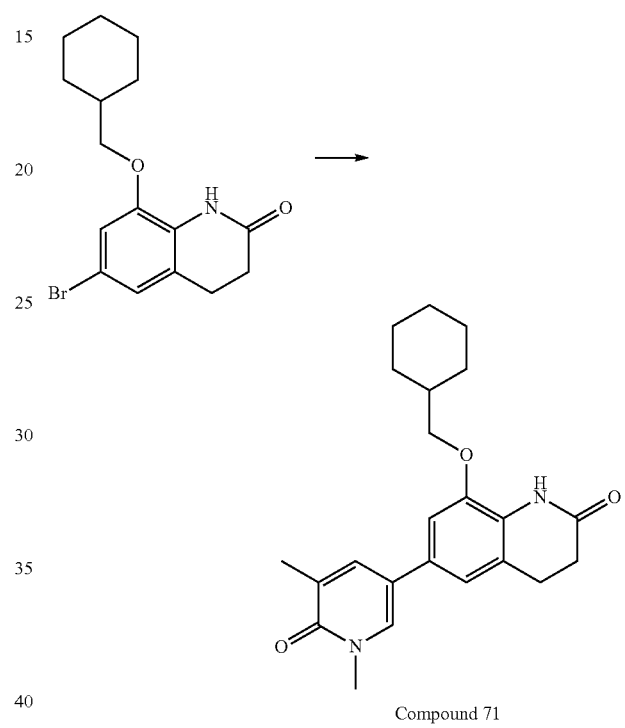

Compound 71

A stirred solution of 6-bromo-8-(cyclohexylmethoxy)-3,4-dihydroquinolin-2(1H)-one (0.20 g, 0.5934 mmol) and 1,3-dimethyl-5-(4,4,5,5-tetramethyl-1,3,2-dioxaborolan-2-yl)pyridin-2(1H)-one (0.18 g, 0.7121 mmol, prepared using procedure described in US20130053362) in 1,4-dioxane (4 mL) was purged with $N_2$ for 10 min. A solution of sodium carbonate (0.19 g, 1.7802 mmol) in water (0.5 mL) was then added and the mixture was further purged with $N_2$ for 10 min. $Pd(PPh_3)_4$ (0.034 g, 0.0297 mmol) was then added and the reaction mixture was heated at 90° C. for 4 h. The solvent was evaporated under vacuum and water (60 mL) was added. The product was extracted using EtOAc (30 mL×3). The combined organic layers were washed with brine solution (30 mL), dried over anhydrous $Na_2SO_4$, filtered and evaporated to afford a crude product, which was purified by flash chromatography using a gradient of 1.5-2% methanol in DCM as eluent, followed by preparative HPLC purification using 38% acetonitrile in water containing 0.1% ammonia as modifier to afford Compound 71 (0.082 g, 36%) as a solid. $^1$H NMR (400 MHz, DMSO) δ 9.01 (s, 1H), 7.94 (d, J=2.4 Hz, 1H), 7.73 (d, J=1.6 Hz, 1H), 7.01 (d, J=1.6 Hz, 1H), 6.99 (d, J=1.2 Hz, 1H), 3.87 (d, J=6.0 Hz, 1H), 3.51 (s, 3H), 2.90 (t, J=7.2 Hz, 2H), 2.47 (m, 2H), 2.08 (s, 4H), 1.91-1.83 (m, 3H), 1.75-1.66 (m, 3H), 1.30-1.18 (m, 3H), 1.10-1.04 (m, 2H). MS (ESI) [M+H]+ 381.6.

Example 49: 6-(1,5-dimethyl-6-oxo-1,6-dihydro-pyridin-3-yl)-8-((tetrahydro-2H-pyran-4-yl) methoxy)-3,4-dihydroquinolin-2(1H)-one

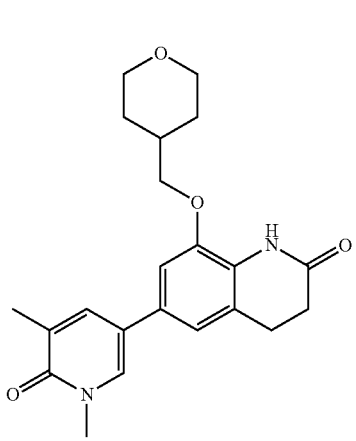

Compound 72

Step 1: Preparation of 6-bromo-8-((tetrahydro-2H-pyran-4-yl)methoxy)-3,4-dihydro-quinolin-2(1H)-one

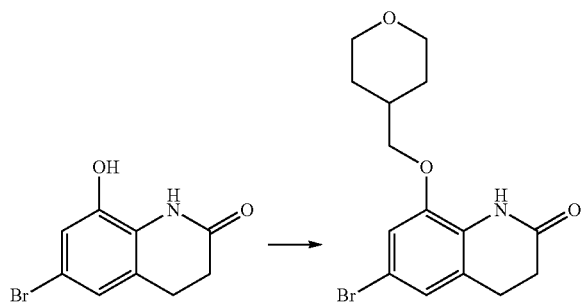 [SMILES: O=C1CCc2cc(Br)cc(O)c2N1 ; O=C1CCc2cc(Br)cc(OCC3CCOCC3)c2N1]

Intermediate 3 (0.3 g, 1.2448 mmol) was added to a suspension of $K_2CO_3$ (0.52 g, 3.7344 mmol) in DMF (3 mL) and the mixture was stirred at rt for 15 min. 4-(bromomethyl)tetrahydro-2H-pyran (0.27 g, 1.4938 mmol) was then added dropwise at rt and the resultant mixture was heated at 70° C. for 4 h. Then, the reaction mixture was diluted with EtOAc (80 mL) and washed with water (40 mL×2) and brine solution (30 mL), dried over anhydrous $Na_2SO_4$, filtered and evaporated to afford a crude product, which was purified by silica gel column chromatography using 40% EtOAc in n-hexane as eluent. The product fractions were collected and evaporated to afford title compound (0.25 g, 59%) as a solid. MS (ESI) $[M+H]^+$ 340.49.

Step 2: Preparation of 6-(1,5-dimethyl-6-oxo-1,6-dihydropyridin-3-yl)-8-((tetrahydro-2H-pyran-4-yl) methoxy)-3,4-dihydroquinolin-2(1H)-one

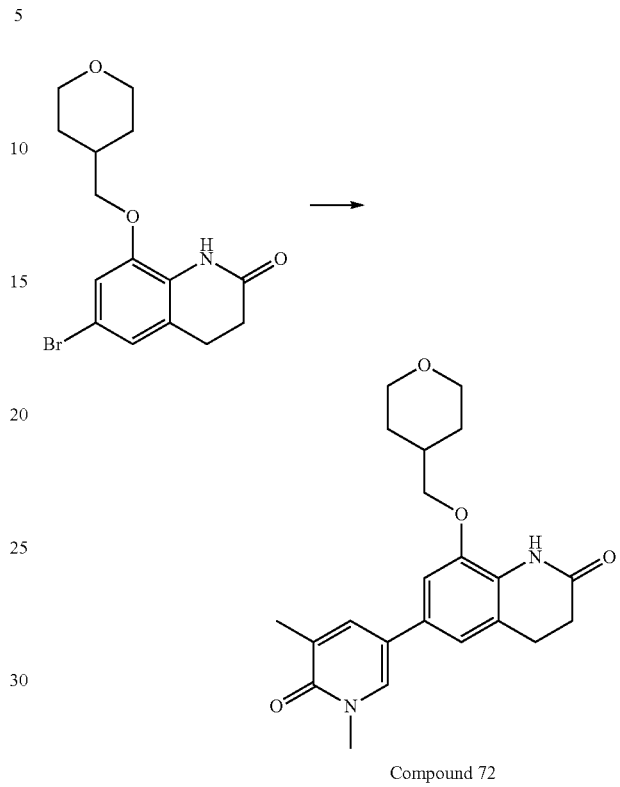

Compound 72

A stirred solution of 6-bromo-8-((tetrahydro-2H-pyran-4-yl)methoxy)-3,4-dihydroquinolin-2(1H)-one (0.25 g, 0.7373 mmol) and 1,3-dimethyl-5-(4,4,5,5-tetramethyl-1,3,2-dioxaborolan-2-yl)pyridin-2(1H)-one (0.28 g, 1.1060 mmol, prepared using procedure described in US20130053362) in 1,4-dioxane (5 mL) was purged with $N_2$ for 10 min. A solution of sodium carbonate (0.24 g, 2.2119 mmol) in water (0.5 mL) was then added and the mixture was further purged with $N_2$ for 10 min. $Pd(PPh_3)_4$ (0.043 g, 0.0368 mmol) was then added and the reaction mixture was heated at 90° C. for 8 h. The solvent was evaporated and water (80 mL) was added. The product was extracted using EtOAc (40 mL×3). The combined organic layers were washed with brine solution (50 mL), dried over anhydrous $Na_2SO_4$, filtered and evaporated to afford a crude product, which was purified by flash chromatography using a gradient of 1.5-2% methanol in DCM as eluent, followed by preparative HPLC purification using 5-19% acetonitrile in water containing 0.1% ammonia as modifier to afford Compound 72 (0.039 g, 14%) as a solid. $^1H$ NMR (400 MHz, DMSO) δ 9.18 (s, 1H), 7.94 (s, 1H), 7.73 (s, 1H), 7.01 (d, J=7.2 Hz, 2H), 3.91 (d, J=6 Hz, 4H), 3.51 (s, 3H), 3.38 (m, 2H), 2.89 (t, J=7.6 Hz, 2H), 2.47 (m, 2H), 2.07 (bs, 4H), 1.82 (d, J=12.8 Hz, 2H), 1.38-1.29 (m, 2H). MS (ESI) $[M+H]^+$ 383.34.

Example 50: 6-(1,5-dimethyl-6-oxo-1,6-dihydropyridin-4-yl)-8-(pyridin-4-ylmethoxy)-3,4-dihydroquinolin-2(1H)-one

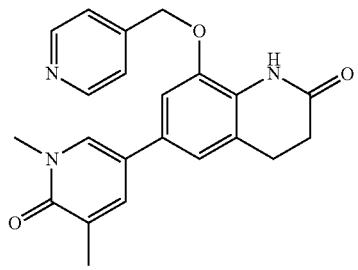

Step 1: Preparation of 6-bromo-8-(pyridin-4-ylmethoxy)-3,4-dihydroquinolin-2(1H)-one

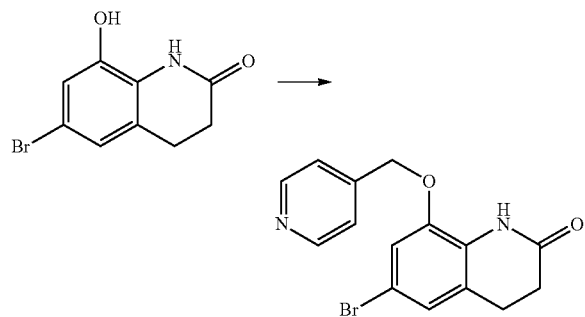

Intermediate 3 (0.3 g, 1.2448 mmol) was added to a suspension of K₂CO₃ (0.35 g, 2.4896 mmol) in DMF (3 mL) and the mixture was stirred at rt for 15 min. 4-(bromomethyl)pyridine hydrobromide (0.47 g, 1.8672 mmol) was then added at rt and the resultant mixture was heated at 70° C. for 8 h. Then, the reaction mixture was diluted with EtOAc (70 mL) and washed with water (30 mL×2) and brine solution (30 mL), dried over anhydrous Na₂SO₄, filtered and evaporated to afford a crude product, which was purified by silica gel column chromatography using a gradient of 1.5-2% MeOH in DCM as eluent. The product fractions were collected and evaporated to afford title compound (0.2 g, 48%) as a solid. MS (ESI) [M+H]⁺ 333.48.

Step 2: Preparation of 6-(1,5-dimethyl-6-oxo-1,6-dihydropyridin-3-yl)-8-(pyridin-4-ylmethoxy)-3,4-dihydroquinolin-2(1H)-one

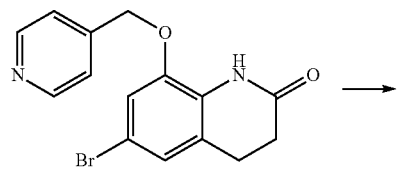

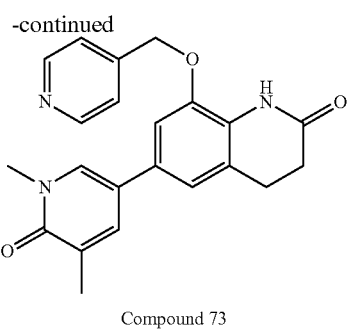

A stirred solution of 6-bromo-8-(pyridin-4-ylmethoxy)-3,4-dihydroquinolin-2(1H)-one (0.20 g, 0.6020 mmol) and 1,3-dimethyl-5-(4,4,5,5-tetramethyl-1,3,2-dioxaborolan-2-yl)pyridin-2(1H)-one (0.20 g, 0.7826 mmol, prepared using procedure described in US20130053362) in 1,4-dioxane (4 mL) was purged with N₂ for 10 min. A solution of sodium carbonate (0.19 g, 1.8060 mmol) in water (0.5 mL) was then added and the mixture was further purged with N₂ for 10 min. Pd(PPh₃)₄ (0.035 g, 0.0301 mmol) was then added and the reaction mixture was heated at 90° C. for 4 h. The solvent was evaporated under vacuum and water (60 mL) was added. The product was extracted using EtOAc (40 mL×3). The combined organic layers were washed with brine solution (30 mL), dried over anhydrous Na₂SO₄, filtered and evaporated to afford a crude product, which was purified by flash chromatography using a gradient of 2.5-3% methanol in DCM as eluent, followed by preparative HPLC purification using 10-19% acetonitrile in water containing 0.1% formic acid as modifier to afford Compound 73 (0.075 g, 33%) as a solid. $^1$H NMR (400 MHz, DMSO) δ 9.42 (s, 1H), 8.59 (d, J=6 Hz, 2H), 7.94 (d, J=2.4 Hz, 1H), 7.72 (d, J=1.6 Hz, 1H), 7.63 (d, J=6 Hz, 2H), 7.16 (d, J=1.6 Hz, 1H), 7.06 (d, J=1.2 Hz, 1H), 5.30 (s, 2H), 3.51 (s, 3H), 2.92 (t, J=6.8 Hz, 2H), 2.48 (t, J=7.2 Hz, 2H), 2.07 (s, 3H). MS (ESI) [M+H]⁺ 376.52.

Example 51: (S)-6-(1,5-dimethyl-6-oxo-1,6-dihydropyridin-3-yl)-8-(1-(pyridin-2-yl)ethoxy)-3,4-dihydroquinolin-2(1H)-one and (R)-6-(1,5-dimethyl-6-oxo-1,6-dihydropyridin-3-yl)-8-(1-(pyridin-2-yl)ethoxy)-3,4-dihydroquinolin-2(1H)-one

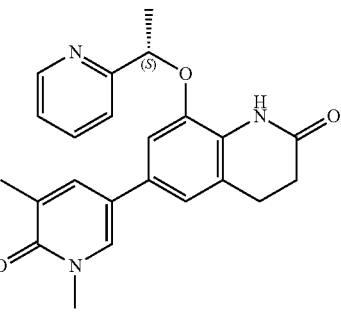

-continued

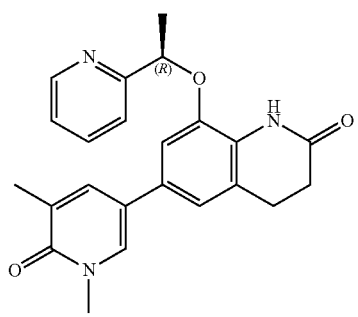
Compound 74b

Procedure A: Preparation of a Racemic Mixture of Compounds 74a and 74b and Separation Thereof Step 1a: Preparation of 1-(pyridin-2-yl)ethyl methanesulfonate

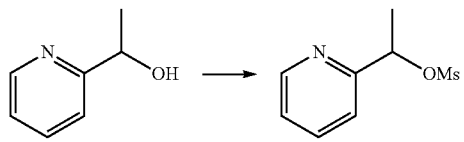

To a solution of 1-(pyridin-2-yl)ethan-1-ol (0.3 g, 2.4376 mmol) in DCM (3 mL), triethylamine (0.68 mL, 4.8752 mmol) was added and the mixture was stirred at rt for 15 min. Methane sulphonyl chloride (0.23 g, 2.9251 mmol) was then added dropwise at rt and the resultant reaction mixture was stirred at same temperature for 3 h. Then, the reaction mixture was diluted with DCM (50 mL), washed with water (40 mL) and brine solution (30 mL), dried over anhydrous Na$_2$SO$_4$, filtered and evaporated to afford title compound (0.48 g, 97%) as an oil. The product was used as such in the next step.

Step 1b: Preparation of 6-bromo-8-(1-(pyridin-2-yl)ethoxy)-3,4-dihydroquinolin-2(1H)-one

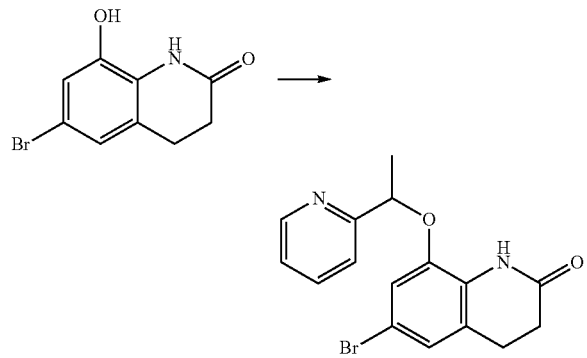

Intermediate 3 (0.5 g, 2.0747 mmol) was added to a suspension of K$_2$CO$_3$ (0.86 g, 6.2241 mmol) in DMF (10 mL) and the mixture was stirred at rt for 15 min. 1-(pyridin-2-yl)ethyl methanesulfonate (0.5 g, 2.4896 mmol) was then added dropwise at rt and the mixture was stirred at rt for 8 h. Then, the reaction mixture was diluted with EtOAc (80 mL), washed with water (40 mL×2) and brine solution (30 mL), dried over anhydrous Na$_2$SO$_4$, filtered and evaporated to afford a crude product, which was purified by silica gel (column chromatography using a gradient of 40-50% EtOAc in n-hexane as eluent. The product fractions were collected and evaporated to afford title compound (0.6 g, 48%) as an oil. MS (ESI) [M+H]$^+$ 349.24. The product was used as such in the next step.

Step 2: Preparation of the Racemic Mixture of Compounds 74a and 74b and Separation Thereof

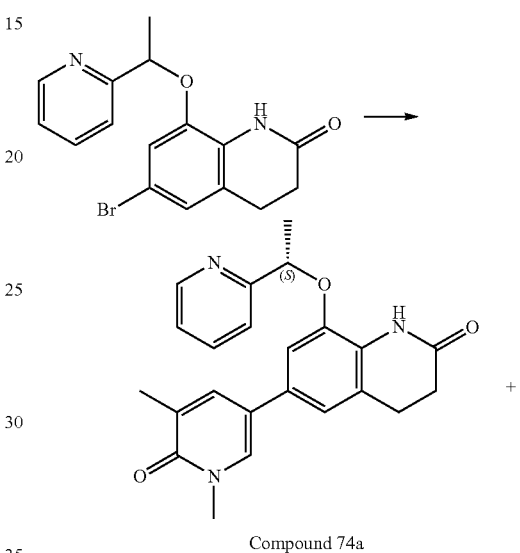

Compound 74a

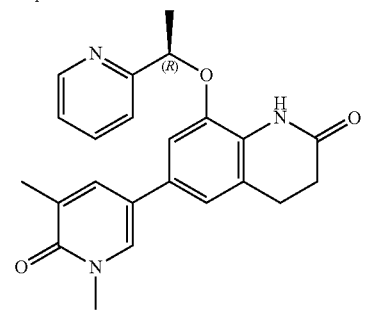

Compound 74b

A stirred solution of 6-bromo-8-(1-(pyridin-2-yl)ethoxy)-3,4-dihydroquinolin-2(1H)-one (0.6 g, 1.7341 mmol) and 1,3-dimethyl-5-(4,4,5,5-tetramethyl-1,3,2-dioxaborolan-2-yl)pyridin-2(1H)-one (0.56 g, 2.2543 mmol, prepared using procedure described in US20130053362) in 1,4-dioxane (10 mL) was purged with N$_2$ for 10 min. A solution of sodium carbonate (0.55 g, 5.2023 mmol) in water (1 mL) was then added and the mixture was further purged with N$_2$ for 10 min. Pd(PPh$_3$)$_4$ (0.1 g, 0.0867 mmol) was then added and the reaction mixture and heated at 90° C. for 8 h. The solvent was evaporated and water (80 mL) was added. The product was extracted using EtOAc (40 mL×3). The combined organic layers were washed with brine solution (50 mL), dried over anhydrous Na$_2$SO$_4$, filtered and evaporated to afford a crude product, which was purified by flash chromatography using a gradient of 1.5-2% methanol in DCM as eluent, followed by preparative HPLC purification using 10-45% methanol in water containing 0.1% formic acid as modifier to afford a racemic mixture of Compounds 74a and 74b (0.088 g) as a solid. The isomers were separated by chiral preparative HPLC purification (ChiralART™ SA (250*4.6)mm, 5 micron, flow 3.0 ml/min) using 5-50% IPA in Liq $CO_2$ to afford Compound 74a (0.03 g) and Compound 74b (0.036 g) as solids.

Compound 74a: retention time=5.51 min: $^1$H NMR (400 MHz, DMSO) δ 9.43 (s, 1H), 8.55 (dd, J=0.8 and 4.8 Hz, 1H), 7.82 (d, J=2.8 Hz, 1H), 7.78 (dd, J=1.6 and 7.6 Hz, 1H), 7.64 (d, J=8 Hz, 1H), 7.55 (d, J=1.2 Hz, 1H), 7.31-7.28 (m, 1H), 6.99 (dd, J=1.6 and 11.2 Hz, 2H), 5.67 (q, J=6.4 Hz, 1H), 3.48 (s, 3H), 2.88 (t, J=7.6 Hz, 2H), 2.48 (t, J=7.2 Hz, 2H), 2.04 (s, 3H), 1.65 (d, J=6.4 Hz, 3H). MS (ESI) [M+H]$^+$ 390.34.

Compound 74b: retention time=5.96 min: $^1$H NMR (400 MHz, DMSO) δ 9.42 (s, 1H), 8.55 (d, J=4.8 Hz, 1H), 7.82 (d, J=2 Hz, 1H), 7.79 (dd, J=1.6 and 7.6 Hz, 1H), 7.64 (d, J=8 Hz, 1H), 7.55 (s, 1H), 7.31-7.30 (m, 1H), 6.99 (d, J=9.6 Hz, 2H), 5.68 (q, J=5.6 Hz, 1H), 3.47 (s, 3H), 2.88 (t, J=7.6 Hz, 2H), 2.47 (t, 2H), 2.05 (s, 3H), 1.65 (d, J=6.4 Hz, 3H). MS (ESI) [M+H]$^+$ 390.34.

Procedure B: Preparation of Compound 74a

Compound 74a

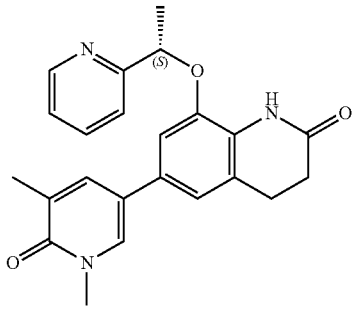

In this example, Intermediate 3 was prepared as detailed in following steps 1 to 5.

Step 1: Preparation of 3-chloro-N-(2-methoxyphenyl)propanamide

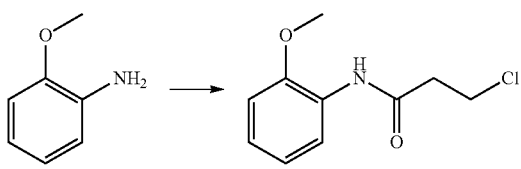

3-chloropropanoyl chloride (48.4 mL, 507.47 mmol) was added dropwise at 5° C. to a stirred solution of 2-methoxyaniline (50 g, 405.97 mmol) and $K_2CO_3$ (84 g, 608.95 mmol) in a mixture of acetone (500 mL) and water (1 L) and the reaction mixture was allowed to stir for 30 min at same temperature. Then, the reaction mixture was transferred into water (1 L) and extracted with EtOAc (500 mL×3). The combined EtOAc layers were washed with water (500 mL), dried over anhydrous $Na_2SO_4$, filtered and evaporated to afford a crude product, which was purified by recrystallization in hexane (500 mL) to afford title compound (85 g, 98%) as a solid. MS (ESI) [M+H]$^+$ 164.12.

Step 2: Preparation of 8-hydroxy-3,4-dihydroquinolin-2(1H)-one

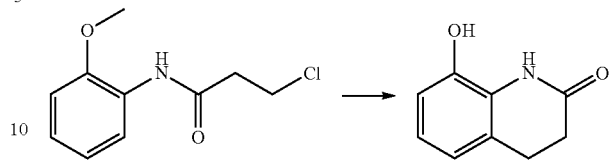

To 3-chloro-N-(2-methoxyphenyl)propanamide (50 g, 234 mmol) was added fine powder of $AlCl_3$ (187 g, 1404 mmol) at rt and the mixture was heated under stirring at 140° C. for 3 h. Then, the reaction mixture was transferred into 12% HCl solution in water (2 L) and extracted with EtOAc (500 mL×3). The combined EtOAc layers were washed with water (500 mL), dried over anhydrous $Na_2SO_4$, filtered and evaporated to afford a crude product, which was purified by silica gel column chromatography using 1% methanol in DCM as eluent. The pure product fractions were collected and evaporated to get solid product which was further triturated with n-pentane to afford title compound (30 g, 78%) as a solid. MS (ESI) [M+H]$^+$ 164.12.

Step 3: Preparation of 8-(methoxymethoxy)-3,4-dihydroquinolin-2(1H)-one

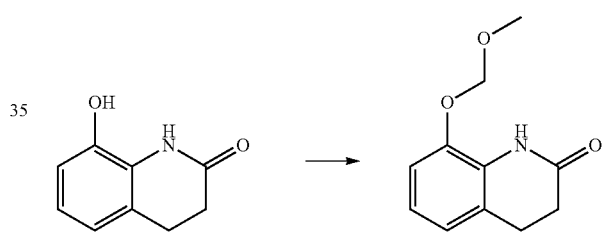

Methoxymethyl chloride (18 mL, 220.61 mmol) was added dropwise at 0° C. to a stirred solution of 8-hydroxy-3,4-dihydroquinolin-2(1H)-one (30 g, 183.85 mmol) and DIPEA (94 mL, 551.55 mmol) in DCM (600 mL) and the reaction mixture was allowed to stir for 1 h at same temperature. Then, the reaction mixture was diluted with water (500 mL) and extracted with DCM (250 mL×3). The combined DCM layers were washed with brine (250 mL), dried over anhydrous $Na_2SO_4$, filtered and evaporated under reduced pressure to afford title compound (25 g, 79%) as an oil. MS (ESI) [M+H]$^+$ 208.23.

Step 4: Preparation of 6-bromo-8-(methoxymethoxy)-3,4-dihydroquinolin-2(1H)-one

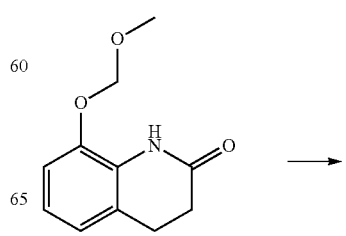

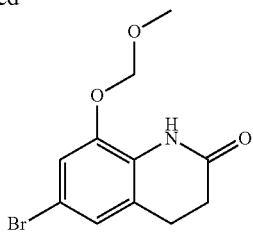

N-bromo succinimide (14.44 g, 81.16 mmol) in DMF (20 mL) was added dropwise at 0° C. to a stirred a solution of 8-(methoxymethoxy)-3,4-dihydroquinolin-2(1H)-one (14 g, 67.63 mmol) in DMF (80 mL) and the reaction mixture was allowed to stir for 3 h at same temperature. Then, the reaction mixture was diluted with water (1 L) and extracted with EtOAc (200 mL×3). The combined EtOAc layers were washed with brine (250 mL), dried over anhydrous $Na_2SO_4$, filtered and evaporated to afford title compound (10 g, 90%) as a solid. $^1$H NMR (400 MHz, DMSO) δ ppm 9.38 (s, 1H) 7.12 (d, J=2 Hz, 1H), 7.07 (d, J=1.6 Hz, 1H), 5.19 (s, 2H), 3.40 (s, 3H), 2.87 (t, J=7.2 Hz, 2H), 2.44 (t, J=7.2 Hz, 2H).

Step 5: Preparation of 6-bromo-8-hydroxy-3,4-dihydroquinolin-2(1H)-one

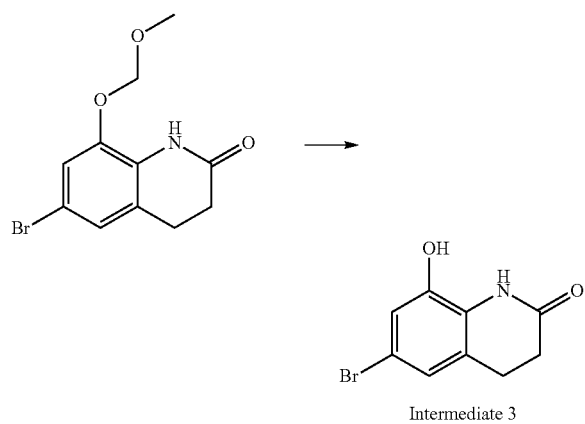

Intermediate 3

4 M HCl in dioxane (50 mL) was added dropwise at 0° C. to a stirred solution of 6-bromo-8-(methoxymethoxy)-3,4-dihydroquinolin-2(1H)-one (10 g, 34.96 mmol) in 1,4-dioxane (50 mL) and the mixture was stirred at rt for 4 h. Then, the reaction mixture was evaporated under vacuum and saturated $NaHCO_3$ solution (500 mL) was added and the mixture stirred at rt for 30 min. The resulting solid was filtered off, washed with water (500 mL) and dried under vacuum to afford Intermediate 3 (7 g, 73%) as a solid. MS (ESI) [M+H]$^+$ 242.

Step 6: Preparation of (S)-6-bromo-8-(1-(pyridin-2-yl)ethoxy)-3,4-dihydroquinolin-2(1H)-one

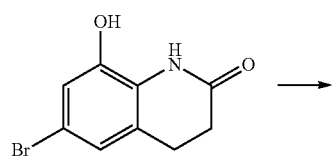

Diisopropyl azodicarboxylate (23.68 g, 117.7 mmol) was added dropwise at 60° C. under nitrogen atmosphere to a solution of 6-bromo-8-hydroxy-3,4-dihydroquinolin-2(1H)-one (19 g, 78.49 mmol), (R)-1-(pyridin-2-yl)ethan-1-ol (9.7 g, 78.49 mmol) and triphenylphosphine (30.9 g, 117.7 mmol) in THF (400 mL) and the mixture was stirred at same temperature for 2 h. Then, the reaction mixture was diluted with EtOAc (500 mL), washed with water (250 mL×2) and brine solution (250 mL), dried over anhydrous $Na_2SO_4$, filtered and evaporated to afford a crude product, which was purified by silica gel column chromatography using a gradient of 40-50% EtOAc in n-hexane as eluent. The product fractions were collected and evaporated to afford a product, which was triturated using diethyl ether (200 mL) and the filtrate was concentrate under vacuum to provide title compound (27 g, 99%) as an oil. MS (ESI) [M+H]$^+$ 349.28.

Step 7: Preparation of (S)-6-(1,5-dimethyl-6-oxo-1,6-dihydropyridin-3-yl)-8-(1-(pyridin-2-yl)ethoxy)-3,4-dihydroquinolin-2(1H)-one (Compound 74a)

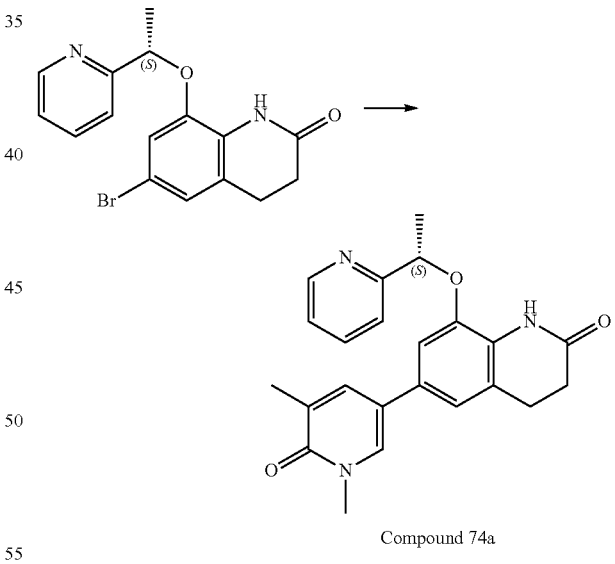

Compound 74a

A stirred solution of (S)-6-bromo-8-(1-(pyridin-2-yl)ethoxy)-3,4-dihydroquinolin-2(1H)-one (contains TPPO) (40 g, 115.2 mmol) and 1,3-dimethyl-5-(4,4,5,5-tetramethyl-1,3,2-dioxaborolan-2-yl)pyridin-2(1H)-one (28.7 g, 115.2 mmol, prepared using procedure described in US20130053362) in 1,4-dioxane (750 mL) was purged with $N_2$ for 10 min. A solution of sodium carbonate (36.6 g, 345.6 mmol) in water (120 mL) was then added and the mixture was further purged with $N_2$ for 10 min. Pd(PPh$_3$)$_4$(6.6 g, 5.76 mmol) was then added and the reaction mixture and heated at 90° C. for 4 h. Then, the reaction mixture was diluted with EtOAc (500 mL) washed with water (250 mL×2) and brine solution (250 mL), dried over anhydrous Na₂SO₄, filtered and evaporated to afford a crude product, which was purified by flash chromatography using a gradient of 2-3% methanol in DCM as eluent. The pure product fractions were collected and evaporated to afford a product, which was recrystallized in acetonitrile (200 mL) to remove undesired isomer at 80° C., cooled to rt, filtered and filtrate was concentrate under vacuum to afford Compound 74a (13.1 g, 28%) as a white solid. $^1$H NMR (400 MHz, DMSO) δ 9.43 (s, 1H), 8.55 (dd, J=0.8 and 4.8 Hz, 1H), 7.82 (d, J=2.8 Hz, 1H), 7.78 (dd, J=1.6 and 7.6 Hz, 1H), 7.64 (d, J=8 Hz, 1H), 7.55 (d, J=1.2 Hz, 1H), 7.31-7.28 (m, 1H), 6.99 (dd, J=1.6 and 11.2 Hz, 2H), 5.67 (q, J=6.4 Hz, 1H), 3.48 (s, 3H), 2.88 (t, J=7.6 Hz, 2H), 2.48 (t, J=7.2 Hz, 2H), 2.04 (s, 3H), 1.65 (d, J=6.4 Hz, 3H). MS (ESI) [M+H]⁺ 390.34.

Example 52: 6-(1,5-dimethyl-6-oxo-1,6-dihydro-pyridin-3-yl)-8-((5-methylpyridin-2-yl)methoxy)-3,4-dihydroquinolin-2(1H)-one

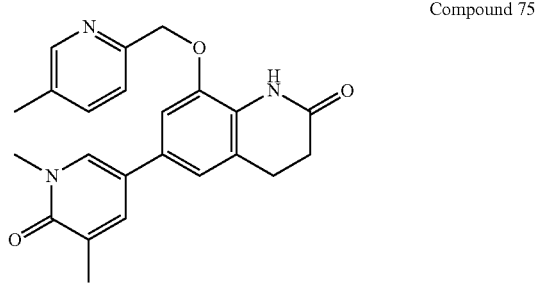 [SMILES: Cc1ccc(COc2cc(-c3cc(C)c(=O)n(C)c3)cc3c2NC(=O)CC3)nc1]

Compound 75

Step 1a: Preparation of (5-methylpyridin-2-yl)methyl methanesulfonate

Triethylamine (0.46 mL, 3.2500 mmol) was added to a solution of (5-methylpyridin-2-yl)methanol (0.2 g, 1.6250 mmol) in DCM (3 mL) and the mixture was stirred at rt for 15 min. Then, methane sulphonyl chloride (0.16 mL, 1.9501 mmol) was added dropwise at rt and the resultant mixture was stirred at rt for 3 h. The reaction mixture was then diluted with DCM (30 mL) and washed with water (40 mL) and brine solution (30 mL), dried over anhydrous Na₂SO₄, filtered and evaporated to afford title compound (0.3 g, 92%) as an oil. The product was used as such in the next step.

Step 1b: Preparation of 6-bromo-8-((5-methylpyridin-2-yl)methoxy)-3,4-dihydroquinolin-2(1H)-one

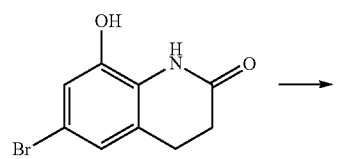

-continued

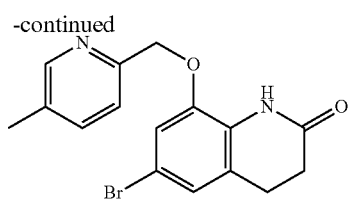

Intermediate 3 (0.3 g, 1.2448 mmol) was added to a suspension of K₂CO₃ (0.52 g, 3.7344 mmol) in DMF (6 mL) and the mixture stirred at rt for 15 min. Then, (5-methylpyridin-2-yl)methyl methanesulfonate (0.33 g, 1.6182 mmol) was added dropwise at rt and the resultant mixture was stirred at rt for 8 h. Then, the reaction mixture was diluted with EtOAc (80 mL) and washed with water (2×40 mL) and brine solution (30 mL), dried over anhydrous Na₂SO₄, filtered and evaporated to afford a crude product, which was purified by silica gel column chromatography using a gradient of 30-40% EtOAc in n-hexane as eluent. The product fractions were collected and evaporated to afford title compound (0.4 g, 60%) as an oil. MS (ESI) [M+H]⁺ 349.19. The product was used as such in the next step.

Step 2: Preparation of 6-(1,5-dimethyl-6-oxo-1,6-dihydropyridin-3-yl)-8-((5-methylpyridin-2-yl)methoxy)-3,4-dihydroquinolin-2(1H)-one

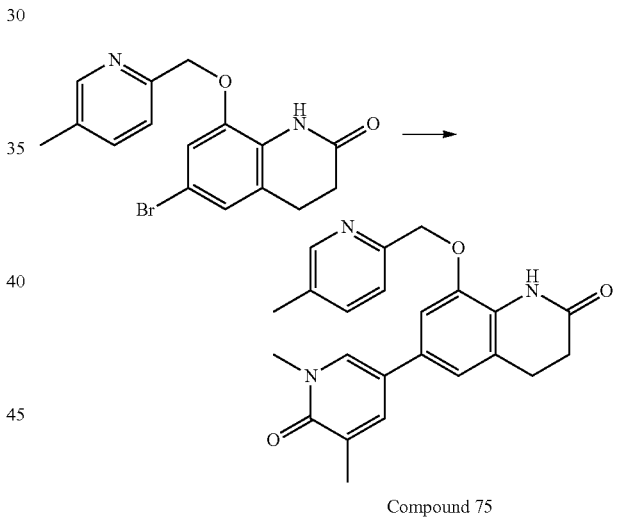

Compound 75

A stirred solution of 6-bromo-8-((5-methylpyridin-2-yl)methoxy)-3,4-dihydroquinolin-2(1H)-one (0.4 g, 1.1560 mmol) and 1,3-dimethyl-5-(4,4,5,5-tetramethyl-1,3,2-dioxaborolan-2-yl)pyridin-2(1H)-one (0.37 g, 1.5028 mmol, prepared using procedure described in US20130053362) in 1,4-dioxane (6 mL) was purged with N₂ for 10 min. A solution of sodium carbonate (0.37 g, 3.4680 mmol) in water (1 mL) was then added and the mixture was further purged with N₂ for 10 min. Pd(PPh₃)₄ (0.07 g, 0.0578 mmol) was then added and the reaction mixture was heated at 90° C. for 8 h. The solvent was evaporated and water (80 mL) was added. The product was extracted using EtOAc (3×40 mL). The combined organic layers were washed with brine solution (50 mL), dried over anhydrous Na₂SO₄, filtered and evaporated to afford a crude product, which was purified by flash chromatography using a gradient of 1.5-2% methanol in DCM as eluent, followed by preparative HPLC purification using 20-25% acetonitrile in water containing 0.1% formic acid as modifier to afford Compound 75 (0.026 g, 12%) as a solid. $^1$H NMR (400 MHz, DMSO) δ 9.32 (s, 1H), 8.42 (s, 1H), 7.95 (d, J=2.4 Hz, 1H), 7.72-7.66 (m, 3H), 7.18 (s, 1H), 7.05 (s, 1H), 5.26 (s, 2H), 3.50 (s, 3H), 2.91 (t, J=15.2 Hz, 2H), 2.50 (m, 2H), 2.33 (s, 3H), 2.07 (s, 3H). MS (ESI) [M+H]$^+$ 390.34.

Example 53: 6-(1,5-dimethyl-6-oxo-1,6-dihydro-pyridin-3-yl)-8-((3-methylpyridin-2-yl)methoxy)-3,4-dihydroquinolin-2(1H)-one Compound 76

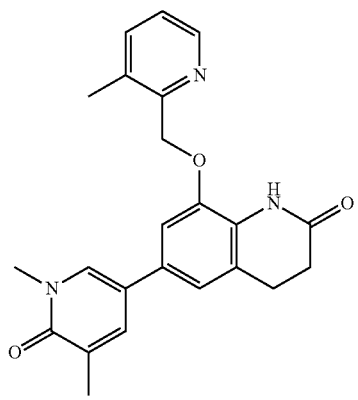

Step 1: Preparation of 2,3-dimethylpyridine 1-oxide

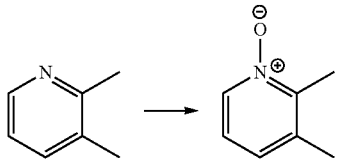

Hydrogen peroxide (30%) (2 mL, 18.66 mmol) was added to a solution of 2,3-dimethylpyridine (2 g, 18.66 mmol) in glacial acetic acid (12 mL) and the mixture was stirred at 80° C. for 12 h. Then, Na$_2$CO$_3$ solution (10 mL) was added and the mixture was evaporated to obtain a residue which was extracted with 10% MeOH in DCM (150 mL), dried over anhydrous Na$_2$SO$_4$, filtered and evaporated to afford title compound (1.6 g, 69%) as a solid. $^1$H NMR (400 MHz, CDCl$_3$) δ 8.17 (d, J=6.4 Hz, 1H), 7.08-7.15 (m, 2H), 2.51 (s, 3H), 2.35 (s, 3H).

Step 2: Preparation of (3-methylpyridin-2-yl)methyl acetate

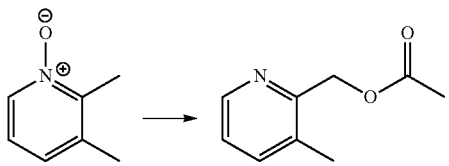

A stirred solution of 2,3-dimethylpyridine 1-oxide (1.6 g, 12.99 mmol) in acetic anhydride (8 mL) was refluxed for 1 h. Then, a saturated NaHCO$_3$ solution (100 mL) was added to the reaction mixture and the product was extracted using EtOAc (40 mL×3). The combined organic layers were washed with brine solution (50 mL), dried over anhydrous Na$_2$SO$_4$, filtered and evaporated to afford title compound (2.0 g, 82%). MS (ESI) [M+H]$^+$ 166.12. The product was used as such in the next step.

Step 3: Preparation of (3-methylpyridin-2-yl)methanol

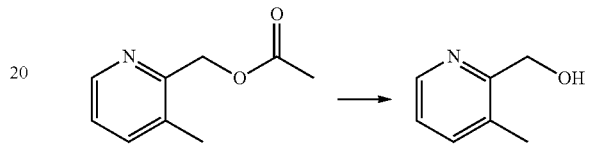

A 1N solution of NaOH (12 mL, 14.5 mmol) was added to a stirred solution of (3-methylpyridin-2-yl)methyl acetate (2 g, 12.12 mmol) in methanol (24 mL) and the mixture was stirred at rt for 2 h. Then, the reaction mixture was diluted with water (100 mL) and extracted with EtOAc (30 mL×3). The combined EtOAc layers were washed with brine (30 mL), dried over anhydrous Na$_2$SO$_4$, filtered and evaporated to afford a crude product, which was purified by silica gel column chromatography using a gradient of 3-5% methanol in DCM as eluent. The product fractions were collected and evaporated to afford title compound (0.6 g, 40%) as an oil. $^1$H NMR (400 MHz, CDCl$_3$) δ 8.34 (d, J=4.8 Hz, 1H), 7.57 (d, J=8.4 Hz, 1H), 7.23-7.20 (m, 1H), 5.03 (t, J=5.4 Hz, 1H), 4.56 (d, J=4.0 Hz, 2H), 2.30 (s, 3H). MS (ESI) [M+H]$^+$ 124.17.

Step 4: Preparation of (3-methylpyridin-2-yl)methyl methanesulfonate

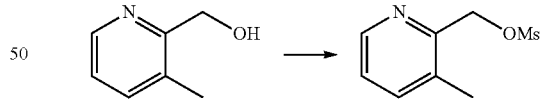

TEA (1.3 mL, 9.6 mmol) was added to a solution of 3-methylpyridin-2-yl)methanol (0.6 g, 4.8 mmol) in DCM (4 mL) and the mixture was stirred for 10 min at 0° C. Mesyl chloride (0.5 mL, 6.3 mmol) in DCM (1 mL) was then added dropwise and the reaction mixture was stirred at same temperature for 3 h. Then, the reaction mixture was diluted with water (50 mL) and extracted with EtOAc (25 mL×3). The combined EtOAc layers were washed with brine (30 mL), dried over anhydrous Na$_2$SO$_4$, filtered and evaporated to afford title compound (0.8 g, 81%) as an oil. MS (ESI) [M+H]$^+$ 202.23. The product was used as such in the next step.

Step 5: Preparation of 6-bromo-8-((3-methylpyridin-2-yl)methoxy)-3,4-dihydro-quinolin-2(1H)-one

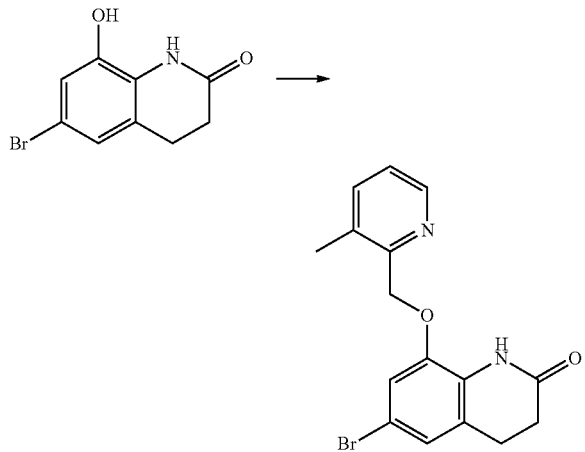

Intermediate 3 (0.3 g, 1.2 mmol) was added to a suspension of K$_2$CO$_3$ (0.24 g, 1.8 mmol) in DMF (4 mL) and the mixture was stirred at rt for 15 min. Then, (3-methylpyridin-2-yl)methyl methanesulfonate (0.3 g, 1.4 mmol) in DMF (1 mL) was added dropwise and the mixture was stirred at rt for 16 h. Then, the reaction mixture was diluted with water (100 mL) and extracted with EtOAc (30 mL×3). The combined EtOAc layers were washed with brine (30 mL), dried over anhydrous Na$_2$SO$_4$, filtered and evaporated to afford a crude product, which was purified by silica gel column chromatography using a gradient of 3-5% methanol in DCM as eluent. The product fractions were collected and evaporated to afford title compound (0.17 g, 40%) as a solid. MS (ESI) [M+H]$^+$ 349.2.

Step 6: Preparation of 6-(1,5-dimethyl-6-oxo-1,6-dihydropyridin-3-yl)-8-((3-methyl-pyridin-2-yl)methoxy)-3,4-dihydroquinolin-2(1H)-one

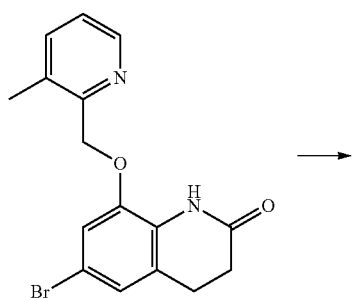

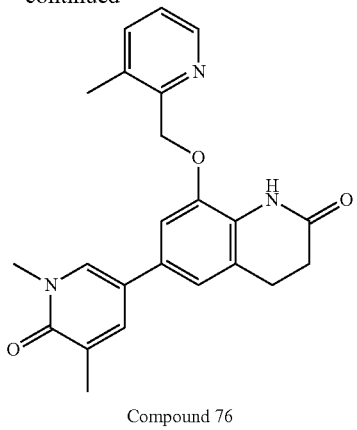

Compound 76

A stirred solution of 6-bromo-8-((3-methylpyridin-2-yl)methoxy)-3,4-dihydroquinolin-2(1H)-one (0.17 g, 0.48 mmol) and 1,3-dimethyl-5-(4,4,5,5-tetramethyl-1,3,2-dioxaborolan-2-yl)pyridin-2(1H)-one (0.18 g, 0.73 mmol, prepared using procedure described in US20130053362) in 1,4-dioxane (4 mL) was purged with N$_2$ for 20 min. A solution of sodium carbonate (0.15 g, 1.46 mmol) in water (0.4 mL) was then added and the mixture was further purged with N$_2$ for 20 min. Pd(PPh$_3$)$_4$(0.03 g, 0.05 mmol) was then added and reaction mixture was heated at 80° C. for 16 h. Then, the reaction mixture was diluted with water (30 mL) and extracted with EtOAc (30 mL×3). The combined EtOAc layers were washed with brine (30 mL), dried over anhydrous Na$_2$SO$_4$, filtered and evaporated to afford a crude product, which was purified by silica gel column chromatography using a gradient of 3-5% methanol in DCM as eluent, followed by preparative HPLC purification using (A) 0.1% Ammonia in Water and (B) 100% Methanol Isocratic: (A):(B)=52:48 for 35 min, to afford Compound 76 (0.020 g, 10%) as a solid. $^1$H NMR (400 MHz, DMSO) 9.33 (s, 1H), 8.42 (d, J=4.8 Hz, 1H), 7.94 (d, J=2.4 Hz, 1H), 7.70 (d, J=1.2 Hz, 1H), 7.67 (d, J=6.8 Hz, 1H), 7.34-7.31 (m, 1H), 7.29 (d, J=1.2 Hz, 1H), 7.05 (s, 1H), 5.31 (s, 2H), 3.51 (s, 3H), 2.90 (t, J=7.4 Hz, 2H), 2.47 (t, J=7.4 Hz, 2H), 2.45 (s, 3H), 2.09 (s, 3H). MS (ESI) [M+H]$^+$ 390.3.

Example 54: 6-(1,5-dimethyl-6-oxo-1,6-dihydropyridin-3-yl)-8-((5-fluoropyridin-2-yl)methoxy)-3,4-dihydroquinolin-2(1H)-one

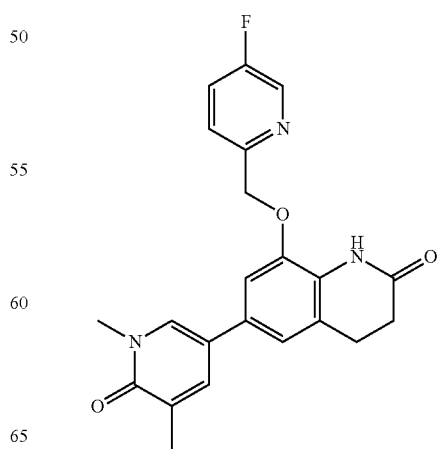

Compound 77

Step 1: Preparation of (5-fluoropyridin-2-yl)methyl methanesulfonate

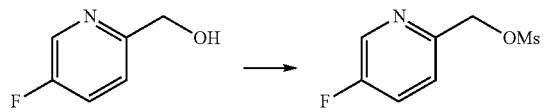 [SMILES: OCc1ccc(F)cn1 ; CS(=O)(=O)OCc1ccc(F)cn1]

Triethylamine (0.55 mL, 3.9360 mmol) was added to a stirred solution of (5-fluoropyridin-2-yl)methanol (0.25 g, 1.9680 mmol) in DCM (3 mL) and the mixture was stirred at 0° C. for 15 min. Methane sulphonyl chloride (0.19 mL, 2.3616 mmol) was then added at same temperature and the resultant mixture was stirred at rt for 3 h. Then, the reaction mixture was diluted with DCM (70 mL) and washed with saturated solution of NaHCO$_3$ (30 mL), water (30 mL) and brine solution (30 mL), dried over anhydrous Na$_2$SO$_4$, filtered and evaporated to afford title compound (0.32 g, 79%) as an oil. The product was used as such in the next step.

Step 2: Preparation of 6-bromo-8-((5-fluoropyridin-2-yl)methoxy)-3,4-dihydro-quinolin-2(1H)-one

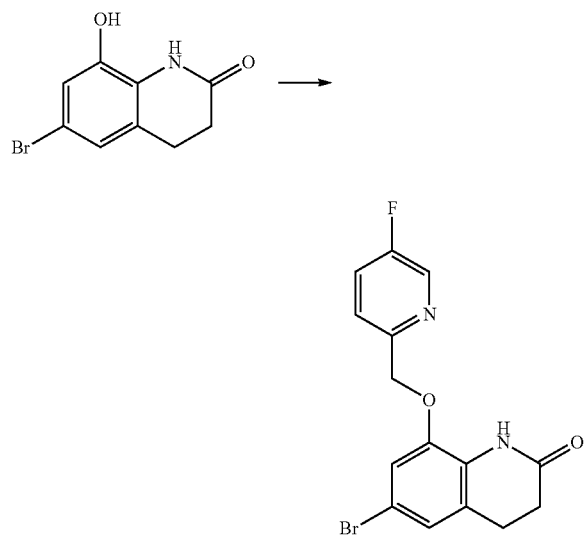

Intermediate 3 (0.30 g, 1.2448 mmol) was added to a suspension of K$_2$CO$_3$ (0.52 g, 3.73 mmol) in DMF (6 mL) and the mixture was stirred at rt for 15 min. Then, (5-fluoropyridin-2-yl)methyl methanesulfonate (0.32 g, 1.6182 mmol) was added at rt and the resultant mixture was stirred at rt for 8 h. Then, the reaction mixture was diluted with EtOAc (70 mL), washed with water (30 mL×2) and brine solution (30 mL), dried over anhydrous Na$_2$SO$_4$, filtered and evaporated to afford a crude product, which was purified by silica gel column chromatography using 20-40% EtOAc in hexane as eluent. The product fractions were collected and evaporated to afford title compound (0.35 g, 52%) as a solid. MS (ESI) [M+H]$^+$ 352.14. The product was used as such in the next step.

Step 3: Preparation of 6-(1,5-dimethyl-6-oxo-1,6-dihydropyridin-3-yl)-8-((5-fluoro-pyridin-2-yl)methoxy)-3,4-dihydroquinolin-2(1H)-one

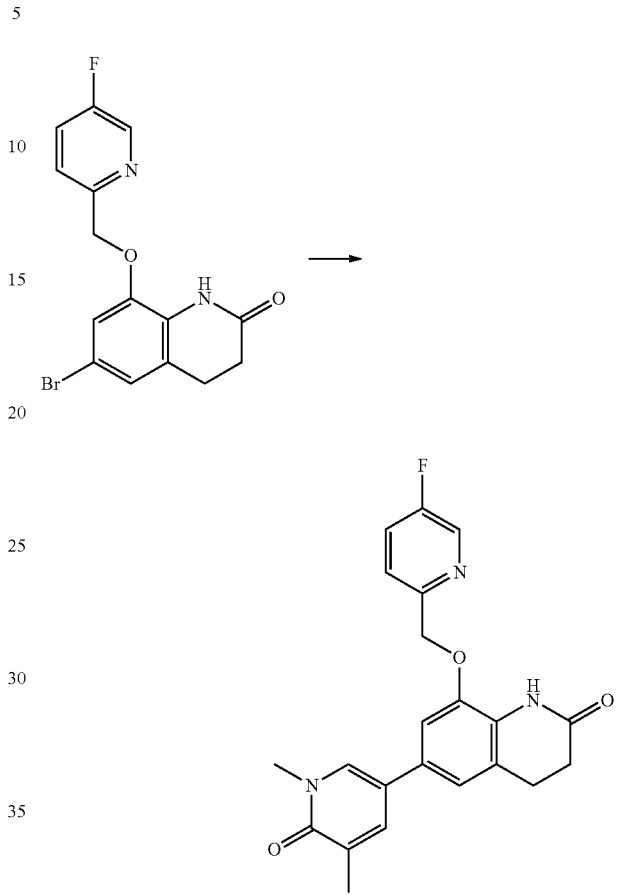

Compound 77

A stirred solution of 6-bromo-8-((5-fluoropyridin-2-yl)methoxy)-3,4-dihydroquinolin-2(1H)-one (0.35 g, 0.9999 mmol) and 1,3-dimethyl-5-(4,4,5,5-tetramethyl-1,3,2-dioxaborolan-2-yl)pyridin-2(1H)-one (0.32 g, 1.2999 mmol, prepared using procedure described in US20130053362) in 1,4-dioxane (10 mL) was purged with N$_2$ for 10 min. A solution ofسodium carbonate (0.32 g, 2.9997 mmol) in water (1 mL) was then added and the mixture was further purged with nitrogen for 10 min. Pd(PPh$_3$)$_4$ (0.058 g, 0.0499 mmol) was then added and the reaction mixture was heated at 90° C. for 6 h. The solvent was evaporated under vacuum and water (60 mL) was added. The product was extracted using EtOAc (40 mL×3). The combined organic layers were washed with brine solution (30 mL), dried over anhydrous Na$_2$SO$_4$, filtered and evaporated to afford a crude product, which was purified by flash chromatography using a gradient of 2.5-3% methanol in DCM as eluent, followed by preparative HPLC purification using 10-57% methanol in water containing 0.1% formic acid as modifier to afford Compound 77 (0.072 g, 18%) as a solid. $^1$H NMR (400 MHz, DMSO) δ 9.38 (s, 1H), 8.59 (d, J=2.8 Hz, 1H), 7.97 (d, J=2.4 Hz, 1H), 7.93 (dd, J=and 4.4 Hz, 1H), 7.84-7.78 (m, 1H), 7.74 (s, 1H), 7.20 (d, J=1.2 Hz, 1H), 7.07 (s, 1H), 5.30 (s, 2H), 3.51 (s, 3H), 2.92 (t, J=7.2 Hz, 2H), 2.50 (m, 2H), 2.08 (s, 3H). MS (ESI) [M+H]$^+$ 394.29.

Example 55: 6-(1,5-dimethyl-6-oxo-1,6-dihydro-pyridin-3-yl)-8-(pyridyl-3-ylmethylamino)-3,4-dihydro-1H-quinolin-2-one Compound 78

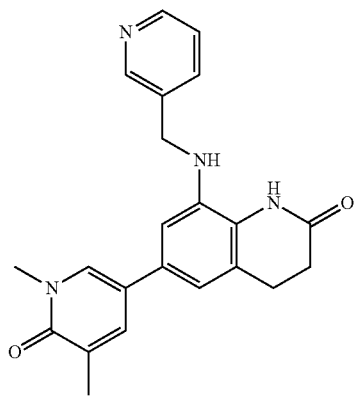

A mixture of AcOH (22 µL, 0.388 mmol), 3-pyridinecarboxaldehyde (36 µL, 0.388 mmol) and Intermediate 2 (100 mg, 0.353 mmol) in DCE (4 mL) was stirred at rt. After 20 h, only the corresponding imine was observed by LCMS. Then, saturated NaHCO$_3$ (10 mL) was added to the mixture and the aqueous layer was extracted with DCM (3×20 mL). The combined organic layers were washed with brine, dried over Na$_2$SO$_4$, filtered and concentrated under reduced pressure. The residue was the dissolved in MeOH (4 mL), NaBH$_4$ (40 mg, 1.06 mmol) was added and the reaction mixture was stirred at rt for 2 h. Saturated NaHCO$_3$ (10 mL) and EtOAc (10 mL) were then added to the mixture. The aqueous phase was extracted with EtOAc (3×10 mL). The combined organic layers were dried over Na$_2$SO$_4$, filtered and concentrated under reduced pressure. The material was purified by flash chromatography on silica gel using a mixture of EtOAc in hexane as eluent, followed by preparative HPLC to afford Compound 78 (21 mg, 16%) as a solid. $^1$H NMR (500 MHz, CDCl$_3$) δ 10.01 (s, 1H), 8.70 (s, 1H), 8.54 (s, 1H), 7.77 (d, J=7.8 Hz, 1H), 7.38 (d, J=1.2 Hz, 1H), 7.29 (dd, J=7.7, 4.8 Hz, 1H), 7.24 (d, J=2.4 Hz, 1H), 6.61 (s, 1H), 6.54 (d, J=1.6 Hz, 1H), 5.10 (s, 1H), 4.43 (s, 2H), 3.59 (s, 3H), 2.95-2.85 (m, 2H), 2.48-2.36 (m, 2H), 2.19 (s, 3H). MS (ESI) [M+H]$^+$ 375.2.

Example 56: 6-(5-chloro-1-methyl-6-oxo-1,6-dihydropyridin-3-yl)-8-(pyridin-2-ylmethoxy)-3,4-dihydroquinolin-2(1H)-one Compound 79

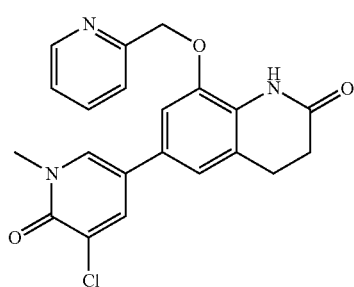

Step 1: Preparation of 5-bromo-3-chloro-1-methylpyridin-2(1H)-one

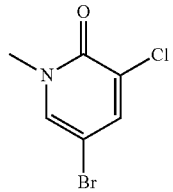

To a rt stirred solution of 5-bromo-3-chloropyridin-2(1H)-one (4 g, 19.19 mmol) in MeOH (80 mL) was added K$_2$CO$_3$ (7.94 g, 57.57 mmol), followed by the addition of methyl iodide (3.6 mL, 57.57 mmol). The reaction mixture was heated to 70° C. for 3 h. The mixture was concentrated under pressure, diluted with water (200 mL), and the aqueous layer was extracted with DCM (3×150 mL). The combined organic layers were washed with brine (100 mL), dried over Na$_2$SO$_4$, filtered and concentrated under reduced pressure to afford the title compound (4 g, 93%) as a solid. MS (ESI) [M+H]$^+$ 223.5.

Step 2: Preparation of 3-chloro-1-methyl-5-(4,4,5,5-tetramethyl-1,3,2-dioxaborolan-2-yl)pyridin-2(1H)-one

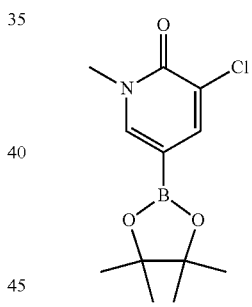

A stirred solution of 5-bromo-3-chloro-1-methylpyridin-2(1H)-one (4 g, 18 mmol) and potassium acetate (5.3 g, 54 mmol) in dioxane (80 mL) was purged with nitrogen for 15 min. Bis(pinacolato)diborane (6.85 g, 27 mmol) was added to the reaction mixture, which was again purged with nitrogen for 30 min. Pd(dppf)Cl$_2$.CH$_2$Cl$_2$ (0.73 g, 0.09 mmol) was added and the resulting mixture was heated at 110° C. for 16 h. The mixture was cooled and filtered through Celite™ and washed with EtOAc (3×50 mL). The organic layer was dried over Na$_2$SO$_4$, filtered and concentrated under reduced pressure. The material was purified by flash chromatography on silica gel using a gradient (0-3%) of MeOH in DCM as eluent and then triturated with Et$_2$O to afford title compound (1.5 g, 31%) as a solid. $^1$H NMR (400 MHz, DMSO) δ ppm 7.81 (d, J=1.6 Hz, 1H), 7.71 (d, J=1.6 Hz, 1H), 3.63 (s, 3H), 1.32 (s, 12H). MS (ESI) [M+H]$^+$ 270.2.

Step 3: Preparation of 6-(5-chloro-1-methyl-6-oxo-1,6-dihydropyridin-3-yl)-8-(pyridin-2-ylmethoxy)-3,4-dihydroquinolin-2(1H)-one

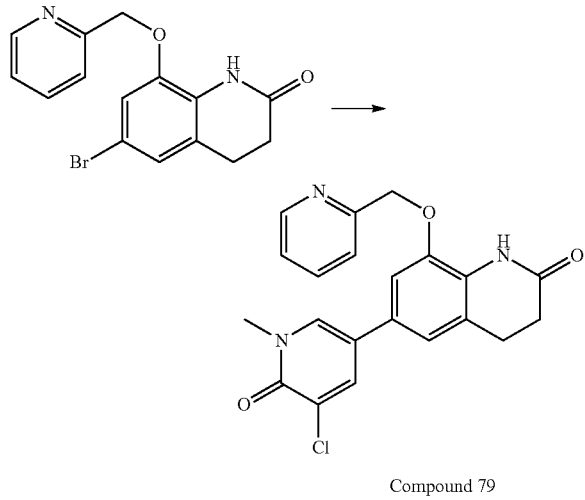

Compound 79

A stirred solution of 6-bromo-8-(pyridin-2-ylmethoxy)-3,4-dihydroquinolin-2(1H)-one (0.3 g, 0.903 mmol, prepared as mentioned in step 1 of Example 23) and 3-chloro-1-methyl-5-(4,4,5,5-tetramethyl-1,3,2-dioxaborolan-2-yl)pyridin-2(1H)-one (0.32 g, 1.173 mmol) in 1,4-dioxane (5 mL) was purged with N₂ for 10 min. A solution of sodium carbonate (0.29 g, 2.709 mmol) in water (0.5 mL) was then added and the mixture was further purged with N₂ for 10 min. Pd(PPh₃)₄(0.052 g, 0.045 mmol) was then added and the reaction mixture was heated at 90° C. for 4 h. Then, the reaction mixture was diluted with water (100 mL) and extracted with EtOAc (100 mL×3). The combined organic layers were dried over anhydrous Na₂SO₄, filtered and evaporated to afford a crude product, which was purified by silica gel column chromatography using a gradient of 2-3% methanol in DCM as eluent, followed by preparative HPLC purification using 17% acetonitrile in water containing 0.1% formic acid as modifier to afford Compound 79 (0.04 g, 11%) as a solid. ¹H NMR (400 MHz, DMSO) δ 9.41 (s, 1H), 8.58 (d, J=4.4 Hz, 1H), 8.18 (dd, J=2.4 and 9.2 Hz, 2H), 7.88 (t, J=7.2 Hz, 1H), 7.85 (d, J=7.6 Hz, 1H), 7.35 (t, J=11.2 Hz, 1H), 7.26 (s, 1H), 7.12 (s, 1H), 5.33 (s, 2H), 3.58 (s, 3H), 2.92 (t, J=7.4 Hz, 2H), 2.47 (s, 2H). MS (ESI) [M+H]⁺ 396.29.

Example 57: 6-(5-chloro-1-methyl-6-oxo-1,6-dihydropyridin-3-yl)-8-(pyridin-3-yl-methoxy)-3,4-dihydroquinolin-2(1H)-one

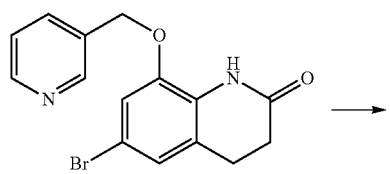

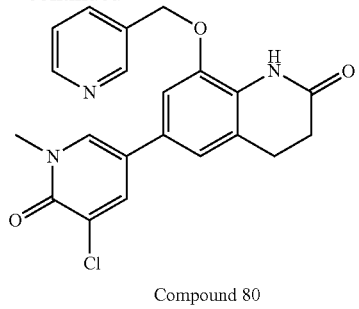

Compound 80

A stirred solution of 6-bromo-8-(pyridin-3-ylmethoxy)-3,4-dihydroquinolin-2(1H)-one (0.3 g, 0.903 mmol, prepared according to step 1 of Example 22) and 3-chloro-1-methyl-5-(4,4,5,5-tetramethyl-1,3,2-dioxaborolan-2-yl)pyridin-2(1H)-one (0.32 g, 1.173 mmol, prepared as in Example 56) in 1,4-dioxane (5 mL) was purged with N₂ for 10 min. A solution of sodium carbonate (0.29 g, 2.709 mmol) in water (0.5 mL) was then added and the mixture was further purged with N₂ for 10 min. Pd(PPh₃)₄(0.052 g, 0.045 mmol) was then added and the reaction mixture was heated at 90° C. for 4 h. After completion of the reaction, reaction mixture was diluted with water (100 mL) and extracted with EtOAc (100 mL×3). The combined organic layers were dried over anhydrous Na₂SO₄, filtered and evaporated to afford a crude product, which was purified by silica gel column chromatography using a gradient of 2-4% methanol in DCM as eluent, followed by preparative HPLC purification using 25% acetonitrile in water containing 0.1% formic acid as modifier to afford Compound 80 (0.02 g, 6%) as a solid. ¹H NMR (400 MHz, MeOD) δ 8.77 (bs, 1H), 8.55 (bs, 1H), 8.11 (d, J=2.4 Hz, 1H), 8.05 (d, J=8 Hz, 1H), 7.97 (d, J=2.4 Hz, 1H), 7.53-7.50 (m, 1H), 7.19 (d, J=1.6 Hz, 1H), 7.06 (s, 1H), 5.36 (s, 2H), 3.72 (s, 3H), 3.03 (t, J=7.6 Hz, 2H), 2.61 (t, J=7.6 Hz, 2H). MS (ESI) [M+H]⁺ 396.2.

Example 58: 6-(1,5-dimethyl-6-oxo-1,6-dihydro-pyridin-3-yl)-8-(oxazol-2-ylmeth oxy)-3,4-dihydroquinolin-2(1H)-one

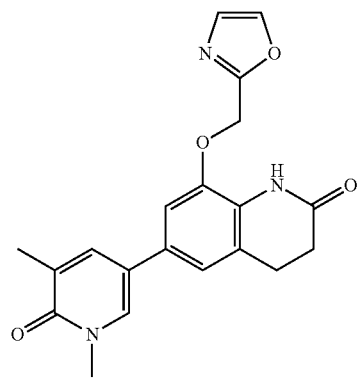

Compound 81

Step 1a: Preparation of oxazol-2-ylmethyl methanesulfonate

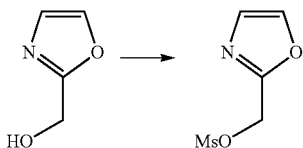 [SMILES: OCc1ncco1 ; CS(=O)(=O)OCc1ncco1]

TEA (0.8 mL, 6.2 mmol) was added to a solution of oxazol-2-ylmethanol (0.25 g, 2.5 mmol) in DCM (4 mL) and the mixture was stirred for 10 min at 0° C. Mesyl chloride (0.25 mL, 3.2 mmol) in DCM (1 mL) was then added dropwise to the reaction mixture, which was stirred at the same temperature for 3 h. Then, the reaction mixture was diluted with water (50 mL) and extracted with EtOAc (25 mL×3). The combined EtOAc layers were washed with brine (30 mL), dried over anhydrous $Na_2SO_4$, filtered and evaporated to afford title compound (0.3 g, 67%) as a solid. MS (ESI) [M+H]$^+$ 178.1. The product was used as such in the next step.

Step 1b: Preparation of 6-bromo-8-(oxazol-2-yl-methoxy)-3,4-dihydroquinolin-2(1H)-one

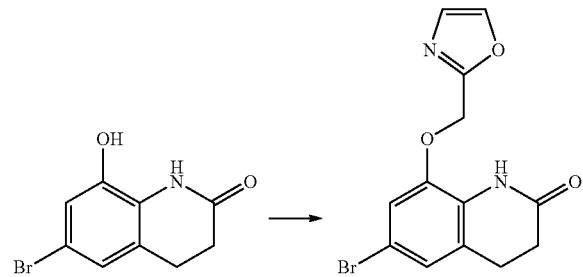 [SMILES: O=C1CCc2cc(Br)cc(O)c2N1 ; O=C1CCc2cc(Br)cc(OCc3ncco3)c2N1]

Intermediate 3 (0.3 g, 1.2 mmol) was added to a suspension of $K_2CO_3$ (0.24 g, 1.8 mmol) in DMF (4 mL) and the mixture was stirred at rt for 15 min. Then, oxazol-2-ylmethyl methanesulfonate (0.26 g, 1.4 mmol) in DMF (1 mL) was added dropwise and the mixture stirred at rt for 16 h. Then, the reaction mixture was diluted with water (100 mL) and extracted with EtOAc (30 mL×3). The combined EtOAc layers were washed with brine (30 mL), dried over anhydrous $Na_2SO_4$, filtered and evaporated to afford a crude product, which was purified by silica gel column chromatography using a gradient of 3-5% methanol in DCM as eluent. The product fractions were collected and evaporated to give title compound (0.24 g, 62%) as a solid. MS (ESI) [M+H]$^+$ 323.29.

Step 2: Preparation of 6-(1,5-dimethyl-6-oxo-1,6-dihydropyridin-3-yl)-8-(oxazol-2-ylmethoxy)-3,4-dihydroquinolin-2(1H)-one

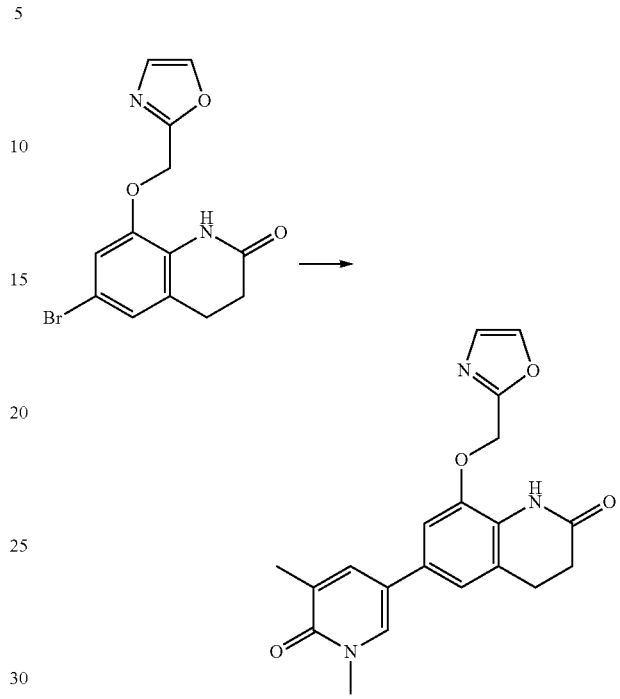

Compound 81

A stirred solution of 6-bromo-8-(oxazol-2-ylmethoxy)-3,4-dihydroquinolin-2(1H)-one (0.24 g, 0.74 mmol) and 1,3-dimethyl-5-(4,4,5,5-tetramethyl-1,3,2-dioxaborolan-2-yl)pyridin-2(1H)-one (0.27 g, 1.1 mmol, prepared using procedure described in US20130053362) in 1,4-dioxane (4 mL) was purged with $N_2$ for 20 min. A solution of sodium carbonate (0.23 g, 2.2 mmol) in water (0.4 mL) was then added and the mixture was further purged with $N_2$ for 20 min. Pd(PPh$_3$)$_4$(0.04 g, 0.037 mmol) was then added and the reaction mixture was heated at 90° C. for 16 h. Then, the reaction mixture was diluted with water (30 mL) and extracted with EtOAc (30 mL×3). The combined EtOAc layers were washed with brine (30 mL), dried over anhydrous $Na_2SO_4$, filtered and evaporated to afford a crude product, which was purified by silica gel column chromatography using a gradient of 3-5% methanol in DCM as eluent, followed by preparative HPLC purification using 20% acetonitrile in water containing 0.1% formic acid as modifier to afford Compound 81 (0.025 g, 9%) as a solid. $^1$H NMR (400 MHz, DMSO) δ 9.17 (s, 1H), 8.20 (s, 1H), 7.95 (d, J=2.4 Hz, 1H), 7.73 (s, 1H), 7.30 (s, 1H), 7.24 (d, J=1.6 Hz, 1H), 7.08 (s, 1H), 5.34 (s, 2H), 3.51 (s, 3H), 2.91 (t, J=14.8 Hz, 2H), 2.47 (m, 2H), 2.08 (s, 3H). MS (ESI) [M+H]$^+$ 366.24.

Example 59: 6-(1,5-dimethyl-6-oxo-1,6-dihydropyridin-3-yl)-8-(thiazol-4-ylmethoxy)-3,4-dihydroquinolin-2(1H)-one

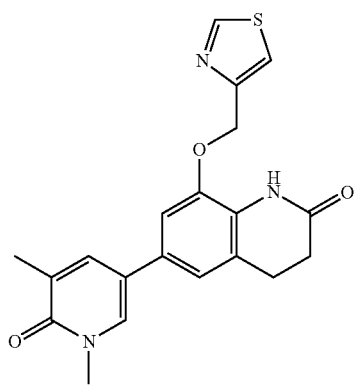

Compound 82

Step 1a: Preparation of thiazol-4-ylmethyl methanesulfonate

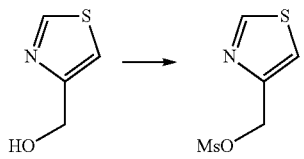

TEA (0.8 mL, 5.2 mmol) was added to a solution of Thiazol-4-ylmethanol (0.25 g, 2.1 mmol) in DCM (4 mL) and the mixture was stirred for 10 min at 0° C. Mesyl chloride (0.25 mL, 2.8 mmol) in DCM (1 mL) was then added dropwise and the mixture stirred at the same temperature for 3 h. Then, the reaction mixture was diluted with water (50 mL) and extracted with EtOAc (25 mL×3). The combined EtOAc layers were washed with brine (30 mL), dried over anhydrous Na$_2$SO$_4$, filtered and evaporated to afford title compound (0.3 g, 71%) as a solid. $^1$H NMR (400 MHz, CDCl$_3$) δ 8.87 (d, J=1.6 Hz, 1H), 7.54 (d, J=2 Hz, 1H), 5.43 (s, 2H), 3.03 (s, 3H). The product was used as such in the next step.

Step 1b: Preparation of 6-bromo-8-(thiazol-4-ylmethoxy)-3,4-dihydroquinolin-2(1H)-one

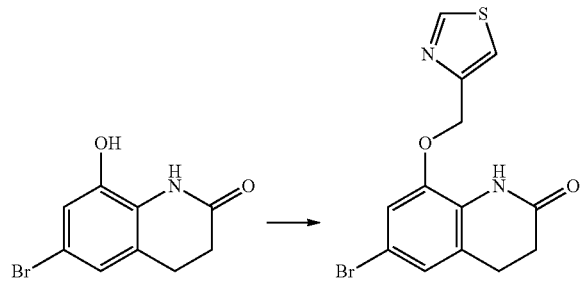 [SMILES: O=C1CCc2cc(Br)cc(O)c2N1 ; O=C1CCc2cc(Br)cc(OCc3cscn3)c2N1]

Intermediate 3 (0.3 g, 1.2 mmol) was added to a suspension of K$_2$CO$_3$ (0.24 g, 1.8 mmol) in DMF (4 mL) and the mixture was stirred at rt for 15 min. Thiazol-4-ylmethyl methanesulfonate (0.27 g, 1.4 mmol) in DMF (1 mL) was then added dropwise and the mixture stirred at rt for 16 h. Then, the reaction mixture was diluted with water (100 mL) and extracted with EtOAc (30 mL×3). The combined EtOAc layers were washed with brine (30 mL), dried over anhydrous Na$_2$SO$_4$, filtered and evaporated to afford a crude product, which was purified by silica gel column chromatography using a gradient of 3-5% methanol in DCM as eluent. The product fractions were collected and evaporated to give title compound (0.25 g, 18%) as a solid. MS (ESI) [M+H]$^+$ 341.1.

Step 2: Preparation of 6-(1,5-dimethyl-6-oxo-1,6-dihydropyridin-3-yl)-8-(thiazol-4-ylmethoxy)-3,4-dihydroquinolin-2(1H)-one

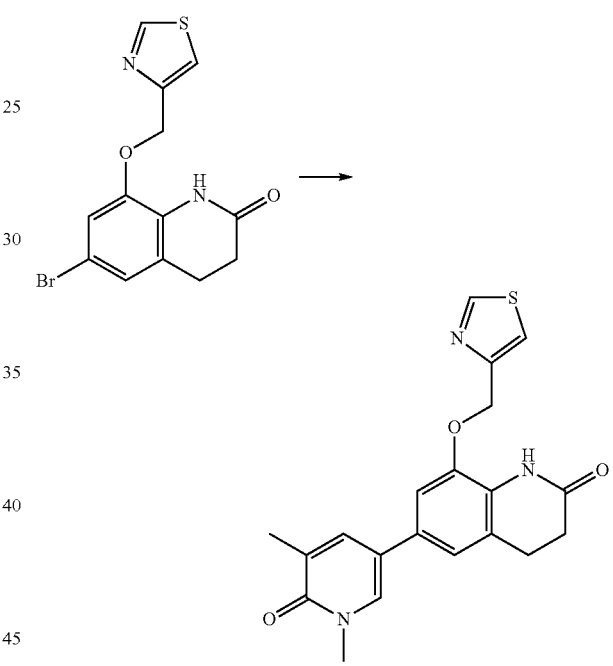

Compound 82

A stirred solution of 6-bromo-8-(thiazol-4-ylmethoxy)-3,4-dihydroquinolin-2(1H)-one (0.24 g, 0.70 mmol) and 1,3-dimethyl-5-(4,4,5,5-tetramethyl-1,3,2-dioxaborolan-2-yl)pyridin-2(1H)-one (0.22 g, 0.80 mmol, prepared using procedure described in US20130053362) in 1,4-dioxane (4 mL) was purged with N$_2$ for 20 min. A solution of sodium carbonate (0.22 g, 2.1 mmol) in water (0.4 mL) was then added and the mixture was further purged with N$_2$ for 20 min. Pd(PPh$_3$)$_4$ (0.04 g, 0.035 mmol) was then added and the reaction mixture was heated at 90° C. for 16 h. Then, the reaction mixture was diluted with water (30 mL) and extracted with EtOAc (30 mL×3). The combined EtOAc layers were washed with brine (30 mL), dried over anhydrous Na$_2$SO$_4$, filtered and evaporated to afford a crude product, which was purified by silica gel column chromatography using a gradient of 3-5% methanol in DCM as eluent, followed by preparative HPLC purification using 30% acetonitrile in water containing 0.1% formic acid as modifier to afford Compound 82 (0.010 g, 3%) as a solid. $^1$H NMR (400 MHz, MeOD) 9.11 (d, J=2 Hz, 1H), 7.84 (d, J=2.4 Hz, 1H), 7.80 (d, J=2 Hz, 1H), 7.77 (d, J=1.2 Hz, 1H), 7.21 (d, J=1.6 Hz, 1H), 7.05 (d, J=1.6 Hz, 1H), 5.40 (s, 2H), 3.67 (s, 3H), 3.15 (t, J=14.8 Hz, 2H), 2.61 (t, J=14.8 Hz, 2H), 2.22 (s, 3H). MS (ESI) [M+H]$^+$ 382.56.

Example 60: 6-(1,5-dimethyl-6-oxo-1,6-dihydropyridin-3-yl)-8-(thiazol-2-ylmethoxy)-3,4-dihydroquinolin-2(1H)-one

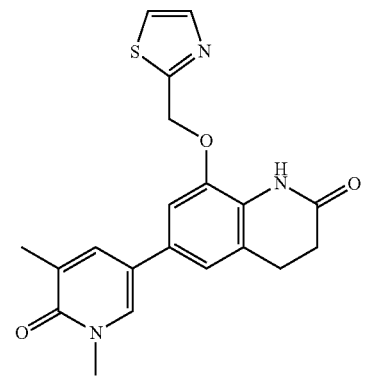

Compound 83

Step 1: Preparation of 6-bromo-8-(thiazol-2-ylmethoxy)-3,4-dihydroquinolin-2(1H)-one

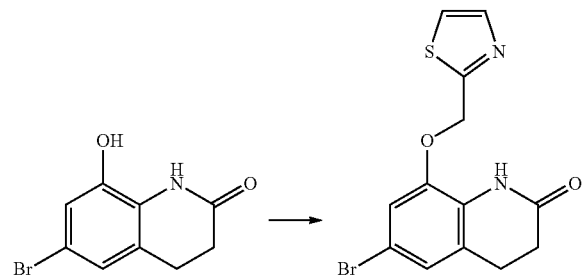 [SMILES: O=C1CCc2cc(Br)cc(O)c2N1 ; O=C1CCc2cc(Br)cc(OCc3nccs3)c2N1]

Intermediate 3 (0.2 g, 0.83 mmol) was added to a suspension of K$_2$CO$_3$ (0.35 g, 2.49 mmol) in DMF (4 mL) and the mixture was stirred at rt for 15 min. Thiazol-2-ylmethyl methanesulfonate (0.33 g, 1.24 mmol) in DMF (1 mL) was then added dropwise at rt and the mixture was heated at 50° C. for 16 h. Then, the reaction mixture was diluted with water (50 mL) and extracted with EtOAc (30 mL×3). The combined EtOAc layers were washed with brine solution (30 mL), dried over anhydrous Na$_2$SO$_4$, filtered and evaporated to afford a crude product, which was purified by silica gel column chromatography using a gradient of 1-2% methanol in DCM as eluent. The product fractions were collected and evaporated to give title compound (0.23 g, 58%) as a solid. MS (ESI) [M+H]$^+$ 338.09.

Step 2: Preparation of 6-(1,5-dimethyl-6-oxo-1,6-dihydropyridin-3-yl)-8-(thiazol-2-ylmethoxy)-3,4-dihydroquinolin-2(1H)-one

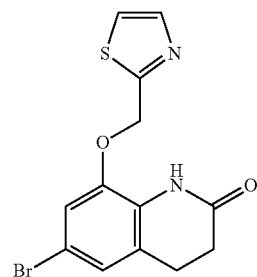

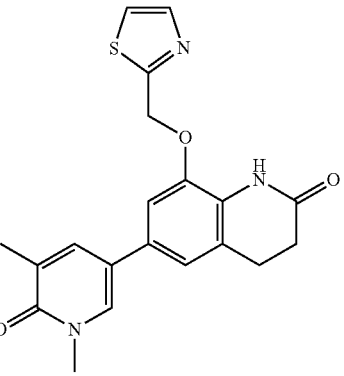

Compound 83

A stirred solution of 6-bromo-8-(thiazol-2-ylmethoxy)-3,4-dihydroquinolin-2(1H)-one (0.23 g, 0.69 mmol) and 1,3-dimethyl-5-(4,4,5,5-tetramethyl-1,3,2-dioxaborolan-2-yl)pyridin-2(1H)-one (0.22 g, 0.90 mmol, prepared using procedure described in US20130053362) in 1,4-dioxane (4 mL) was purged with N$_2$ for 20 min. A solution of sodium carbonate (0.22 g, 2.70 mmol) in water (0.5 mL) was then added and the mixture was further purged with N$_2$ for 20 min. Pd(PPh$_3$)$_4$(0.04 g, 0.034 mmol) was then added and the reaction mixture was heated at 90° C. for 16 h. Then, the reaction mixture was diluted with water (30 mL) and extracted with EtOAc (30 mL×3). The combined EtOAc layers were washed with brine solution (30 mL), dried over anhydrous Na$_2$SO$_4$, filtered and evaporated to afford a crude product, which was purified by silica gel column chromatography using a gradient of 2-3% methanol in DCM as eluent, followed by preparative HPLC purification using 15-25% acetonitrile:methanol (1:1) in 0.1% formic acid in water to afford Compound 83 (0.025 g, 9%) as a solid. $^1$H NMR (400 MHz, DMSO) 9.13 (s, 1H), 7.96 (d, J=2 Hz, 1H), 7.86 (d, J=3.2 Hz, 1H), 7.80 (d, J=3.2 Hz, 1H), 7.39 (s, 1H), 7.27 (d, J=1.6 Hz, 1H), 7.09 (s, 1H), 5.57 (s, 2H), 3.50 (s, 3H), 2.92 (t, J=7.4 Hz, 2H), 2.47 (m, 2H), 2.07 (s, 3H). MS (ESI) [M+H]$^+$ 382.29.

Example 61: 6-(1,5-dimethyl-6-oxo-1,6-dihydropyridin-3-yl)-8-(oxazol-4-ylmethoxy)-3,4-dihydroquinolin-2(1H)-one

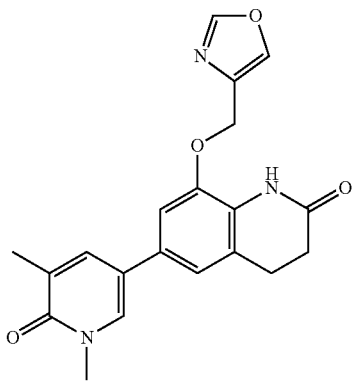

Compound 84

Step 1a: Preparation of oxazol-4-ylmethyl methanesulfonate

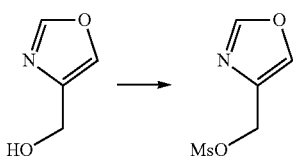 [SMILES: OCc1cocn1 ; CS(=O)(=O)OCc1cocn1]

TEA (0.8 mL, 6.2 mmol) was added to a solution of oxazol-4-ylmethanol (0.25 g, 2.5 mmol) in DCM (4 mL) at 0° C. and the mixture was stirred for 10 min at 0° C. Mesyl chloride (0.25 mL, 3.2 mmol) in DCM (1 mL) was then added dropwise and the mixture stirred at 0° C. for 3 h. Then, the reaction mixture was diluted with water (50 mL) and extracted with EtOAc (25 mL×3). The combined EtOAc layers were washed with brine (30 mL), dried over anhydrous Na$_2$SO$_4$, filtered and evaporated to afford title compound (0.3 g, 67%) as a solid. MS (ESI) [M+H]$^+$ 178.1.

Step 1b: Preparation of 6-bromo-8-(oxazol-4-ylmethoxy)-3,4-dihydroquinolin-2(1H)-one

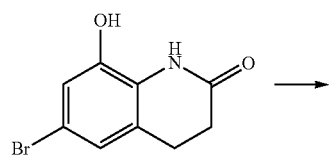

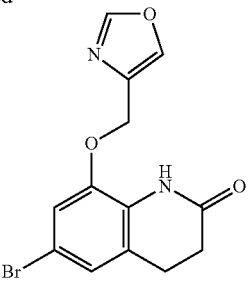

Intermediate 3 (0.25 g, 1.0 mmol) was added to a suspension of K$_2$CO$_3$ (0.41 g, 3.0 mmol) in DMF (4 mL) and the mixture was stirred at rt for 15 min. Oxazol-4-ylmethyl methanesulfonate (0.21 g, 1.2 mmol) in DMF (1 mL) was then added dropwise and the mixture stirred at rt for 16 h. Then, the reaction mixture was diluted with water (100 mL) and extracted with EtOAc (30 mL×3). The combined EtOAc layers were washed with brine (30 mL), dried over anhydrous Na$_2$SO$_4$, filtered and evaporated to afford a crude product, which was purified by silica gel column chromatography using a gradient of 3-5% methanol in DCM as eluent. The product fractions were collected and evaporated to give title compound (0.24 g, 54%) as a solid. MS (ESI) [M+H]$^+$ 325.

Step 2: Preparation of 6-(1,5-dimethyl-6-oxo-1,6-dihydropyridin-3-yl)-8-(oxazol-4-ylmethoxy)-3,4-dihydroquinolin-2(1H)-one

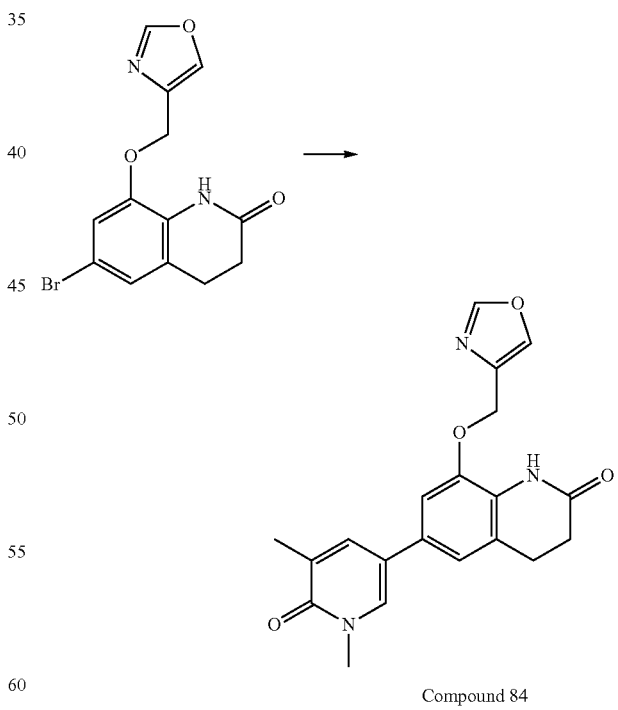

Compound 84

A stirred solution of 6-bromo-8-(oxazol-4-ylmethoxy)-3,4-dihydroquinolin-2(1H)-one (0.23 g, 0.71 mmol) and 1,3-dimethyl-5-(4,4,5,5-tetramethyl-1,3,2-dioxaborolan-2-yl)pyridin-2(1H)-one (0.26 g, 1.0 mmol, prepared using procedure described in US20130053362 in 1,4-dioxane (4 mL) was purged with N$_2$ for 20 min. A solution of sodium carbonate (0.22 g, 2.1 mmol) in water (0.4 mL) was then added and the mixture was further purged with N$_2$ for 20 min. Pd(PPh$_3$)$_4$ (0.04 g, 0.035 mmol) was then added and the reaction mixture was heated at 90° C. for 16 h. Then, the reaction mixture was diluted with water (30 mL) and extracted with EtOAc (30 mL×3). The combined EtOAc layer was washed with brine (30 mL), dried over anhydrous Na$_2$SO$_4$, filtered and evaporated to afford a crude product, which was purified by silica gel column chromatography using a gradient of 3-5% methanol in DCM as eluent, followed by preparative HPLC purification using 30% acetonitrile in water containing 0.1% formic acid as modifier to afford Compound 84 (0.005 g, 2%) as a solid. $^1$H NMR (400 MHz, MeOD) δ 8.32 (s, 1H), 8.13 (s, 1H), 7.85 (d, J=2.4 Hz, 1H), 7.79 (J=1.2 Hz, 1H), 7.23 (d, J=2 Hz, 1H), 7.06 (d, J=1.6 Hz, 1H), 5.21 (s, 2H), 3.68 (s, 3H), 3.02 (t, J=7.2 Hz, 2H), 2.61 (t, J=6 Hz, 2H), 2.22 (s, 3H). MS (ESI) [M+H]$^+$ 366.3.

Example 62: 6-(1,5-dimethyl-6-oxo-1,6-dihydropyridin-3-yl)-7-(3-fluorobenzyl)-3,4-dihydroquinolin-2(1H)-one and 6-(1,5-dimethyl-6-oxo-1,6-dihydropyridin-3-yl)-5-(3-fluorobenzyl)-3,4-dihydroquinolin-2(1H)-one

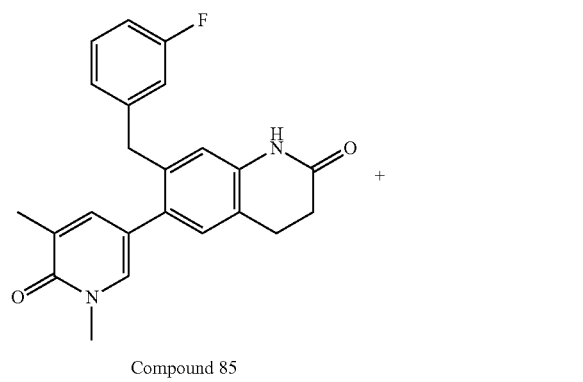

Compound 85

Compound 86

Step 1: Preparation of Mixture of 6-chloro-7-(3-fluorobenzyl)-3,4-dihydroquinolin-2(1H)-one and 6-chloro-5-(3-fluorobenzyl)-3,4-dihydroquinolin-2(1H)-one

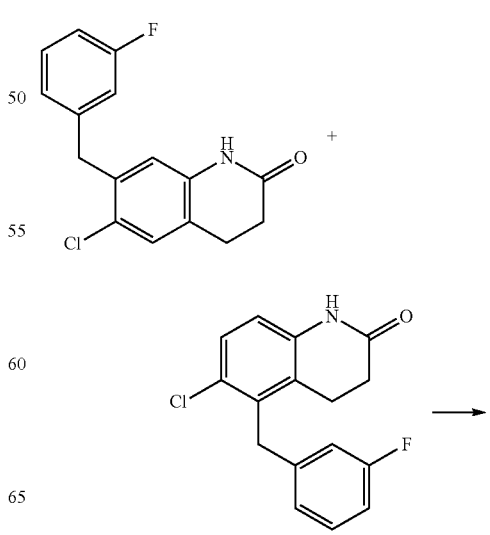

A stirred solution of mixture of 7-bromo-6-chloro-3,4-dihydroquinolin-2(1H)-one and 5-bromo-6-chloro-3,4-dihydroquinolin-2(1H)-one (0.3 g, 1.15 mmol, prepared as in step 1b of Example 42) and 2-(3-fluorobenzyl)-4,4,5,5-tetramethyl-1,3,2-dioxaborolane (0.408 g, 1.73 mmol) in 1,4-dioxane (5 mL) was purged with N$_2$ for 10 min. A solution of Cs$_2$CO$_3$ (1.125 g, 3.45 mmol) in water (0.5 mL) was then added and the mixture was further purged with N$_2$ for 10 min. PdCl$_2$(dppf).CH$_2$Cl$_2$ (0.047 g, 0.06 mmol) was then added and the reaction mixture was heated at 150° C. for 3 h under microwave irradiation. Then, the reaction mixture was evaporated to afford a crude product, which was purified by silica gel column chromatography using a gradient of 50-70% EtOAc in hexane as eluent. The product fractions were collected and evaporated to afford a mixture of title compounds (0.4 g, 72%) as a semi-solid. MS (ESI) [M+H]$^+$ 290.34.

Step 2: Preparation of 6-(1,5-dimethyl-6-oxo-1,6-dihydropyridin-3-yl)-7-(3-fluorobenzyl)-3,4-dihydroquinolin-2(1H)-one and 6-(1,5-dimethyl-6-oxo-1,6-dihydropyridin-3-yl)-5-(3-fluorobenzyl)-3,4-dihydroquinolin-2(1H)-one

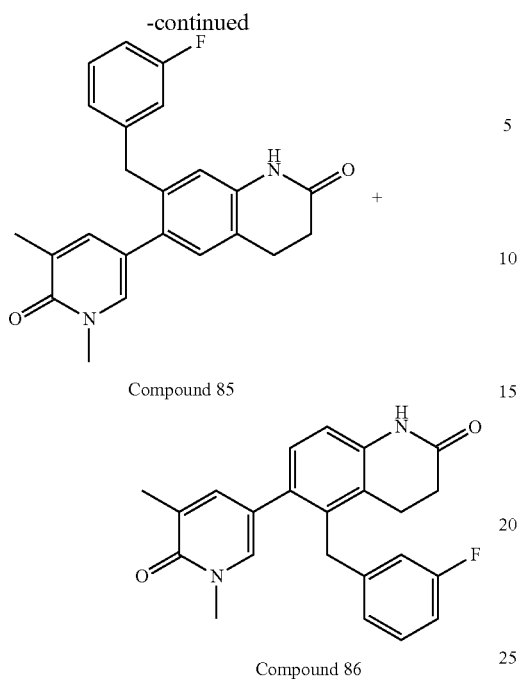

Compound 85

Compound 86

A stirred solution of a mixture of 6-chloro-7-(3-fluorobenzyl)-3,4-dihydroquinolin-2(1H)-one and 6-chloro-5-(3-fluorobenzyl)-3,4-dihydroquinolin-2(1H)-one (0.35 g, 1.21 mmol) and 1,3-dimethyl-5-(4,4,5,5-tetramethyl-1,3,2-dioxaborolan-2-yl)pyridin-2(1H)-one (0.602 g, 2.42 mmol, prepared using procedure described in US20130053362) in 1,4-dioxane (5 mL) was purged with $N_2$ for 10 min. A solution of $K_3PO_4$ (0.769 g, 3.62 mmol) in water (0.5 mL) was then added and the mixture was further purged with $N_2$ for 10 min. $Pd(t-Bu_3P)_2$ (0.032 g, 0.06 mmol) was then added and the reaction mixture was heated at 150° C. under microwave irradiation for 4 h. Then, the reaction mixture was evaporated to afford a crude product, which was purified by silica gel column chromatography using a gradient of 1-2% methanol in DCM as eluent. The pure product fractions were collected and evaporated to afford a mixture of the title compounds (0.075 g) as a solid. The compounds were isolated by preparative HPLC purification using 30% ACN in water containing 0.1% formic acid as modifier to afford Compound 85 (0.030 g) and Compound 86 (0.023 g) as solids.

Compound 85: $^1$H NMR (400 MHz, DMSO-d6) δ ppm 10.05 (s, 1H), 7.41 (d, J=2.4 Hz, 1H), 7.32-7.26 (m, 1H), 7.16 (t, J=1.2 Hz, 1H), 7.04 (s, 1H), 7.03-6.98 (m, 1H), 6.83 (d, J=7.6 Hz, 1H), 6.81-6.78 (m, 1H), 6.69 (s, 1H), 3.90 (s, 2H), 3.42 (s, 3H), 2.88-2.84 (m, 2H), 2.47-2.43 (m, 2H), 1.98 (s, 3H). MS (ESI) [M+H]$^+$ 377.29.

Compound 86: $^1$H NMR (400 MHz, DMSO-d6) δ ppm 10.16 (s, 1H), 7.34 (d, J=2.4 Hz, 1H), 7.31-7.26 (m, 1H), 7.07 (d, J=8 Hz, 1H), 7.05 (d, J=1.2 Hz, 1H), 7.02-6.97 (m, 1H), 6.86 (d, J=8 Hz, 1H), 6.76 (d, J=7.6 Hz, 1H), 6.72 (s, 1H), 4.01 (s, 2H), 3.37 (s, 3H), 2.72-2.68 (m, 2H), 2.40-2.36 (m, 2H), 1.91 (s, 3H). MS (ESI) [M+H]$^+$ 377.29.

Example 63: 4-((6-(1,5-dimethyl-6-oxo-1,6-dihydropyridin-3-yl)-2-oxo-1,2,3,4-tetrahydroquinolin-5-yl)methyl)benzonitrile

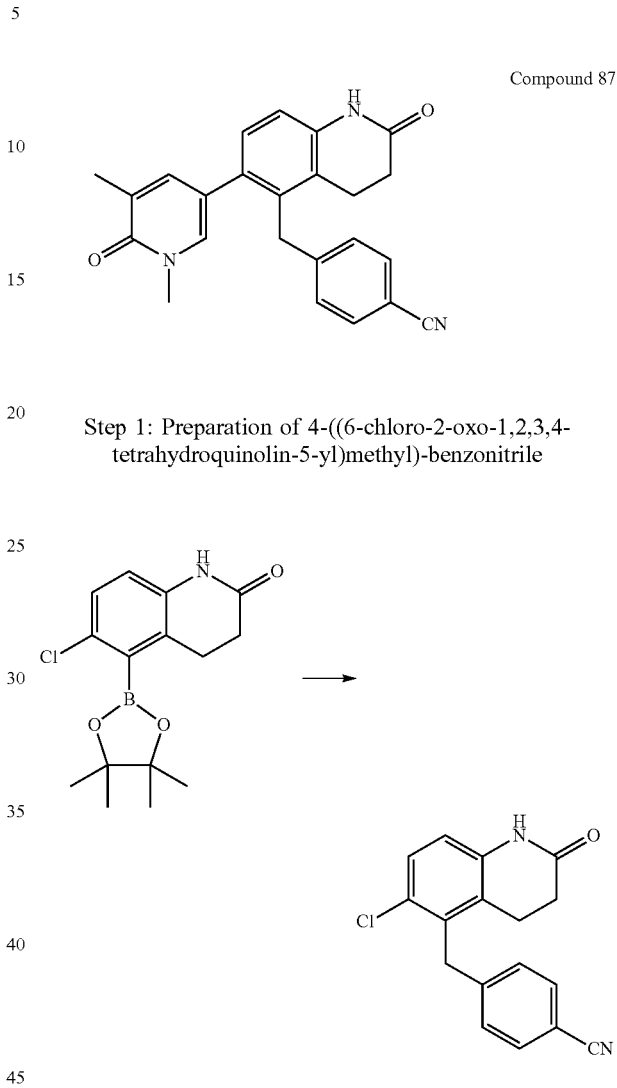

Compound 87

Step 1: Preparation of 4-((6-chloro-2-oxo-1,2,3,4-tetrahydroquinolin-5-yl)methyl)-benzonitrile A stirred solution of 6-chloro-5-(4,4,5,5-tetramethyl-1,3,2-dioxaborolan-2-yl)-3,4-dihydroquinolin-2(1H)-one (0.2 g, 0.65 mmol, prepared as in step 1 of Example 42) and 4-(bromomethyl)benzonitrile (0.191 g, 0.98 mmol) in 1,4-dioxane (5 mL) was purged with $N_2$ for 10 min. A solution of $Cs_2CO_3$ (0.636 g, 1.95 mmol) in water (0.5 mL) was then added and the mixture was further purged with $N_2$ for 10 min. $PdCl_2(dppf) \cdot CH_2Cl_2$ (0.027 g, 0.03 mmol) was then added and the reaction mixture was heated at 100° C. for 5 h. Then, the reaction mixture was evaporated to afford a crude product, which was purified by silica gel column chromatography using a gradient of 40-70% EtOAc in hexane as eluent. The product fractions were collected and evaporated to afford title compound (0.15 g, 67%) as a solid. MS (ESI) [M+H]$^+$ 295.23.

Step 2: Preparation of 4-((6-(1,5-dimethyl-6-oxo-1,6-dihydropyridin-3-yl)-2-oxo-1,2,3,4-tetrahydroquinolin-5-yl)methyl)benzonitrile

Step 1: Preparation of 3-((6-chloro-2-oxo-1,2,3,4-tetrahydroquinolin-5-ylmethyl)-benzonitrile

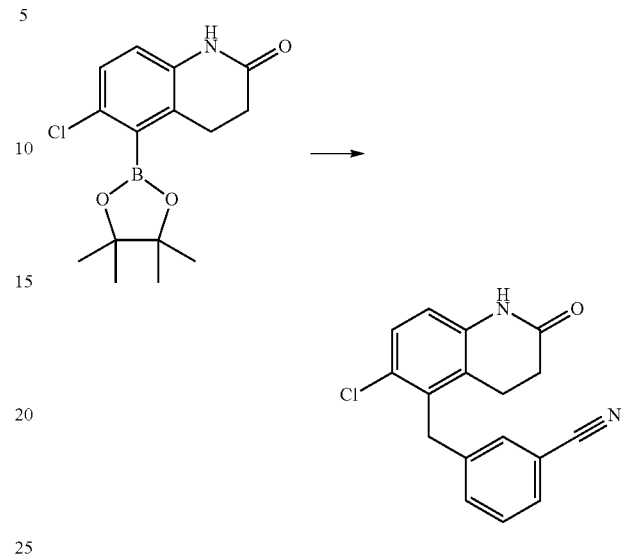

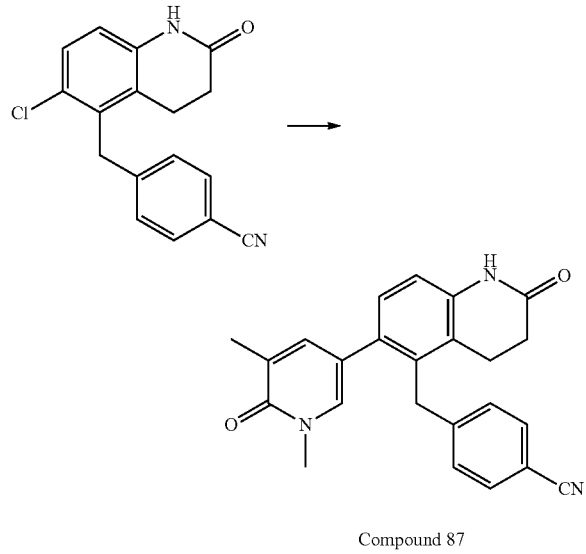

Compound 87

A stirred solution of 6-chloro-5-(4,4,5,5-tetramethyl-1,3,2-dioxaborolan-2-yl)-3,4-dihydroquinolin-2(1H)-one (0.2 g, 0.65 mmol) and 3-(bromomethyl)benzonitrile (0.191 g, 0.98 mmol) in 1,4-dioxane (5 mL) was purged with $N_2$ for 10 min. A solution of $Cs_2CO_3$ (0.636 g, 1.95 mmol) in water (0.5 mL) was then added and the mixture was further purged with $N_2$ for 10 min. $PdCl_2(dppf) \cdot CH_2Cl_2$ (0.027 g, 0.03 mmol) was then added and the reaction mixture was heated at 100° C. for 5 h. Then, the reaction mixture was evaporated to afford a crude product, which was purified by silica gel column chromatography using a gradient of 40-70% EtOAc in hexane as eluent. The product fractions were collected and evaporated to afford title compound (0.15 g, 68%) as a solid. MS (ESI) [M+H]⁺ 297.23.

A stirred solution of 4-((6-chloro-2-oxo-1,2,3,4-tetrahydroquinolin-5-yl)methyl)benzonitrile (0.15 g, 0.51 mmol) and 1,3-dimethyl-5-(4,4,5,5-tetramethyl-1,3,2-dioxaborolan-2-yl)pyridin-2(1H)-one (0.189 g, 0.76 mmol, prepared using procedure described in US20130053362) in 1,4-dioxane (5 mL) was purged with $N_2$ for 10 min. A solution of $K_3PO_4$ (0.322 g, 1.52 mmol) in water (0.5 mL) was then added and the mixture was further purged with $N_2$ for 10 min. $Pd(t-Bu_3P)_2$ (0.013 g, 0.03 mmol) was then added and the reaction mixture was heated at 150° C. under microwave irradiation for 4 h. Then, the reaction mixture was evaporated to afford a crude product, which was purified by silica gel column chromatography using a gradient of 1-2% methanol in DCM as eluent, followed by preparative HPLC purification using 28% ACN in water containing 0.1% $NH_3$ as modifier to afford Compound 87 (0.025 g, 13%) as a solid. ¹H NMR (400 MHz, MeOD) δ ppm 7.64 (s, 1H), 7.62 (s, 1H), 7.27 (d, J=2.4 Hz, 1H), 7.16-7.27 (m, 4H), 6.93 (d, J=8 Hz, 1H), 4.16 (s, 2H), 3.51 (s, 3H), 2.86-2.82 (m, 2H), 2.55-2.51 (m, 2H), 2.05 (s, 3H). MS (ESI) [M+H]⁺ 384.28.

Step 2: Preparation of 3-((6-(1,5-dimethyl-6-oxo-1,6-dihydropyridin-3-yl)-2-oxo-1,2,3,4-tetrahydroquinolin-5-yl)methyl)benzonitrile

Example 64: 3-((6-(1,5-dimethyl-6-oxo-1,6-dihydropyridin-3-yl)-2-oxo-1,2,3,4-tetrahydroquinolin-5-yl)methyl)benzonitrile

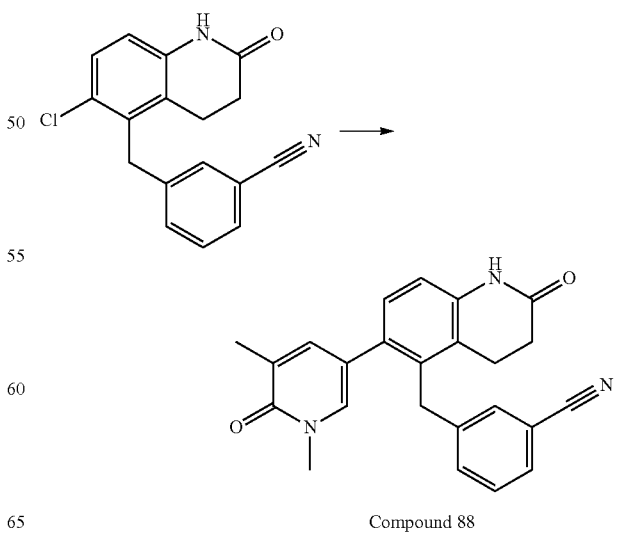

Compound 88

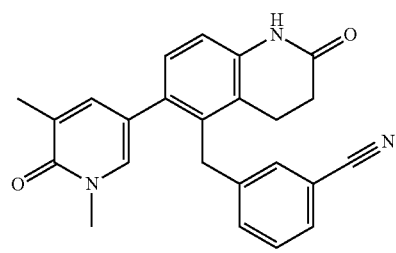

Compound 88

A stirred solution of 3-((6-chloro-2-oxo-1,2,3,4-tetrahydroquinolin-5-yl)methyl)benzonitrile (0.15 g, 0.51 mmol) and 1,3-dimethyl-5-(4,4,5,5-tetramethyl-1,3,2-dioxaborolan-2-yl)pyridin-2(1H)-one (0.189 g, 0.76 mmol, prepared using procedure described in US20130053362) in 1,4-dioxane (5 mL) was purged with $N_2$ for 10 min. A solution of $K_3PO_4$ (0.322 g, 1.52 mmol) in water (0.5 mL) was then added and the mixture was again purged with $N_2$ for 10 min. Pd (t-But$_3$P)$_2$ (0.013 g, 0.03 mmol) was then added and the reaction mixture was heated at 150° C. under microwave irradiation for 4 h. Then, the reaction mixture was evaporated to afford a crude product, which was purified by silica gel column chromatography using a gradient of 1-2% methanol in DCM as eluent. The pure product fractions were collected and evaporated to afford Compound 88 (0.015 g, 8%) as a solid. $^1$H NMR (400 MHz, MeOD) δ ppm 7.56 (d, J=7.6 Hz, 1H), 7.44 (t, J=8 and 7.6 Hz, 1H), 7.29 (s, 1H), 7.28 (d, J=2 Hz, 1H), 7.26 (d, J=7.6 Hz, 1H), 7.16 (s, 1H), 7.14 (s, 1H), 6.93 (d, J=8 Hz, 1H), 4.14 (s, 2H), 3.52 (s, 3H), 2.86 (m, 2H), 2.54 (m, 2H), 2.06 (s, 3H). MS (ESI) [M+H]$^+$ 384.33.

Example 65: 2-((6-(1,5-dimethyl-6-oxo-1,6-dihydropyridin-3-yl)-2-oxo-1,2,3,4-tetrahydroquinolin-5-yl)methyl)benzonitrile

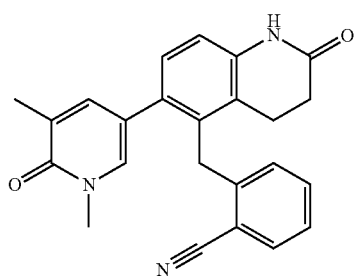

Compound 89

Step 1: Preparation of 2-((6-chloro-2-oxo-1,2,3,4-tetrahydroquinolin-5-yl)methyl)-benzonitrile

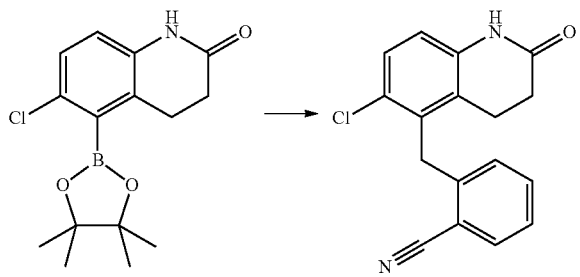 [SMILES: CC1(C)OB(c2c(Cl)ccc3c2CCC(=O)N3)OC1(C)C ; N#Cc1ccccc1Cc1c(Cl)ccc2c1CCC(=O)N2]

A stirred solution of 6-chloro-5-(4,4,5,5-tetramethyl-1,3,2-dioxaborolan-2-yl)-3,4-dihydroquinolin-2(1H)-one (0.2 g, 0.65 mmol) and 2-(bromomethyl)benzonitrile (0.191 g, 0.98 mmol) in 1,4-dioxane (5 mL) was purged with $N_2$ for 10 min. A solution of $Cs_2CO_3$ (0.636 g, 1.95 mmol) in water (0.5 mL) was then added the mixture was further purged with $N_2$ for 10 min. PdCl$_2$(dppf).CH$_2$Cl$_2$ (0.027 g, 0.03 mmol) was then added and the reaction mixture was heated at 100° C. for 5 h. Then, the reaction mixture was evaporated to afford a crude product, which was purified by silica gel column chromatography using a gradient of 40-70% EtOAc in hexane as eluent. The product fractions were collected and evaporated to afford title compound (0.13 g, 51%) as a solid. MS (ESI) [M+H]$^+$ 297.18.

Step 2: Preparation of 2-((6-(1,5-dimethyl-6-oxo-1,6-dihydropyridin-3-yl)-2-oxo-1,2,3,4-tetrahydroquinolin-5-yl)methyl)benzonitrile

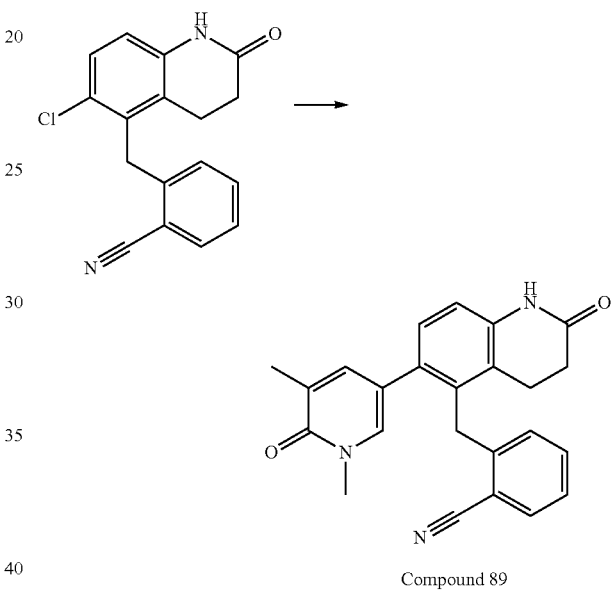

Compound 89

A stirred solution of 2-((6-chloro-2-oxo-1,2,3,4-tetrahydroquinolin-5-yl)methyl)benzonitrile (0.13 g, 0.44 mmol) and 1,3-dimethyl-5-(4,4,5,5-tetramethyl-1,3,2-dioxaborolan-2-yl)pyridin-2(1H)-one (0.164 g, 0.66 mmol, prepared using procedure described in US20130053362) in 1,4-dioxane (5 mL) was purged with $N_2$ for 10 min. A solution of $K_3PO_4$ (0.279 g, 1.31 mmol) in water (0.5 mL) was then added and the mixture was further purged with $N_2$ for 10 min. Pd(t-But$_3$P)$_2$ (0.012 g, 0.02 mmol) was then added and the reaction mixture was heated at 150° C. under microwave irradiation for 4 h. Then, the reaction mixture was evaporated to afford a crude product which was purified by silica gel column chromatography using a gradient of 1-2% methanol in DCM as eluent, followed by preparative HPLC purification using 30% ACN in water containing 0.1% NH$_3$ as modifier to afford Compound 89 (0.015 g, 9%) as a solid. $^1$H NMR (400 MHz, MeOD) δ ppm 7.65 (d, J=7.6 Hz, 1H), 7.53 (t, J=7.6 Hz, 1H), 7.36 (t, J=7.6 Hz, 1H), 7.24 (d, J=1.6 Hz, 1H), 7.11 (d, J=8.4 Hz, 1H), 6.97-6.93 (m, 3H), 4.27 (s, 2H), 3.51 (s, 3H), 2.96 (t, J=7.6 Hz, 2H), 2.59 (t, J=7.6 Hz, 2H), 1.99 (s, 3H). MS (ESI) [M+H]$^+$ 384.33.

Example 66: 6-(1,5-dimethyl-6-oxo-1,6-dihydro-pyridin-3-yl)-7-(4-fluorobenzyl)-3,4-dihydroquinolin-2(1H)-one and 6-(1,5-dimethyl-6-oxo-1,6-dihydropyridin-3-yl)-5-(4-fluorobenzyl)-3,4-dihydroquinolin-2(1H)-one

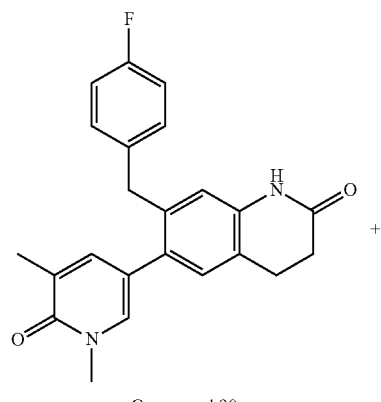

Compound 90

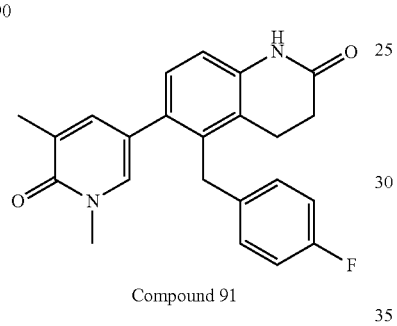

Compound 91

Step 1: Preparation of Mixture of 6-chloro-7-(4-fluorobenzyl)-3,4-dihydroquinolin-2(1H)-one and 6-chloro-5-(4-fluorobenzyl)-3,4-dihydroquinolin-2(1H)-one A stirred solution of a mixture of 7-bromo-6-chloro-3,4-dihydroquinolin-2(1H)-one and 5-bromo-6-chloro-3,4-dihydroquinolin-2(1H)-one (0.3 g, 1.15 mmol, prepared as in step 1b of Example 42) and 2-(4-fluorobenzyl)-4,4,5,5-tetramethyl-1,3,2-dioxaborolane (0.32 g, 1.38 mmol) in 1,4-dioxane (5 mL) was purged with $N_2$ for 10 min. A solution of $Cs_2CO_3$ (1.12 g, 3.45 mmol) in water (0.5 mL) was then added and the mixture was further purged with $N_2$ for 10 min. $PdCl_2(dppf) \cdot CH_2Cl_2$ (0.046 g, 0.05 mmol) was then added and the reaction mixture was heated at 150° C. for 3 h under microwave irradiation. Then, the reaction mixture was evaporated to afford a crude product, which was purified by silica gel (100-200#) column chromatography using a gradient of 40-70% EtOAc in hexane as eluent. The pure product fractions were collected and evaporated under vacuum to afford a mixture of title compounds (0.3 g, 90%) as a semi-solid. MS (ESI) $[M+H]^+$ 289.73.

Step 2: Preparation of 6-(1,5-dimethyl-6-oxo-1,6-dihydropyridin-3-yl)-7-(4-fluorobenzyl)-3,4-dihydroquinolin-2(1H)-one and 6-(1,5-dimethyl-6-oxo-1,6-dihydropyridin-3-yl)-5-(4-fluorobenzyl)-3,4-dihydroquinolin-2(1H)-one

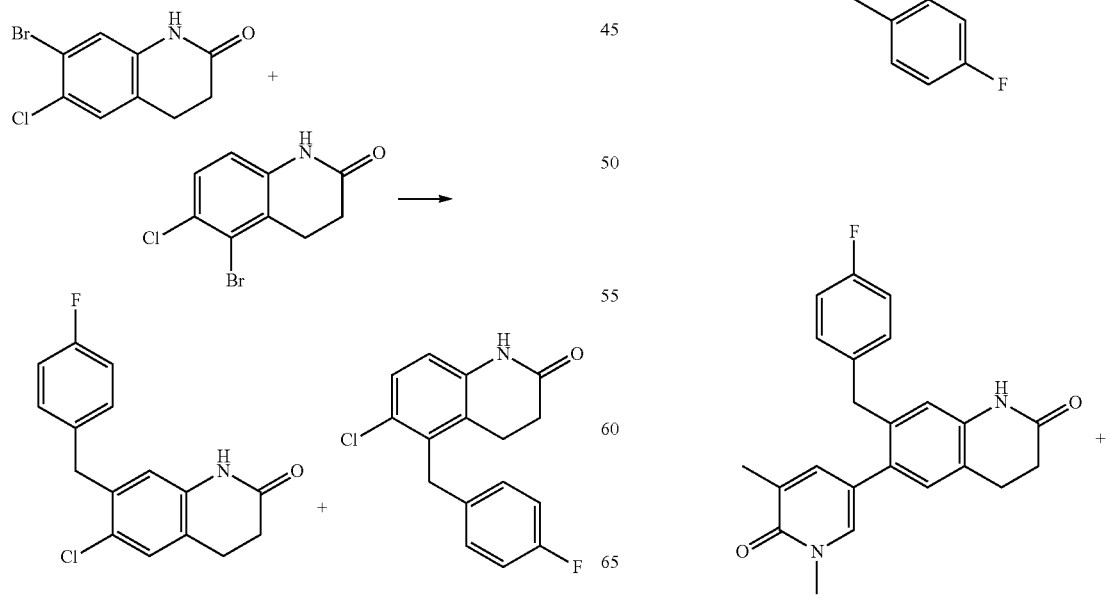

199
-continued

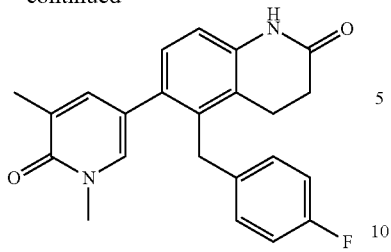

A stirred solution of mixture of 6-chloro-7-(4-fluorobenzyl)-3,4-dihydroquinolin-2(1H)-one and 6-chloro-5-(4-fluorobenzyl)-3,4-dihydroquinolin-2(1H)-one (0.23 g, 0.79 mmol) and 1,3-dimethyl-5-(4,4,5,5-tetramethyl-1,3,2-dioxaborolan-2-yl)pyridin-2(1H)-one (0.39 g, 1.58 mmol, prepared using procedure described in US20130053362) in 1,4-dioxane (5 mL) was purged with $N_2$ for 10 min. A solution of $K_3PO_4$ (0.50 g, 2.38 mmol) in water (0.5 mL) was then added and the mixture was further purged with $N_2$ for 10 min. Pd(t-Bu$_3$P)$_2$ (0.02 g, 0.03 mmol) was then added and the reaction mixture was heated at 150° C. under microwave irradiation for 4 h. Then, the reaction mixture was evaporated to afford a crude product, which was purified by silica gel column chromatography using a gradient of 1-2% methanol in DCM as eluent, followed by preparative HPLC purification using 10-60% Acetonitrile:Methanol (1:1) in water containing 0.1% Formic Acid as a modifier to afford Compound 90 (0.020 g) and Compound 91 (0.015 g) as solids.

Compound 90: $^1$H NMR (400 MHz, MeOH-d$_4$) δ ppm 1H NMR (400 MHz, DMSO-d$_6$) δ ppm 7.23 (d, J=2.4 Hz, 1H), 7.20 (s, 1H), 7.06 (s, 1H), 7.00-6.92 (m, 4H), 6.80 (s, 1H), 3.91 (s, 2H), 3.50 (s, 3H), 2.97 (t, J=7.4 Hz, 2H), 2.60 (t, J=7.6 Hz, 2H), 2.10 (s, 3H), —NH was not visible. MS (ESI) [M+H]$^+$ 377.27

Compound 91: $^1$H NMR (400 MHz, MeOH-d$_4$) δ ppm 7.24 (d, J=2.4 Hz, 1H), 7.17 (s, 1H), 7.13 (d, J=8 Hz, 1H), 7.02-6.96 (m, 4H), 6.90 (d, J=8 Hz, 1H), 4.03 (s, 2H), 3.50 (s, 3H), 2.86 (t, J=7.4 Hz, 2H), 2.52 (t, J=7.6 Hz, 2H), 2.04 (s, 3H), —NH was not visible. MS (ESI) [M+H]$^+$ 377.27.

Example 67: 6-(1,5-dimethyl-6-oxo-1,6-dihydropyridin-3-yl)-8-(1-(pyridin-3-yl)ethoxy)-3,4-dihydroquinolin-2(1H)-one Compound 92a and 92b

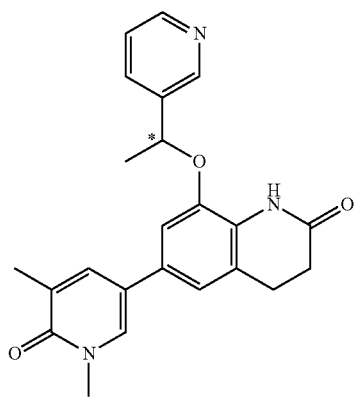

200

Step 1a: Preparation of 1-(pyridin-3-yl)ethyl methanesulfonate

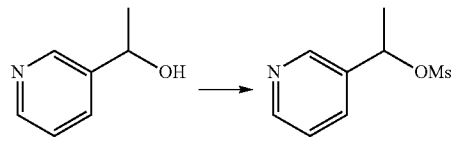

Triethylamine (1.2 mL, 8.12 mmol) was added to a solution of 1-(pyridin-3-yl)ethan-1-ol (0.5 g, 4.06 mmol) in DCM (8 mL) and the mixture was stirred at rt for 15 min. After 15 min, methane sulphonyl chloride (0.4 mL, 4.87 mmol) was added dropwise at rt and the resultant mixture was stirred at same temperature for 3 h. Then, the reaction mixture was diluted with DCM (50 mL), washed with water (40 mL) and brine solution (30 mL), dried over anhydrous Na$_2$SO$_4$, filtered and evaporated to afford title compound (0.5 g, 61%) as an oil. The product was used as such in the next step.

Step 1b: Preparation of 6-bromo-8-(1-(pyridine-3-yl)ethoxy)-3,4-dihydroquinolin-2(1H)-one

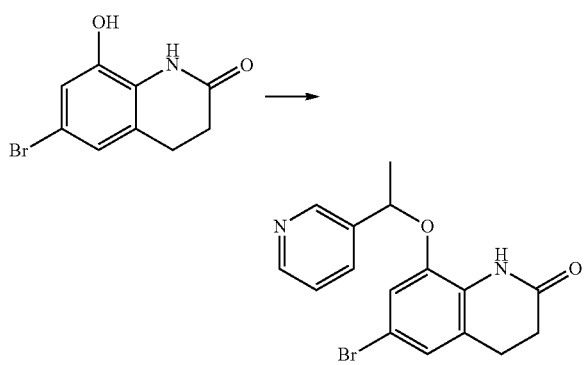

Intermediate 3 (0.5 g, 2.0747 mmol) was added to a suspension of K$_2$CO$_3$ (0.86 g, 6.2241 mmol) in DMF (5 mL) and the mixture was stirred at rt for 15 min. 1-(pyridin-3-yl)ethyl methanesulfonate (0.5 g, 2.4896 mmol) was then added dropwise at rt and the resultant mixture was stirred at rt for 15 h. Then, the reaction mixture was diluted with EtOAc (80 mL), washed with water (40 mL×3) and brine solution (40 mL), dried over anhydrous Na$_2$SO$_4$, filtered and evaporated to afford a crude product, which was purified by silica gel column chromatography using a gradient of 30-50% EtOAc in n-hexane as eluent. The product fractions were collected and evaporated to afford title compound (0.65 g, 54%) as an oil. MS (ESI) [M+H]$^+$ 349.19. The product was used as such in the next step.

Step 2: Preparation of 6-(1,5-dimethyl-6-oxo-1,6-dihydropyridin-3-yl)-8-(1-(pyridin-3-yl)ethoxy)-3,4-dihydroquinolin-2(1H)-one

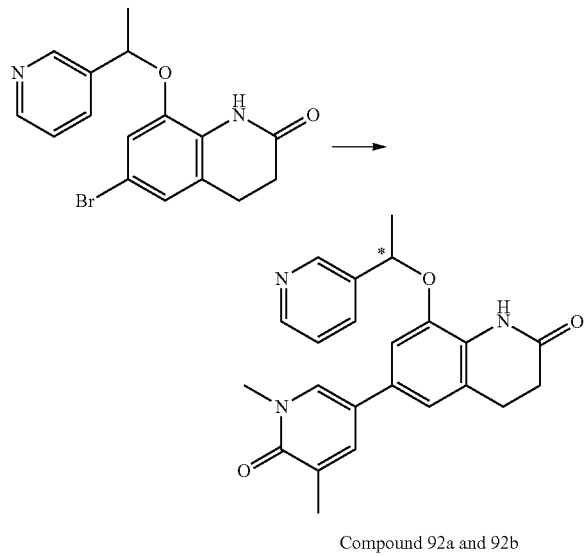

Compound 92a and 92b

A stirred solution of 6-bromo-8-(1-(pyridin-3-yl)ethoxy)-3,4-dihydroquinolin-2(1H)-one (0.65 g, 1.81 mmol) and 1,3-dimethyl-5-(4,4,5,5-tetramethyl-1,3,2-dioxaborolan-2-yl)pyridin-2(1H)-one (0.61 g, 2.44 mmol, prepared using procedure described in US20130053362) in 1,4-dioxane (6 mL) was purged with $N_2$ for 10 min. A solution of sodium carbonate (0.60 g, 5.61 mmol) in water (1 mL) was then added and the mixture was further purged with $N_2$ for 10 min. Pd(PPh$_3$)$_4$ (0.1 g, 0.09 mmol) was then added and the reaction mixture and heated at 100° C. for 8 h. The solvent was evaporated and water (80 mL) was added. The product was extracted using EtOAc (30 mL×3). The combined organic layers were washed with brine solution (40 mL), dried over anhydrous Na$_2$SO$_4$, filtered and evaporated to afford a crude product, which was purified by flash chromatography using a gradient of 1.8-2% methanol in DCM as eluent, followed by preparative HPLC purification using 10-45% methanol in water containing 0.1% formic acid as modifier to afford a racemic mixture of Compounds 92 and 92b (0.088 g) as a solid. The mixture was further purified by chiral preparative HPLC purification using 5-50% IPA in Liq CO$_2$ to afford Compound 92a (0.026 g) and Compound 92b (0.028 g) as separated solids.

Compound 92a: retention time=4.63 min: $^1$H NMR (400 MHz, DMSO) 9.47 (s, 1H), 8.80 (s, 1H), 8.46 (d, J=3.6 Hz, 1H), 8.05 (d, J=7.6 Hz, 1H), 7.84 (s, 1H), 7.61 (s, 1H), 7.38-7.35 (m, 1H), 7.08 (s, 1H), 6.94 (s, 1H), 5.83-5.82 (m, 1H), 3.49 (s, 3H), 2.86 (t, J=7.6 Hz, 2H), 2.48 (m, 2H), 2.06 (s, 3H), 1.65 (d, J=6.0 Hz, 3H). MS (ESI) [M+H]$^+$ 390.33.

Compound 92b: retention time=5.7 min: $^1$H NMR (400 MHz, DMSO) δ 9.47 (s, 1H), 8.80 (s, 1H), 8.46 (d, J=3.6 Hz, 1H), 8.05 (d, J=7.6 Hz, 1H), 7.84 (s, 1H), 7.61 (s, 1H), 7.38-7.35 (m, 1H), 7.08 (s, 1H), 6.94 (s, 1H), 5.85-5.80 (m, 1H), 3.49 (s, 3H), 2.86 (t, J=7.6 Hz, 2H), 2.48 (t, merge with DMSO, 2H), 2.06 (s, 3H), 1.65 (d, J=6.0 Hz, 3H). MS (ESI) [M+H]$^+$ 390.33.

Example 68: (E)-6-(1,5-dimethyl-6-oxo-1,6-dihydropyridin-3-yl)-7-styryl-3,4-dihydroquinolin-2(1H)-one, (E)-6-(1,5-dimethyl-6-oxo-1,6-dihydropyridin-3-yl)-5-styryl-3,4-dihydroquinolin-2(1H)-one, 6-(1,5-dimethyl-6-oxo-1,6-dihydropyridin-3-yl)-5-(1-phenylethyl)-3,4-dihydro-quinolin-2(1H)-one and 6-(1,5-dimethyl-6-oxo-1,6-dihydropyridin-3-yl)-5-phenethyl-3,4-dihydroquinolin-2(1H)-one

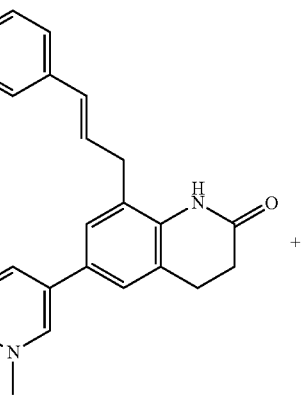

Compound 93

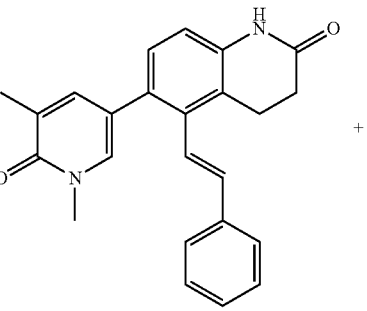

Compound 94

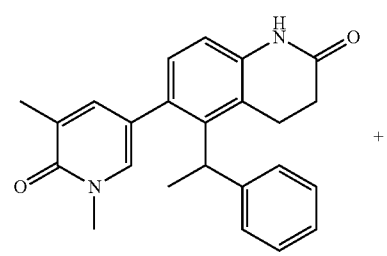

Compound 95

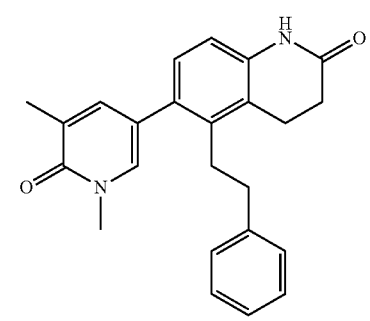

Compound 96

Step 1: Preparation of Mixture of (E)-6-chloro-7-styryl-3,4-dihydroquinolin-2(1H)-one, (E)-6-chloro-5-styryl-3,4-dihydroquinolin-2(1H)-one, 6-chloro-5-(1-phenylethyl)-3,4-dihydro-quinolin-2(1H)-one and 6-chloro-5-phenethyl-3,4-dihydroquinolin-2(1H)-one

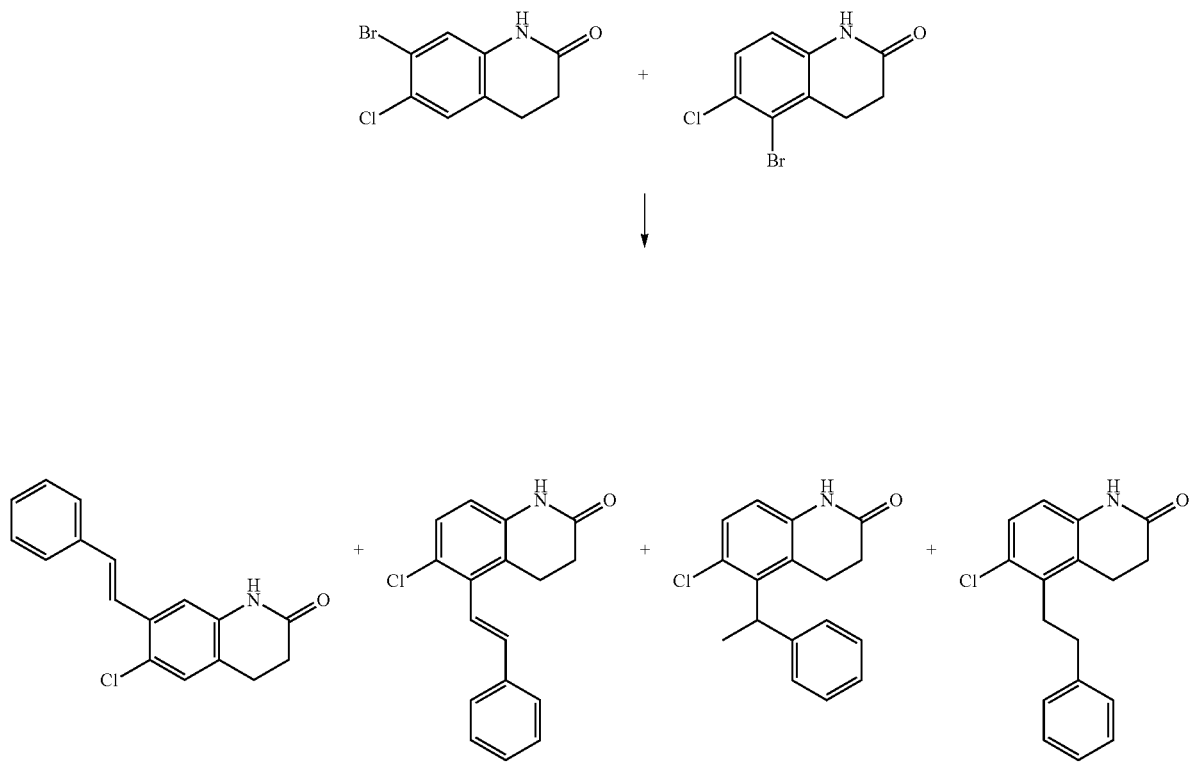

A stirred solution of mixture of 7-bromo-6-chloro-3,4-dihydroquinolin-2(1H)-one and 5-bromo-6-chloro-3,4-dihydroquinolin-2(1H)-one (0.4 g, 1.54 mmol, prepared as in step 1b of Example 42) and 4,4,5,5-tetramethyl-2-phenethyl-1,3,2-dioxaborolane (0.535 g, 2.30 mmol) in 1,4-dioxane (5 mL) was purged with $N_2$ for 10 min. A solution of $Cs_2CO_3$ (1.5 g, 4.61 mmol) in water (0.5 mL) was then added and the mixture was further purged with $N_2$ for 10 min. $PdCl_2(dppf).CH_2Cl_2$ (0.063 g, 0.08 mmol) was then added and the reaction mixture was heated at 150° C. for 3 h under microwave irradiation. Then, the reaction mixture was evaporated to afford a crude product, which was purified by silica gel column chromatography using a gradient of 40-70% EtOAc in hexane as eluent. The product fractions were collected and evaporated to afford the title mixture (0.35 g, 38%) as a semi-solid. MS (ESI) $[M+H]^+$ 286.13.

Step 2: Preparation of (E)-6-(1,5-dimethyl-6-oxo-1,6-dihydropyridin-3-yl)-7-styryl-3,4-dihydroquinolin-2(1H)-one, (E)-6-(1,5-dimethyl-6-oxo-1,6-dihydropyridin-3-yl)-5-styryl-3,4-dihydroquinolin-2(1H)-one, 6-(1,5-dimethyl-6-oxo-1,6-dihydropyridin-3-yl)-5-(1-phenylethyl)-3,4-dihydroquinolin-2(1H)-one and 6-(1,5-dimethyl-6-oxo-1,6-dihydropyridin-3-yl)-5-phenethyl-3,4-dihydroquinolin-2(1H)-one

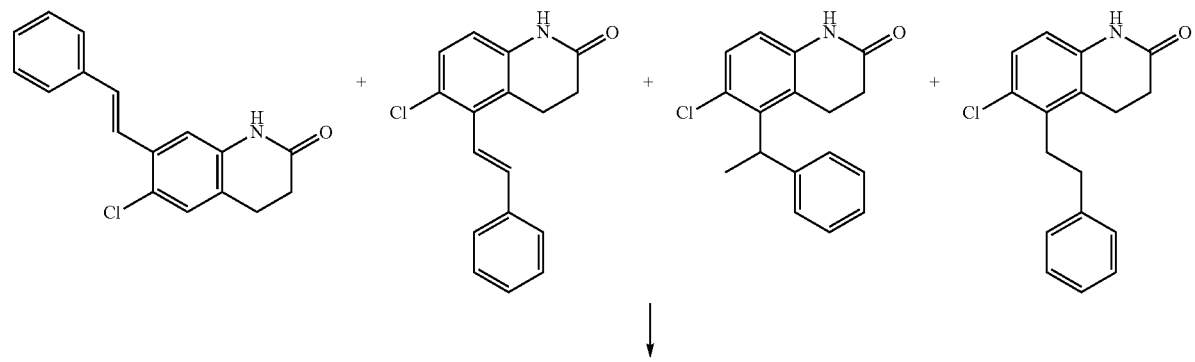

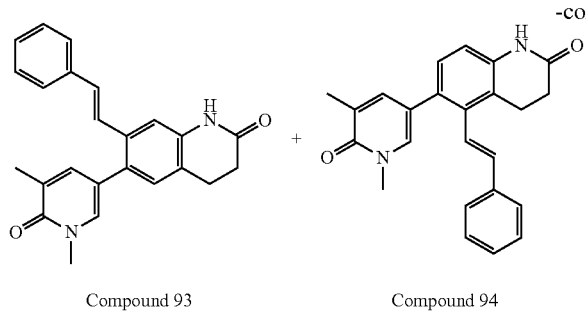

Compound 93

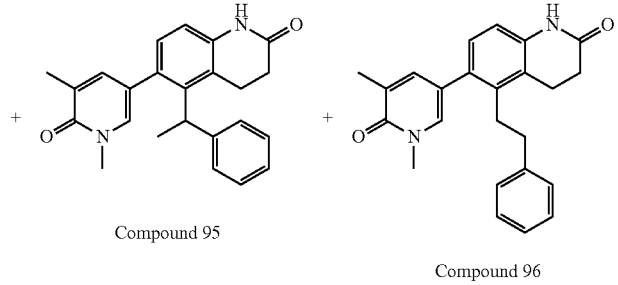

Compound 94   Compound 95   Compound 96

A stirred solution of mixture of (E)-6-chloro-7-styryl-3,4-dihydroquinolin-2(1H)-one, (E)-6-chloro-5-styryl-3,4-dihydroquinolin-2(1H)-one, 6-chloro-7-phenethyl-3,4-dihydroquinolin-2(1H)-one and 6-chloro-5-phenethyl-3,4-dihydroquinolin-2(1H)-one (0.35 g, 1.22 mmol) and 1,3-dimethyl-5-(4,4,5,5-tetramethyl-1,3,2-dioxaborolan-2-yl)pyridin-2(1H)-one (0.458 g, 1.84 mmol, prepared using procedure described in US20130053362) in 1,4-dioxane (5 mL) was purged with $N_2$ for 10 min. A solution of $K_3PO_4$ (0.78 g, 3.67 mmol) in water (1 mL) was then added and the mixture was further purged with $N_2$ for 10 min. $Pd(t-Bu_3P)_2$ (0.032 g, 0.06 mmol) was then added and the reaction mixture was heated at 150° C. under microwave irradiation for 4 h. Then, the reaction mixture was evaporated to afford a crude product, which was purified by silica gel column chromatography using a gradient of 1-2% methanol in DCM as eluent, followed by preparative HPLC purification using 40% ACN in water containing 0.1% formic acid as modifier to afford Compound 93 (0.015 g), Compound 94 (0.025 g), Compound 95 (0.01 g) and 0.06 g of a solid fraction of a mixture of compounds. The mixture of unknown isomers was repurified by preparative HPLC purification using 5-50% ACN in water containing 0.1% formic acid as modifier to afford Compound 96 (0.005 g).

Compound 93: 1H NMR (400 MHz, DMSO-$d_6$) δ ppm 10.17 (s, 1H), 7.56 (s, 1H), 7.48 (s, 1H), 7.46 (s, 1H), 7.38-7.34 (m, 2H), 7.32 (s, 1H), 7.28 (d, J=6.8 Hz, 1H), 7.24 (s, 1H), 7.14 (s, 1H), 7.10 (d, J=16.4 Hz, 1H), 6.96 (d, J=16.4 Hz, 1H), 3.45 (s, 3H), 2.91 (t, J=7.2 Hz, 2H), 2.45 (m, 2H), 2.04 (s, 3H); MS (ESI) [M+H]$^+$ 371.31.

Compound 94: 1H NMR (400 MHz, MeOH-$d_4$) δ ppm 7.53 (s, 1H), 7.45-7.41 (m, 3H), 7.36-7.32 (m, 2H), 7.29-7.25 (m, 1H), 7.19 (d, J=8.0 Hz, 1H), 7.05 (d, J=16.8 Hz, 1H), 6.92 (d, J=8.0 Hz, 1H), 6.53 (d, J=16.8 Hz, 1H), 3.60 (s, 3H), 3.16 (t, J=7.4 Hz, 2H), 2.57 (t, J=7.4 Hz, 2H), 2.08 (s, 3H), MS (ESI) [M+H]$^+$ 371.31.

Compound 95: 1H NMR (400 MHz, MeOH-$d_4$) δ ppm 7.42-7.25 (m, 4H), 7.20-7.13 (m, 3H), 7.09 (d, J=8.0 Hz, 1H), 6.87 (d, J=8.4 Hz, 1H), 4.51-4.46 (m, 1H), 3.55 (s, 3H), 2.82-2.74 (m, 1H), 2.53-2.45 (m, 1H), 2.39-2.32 (m, 1H), 2.25-2.16 (m, 1H), 2.09 (s, 3H), 1.66 (d, J=7.2 Hz, 3H), MS (ESI) [M+H]$^+$ 373.36.

Compound 96: 1H NMR (400 MHz, DMSO-$d_6$) δ ppm 10.10 (bs, 1H), 7.31 (s, 1H), 7.24-7.15 (m, 4H), 7.01 (s, 1H), 6.99 (s, 1H), 6.94 (d, J=8.0 Hz, 1H), 6.77 (d, J=8.0 Hz, 1H), 3.45 (s, 3H), 2.97-2.94 (m, 2H), 2.80-2.78 (m, 2H), 2.32-2.71 (m, 2H), 2.45-2.41 (m, 2H), 2.03 (s, 3H). MS (ESI) [M+H]$^+$ 373.31.

Example 69: 8-((cyclopentyl(methyl)amino)methyl)-6-(1,5-dimethyl-6-oxo-1,6-dihydro-pyridin-3-yl)-3,4-dihydroquinolin-2(1H)-one

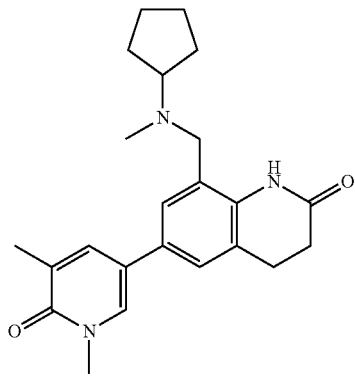

Compound 97

Step 1a: Preparation of potassium ((cyclopentylamino)methyl)trifluoroborate

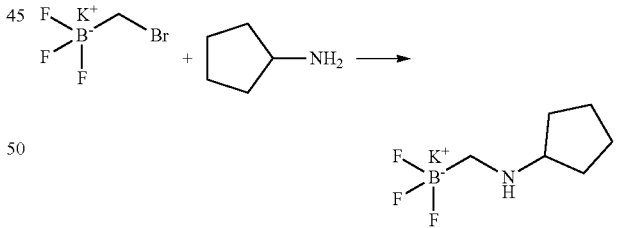

Cyclopentanamine (0.26 g, 2.99 mmol), THF (2 mL) and t-BuOH (1 mL) were added to potassium (bromomethyl)trifluoroborate (0.5 g, 2.49 mmol) in a sealed tube. The mixture was heated at 60° C. for 20 h and then evaporated under vacuum to obtain a crude product, which was suspended into acetonitrile (25 mL) and filtered. The filtrate was evaporated and the product was precipitated in diethyl ether (10 mL). The obtained precipitate was filtered and vacuum dried to afford title compound (0.35 g, 69%) as a solid. $^1$H NMR (400 MHz, DMSO) δ ppm 7.58 (s, 1H), 3.26-3.21 (m, 1H), 1.93-1.81 (m, 2H), 1.72-1.63 (m, 4H), 1.58-1.45 (m, 4H).

Step 1 b: Preparation of 8-((cyclopentylamino)methyl)-6-(1,5-dimethyl-6-oxo-1,6-dihydropyridin-3-yl)-3,4-dihydroquinolin-2(1H)-one

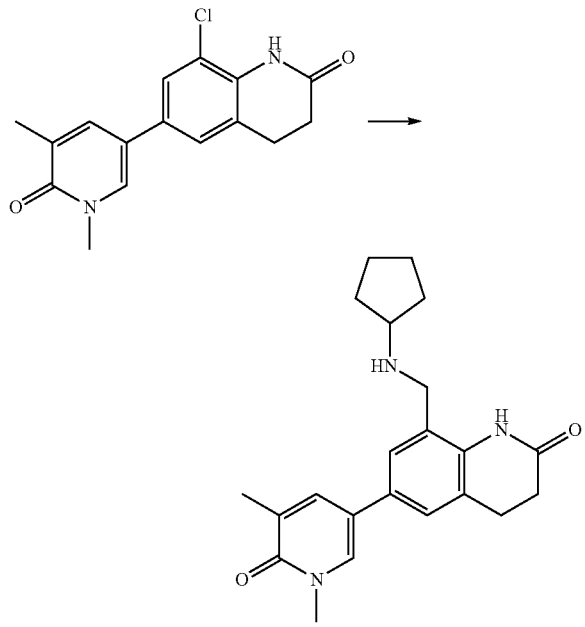

Cs₂CO₃ (0.97 g, 2.97 mmol) was added to a stirred solution of Intermediate 1 (0.3 g, 0.99 mmol) and potassium ((cyclopentylamino)methyl)trifluoroborate (0.3 g, 1.49 mmol) in 1,4-dioxane (5 mL) and water (1 mL) and the mixture was degassed with N₂ for 10 min. Pd(OAc)₂ (0.022 g, 0.1 mmol) and X-phos (0.24 g, 0.5 mmol) were then added and the reaction mixture was heated at 120° C. for 2 h under microwave irradiation. Then, the reaction mixture was evaporated under vacuum to get a crude product, which was purified by column chromatography using a gradient of 1-2% methanol in DCM as eluent, followed by preparative HPLC purification using 32-40% acetonitrile in water using 0.1% ammonia as a modifier to afford title compound (0.06 g, 33%). MS (ESI) [M+H]⁺ 366.36.

Step 2: Preparation of 8-((cyclopentyl(methyl)amino)methyl)-6-(1,5-dimethyl-6-oxo-1,6-dihydropyridin-3-yl)-3,4-dihydroquinolin-2(1H)-one

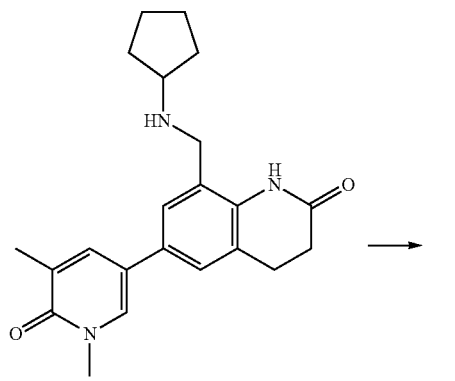

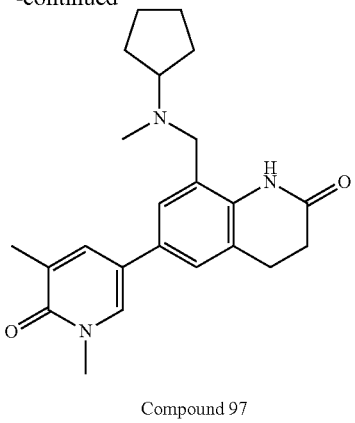

Compound 97

K₂CO₃ (0.068 g, 0.49 mmol) was added to a stirred solution of 8-((cyclopentylamino)methyl)-6-(1,5-dimethyl-6-oxo-1,6-dihydropyridin-3-yl)-3,4-dihydroquinolin-2(1H)-one (0.06 g, 0.16 mmol) in DMF (1 mL). Methyl iodide (0.047 g, 0.33 mmol) was then added at 0° C. and the mixture heated at 120° C. for 1 h under microwave irradiation. Then, the reaction mixture was diluted with water (50 mL) and the product extracted using EtOAc (3×50 mL). The organic layers were combined, dried over anhydrous Na₂SO₄, filtered and evaporated to afford a crude product, which was purified by column chromatography using a gradient of 1-2% methanol in DCM as eluent, followed by preparative HPLC purification using 35-85% acetonitrile in water using 5 mM ammonium acetate as a modifier to afford Compound 97 (0.012 g, 19%) as a solid. ¹H NMR (400 MHz, DMSO) δ ppm 10.14 (s, 1H), 7.93 (s, 1H), 7.72 (s, 1H), 7.35 (s, 1H), 7.26 (s, 1H), 3.65 (s, 2H), 3.50 (s, 3H), 2.93 (t, J=7.4 Hz, 2H), 2.79-2.75 (m, 1H), 2.50 (m, 2H), 2.08 (s, 3H), 2.07 (s, 3H), 1.90-1.83 (m, 2H), 1.67-1.48 (m, 6H). MS (ESI) [M+H]⁺ 380.04.

Example 70: N-cyclopentyl-N-((6-(1,5-dimethyl-6-oxo-1,6-dihydropyridin-3-yl)-2-oxo-1,2,3,4-tetrahydroquinolin-8-yl)methyl)acetamide

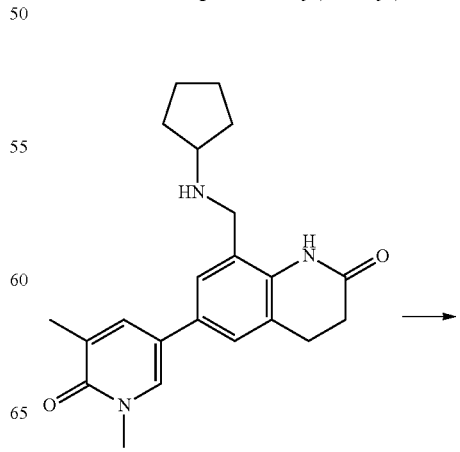

-continued

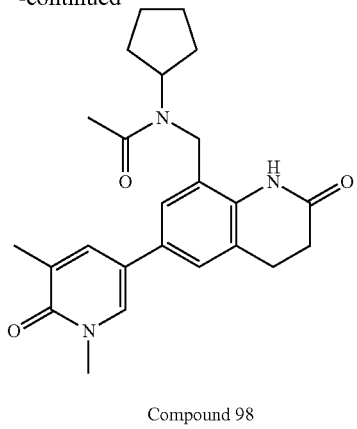

Compound 98

Acetyl chloride (0.06 mL, 0.82 mmol) was added dropwise at 0° C. to a stirred solution of 8-((cyclopentylamino)methyl)-6-(1,5-dimethyl-6-oxo-1,6-dihydropyridin-3-yl)-3,4-dihydroquinolin-2(1H)-one (0.2 g, 0.55 mmol, prepared according to Example 69) and TEA (0.23 mL, 1.65 mmol) in DCM (10 mL) and the mixture was stirred at rt for 2 h. Then, the reaction mixture was evaporated under reduced pressure to afford a crude product, which was purified by silica gel column chromatography using a gradient of 1-3% methanol in DCM as eluent, followed by preparative HPLC purification using 10-40% ACN in water containing 0.02% ammonia as modifier to afford Compound 98 (0.03 g, 13%) as a solid. $^1$H NMR (400 MHz, DMSO) δ 9.49 (s, 1H), 7.69 (s, 1H), 7.50 (s, 1H), 7.27 (s, 1H), 6.99 (s, 1H), 4.30-4.60 (m, 3H), 3.52 (s, 3H), 2.94 (t, J=7.2 Hz, 2H), 2.50 (s, 3H), 2.20-2.00 (m, 5H), 1.90-1.70 (m, 2H), 1.70-1.60 (m, 2H), 1.60-1.40 (m, 4H). MS (ESI) [M+H]$^+$ 408.34.

Example 71: 5-benzyl-7-(1,5-dimethyl-6-oxo-1,6-dihydropyridin-3-yl)-3,4-dihydro-quinolin-2(1H)-one Compound 99

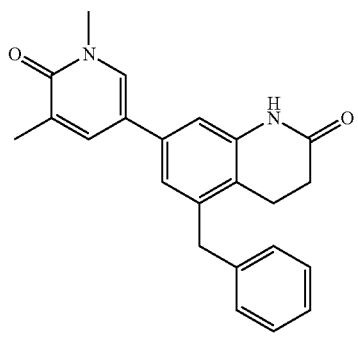

Step 1: Preparation of N-(3-bromo-5-chlorophenyl)-3-chloropropanamide

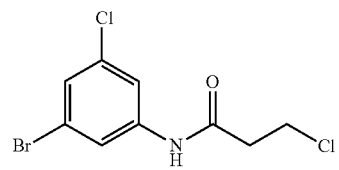

3-chloropropanoyl chloride (3.8 g, 3.03 mmol) was added dropwise to a stirred solution of 3-bromo-5-chloroaniline (5 g, 2.42 mmol) and K$_2$CO$_3$ (5 g, 3.35 mmol) in acetone (12.5 mL) and water (25 mL) at 00° C. and the mixture was stirred for 15 min. Then, the reaction mixture was filtered, evaporated under vacuum, washed with water (300 mL) and dried under vacuum to afford title compound (7 g, 94%) as a solid. MS (ESI) [M+H]$^+$ 296.49

Step 2: Preparation of Mixture of 7-bromo-5-chloro-3,4-dihydroquinolin-2(1H)-one and 5-bromo-7-chloro-3,4-dihydroquinolin-2(1H)-one

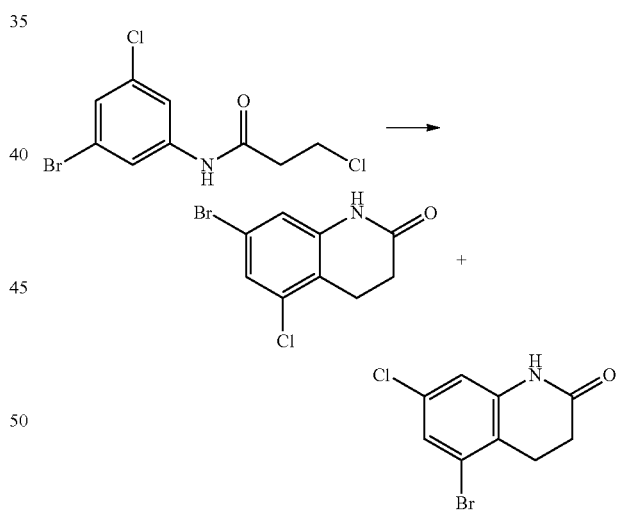

A mixture of N-(3-bromo-5-chlorophenyl)-3-chloropropanamide (7 g, 23.5 mmol) and AlCl$_3$ (14 g, 105 mmol) were heated at 140° C. for 3 h. Then, the reaction mixture was quenched in ice, neutralized with diluted HCl (200 mL) and extracted with EtOAc (500 mL×2). The combined organic layers were dried over anhydrous Na$_2$SO$_4$, filtered and evaporated to afford a crude product, which was purified by silica gel column chromatography using a gradient of 20-30% EtOAc in hexane as eluent. The pure product fractions (regioisomers) were collected and evaporated to afford the title mixture (2.3 g, 37%) as a solid. MS (ESI) [M+H]$^+$ 260.49.

211

Step 3: Preparation of 7-chloro-5-(1,5-dimethyl-6-oxo-1,6-dihydropyridin-3-yl)-3,4-dihydroquinolin-2(1H)-one

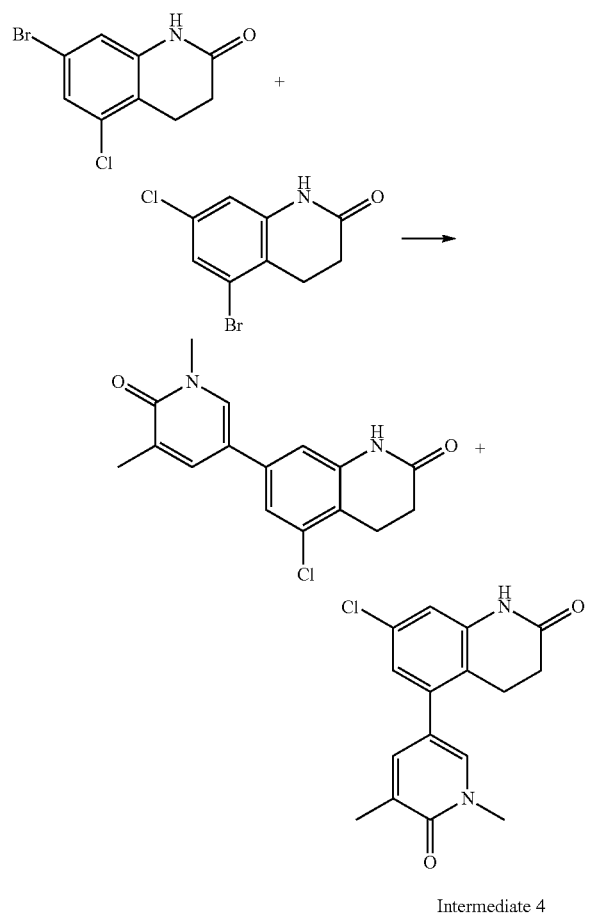

Intermediate 4

A stirred solution of mixture of 7-bromo-5-chloro-3,4-dihydroquinolin-2(1H)-one and 5-bromo-7-chloro-3,4-dihydroquinolin-2(1H)-one (0.5 g, 1.45 mmol) and 1,3-dimethyl-5-(4,4,5-trimethyl-1,3,2-dioxaborolan-2-yl)pyridin-2(1H)-one (0.43 g, 1.73 mmol) in 1,4-dioxane (5 mL) was purged with N₂ for 20 min at rt. A solution of sodium carbonate (0.45 g, 4.34 mmol) in water (0.5 mL) was then added and the mixture was further purged with N₂ for 20 min. Pd(PPh₃)₄ (0.08 g, 0.077 mmol) was then added and the reaction mixture was heated at 90° C. for 6 h. Then, the reaction mixture was diluted with water (50 mL) and extracted with EtOAc (100 mL×3). The combined organic layers were dried over anhydrous Na₂SO₄, filtered and evaporated to afford a crude product, which was purified by silica gel column chromatography using a gradient of 1-2% methanol in DCM as eluent. The pure product fractions were collected and evaporated to afford 0.064 g of 7-chloro-5-(1,5-dimethyl-6-oxo-1,6-dihydropyridin-3-yl)-3,4-dihydroquinolin-2(1H)-one in 11% yield and 0.112 g of 5-chloro-7-(1,5-dimethyl-6-oxo-1,6-dihydropyridin-3-yl)-3,4-dihydroquinolin-2(1H)-one (Intermediate 4) in 19% yield.

212

Intermediate 4: ¹H NMR (400 MHz, DMSO) δ ppm 10.26 (s, 1H), 7.66 (s, 1H), 7.39 (s, 1H), 6.94 (s, 1H), 6.91 (s, 1H) 3.48 (s, 3H), 2.82 (t, J=7.2 Hz, 2H), 2.39 (t, J=7.2 Hz, 2H), 2.04 (s, 3H). MS (ESI) [M+H]⁺ 303.60.

Step 4: Preparation of 5-benzyl-7-(1,5-dimethyl-6-oxo-1,6-dihydropyridin-3-yl)-3,4-dihydroquinolin-2(1H)-one

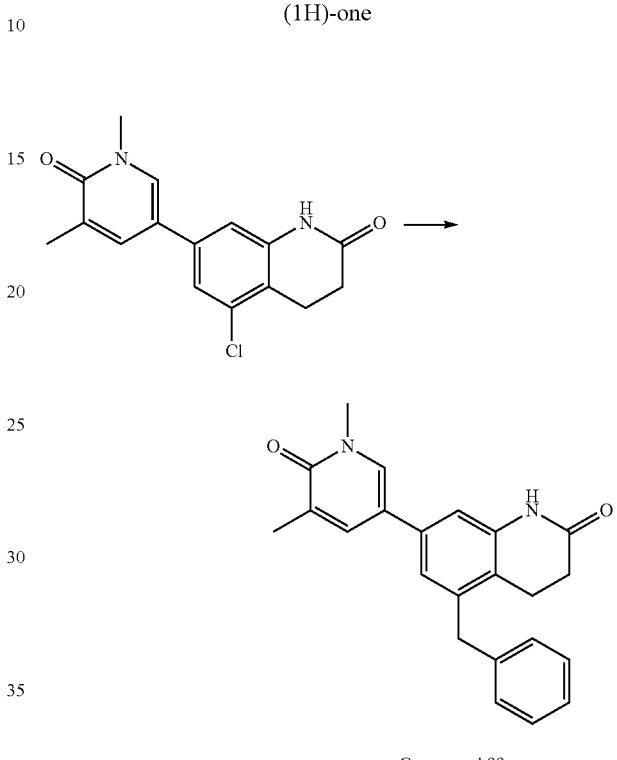

Compound 99

A stirred solution of Intermediate 4 (0.2 g, 0.66 mmol) and 2-benzyl-4,4,5,5-tetramethyl-1,3,2-dioxaborolane (0.28 g, 1.31 mmol) in 1,4-dioxane (4 mL) was purged with N₂ for 20 min. A solution of potassium phosphate (0.4 g, 1.98 mmol) in water (0.8 mL) was then added and the mixture was further purged with N₂ for 20 min. Pd(t-But₃P)₂ (0.016 g, 0.033 mmol) was then added and the reaction mixture was heated at 120° C. for 1 h under microwave irradiation. Then, the reaction mixture was diluted with water (50 mL) and extracted with EtOAc (50 mL×3). The combined EtOAc layer was washed with brine (30 mL), dried over anhydrous Na₂SO₄, filtered and evaporated to afford a crude product, which was purified by silica gel column chromatography using a gradient of in 1-2% methanol in DCM as eluent, followed by preparative HPLC purification using 40-60% acetonitrile in water containing 0.1% formic acid as modifier to afford Compound 99 (0.03 g, 12%) as a solid. ¹H NMR (400 MHz, DMSO) δ ppm 10.04 (s, 1H), 7.86 (s, 1H), 7.57 (s, 1H}, 7.27 (t, J=8 Hz, 2H), 7.17 (d, J=7.2 Hz, 3H), 7.11 (s, 1H), 6.89 (s, 1H), 4.01 (s, 2H), 3.51 (s, 3H), 2.73 (t, J=7.2 Hz, 2H), 2.37 (t, J=7.2 Hz, 2H), 2.07 (s, 3H). MS (ESI) [M+H]⁺ 359.29.

Example 72: 5-((cyclopentyloxy)methyl)-7-(1,5-dimethyl-6-oxo-1,6-dihydropyridin-3-yl)-3,4-dihydroquinolin-2(1H)-one

Example 73: 7-(1,5-dimethyl-6-oxo-1,6-dihydropyridin-3-yl)-6-(pyridin-3-ylmethyl)-3,4-dihydroquinolin-2(1H)-one

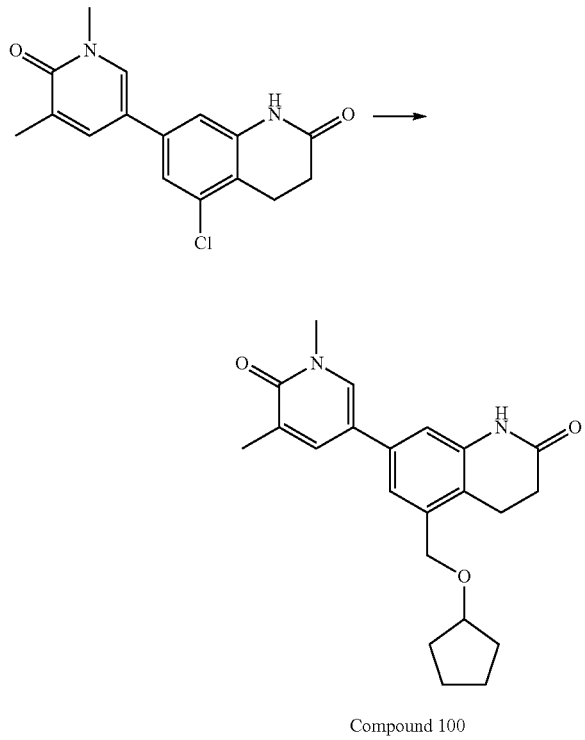

Compound 100

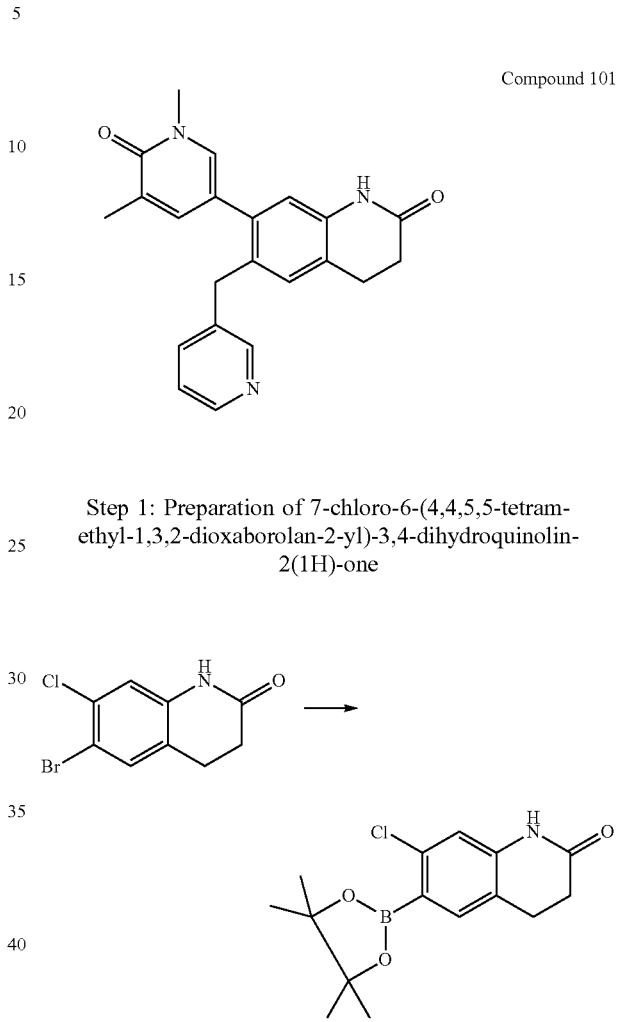

Compound 101

Step 1: Preparation of 7-chloro-6-(4,4,5,5-tetramethyl-1,3,2-dioxaborolan-2-yl)-3,4-dihydroquinolin-2(1H)-one A stirred solution of Intermediate 4 (0.1 g, 0.33 mmol) and potassium((cyclopentyloxy)methyl) trifluoroborate (0.135 g, 0.66 mmol) in THF (3 mL) was purged with $N_2$ for 20 min. A solution of $Cs_2CO_3$ (0.325 g, 0.99 mmol) in water (0.3 mL) was then added and the mixture was further purged with $N_2$ for 20 min. $Pd(OAc)_2$ (0.025 g, 0.099 mmol) and X-Phos (0.08 g, 0.165 mmol) were then added and the reaction mixture was heated at 100° C. for 16 h. Then, the reaction mixture was diluted with water (50 mL) and extracted with EtOAc (50 mL×3). The combined organic layers were dried over anhydrous $Na_2SO_4$, filtered and evaporated to afford a crude product, which was purified by silica gel column chromatography using a gradient of 1-2% methanol in DCM as eluent, followed by preparative HPLC purification using 47-50% acetonitrile in water containing 0.1% Ammonia as modifier to afford Compound 100 (0.019 g, 16%) as a solid. $^1$H NMR (400 MHz, DMSO) δ ppm 10.06 (s, 1H), 7.85 (d, J=2.4 Hz, 1H), 7.57 (s, 1H), 7.11 (d, J=1.2 Hz, 1H), 6.93 (s, 1H), 4.41 (s, 2H), 3.98-3.96 (m, 1H), 3.51 (s, 3H), 2.86 (t, J=7.2 Hz, 2H), 2.50 (t, J=7.2 Hz, 2H), 2.07 (s, 3H), 1.69-1.62 (m, 6H), 1.50-1.49 (m, 2H). MS (ESI) [M+H]$^+$ 367.29.

A stirred solution of 6-bromo-7-chloro-3,4-dihydroquinolin-2(1H)-one (1 g, 3.84 mmol, prepared as detailed in Example 30) and potassium acetate (1.13 g, 11.51 mmol) in 1,4-dioxane (20 mL) was purged with $N_2$ for 15 min. Then, 4,4',4',5,5,5',5'-octamethyl-2,2'-bi(1,3,2-dioxaborolane) (4.9 g, 19.19 mmol) was added and the mixture was further purged with $N_2$ for 15 min. $Pd(dppf)Cl_2 \cdot CH_2Cl_2$ (0.15 g, 0.02 mmol) was then added and the reaction mixture was stirred under microwave irradiation at 100° C. for 30 min. The mixture was then filtered through Celite™ bed and washed with EtOAc (20 mL×3). The combined organic layers were evaporated under vacuum to get a crude product, which was purified by flash chromatography using 25% EtOAc in hexane as eluent. The pure product fractions were collected and evaporated to afford title compound (0.65 g, 55%) as a solid. MS (ESI) [M+H]$^+$ 308.29

Step 2: Preparation of 7-chloro-6-(pyridin-3-ylmethyl)-3,4-dihydroquinolin-2(1H)-one

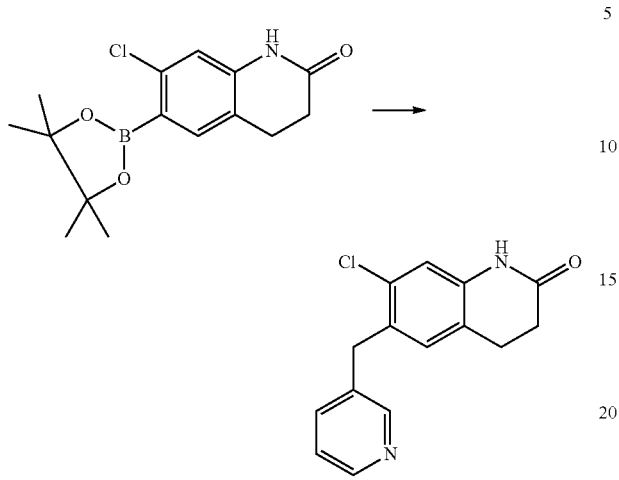

A stirred solution of 7-chloro-6-(4,4,5,5-tetramethyl-1,3,2-dioxaborolan-2-yl)-3,4-dihydroquinolin-2(1H)-one (0.25 g, 0.81 mmol) and 3-(bromomethyl)pyridine hydrobromide (0.31 g, 1.22 mmol) in 1,4-dioxane (5 mL) was purged with $N_2$ for 10 min. A solution of sodium carbonate (0.26 g, 2.43 mmol) in water (2 mL) was then added and the mixture was further purged with $N_2$ for 10 min. Pd(PPh$_3$)$_4$ (0.047 g, 0.04 mmol) was then added and the reaction mixture was heated at 100° C. for 3 h. The solvent was evaporated under vacuum and the product was extracted using EtOAc (10 mL×3). The combined organic layers were washed with water (20 mL) and brine solution (20 mL), dried over anhydrous Na$_2$SO$_4$, filtered and evaporated to afford a crude product, which was purified by flash chromatography using a gradient of 2-3% methanol in DCM as eluent. The pure product fractions were collected and evaporated to afford title compound (0.1 g, 45%) as a solid. $^1$H NMR (400 MHz, MeOD) δ ppm 8.42 (d, J=1.6 Hz, 1H), 8.38 (dd, J=1.6 Hz, 1H), 7.67 (d, J=8.0 Hz, 1H), 7.39-7.35 (m, 1H), 7.19 (s, 1H), 6.95 (s, 1H), 4.64 (s, 1H), 4.10 (s, 2H), 2.94 (t, J=7.4 Hz, 2H), 2.60-2.56 (m, 2H). MS (ESI) [M+H]$^+$ 273.23.

Step 3: Preparation of 7-(1,5-dimethyl-6-oxo-1,6-dihydropyridin-3-yl)-6-(pyridin-3-ylmethyl)-3,4-dihydroquinolin-2(1H)-one

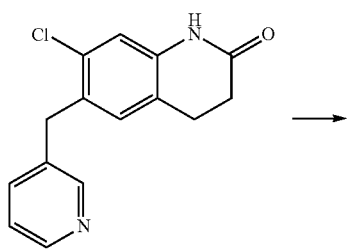

-continued

Compound 101

A stirred solution of 7-chloro-6-(pyridin-3-ylmethyl)-3,4-dihydroquinolin-2(1H)-one (0.1 g, 0.37 mmol) and 1,3-dimethyl-5-(4,4,5,5-tetramethyl-1,3,2-dioxaborolan-2-yl)pyridin-2(1H)-one (0.11 g, 0.44 mmol, prepared using procedure described in US20130053362) in 1,4-dioxane (2 mL) was purged with $N_2$ for 10 min. A solution of $K_3PO_4$ (0.23 g, 1.10 mmol) in water (0.7 mL) was then added and the mixture was further purged with $N_2$ for 10 min. Pd(t-But$_3$P)$_2$ (0.01 g, 0.02 mmol) was then added and the reaction mixture was heated at 150° C. in microwave for 9 h. The solvent was evaporated under vacuum and the product was extracted using EtOAc (10 mL×3). The combined organic layers were washed with water (15 mL) and brine solution (15 mL), dried over anhydrous Na$_2$SO$_4$, filtered and evaporated to afford a crude product, which was purified by flash chromatography using 3% methanol in DCM as eluent. The pure product fractions were collected and evaporated under vacuum to afford Compound 101 (0.03 g, 20%) as a solid. $^1$H NMR (400 MHz, MeOD) δ ppm 8.33 (dd, J=4.8, 1.5 Hz, 1H), 8.13 (d, J=2.2 Hz, 1H), 7.45 (dt, J=8.1, 1.9 Hz, 1H), 7.34-7.26 (m, 2H), 7.23-7.16 (m, 2H), 6.74 (s, 1H), 4.00 (s, 2H), 3.55 (s, 3H), 3.00 (t, J=7.6 Hz, 2H), 2.61 (dd, J=8.5, 6.7 Hz, 2H), 2.11 (s, 3H). MS (ESI) [M+H]$^+$ 360.18.

Example 74: Biological Activity a) In Vitro Bromodomain Inhibition Assay

To measure activity of bromodomain inhibitors, a His-epitope tagged BRD4 BD149-170 is purchased from BPS Bioscience. BRD4 binding and inhibition is assessed by monitoring the engagement of biotinylated H4-tetraacetyl peptide (H4K5/8/12/16; AnaSpec #64989-025) with the target using the AlphaLISA technology (Perkin-Elmer). Specifically, in a 384 well OptiPlate, BRD4(BD1) (200 nM final) is pre-incubated with either DMSO (final 1.0% DMSO) or a compound dilution series in DMSO. All reagents are diluted in assay buffer containing 50 mM HEPES (pH 7.4), 100 mM NaCl, 0.1% (w/v) BSA, and 0.05% (w/v) CHAPS. After a 30 min incubation at rt, H4 peptide is added (200 nM final) and the reaction is incubated an additional 30 min at rt. Alpha streptavidin donor beads and AlphaLISA nickel chelate acceptor beads are then added to a final concentration of 10 µg/mL each. After one hour, equilibration plates are read on an Envision instrument and IC$_{50}$s calculated using a four parameter non-linear curve fit (results are shown in Table 2).

b) Transcription of Human C-Myc in Human Leukemic MV-4-11 Cells:

The effect of compounds on transcription of human C-Myc gene is monitored in human B-myelomonocytic leukemia cell line MV-4-11 (from American Type Culture Collection (ATCC), Manassas, Va., USA) using QuantiGene 2.0 assay kit (Affymetrix, Santa Clara, Calif., USA).

Typically, 8,000 MV-4-11 cells are plated in sterile 96-well plates (Costar #3598 from Fisher Scientific Canada, Ottawa, Ontario, Canada) in Iscove's medium supplemented with 10% fetal bovine serum, glutamine (2 mM), and penicillin (100 I.U.) and streptomycin (100 µg/mL) (all from Wisent Inc., St. Bruno, Quebec, Canada). Compounds are dissolved in DMSO at 30 mM. A series of 1:3 dilutions are first made in DMSO, and further 1:100 dilutions are made in serum-containing cell culture media. The final concentration of DMSO is 0.1% in cell culture media. After cells are treated with various concentrations of test compound for 4 hours, cells are lysed using Quantigene 2.0 sample processing kit (#QS0100). C-Myc mRNA is detected using a QuantiGene 2.0 assay kit (#QS0009) with gene-specific probe to human C-Myc (#SA-50182) following the manufacturer's recommendations. Luminescene signals are read on Flexstation II microplate reader (Molecular Devices, Sunnyvale, Calif., USA). Percentage of inhibition of C-Myc transcription is analyzed using EXCEL (2010 version) (results shown in Table 2).

TABLE 2

| Compound No | IC$_{50}$ BRD4 (µM) | IC50 MV-4-11 cells (µM) |
|---|---|---|
| 1 | 0.41 | 0.16 |
| 2 | 0.56 | 0.21 |
| 3 | 0.51 | 0.58 |
| 4 | 0.28 | 0.09 |
| 5 | N/A | 0.25 |
| 6 | 0.81 | 0.75 |
| 7 | 0.14 | 0.09 |
| 8 | 0.28 | 0.24 |
| 9 | 0.27 | 0.26 |
| 10 | 0.48 | 0.25 |
| 11 | 0.35 | 2.12 |
| 12 | 0.11 | 0.09 |
| 13 | 1.30 | 1.58 |
| 14 | 0.35 | 0.19 |
| 15 | N/A | 2.62 |
| 16 | N/A | 0.53 |
| 17 | 0.18 | 0.24 |
| 18 | 0.42 | 0.79 |
| 19 | 0.70 | 0.90 |
| 20 | N/A | 0.79 |
| 21 | N/A | 0.28 |
| 22 | N/A | 0.24 |
| 23 | N/A | 0.24 |
| 24 | N/A | 0.83 |
| 25 | N/A | 0.15 |
| 26 | N/A | 0.28 |
| 27 | N/A | 0.15 |
| 28 | N/A | 0.42 |
| 29 | N/A | 0.19 |
| 30 | N/A | 0.25 |
| 31 | N/A | 0.29 |
| 32 | N/A | 2.23 |
| 34 | N/A | 2.82 |
| 38 | N/A | 0.54 |
| 39 | N/A | 9.85 |
| 44 | N/A | 0.27 |
| 46 | N/A | 0.91 |
| 47 | N/A | 0.94 |
| 48a | N/A | 2.12 |
| 48b | N/A | 2.74 |
| 52 | N/A | 0.55 |
| 53 | N/A | 2.08 |
| 54a | N/A | 0.55 |
| 54b | N/A | 0.80 |
| 55a | N/A | 0.58 |
| 55b | N/A | 0.80 |
| 57 | N/A | 0.24 |
| 58 | N/A | 0.25 |

TABLE 2-continued

| Compound No | IC$_{50}$ BRD4 (µM) | IC50 MV-4-11 cells (µM) |
|---|---|---|
| 59 | N/A | 0.27 |
| 61 | N/A | 0.89 |
| 62 | N/A | 0.86 |
| 67 | N/A | 2.03 |
| 68 | N/A | 8.56 |
| 69 | N/A | 1.25 |
| 70 | N/A | 7.82 |
| 71 | N/A | 0.54 |
| 72 | N/A | >6.14 |
| 73 | N/A | 0.50 |
| 74a | N/A | 0.12 |
| 74b | N/A | 0.41 |
| 75 | N/A | 0.18 |
| 76 | N/A | 0.56 |
| 77 | N/A | 2.28 |
| 78 | N/A | 0.10 |
| 79 | N/A | 0.24 |
| 80 | N/A | 0.52 |
| 81 | N/A | 0.53 |
| 82 | N/A | 0.25 |
| 83 | N/A | 0.51 |
| 84 | N/A | 0.51 |
| 85 | N/A | 0.35 |
| 86 | N/A | 0.37 |
| 87 | N/A | 0.10 |
| 88 | N/A | 0.26 |
| 89 | N/A | 0.56 |
| 90 | N/A | 0.24 |
| 91 | N/A | 0.10 |
| 92a | N/A | 0.09 |
| 92b | N/A | 0.51 |
| 93 | N/A | 0.76 |
| 94 | N/A | 0.73 |
| 95 | N/A | 0.03 |
| 96 | N/A | 0.78 |
| 97 | N/A | 0.79 |
| 98 | N/A | 0.09 |
| 99 | N/A | 0.84 |
| 100 | N/A | 0.61 |
| 101 | N/A | 2.68 |

N/A: not available

Although the invention has been illustrated and described with respect to one or more implementations, equivalent alterations and modifications will occur to others skilled in the art upon the reading and understanding of this specification. In addition, while a particular feature of the invention may have been disclosed with respect to only one of several implementations, such feature may be combined with one or more other features of the other implementations as may be desired and advantageous for any given or particular application.

Accordingly, it is understood that the examples and embodiments described herein are for illustrative purposes only and that various modifications or changes in light thereof will be suggested to persons skilled in the art and are to be included within the spirit and purview of this application and scope of the appended claims. Any publication, document, patent, patent application or publication referred to herein should be construed as incorporated by reference each in their entirety for all purposes.

The invention claimed is:
1. A compound of formula (I):

(I)

or a pharmaceutically acceptable salt, solvate, ester or prodrug thereof,
wherein:
A is —$CH_2$;
$R^1$ is hydrogen or methyl;
$R^2$ and $R^5$ independently represent hydrogen, halogen, —$CH_3$, —$C(R^a)(R^b)(R^c)$, —$N(R^d)(R^e)$ or —$O(R^f)$, wherein
$R^a$ is hydrogen or $C_1$-$C_6$ alkyl;
$R^b$ is hydrogen, hydroxyl or $C_1$-$C_6$ alkyl;
$R^c$ is $C_3$-$C_6$ cycloalkyl, $C_6$-$C_{10}$ aryl, 3-7 membered heterocycloalkyl, 5-10 membered heteroaryl, ($C_3$-$C_6$ cycloalkyl)$C_1$-$C_6$ alkyl, (3-7 membered heterocycloalkyl)$C_1$-$C_6$ alkyl, ($C_6$-$C_{10}$ aryl)$C_1$-$C_6$ alkyl or (5-10 membered heteroaryl)$C_1$-$C_6$ alkyl, —$O(R^g)$ or —$N(R^g)(R^h)$;
$R^d$ is hydrogen or $C_1$-$C_6$ alkyl;
$R^e$ is $C_1$-$C_6$ alkyl, $C_3$-$C_6$ cycloalkyl, $C_6$-$C_{10}$ aryl, 3-7 membered heterocycloalkyl, 5-10 membered heteroaryl, ($C_3$-$C_6$ cycloalkyl)$C_1$-$C_6$ alkyl, (3-7 membered heterocycloalkyl)$C_1$-$C_6$ alkyl, ($C_6$-$C_{10}$ aryl)$C_1$-$C_6$ alkyl, (5-10 membered heteroaryl)$C_1$-$C_6$ alkyl, keto($C_6$-$C_{10}$ aryl) or keto(5-10 membered heteroaryl);
$R^f$ is $C_1$-$C_6$ alkyl, $C_3$-$C_6$cycloalkyl, 3-7 membered heterocycloalkyl, $C_6$-$C_{10}$ aryl, 5-10 membered heteroaryl, ($C_3$-$C_6$ cycloalkyl)$C_1$-$C_6$ alkyl, (3-7 membered heterocycloalkyl)$C_1$-$C_6$ alkyl, ($C_6$-$C_{10}$ aryl)$C_1$-$C_6$ alkyl or (5-10 membered heteroaryl)$C_1$-$C_6$ alkyl;
$R^g$ is $C_1$-$C_6$ alkyl, $C_3$-$C_6$ cycloalkyl, $C_6$-$C_{10}$ aryl, 3-7 membered heterocycloalkyl, 5-10 membered heteroaryl, ($C_3$-$C_6$ cycloalkyl)$C_1$-$C_6$ alkyl, (3-7 membered heterocycloalkyl)$C_1$-$C_6$ alkyl, ($C_6$-$C_{10}$ aryl)$C_1$-$C_6$ alkyl or (5-10 membered heteroaryl)$C_1$-$C_6$ alkyl;
$R^h$ is hydrogen, $C_1$-$C_4$ alkyl, —$C(O)(R^6)$; —$C(O)NH_2$, —$C(O)NH(R^6)$ or —$C(O)N(R^6)(R^{6'})$;
one of $R^3$ and $R^4$ represents a group of formula (II), provided that when $R^3$ is a group of formula (II), then $R^4$ has the same definition than $R^2$ and $R^5$, and when $R^4$ is a group of formula (II), then $R^3$ has the same definition than $R^2$ and $R^5$;
the group of formula (II) has the following structure:

(II)

wherein:
$X^1$, $X^2$ and $X^3$ are each independently N or C, wherein when $X^1$, $X^2$ or $X^3$ is N, then the $R^7$, $R^8$ or $R^{10}$ attached thereto is absent, provided that at least two of $X^1$, $X^2$ and $X^3$ are C;
$R^7$ and $R^{10}$ are each independently hydrogen, halogen, CN, linear or branched $C_1$-$C_6$alkyl, $C_3$-$C_6$cycloalkyl, $OR^6$, $SR^6$, $NHR^6$, $N(R^6)(R^{6'})$, $NHC(O)R^6$ or $N(R^6)C(O)R^{6'}$;
$R^8$ is halogen, CN, linear or branched $C_1$-$C_6$alkyl, $C_3$-$C_6$cycloalkyl, $OR^6$, $SR^6$, $NHR^6$, $N(R^6)(R^{6'})$, $NHC(O)R^6$ or $N(R^6)C(O)R^{6'}$;
$R^6$ and $R^{6'}$, which are the same or different, represent a $C_1$-$C_6$ alkyl group;
$R^9$ is a $C_1$-$C_3$alkyl or $C_3$-$C_5$cycloalkyl group;
each alkyl group is linear or branched and optionally substituted with 1 to 3 groups being halogen, CN, alkoxy or haloalkoxy, and each of cycloalkyl, aryl, heterocycloalkyl and heteroaryl is optionally substituted by 1 to 3 groups being halogen, CN, alkyl, haloalkyl, alkoxy or haloalkoxy;
and
when $R^3$ is the group of formula (II), one of $R^2$, $R^4$ and $R^5$ is —$C(R^a)(R^b)(R^c)$, —$N(R^d)(R^e)$ or —$O(R^f)$ and the other two of $R^2$, $R^4$ and $R^5$ are independently hydrogen, halogen or —$CH_3$; or
when $R^4$ is the group of formula (II), one of $R^2$, $R^3$ and $R^5$ is —$C(R^a)(R^b)(R^c)$, —$N(R^d)(R^e)$ or —$O(R^f)$ and the other two of $R^2$, $R^3$ and $R^5$ are independently hydrogen, halogen or —$CH_3$.

2. The compound of claim 1, wherein $R^1$ is hydrogen.
3. The compound of claim 1, wherein $R^2$, $R^3$, $R^4$ or $R^5$ represent —$O(R^a)(R^b)(R^c)$, —$C(R^a)(R^b)O(R^g)$, —$C(R^a)(R^b)N(R^g)(R^h)$, —$N(R^d)(R^e)$ or —$O(R^f)$, wherein:
$R^a$ is H;
$R^b$ is H or methyl;
$R^c$ is a group benzyl, cyclobutyl, cyclopentyl, cyclohexyl, phenyl, thienyl, furanyl, pyrrolyl, imidazolyl, pyrazolyl, triazolyl, tetrazolyl, oxazolyl, isoxazolyl, oxadiazolyl, thiazolyl, isothiazolyl, thiadiazolyl, pyridyl, pyridazinyl, pyrimidinyl, pyrazinyl, indolizinyl, purinyl, naphthyridinyl, pteridinyl, [1,3]dioxolane, pyrrolidinyl, pyrazolinyl, pyrazolidinyl, imidazolinyl, imidazolidinyl, piperidinyl, piperazinyl, oxazolidinyl, isoxazolidinyl, morpholinyl, thiazolidinyl, isothiazolidinyl, tetrahydrofuryl or tetrahydropyranyl, each group $R^c$ being optionally substituted by 1 to 3 groups being halogen, CN, alkyl, haloalkyl, alkoxy or haloalkoxy;
$R^d$ is hydrogen or methyl;
$R^e$ is a group cyclobutyl, cyclopentyl, cyclohexyl, phenyl, thienyl, furanyl, pyrrolyl, imidazolyl, pyrazolyl, triazolyl, tetrazolyl, oxazolyl, isoxazolyl, oxadiazolyl, thiazolyl, isothiazolyl, thiadiazolyl, pyridyl, pyridazinyl, pyrimidinyl, pyrazinyl, indolizinyl, purinyl, naphthyridinyl, pteridinyl, [1,3]dioxolane, pyrrolidinyl, pyrazolinyl, pyrazolidinyl, imidazolinyl, imidazolidinyl, piperidinyl, piperazinyl, oxazolidinyl, isoxazolidinyl, morpholinyl, thiazolidinyl, isothiazolidinyl, tetrahydrofuryl, or tetrahydropyranyl, each of these groups being optionally substituted by 1 to 3 groups being halogen, CN, alkyl, haloalkyl, alkoxy or haloalkoxy, or $R^e$ is a group —$CH(R^h)(C_3$-$C_6$ aryl) or —$CH(R^h)$(5-10 membered heteroaryl);
$R^f$ is $C_3$-$C_6$ cycloalkyl, $C_6$-$C_{10}$ aryl, 3-10 membered heterocycloalkyl, 5-10 membered heteroaryl, —$CH(R^h)$ (C₃-C₆ cycloalkyl), —CH(Rʰ)(C₃-C₆ aryl), —CH(Rʰ)(3-7 membered heterocycloalkyl) or —CH(Rʰ)(5-10 membered heteroaryl);

Rᵍ is a group methyl, ethyl, propyl, cyclobutyl, cyclopentyl, cyclohexyl, phenyl, thienyl, furanyl, pyrrolyl, imidazolyl, pyrazolyl, triazolyl, tetrazolyl, oxazolyl, isoxazolyl, oxadiazolyl, thiazolyl, isothiazolyl, thiadiazolyl, pyridyl, pyridazinyl, pyrimidinyl, pyrazinyl, indolizinyl, purinyl, naphthyridinyl, pteridinyl, [1,3]dioxolane, pyrrolidinyl, pyrazolinyl, pyrazolidinyl, imidazolinyl, imidazolidinyl, piperidinyl, piperazinyl, oxazolidinyl, isoxazolidinyl, morpholinyl, thiazolidinyl, isothiazolidinyl, tetrahydrofuryl or tetrahydropyranyl, each group Rᵍ being optionally substituted by 1 to 3 groups being halogen, CN, alkyl, haloalkyl, alkoxy or haloalkoxy;

Rʰ is hydrogen, linear or branched C₁-C₄ alkyl or —(CO)R⁶ with R⁶ being a C₁-C₃ alkyl group; and wherein each of cycloalkyl, heterocycloalkyl, aryl and heteroaryl is optionally substituted by 1 to 3 groups being halogen, CN, alkyl, haloalkyl, alkoxy or haloalkoxy.

4. The compound of claim 1, wherein R², R³, R⁴ or R⁵ represent —C(Rᵃ)(Rᵇ)(Rᶜ), —C(Rᵃ)(Rᵇ)O(Rᵍ), —C(Rᵃ)(Rᵇ)N(Rᵍ)(Rʰ), —N(Rᵈ)(Rᵉ) or —O(Rᶠ), wherein:
Rᵃ is H;
Rᵇ is H or methyl;
Rᶜ is a group phenyl, benzyl, piperidinyl, tetrahydropyranyl or pyridyl;
Rᵈ is hydrogen or methyl;
Rᵉ is cyclohexyl, phenyl, benzyl, pyridyl, tetrahydropyranyl, —CH₂(pyridyl) or —CH(CH₃)(pyridyl);
Rᶠ is phenyl, cyclobutyl, cyclopentyl, cyclohexyl, benzyl, —CH₂(pyridyl), —CH(CH₃)(pyridyl), —CH₂(pyrazinyl), —CH₂(pyrimidinyl), —CH₂(tetrahydropyranyl), —CH₂(cyclopentyl), —CH₂(cyclohexyl), —CH₂(oxazolyl) or —CH₂(thiazolyl);
Rᵍ is ethyl, phenyl, cyclobutyl, cyclopentyl, cyclohexyl or tetrahydropyranyl;
Rʰ is hydrogen, methyl or acetyl;
wherein each of Rᶜ, Rᵉ, Rᶠ and Rᵍ is optionally substituted by 1 to 3 groups being halogen, CN, C₁-C₆ alkyl or C₁-C₆ alkoxy.

5. The compound of claim 1, wherein R², R³, R⁴ or R⁵ represent a group:

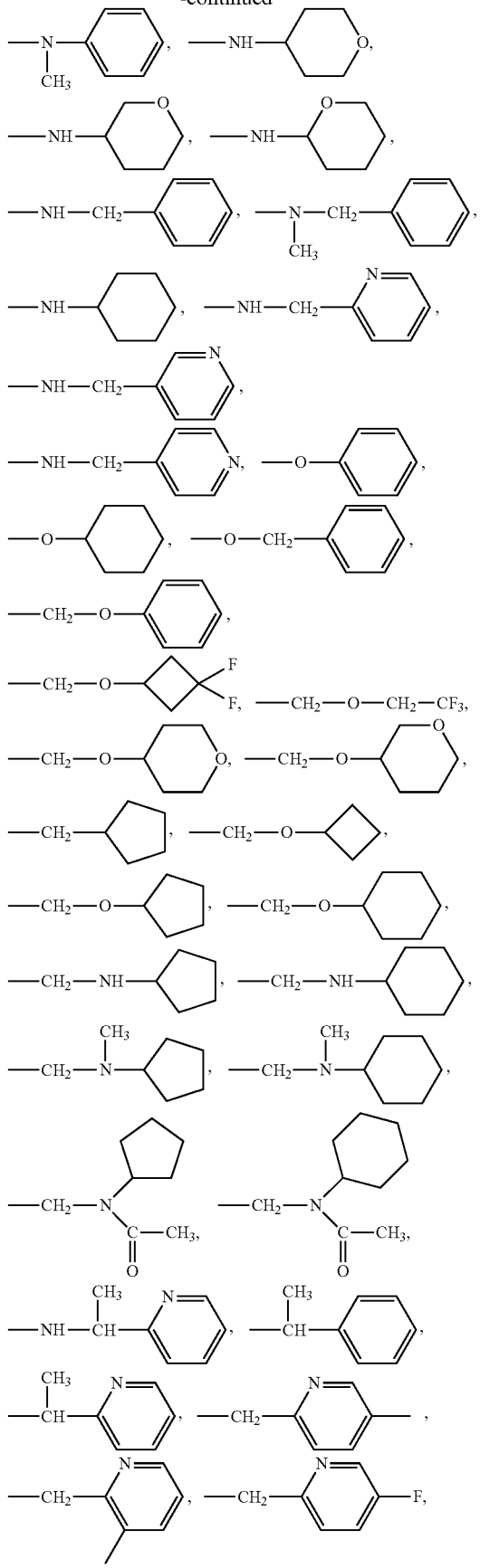

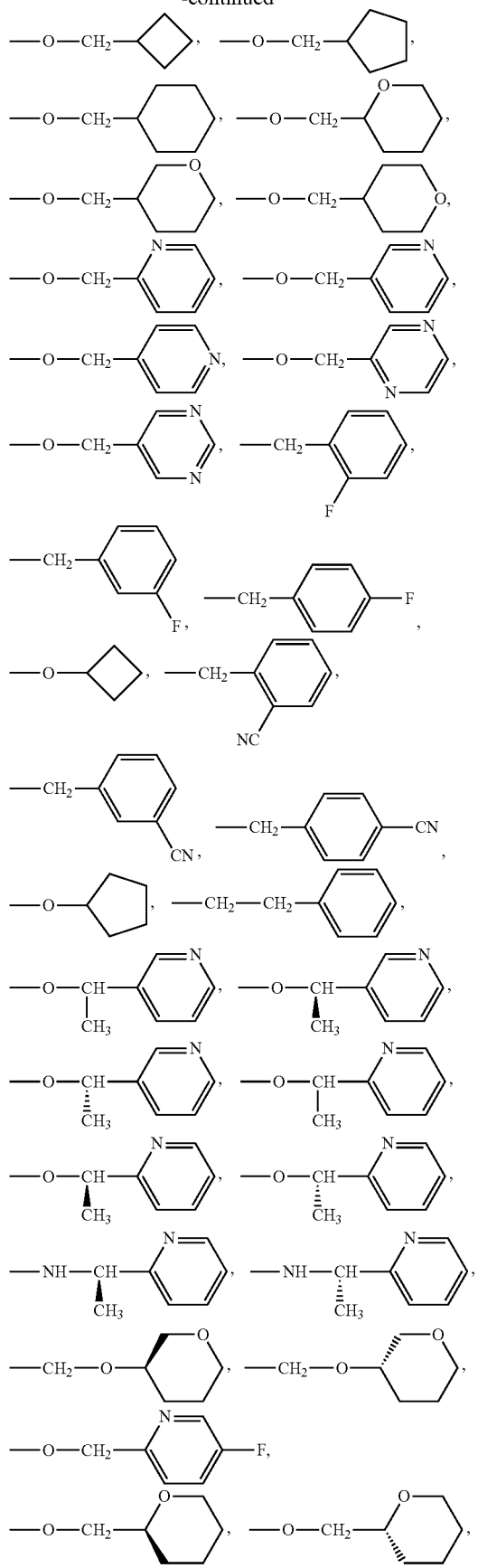
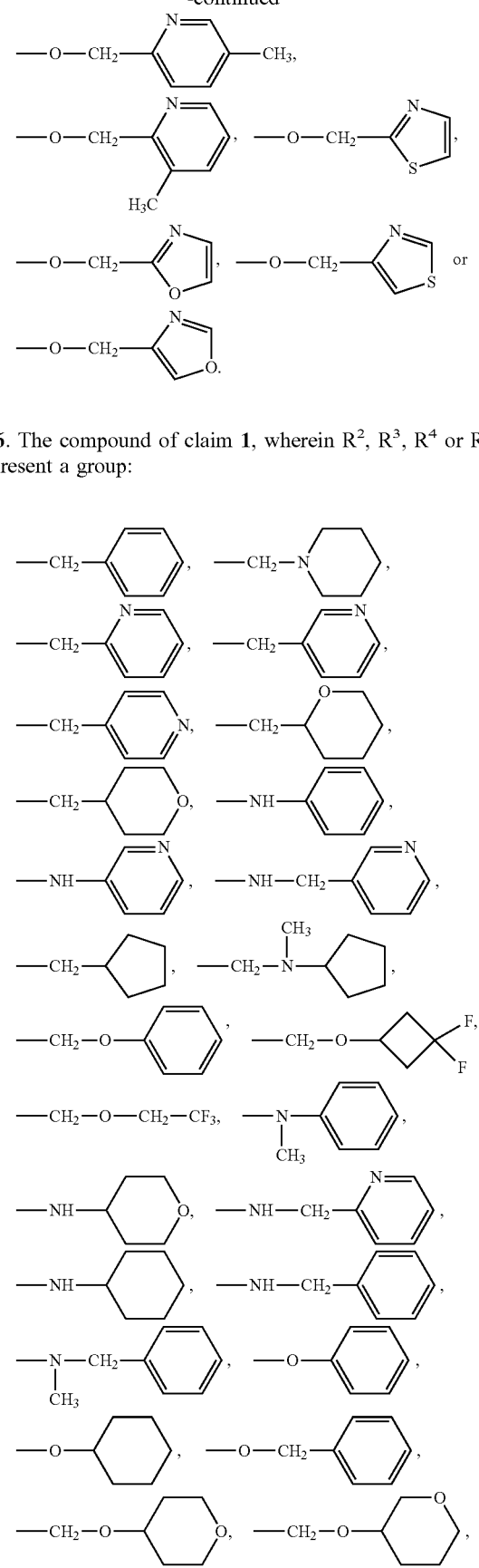
6. The compound of claim 1, wherein $R^2$, $R^3$, $R^4$ or $R^5$ represent a group:

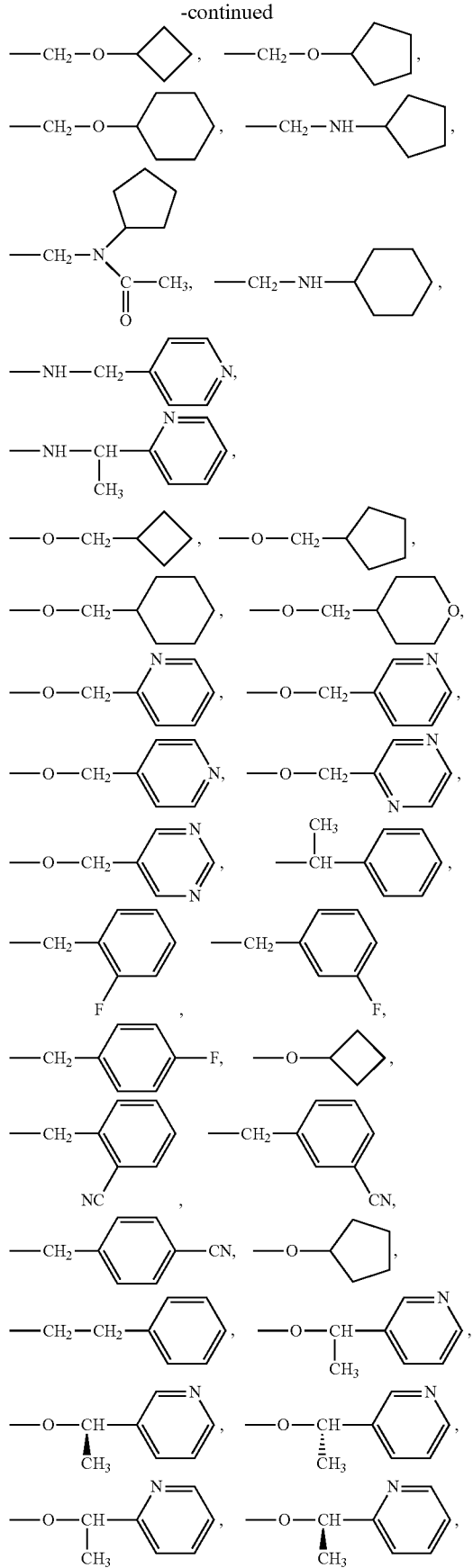
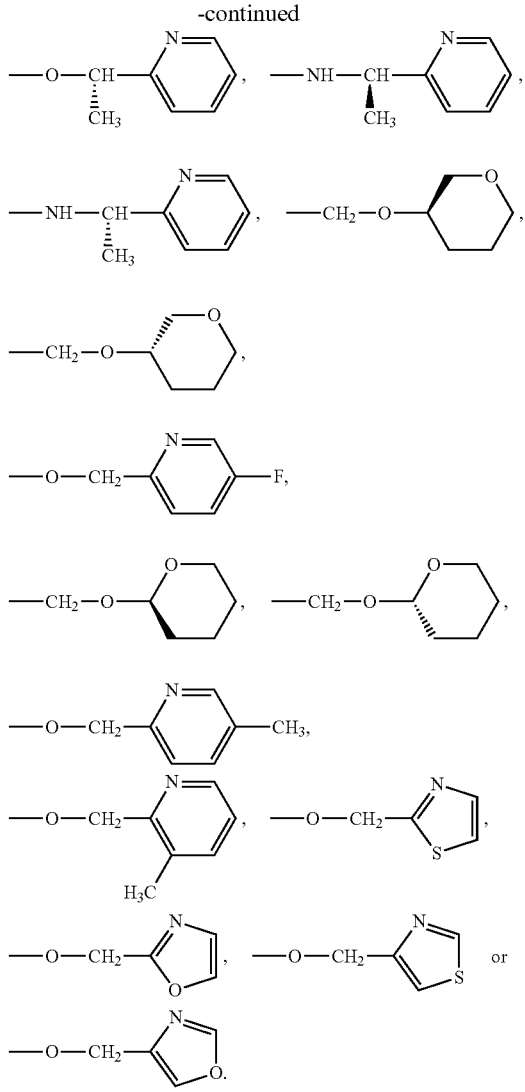

7. The compound of claim 1, wherein $X^1$, $X^2$ and $X^3$ are all carbon atoms.

8. The compound of claim 1, wherein $R^9$ is methyl, ethyl, n-propyl, isopropyl or cyclopropyl.

9. The compound of claim 7, wherein $R^7$ and $R^{10}$ are each hydrogen atoms and $R^8$ is Cl, CN, $NHR^6$ or a substituted or unsubstituted $C_1$-$C_6$alkyl or $C_3$-$C_6$cycloalkyl group.

10. The compound of claim 1, having the following formula (IIIa), (IIIb) or (IIIc):

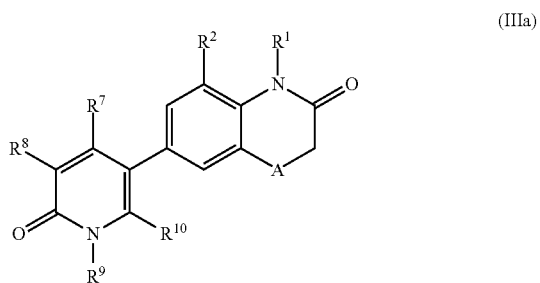

-continued

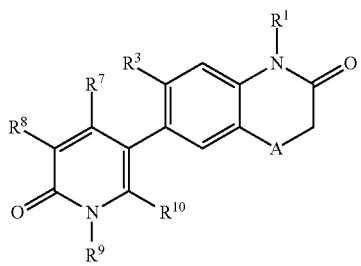
(IIIb)

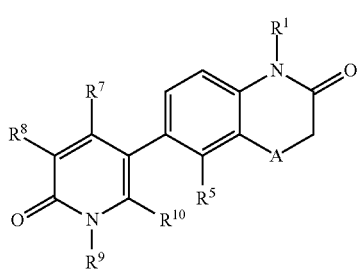
(IIIc)

wherein A, $R^1$, $R^2$, $R^3$, $R^5$, $R^7$, $R^8$, $R^9$ and $R^{10}$ are as defined in claim 1, or a pharmaceutically acceptable salt, solvate, ester or prodrug thereof.

11. The compound of claim 1, having the following formula (IVa) (IVb) or (IVc):

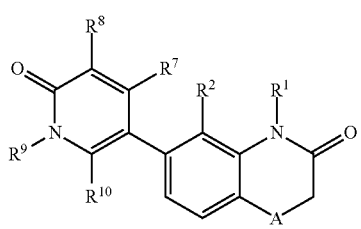
(IVa)

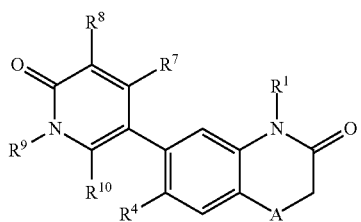
(IVb)

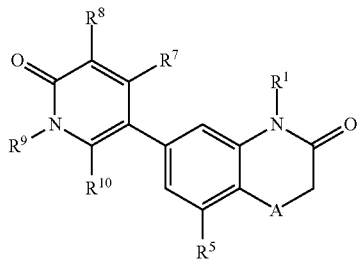
(IVc)

wherein A, $R^1$, $R^2$, $R^4$, $R^5$, $R^7$, $R^8$, $R^9$, $R^{10}$ are as defined in claim 1, or a pharmaceutically acceptable salt, solvate, ester or prodrug thereof.

12. The compound of claim 1, having the following formula (IIId), (IIIe) or (IIIf):

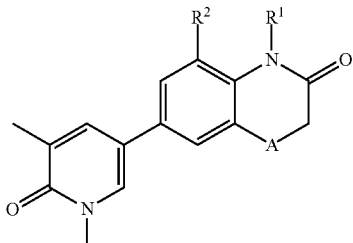
(IIId)

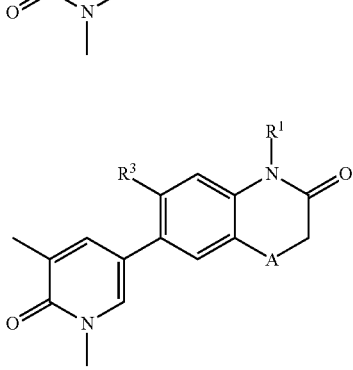
(IIIe)

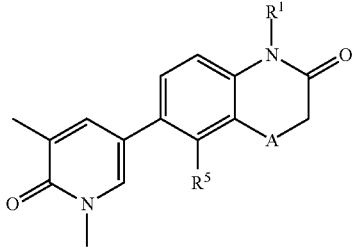
(IIIf)

wherein A, $R^1$, $R^2$, $R^3$ and $R^5$ are as defined in claim 1, or a pharmaceutically acceptable salt, solvate, ester or prodrug thereof.

13. The compound of claim 1, having the following formula (IVd), (IVe) or (IVf):

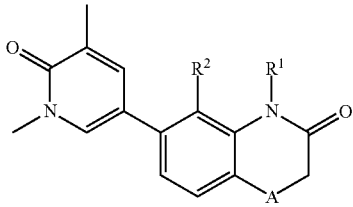
(IVd)

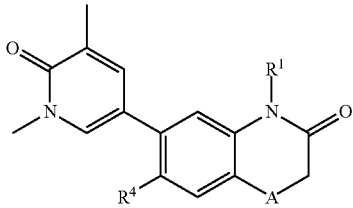
(IVe)

(IVf)
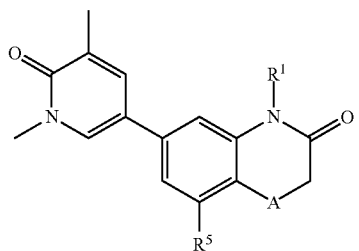
wherein A, $R^1$, $R^2$, $R^4$ and $R^5$ are as defined in claim 1, or a pharmaceutically acceptable salt, solvate, ester or prodrug thereof.
14. The compound of claim 1, wherein the compound is selected from the following compounds
Compound 1
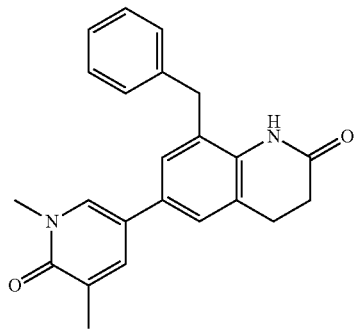
Compound 2
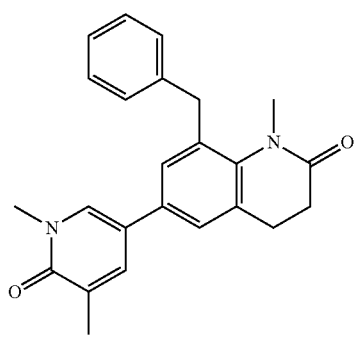
Compound 3
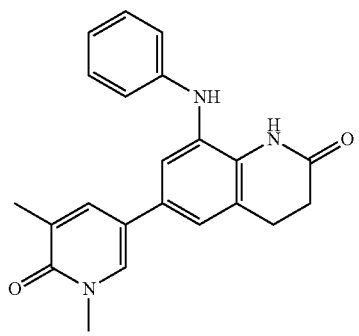
Compound 4
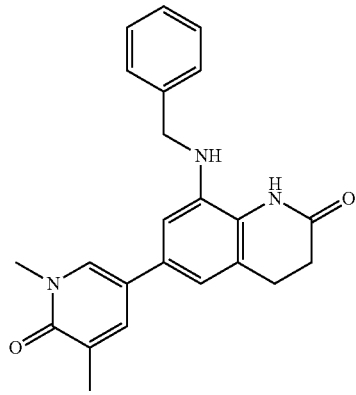
Compound 5
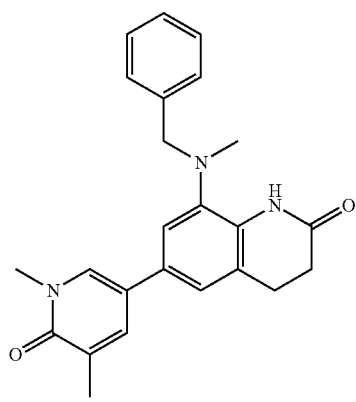
Compound 6
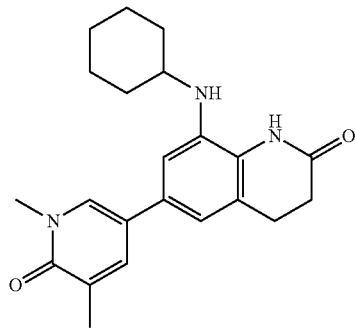
Compound 7
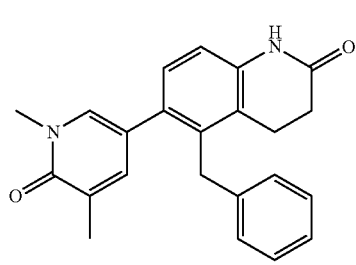

Compound 8
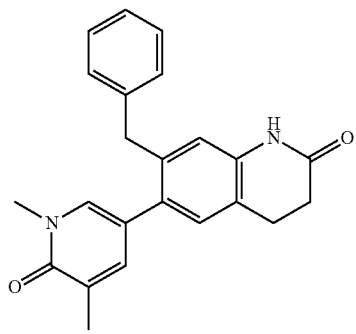
Compound 9
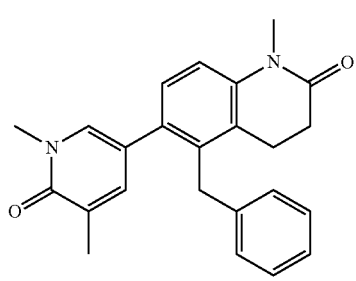
Compound 10
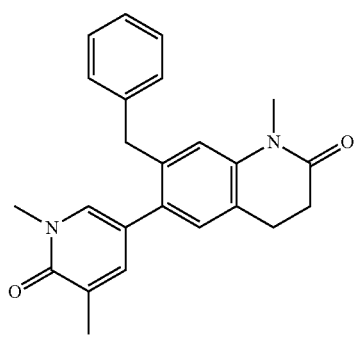
Compound 11
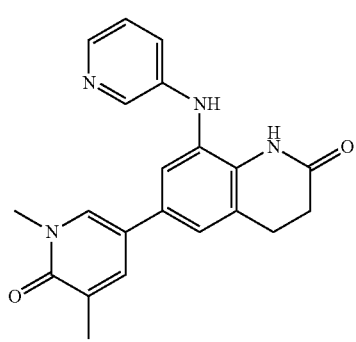
Compound 12
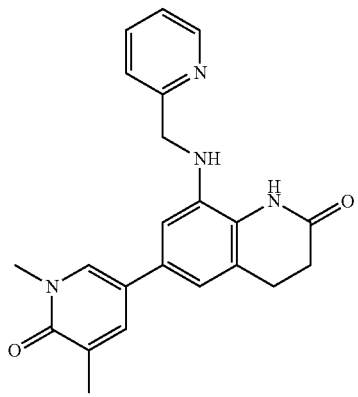
Compound 13
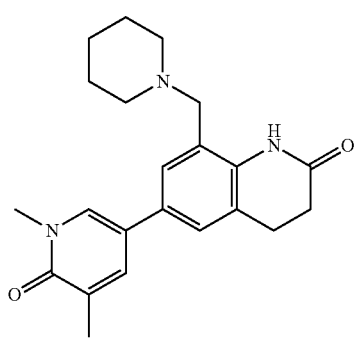
Compound 14
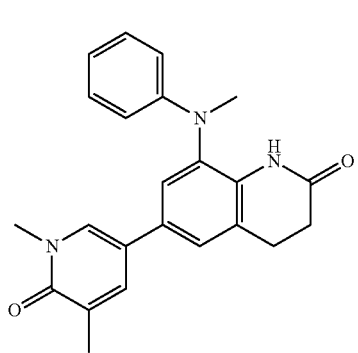
Compound 15
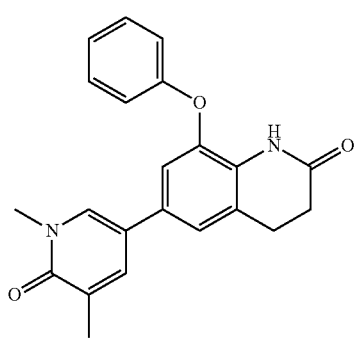

Compound 16
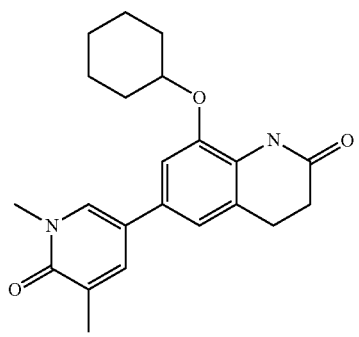
Compound 17
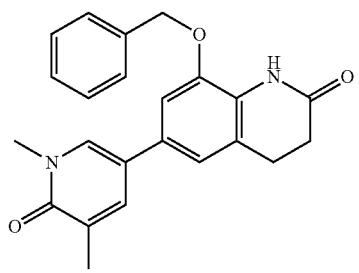
Compound 18
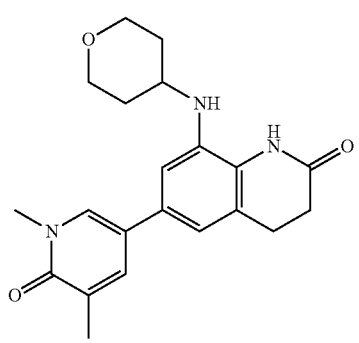
Compound 19
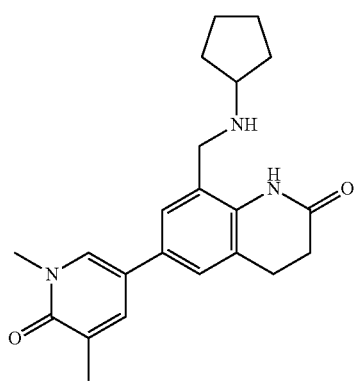
Compound 20
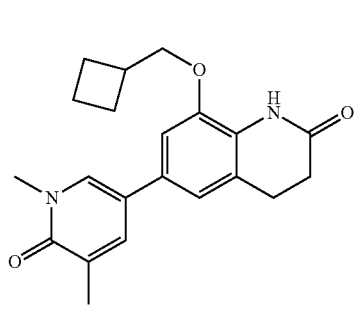
Compound 21
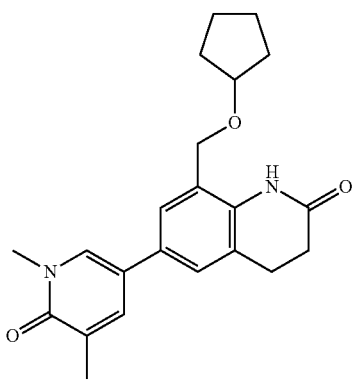
Compounds 22 and 23
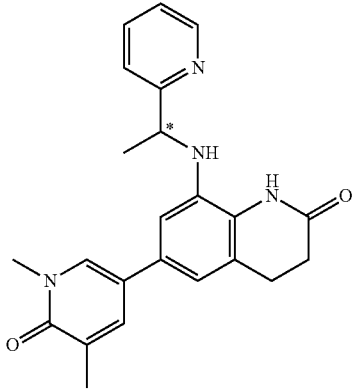
where compounds 22 and 23 are enantiomers
Compound 24
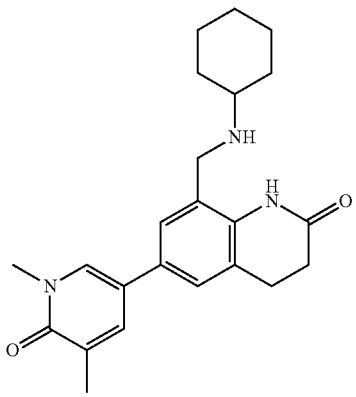
Compound 25
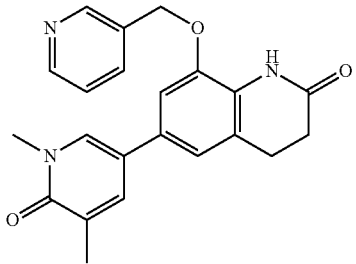

Compound 26
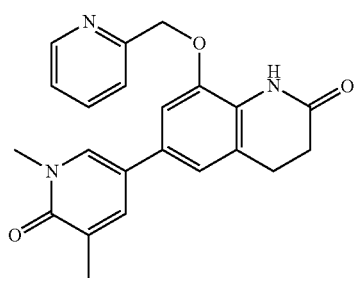
Compound 27
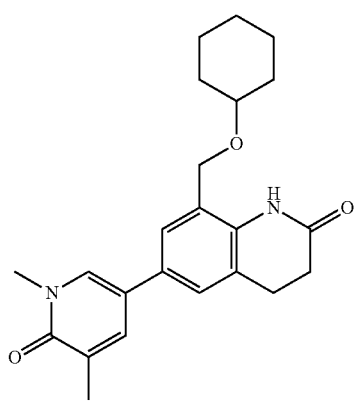
Compound 28
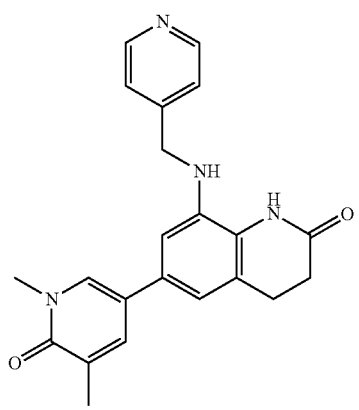
Compound 29
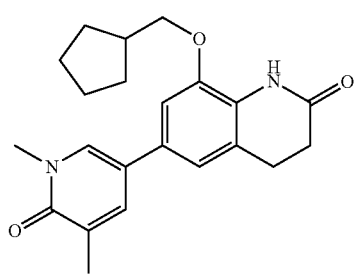
Compound 30
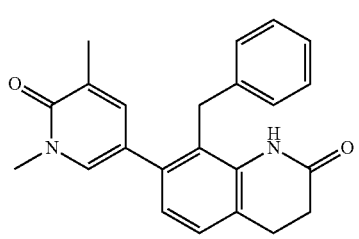
Compound 31
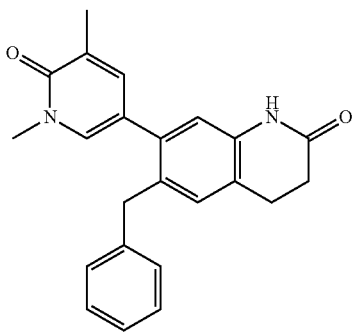
Compound 32
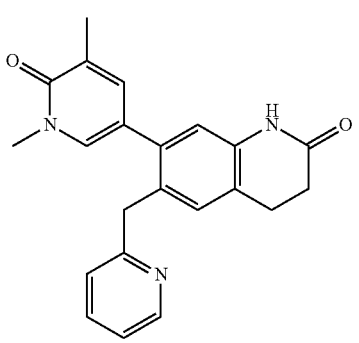
Compound 33
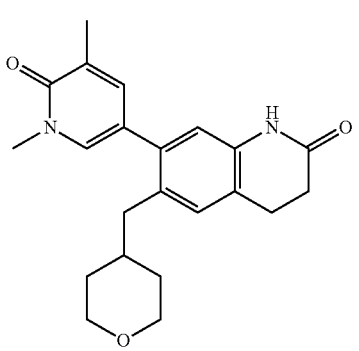
Compound 34
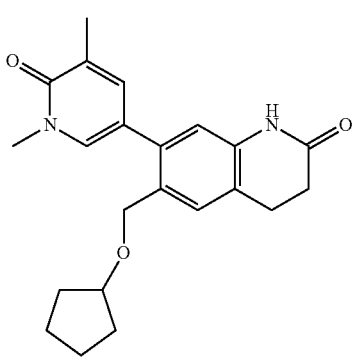

Compound 35
Compound 36
Compound 37
Compound 38
Compound 39
Compound 40
Compound 41
Compound 42
Compound 43
Compound 44

Compound 45
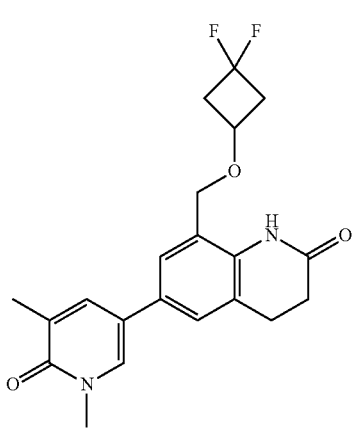
Compound 49
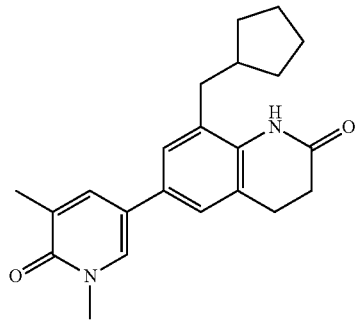
Compound 46
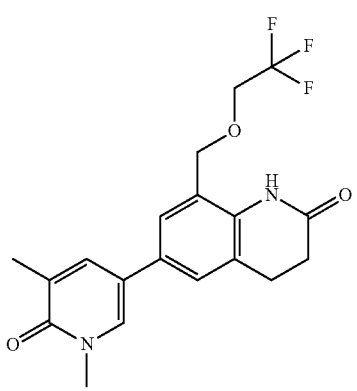
Compound 50
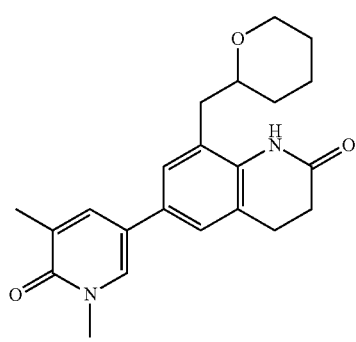
Compound 47
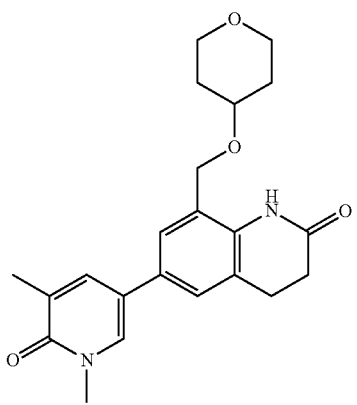
Compound 51
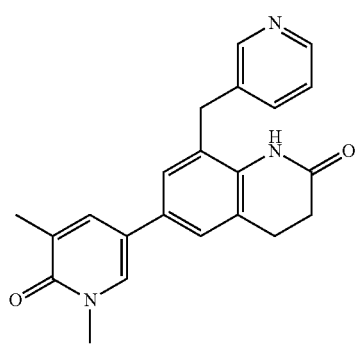
Compounds 48a and 48b
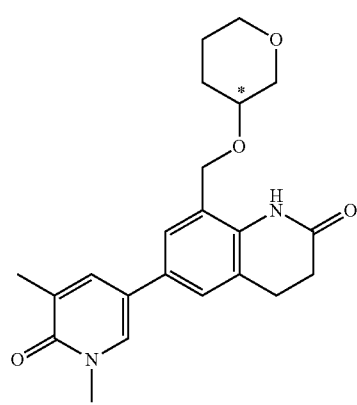
where compounds 48a and 48b are enantiomers
Compound 52
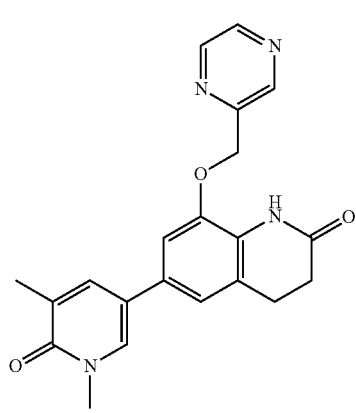

Compound 53
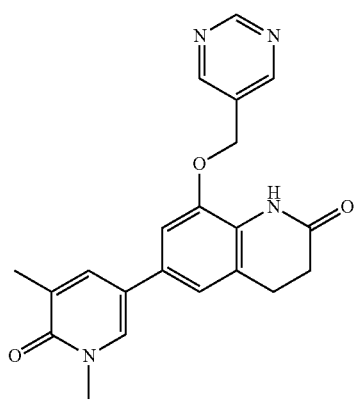
Compounds 54a and 54b
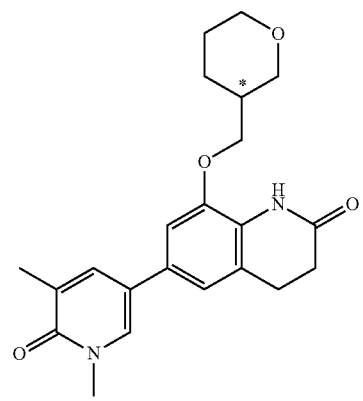
where compounds 54a and 54b are enantiomers
Compounds 55a and 55b
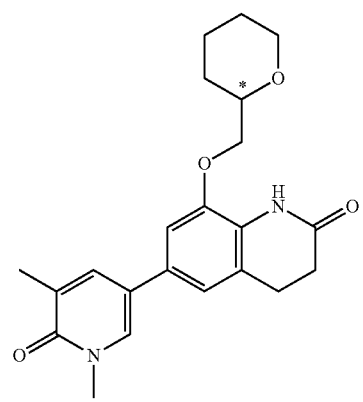
Where compounds 55a and 55b are enantiomers
Compound 56
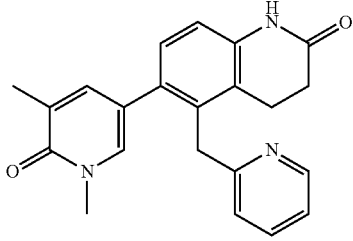
Compound 57
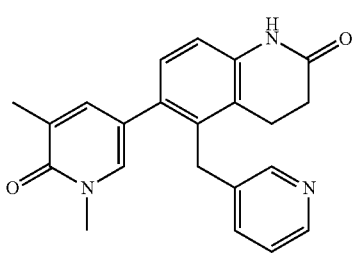
Compound 58
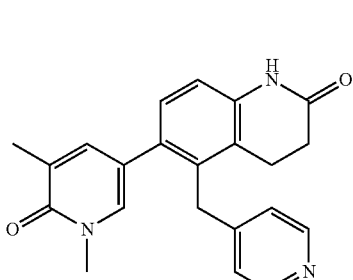
Compound 59
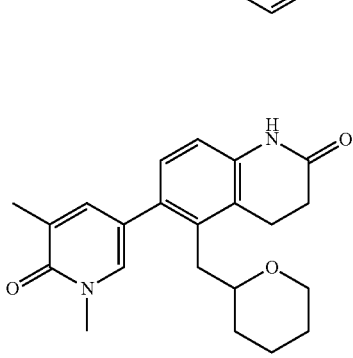
Compound 60
Compound 61
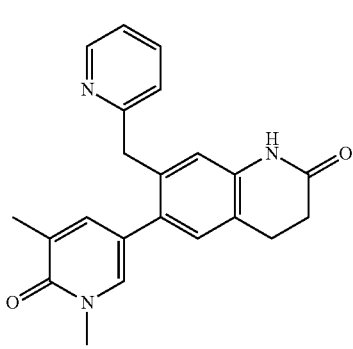

243
-continued
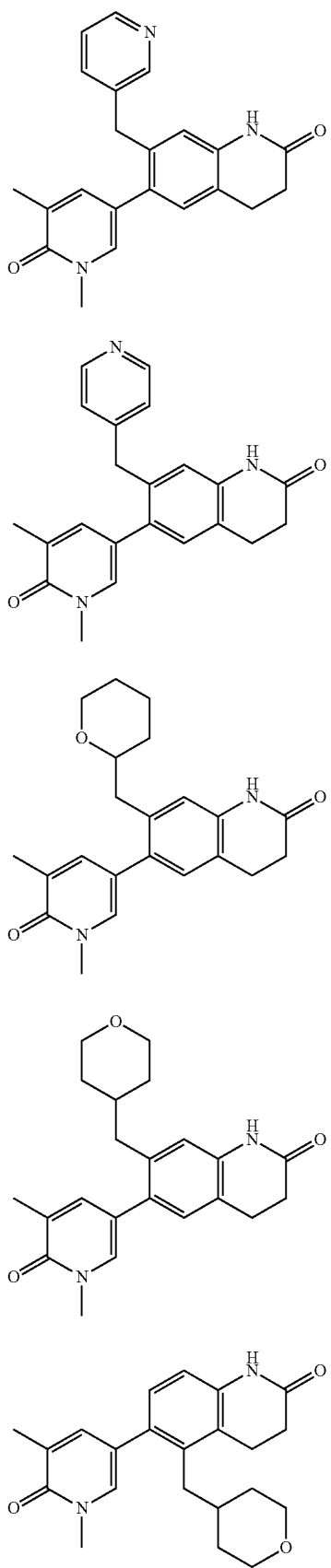
Compound 62
Compound 63
Compound 64
Compound 65
Compound 66
244
-continued
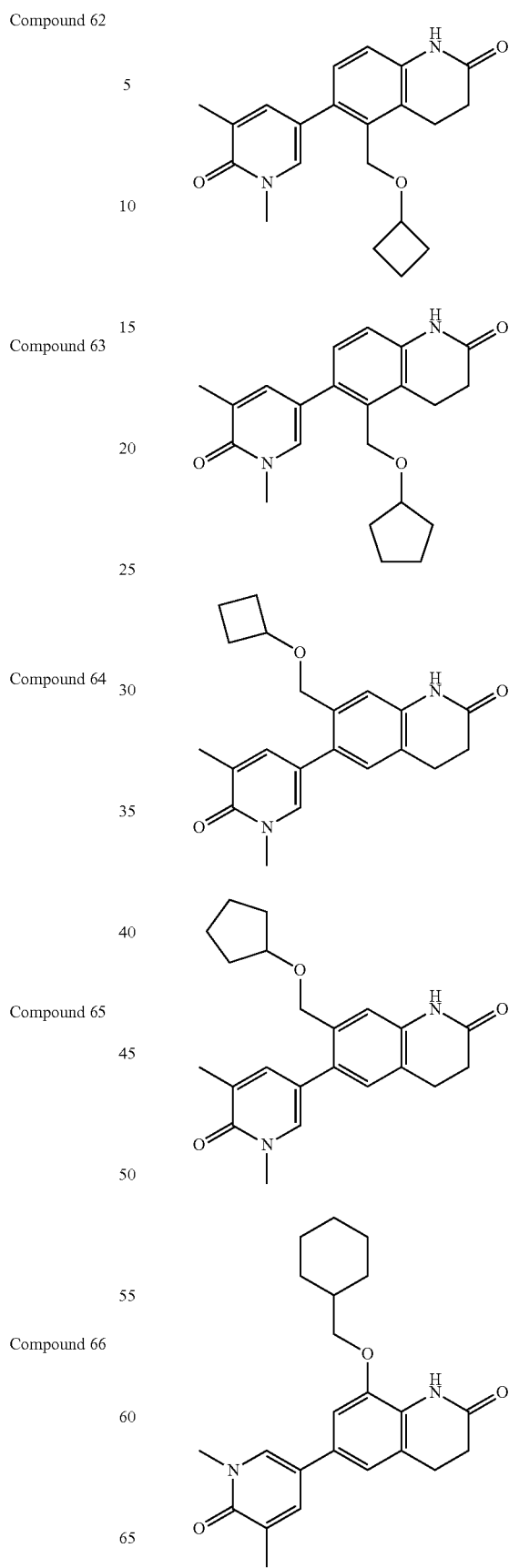
Compound 67
Compound 68
Compound 69
Compound 70
Compound 71

Compound 72
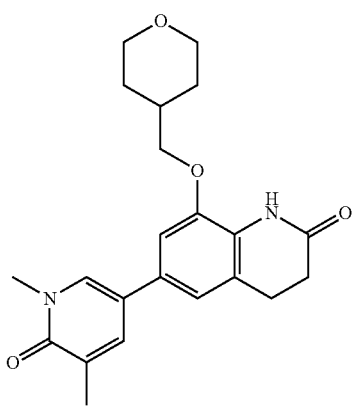
Compound 73
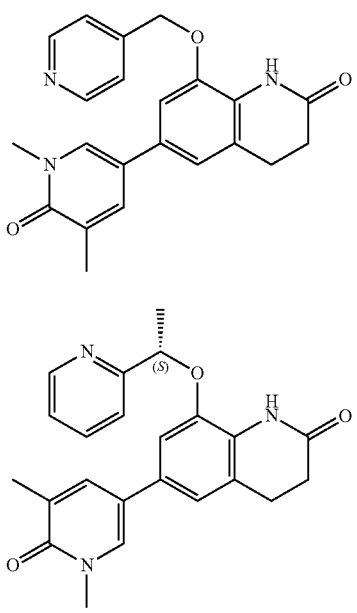
Compound 74a
Compound 74b
Compound 75
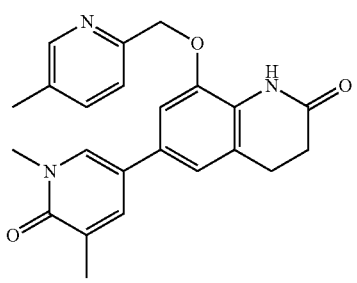
Compound 76
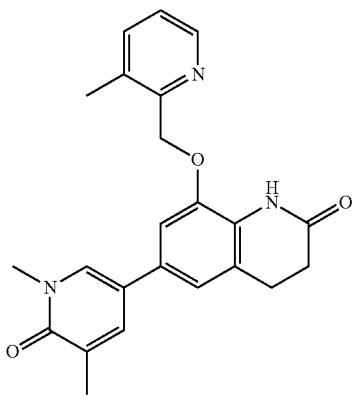
Compound 77
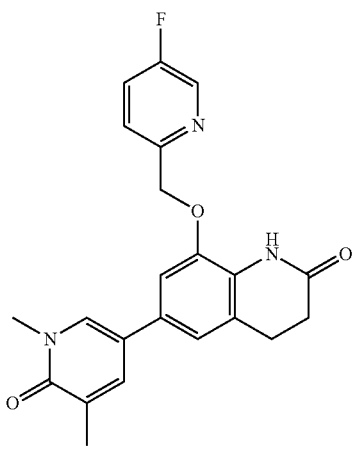
Compound 78
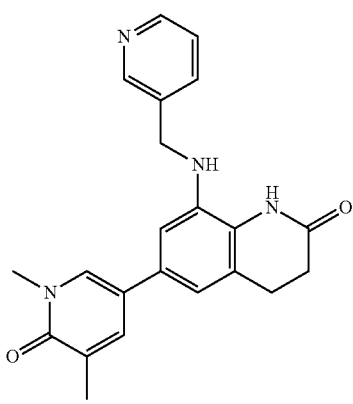
Compound 79
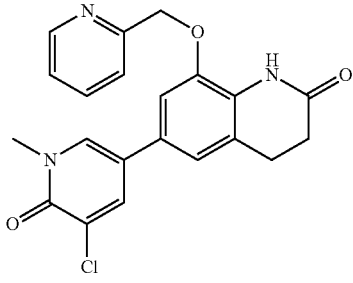

Compound 80
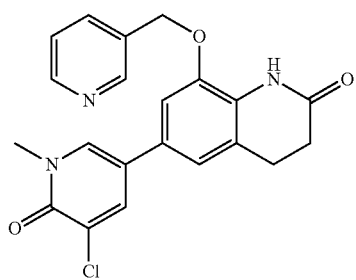
Compound 81
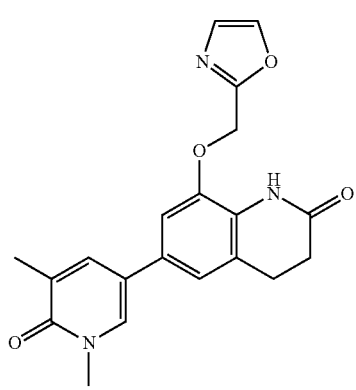
Compound 82
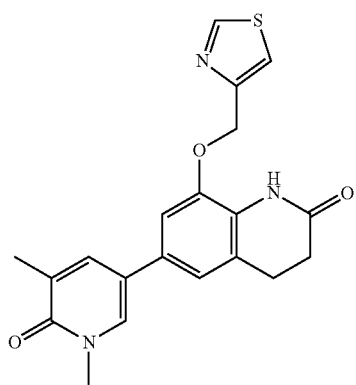
Compound 83
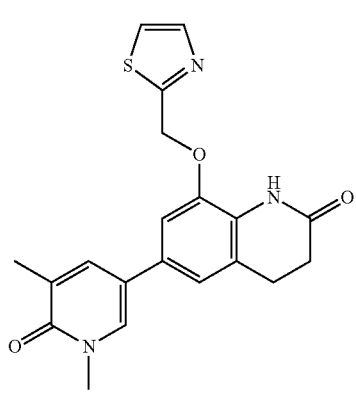
Compound 84
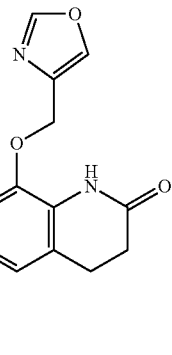
Compound 85
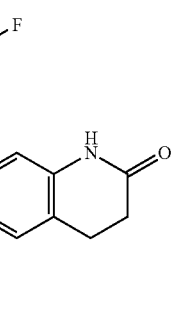
Compound 86
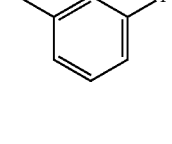
Compound 87
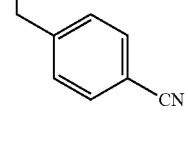
Compound 88
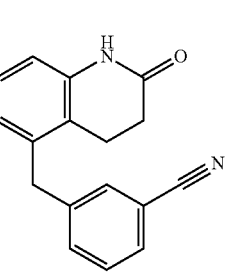

Compound 89
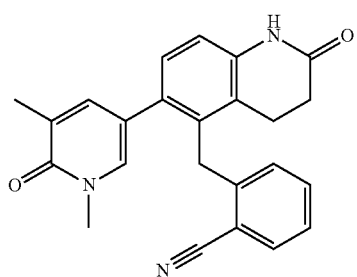
Compound 90
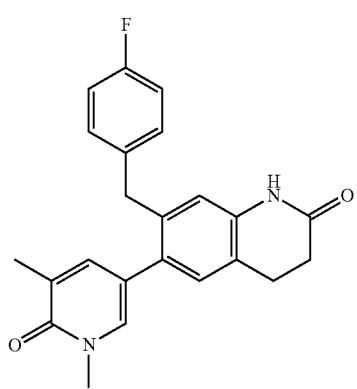
Compound 91
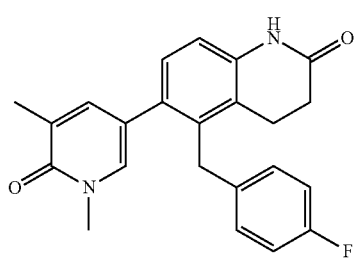
Compounds 92a and 92b
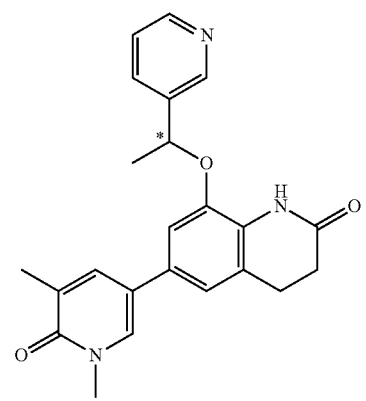
where Compounds 92a and 92b are enantiomers
Compound 93
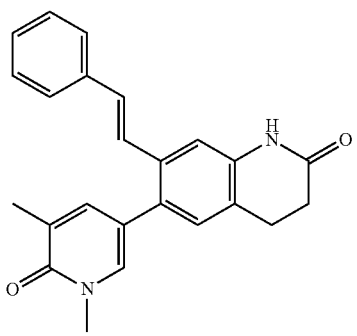
Compound 94
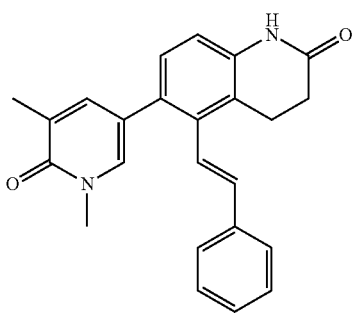
Compound 95
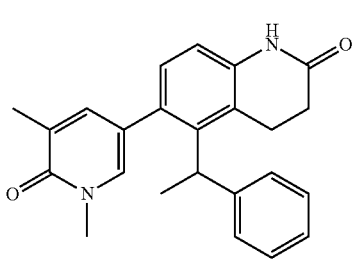
Compound 96
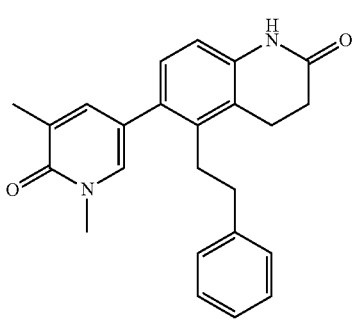
Compound 97
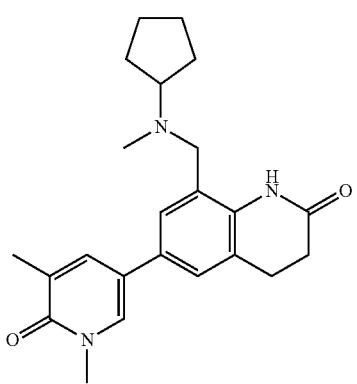

251
-continued

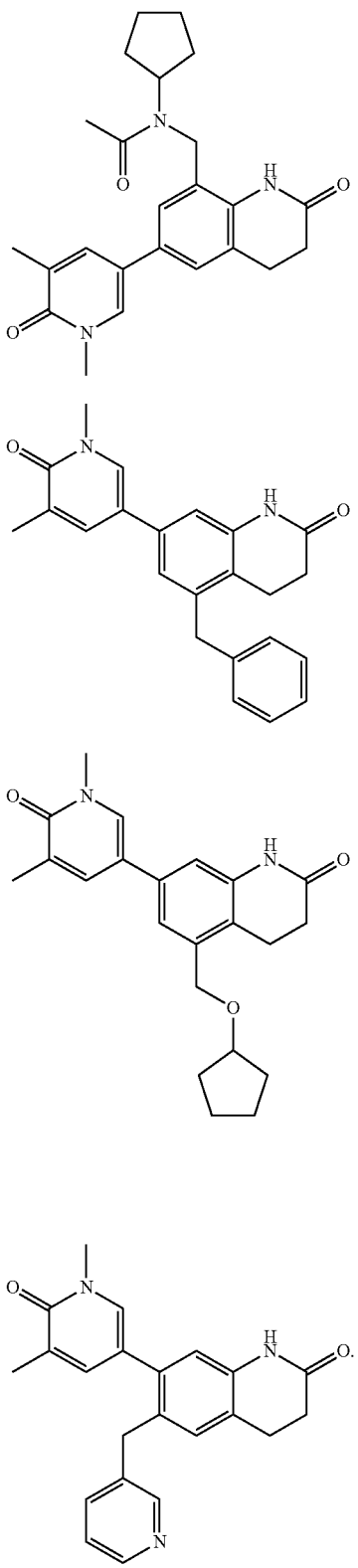

Compound 98

Compound 99

Compound 100

Compound 101

15. The compound of claim 14, wherein the compound is selected from Compounds 1-29, 30-32, 34, 38, 39, 44, 46, 47, 48a, 48b, 52, 53, 54a, 54b, 55a, 55b, 57, 58, 61, 62, 67-73, 74a, 74b, 75-91, 92a, 92b and 93-101.

252

16. The compound of claim 1, which is:

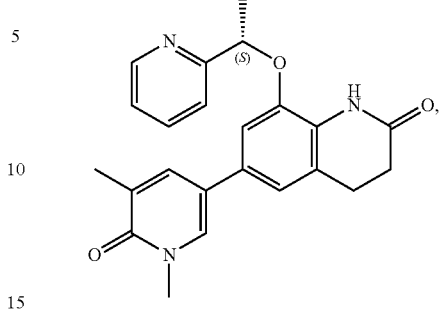

or a pharmaceutically acceptable salt thereof.

17. A method for the treatment of rheumatoid arthritis, irritable bowel syndrome or psoriasis which comprises administering to a subject in need thereof, a therapeutically effective amount of a compound according to claim 1.

18. A method for the treatment of rheumatoid arthritis, irritable bowel syndrome or psoriasis which comprises administering to a subject in need thereof, a therapeutically effective amount of a compound according to claim 14.

19. The method of claim 17, wherein the compound is:

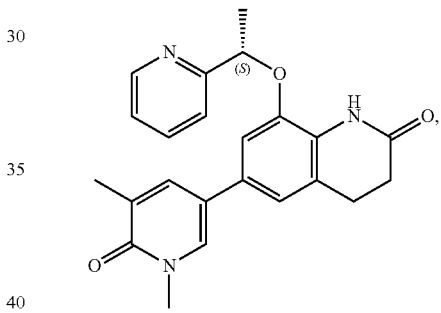

or a pharmaceutically acceptable salt thereof.

20. A method for the treatment of cancer, which comprises administering to a subject in need thereof, a therapeutically effective amount of a compound according to claim 1, wherein the cancer is selected from the group consisting of bladder cancer, leukemia, lymphoma, brain cancer, central nervous system cancer, breast cancer, cervix cancer, colorectal cancer, colon cancer, kidney cancer, liver cancer, lung cancer, mesothelioma, ovarian cancer, pancreatic cancer, prostate cancer, skin cancer and gastric cancer.

21. The method of claim 20, wherein the cancer is selected from the group consisting of breast cancer, bladder cancer, colon cancer, lung cancer, lymphoma, leukemia, mesothelioma, ovarian cancer and prostate cancer.

22. The method of claim 20, wherein the cancer is prostate cancer.

23. A method for the treatment of cancer, which comprises administering to a subject in need thereof, a therapeutically effective amount of a compound according to claim 14, wherein the cancer is selected from the group consisting of bladder cancer, leukemia, lymphoma, brain cancer, central nervous system cancer, breast cancer, cervix cancer, colorectal cancer, colon cancer, kidney cancer, liver cancer, lung cancer, mesothelioma, ovarian cancer, pancreatic cancer, prostate cancer, skin cancer and gastric cancer.

24. The method of claim 20, wherein the compound is:
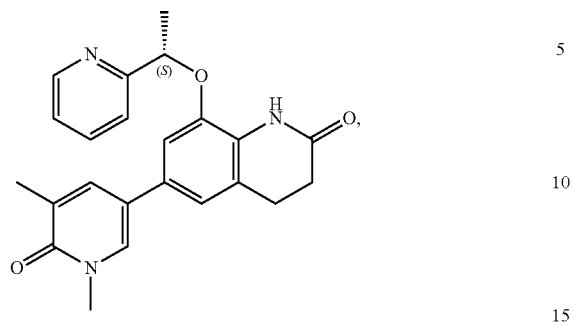
or a pharmaceutically acceptable salt thereof.
25. The method of claim 24, wherein the cancer is prostate cancer.
* * * * *

UNITED STATES PATENT AND TRADEMARK OFFICE
CERTIFICATE OF CORRECTION

PATENT NO. : 10,501,438 B2
APPLICATION NO. : 15/751800
DATED : December 10, 2019
INVENTOR(S) : Guilluame Jacquemot et al.

Page 1 of 1

It is certified that error appears in the above-identified patent and that said Letters Patent is hereby corrected as shown below:

In the Claims

In Column 220, Claim 3, Line 33, delete "O($R^a$)($R^b$)($R^c$)" and in its place insert -- C($R^a$)($R^b$)($R^c$) --

In Column 226, Claim 6, in both formulas between Lines 20-25, delete "——$CH_2$—O" in two places, and insert in its place -- ——O—$CH_2$ --

In Column 227, Claim 11, Line 30, insert a -- , -- between "(IVa)" and "(IVb)"

Signed and Sealed this
Tenth Day of March, 2020

Andrei Iancu
*Director of the United States Patent and Trademark Office*